United States Patent
Nedergaard et al.

(10) Patent No.: US 9,901,650 B2
(45) Date of Patent: Feb. 27, 2018

(54) METHODS FOR EVALUATING BRAIN-WIDE PARAVASCULAR PATHWAY FOR WASTE CLEARANCE FUNCTION AND METHODS FOR TREATING NEURODEGENERATIVE DISORDERS BASED THEREON

(71) Applicants: University of Rochester, Rochester, NY (US); The Research Foundation for The State University of New York, Albany, NY (US)

(72) Inventors: Maiken Nedergaard, Webster, NY (US); Jeffrey J. Iliff, Portland, OR (US); Helene Benveniste, Northport, NY (US); Rashid Deane, Rochester, NY (US)

(73) Assignees: University of Rochester, Rochester, NY (US); The Research Foundation for The State University of New York, Albany, NY (US)

( * ) Notice: Subject to any disclaimer, the term of this patent is extended or adjusted under 35 U.S.C. 154(b) by 0 days.

(21) Appl. No.: 14/769,396

(22) PCT Filed: Feb. 21, 2014

(86) PCT No.: PCT/US2014/017606
§ 371 (c)(1),
(2) Date: Aug. 20, 2015

(87) PCT Pub. No.: WO2014/130777
PCT Pub. Date: Aug. 28, 2014

(65) Prior Publication Data
US 2016/0000945 A1    Jan. 7, 2016

Related U.S. Application Data

(60) Provisional application No. 61/767,546, filed on Feb. 21, 2013, provisional application No. 61/862,321, filed on Aug. 5, 2013, provisional application No. 61/942,447, filed on Feb. 20, 2014.

(51) Int. Cl.
| | | |
|---|---|---|
| A61K 51/04 | (2006.01) | |
| A61K 49/00 | (2006.01) | |
| A61K 31/41 | (2006.01) | |
| A61K 38/10 | (2006.01) | |
| A61B 5/055 | (2006.01) | |
| A61B 5/00 | (2006.01) | |
| G01N 33/68 | (2006.01) | |
| A61K 31/4178 | (2006.01) | |
| A61K 31/437 | (2006.01) | |
| A61K 31/55 | (2006.01) | |
| A61K 31/551 | (2006.01) | |
| A61K 49/06 | (2006.01) | |
| A61M 27/00 | (2006.01) | |
| A61B 6/03 | (2006.01) | |

(52) U.S. Cl.
CPC .......... *A61K 51/0491* (2013.01); *A61B 5/055* (2013.01); *A61B 5/4064* (2013.01); *A61B 5/4082* (2013.01); *A61K 31/41* (2013.01); *A61K 31/4178* (2013.01); *A61K 31/437* (2013.01); *A61K 31/55* (2013.01); *A61K 31/551* (2013.01); *A61K 38/10* (2013.01); *A61K 49/0032* (2013.01); *A61K 49/0054* (2013.01); *A61K 49/06* (2013.01); *A61M 27/00* (2013.01); *G01N 33/6896* (2013.01); *A61B 6/037* (2013.01); *A61B 2576/026* (2013.01); *G01N 2800/2814* (2013.01); *G01N 2800/50* (2013.01)

(58) Field of Classification Search
None
See application file for complete search history.

(56) References Cited

U.S. PATENT DOCUMENTS

| | | |
|---|---|---|
| 6,321,105 B1 | 11/2001 | Jenkins et al. |
| 6,689,085 B1 | 2/2004 | Rubenstein et al. |
| 2005/0215770 A1* | 9/2005 | Bell ............... C07K 16/28 530/388.22 |
| 2007/0104650 A1 | 5/2007 | Cunningham et al. |
| 2009/0296998 A1 | 12/2009 | Fox et al. |
| 2010/0215587 A1 | 8/2010 | Huang et al. |

(Continued)

OTHER PUBLICATIONS

Kienlen-campard 2002 "intracellular amyloid-b1-42 but not extracellular soluble amyloid-b peptides induces neuronal apoptosis" JBC 277(18):15666-15670.*
Raghavan 2011 "predictive models for pressure-driven fluid infusions into brain parenchyma" PMB 56(19):6179-6204.*
Reitz 2016 "toward precision medicine in alzheimer's disease" Annals Trans Med 4(6):107.*
Stanford 2016 "alzheimer's prevention treatment and research" accessed from stanfordhealthcare.org on May 3, 2016.*
(Continued)

*Primary Examiner* — Adam Weidner
(74) *Attorney, Agent, or Firm* — Harris Beach PLLC

(57) ABSTRACT

Methods are provided for measuring glio-vascular pathway ("glymphatic system") function in the brain of a mammal which include performing imaging of the brain and measuring cerebrospinal fluid-interstitial fluid (CSF-ISF) exchange in the brain. The methods can be used to track the exchange between CSF and ISF compartments. An imaging agent is optionally administered intrathecally. The imaging agent can be a negative or positive (paramagnetic) contrast agent and dynamic or contrast-enhanced magnetic resonance imaging (MRI) of the brain can be performed. The imaging agent can be a positron-emitting radionuclide tracer and positron emission tomography (PET) can be performed. Methods for treating diseases or disorders of the mammalian brain are also provided, in which the methods increase or decrease glymphatic clearance.

6 Claims, 116 Drawing Sheets

(56) References Cited

U.S. PATENT DOCUMENTS

Figure 2A:
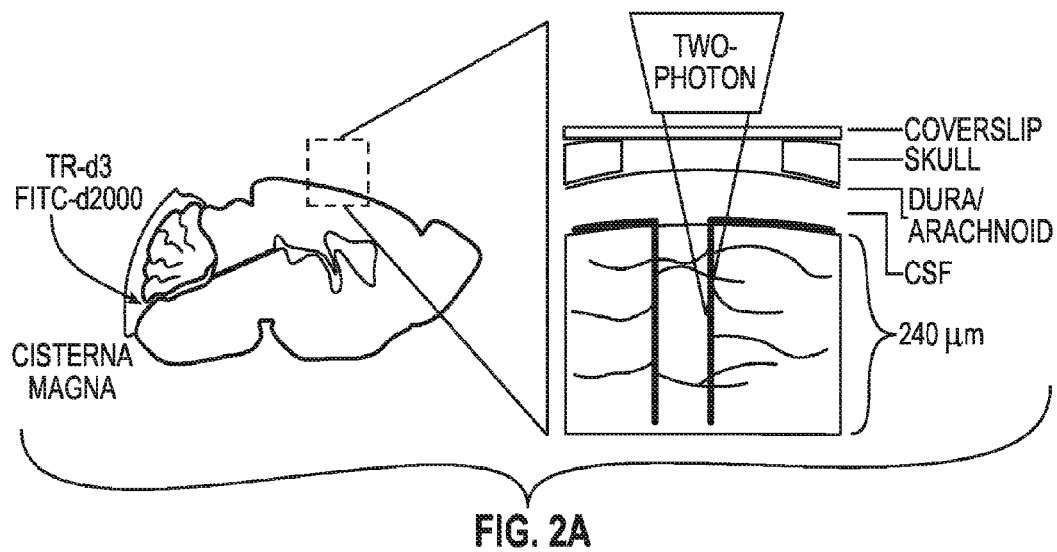

| | | | |
|---|---|---|---|
| 2011/0183904 A1* | 7/2011 | Jacobson | A61K 38/11 514/10.9 |
| 2011/0256150 A1* | 10/2011 | Watts | A61K 31/7105 424/158.1 |
| 2013/0022622 A1* | 1/2013 | Ben-Ari | G01N 33/5058 424/172.1 |

OTHER PUBLICATIONS

Weller "Lymphatic drainage of the brain and the pathophysiology of neurological disease" Acta Neuropathol 117:1-14 (Year: 2009).*

Abbott, N.J., "Evidence for bulk flow of brain interstitial fluid: significance for physiology and pathology," Jan. 24, 2004 Neurochemistry International, vol. 45 (pp. 545-552).

Amiry-Moghaddam, M., et al., "An α-syntrophin-dependent pool of AQP4 in astroglial end-feet confers bidirectional water flow between blood and brain," 2003 PNAS vol. 100 No. 4 (pp. 2106-2111).

Ball, K., et al., "Trafficking of glucose, lactate, and amyloid-β from the inferior colliculus through perivascular routes," 2010 Journal of Cerebral Blood Flow & Metabolism vol. 30 (pp. 162-176).

Bero, A., et al., "Neuronal activity regulates the regional vulnerability to amyloid-β deposition," 2011 Nat Neurosci vol. 14 No. 6 (pp. 750-756).

Chiu, C., et al., "Temporal course of cerebrospinal fluid dynamics and amyloid accumulation in the aging rat brain from three to thirty months," 2012 Fluids and Barriers of the CNS, vol. 9 No. 3 (pp. 1-8).

Deane, R., et al., Clearance of amyloid-β peptide across the blood-brain barrier: Implication for therapies in Alzheimer's disease, 2009 CNS Neurol Disord Drug Targets, vol. 8 No. 1 (pp. 16-30).

Eilert-Olsen, M, et al., "Deletion of Aquaporin-4 Changes the Perivascular Glial Protein Scaffold Without Disrupting the Brain Endothelial Barrier," 2012 GLIA, vol. 60 (pp. 432-440).

Groothuis, D., et al., "Efflux of drugs and solutes from brain: the interactive roles of diffusional transcapillary transport, bulk flow and capillary transporters," 2007 Journal of Cerebral Blood Flow & Metabolism, vol. 27 (pp. 43-56).

Hadaczek, P., et al., "The "Perivascular Pump" Driven by Arterial Pulsation is a Powerful Mechanism for the Distribution of Therapeutic Molecules within the Brain," 2006 Mol Ther, vol. 14 No. 1 (pp. 69-78).

Haj-Yasein, N.N., et al., "Glial-conditional deletion of aquaporin-4 (Aqp4) reduces blood-brain water uptake and confers barrier function on perivascular astrocyte endfeet," 2011 PNAS vol. 108 No. 43 (pp. 17815-17820).

Hardy, John, et al., "A Hundred Years of Alzheimer's Disease Research," 2006 Neuron, vol. 52 (pp. 3-13).

Hardy, John, "The amyloid hypothesis for Alzheimer's disease: a critical reappraisal," 2009 Journal of Neurochemistry, vol. 110 (pp. 1129-1134).

Hardy, John, et al., "The Amyloid Hypothesis of Alzheimer's Disease: Progress and Problems on the Road to Therapeutics," 2002 Science, vol. 297 (pp. 353-358).

Mawuenyega, K., et al., "Decreased Clearance of CNS Amyloid-β in Alzheimer's Disease," 2010 Science, vol. 330 No. 6012 (6 pgs).

Papadopoulos, M., et al., "Aquaporin-4 and brain edema," 2007 Pediatr Nephrol, vol. 22 (pp. 778-784).

Pullen, R., et al., "Bulk flow of cerebrospinal fluid into brain in response to acute hyperosmolality," 1987 The American Physiological Society, (pp. F538-F545).

Rennels, M., et al., "Evidence for a 'Paravascular' Fluid Circulation in the Mammalian Central Nervous System, Provided by the Rapid Distribution of Tracer Protein Throughout the Brain from the Subarachnoid Space," 1985 Brain Research, vol. 326 (pp. 47-63).

Schley, D., et al., "Mechanisms to explain the reverse perivascular transport of solutes out of the brain," 2006 Journal of Theoretical Biology, vol. 238 (pp. 962-974).

Selkoe, Dennis, "Clearing the Brain's Amyloid Cobwebs," 2001 Neuron vol. 32 (pp. 177-180).

Serot, J., "Choroid plexus, aging of the brain, and Alzheimer's disease," 2003 Frontiers in Bioscience vol. 8 (pp. s515-521).

Serot, J., et al., "A Possible Role for CSF Turnover and Choroid Plexus in the Pathogenesis of Late Onset Alzheimer's Disease," 2012 Journal of Alzheimer's Disease vol. 30 (pp. 17-26).

Silverberg, G.D., "Continuous CSF drainage in AD: Results of a double-blind, randomized, placebo-controlled study," 2008 Neurology vol. 71 (pp. 202-209).

Silverberg, G.D., "Amyloid and Tau accumulate in the brains of aged hydrocephalic rats," 2010 Brain Research vol. 1317 (pp. 286-296).

Sykova, E. et al., "Diffusion in Brain Extracellular Space," 2008 Physiol Rev. vol. 88 No. 4 (pp. 1277-1340).

Takano, T., et al., "Astrocyte-mediated control of cerebral blood flow," 2006 Nature Neuroscience vol. 9 No. 2 (pp. 260-267).

Tanzi, Rudolph E., "The synaptic Aβ hypothesis of Alzheimer disease," 2005 Nature Neuroscience vol. 8 No. 8 (pp. 977-979).

Tanzi, R.E., et al., "Clearance of Alzheimer's Aβ Peptide: The Many Roads to Perdition," 2004 Neuron vol. 43 (pp. 605-608).

Thrane, A., et al., "Critical role of aquaporin-4 (AQP4) in astrocytic $Ca^{2+}$ signaling events elicited by cerebral edema," 2011 PNAS vol. 108 No. 2 (pp. 846-851).

Wang, J., et al., "Valsartan lowers brain β-amyloid protein levels and improves spatial learning in a mouse model of Alzheimer disease," 2007 The Journal of Clinical Investigation vol. 117 No. 11 (pp. 3393-3402).

Weller, R., et al., "Perivascular Drainage of Amyloid-β Peptides from the Brain and Its Failure in Cerebral Amyloid Angiopathy and Alzheimer's Disease," 2008 Brain Pathology vol. 18 (pp. 253-266).

Xie, L., et al., "Sleep Drives Metabolite Clearance from the Adult Brain," 2013 Science vol. 342 (11 pages).

Zhou, J., et al., "Altered blood-brain barrier integrity in adult aquaporin-4 knockout mice," 2008 NeuroReport vol. 19 No. 8 (pp. 1-5).

Zlokovic, B., et al., "Low-density lipoprotein receptor-related protein-1: a serial clearance homeostatic mechanism controlling Alzheimer's amyloid β-peptide elimination from the brain," 2010 J. Neurochem vol. 115 No. 5 (pp. 1077-1089).

Alvira-Botero, X., et al., "Clearance of Amyloid-β Peptide Across the Choroid Plexus in Alzheimer's Disease," 2010 Current Aging Science vol. 3 (pp. 219-229).

Deane, R., et al., "Role of the Blood-Brain Barrier in the Pathogenesis of Alzheimer's Disease," 2007 Current Alzheimer Research vol. 4 (pp. 191-197).

Oshio, K., et al., "Aquaporin-1 deletion reduces osmotic water permeability and cerebrospinal fluid production," 2003 Acta Neurochir vol. 86 (pp. 525-528).

Iliff, J., et al., "A Paravascular Pathway Facilitiates CSF Flow Through the Brain Parenchyma and the Clearance of Interstitial Solutes, Including Amyloid β," 2012 Sci Transl Med vol. 4 Issue 147; 147ra111 (22 pages).

Johanson, CE., et al., "Multiplicity of cerebrospinal fluid functions: New challenges in health and disease," 2008 Cerebrospinal Fluid Research vol. 5 No. 10 (pp. 1-32).

Walter, BA., et al., "The olfactory route for cerebrospinal fluid drainage into the peripheral lymphatic system," 2006 Neuropathol Appl Neurobiol vol. 32 No. 4 (abstract).

Gao, X., et al., "Prospective study of dietary pattern and risk of Parkinson disease," 2007 The American Journal of Clinical Nutrition, vol. 86 (pp. 1486-1494).

Jordan, B., et al., "Apolipoprotein E ∈4 Associated With Chronic Traumatic Brain Injury in Boxing," 1997 Journal of the American Medical Association vol. 278 No. 2 (Abstract—2 pp).

International Search Report and Written Opinion of the International Searching Authority for corresponding International Patent Application No. PCT/US14/17606 dated Jul. 14, 2014 (13 pages).

Kang, J.-E., et al. 2009. Amyloid-β Dynamics Are Regulated by Orexin and the Sleep-Wake Cycle, Science 326, 1005-1007.

(56) References Cited

OTHER PUBLICATIONS

Yamada, K. et al. 2011. In Vivo Microdialysis Reveals Age-Dependent Decrease of Brain Interstitial Fluid Tau Levels in P301S Human Tau Transgenic Mice. The Journal of Neuroscience, Sep. 14, 2011, 31(37):13110-13117.
Emmanouilidou, E. et al. 2011. Assessment of α-Synuclein Secretion in Mouse and Human Brain Parenchyma, PLoS One 6(7): e22225. doi:10.1371/journal.pone.0022225.
Kang, J., et al., "Amyloid-β Dynamics are Regulard by Orexin and the Sleep-Wake Cycle," Sep. 24, 2009, Scienceexpress, vol. 1126 (10), pp. 1180962-1180970.
Mogi, M., et al., "Roles of Brain Angiotensin II in Cognitive Function and Dementia," Sep. 14, 2012, International Journal of Hypertension, vol. 2012 (3), pp. 1-7.
Sakka, L., "Anatomy and physiology of cerebrospinal fluid," Nov. 18, 2011, European Annals of Otorhinolaryngology, Head and Neck diseases, vol. 2011 (128), pp. 309-316.

\* cited by examiner

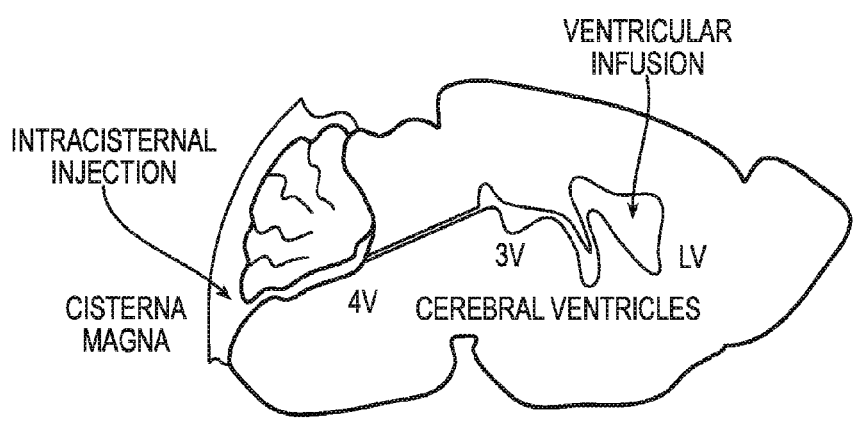
FIG. 1A
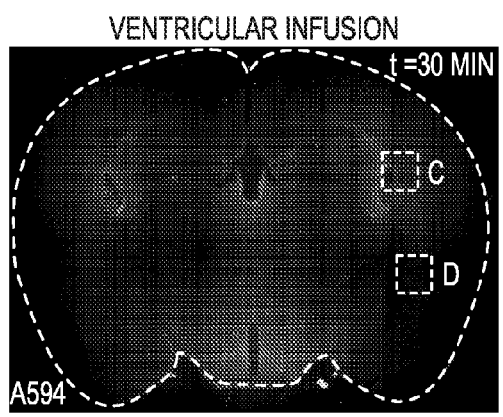
FIG. 1B
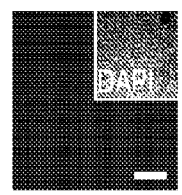
FIG. 1C   FIG. 1D
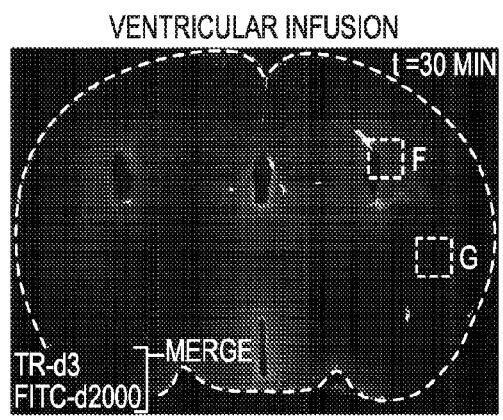
FIG. 1E
 
FIG. 1F   FIG. 1G

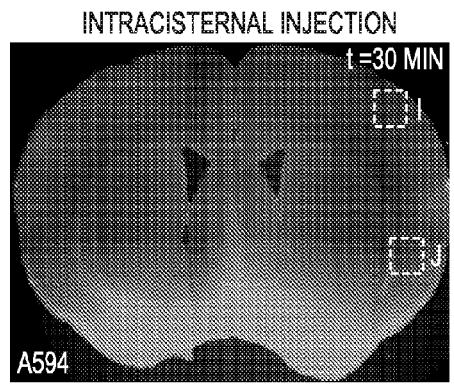
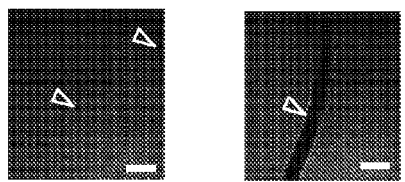
FIG. 1H | FIG. 1I | FIG. 1J
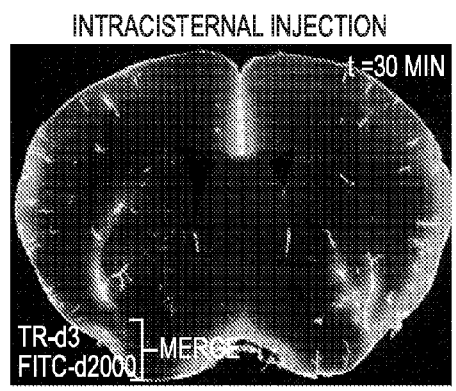
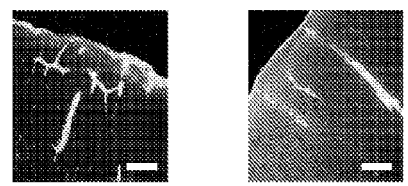
FIG. 1K | FIG. 1L | FIG. 1M
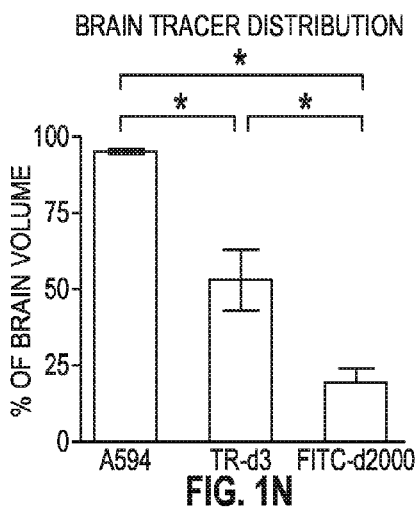
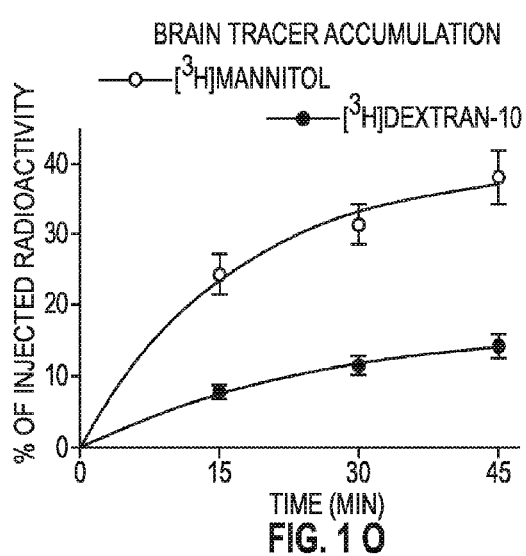
FIG. 1N | FIG. 1O

SURFACE

100 μm BELOW CORTICAL SURFACE

100 μm BELOW CORTICAL SURFACE

100 μm BELOW CORTICAL SURFACE

SURFACE ARTERY

SURFACE ARTERY

SURFACE ARTERY

PENETRATING ARTERIOLE

PENETRATING ARTERIOLE

PENETRATING ARTERIOLE

PENETRATING ARTERIOLE

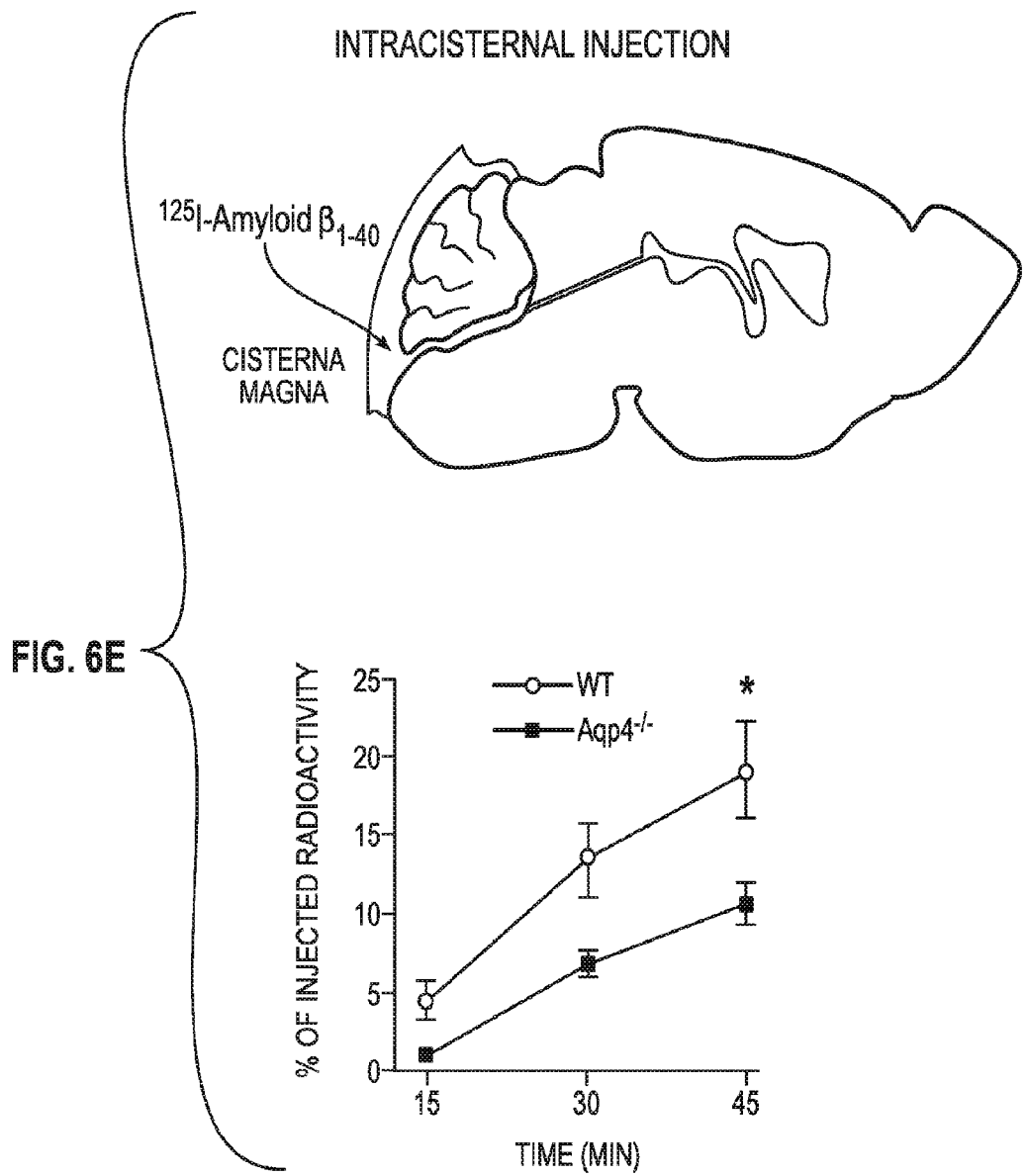

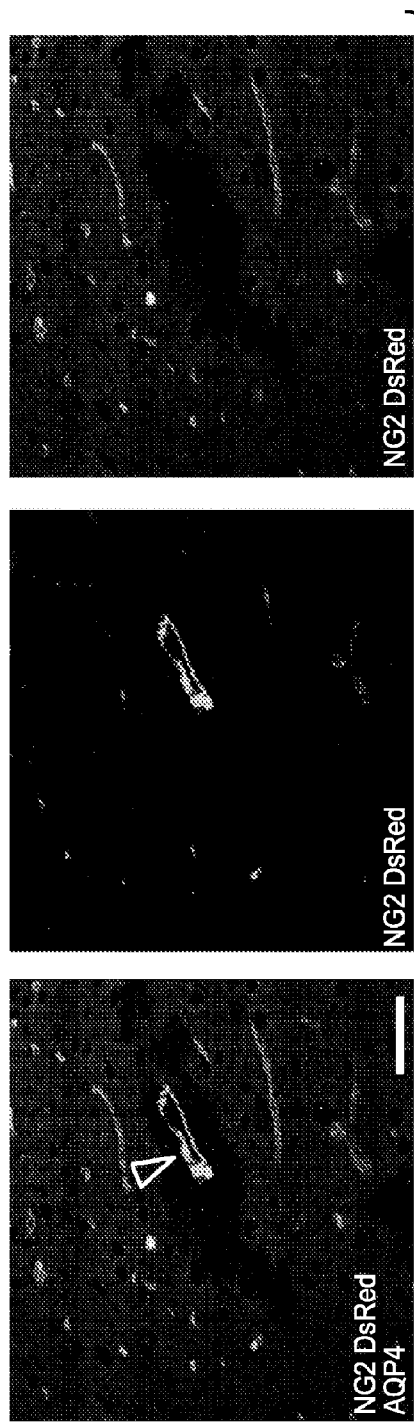

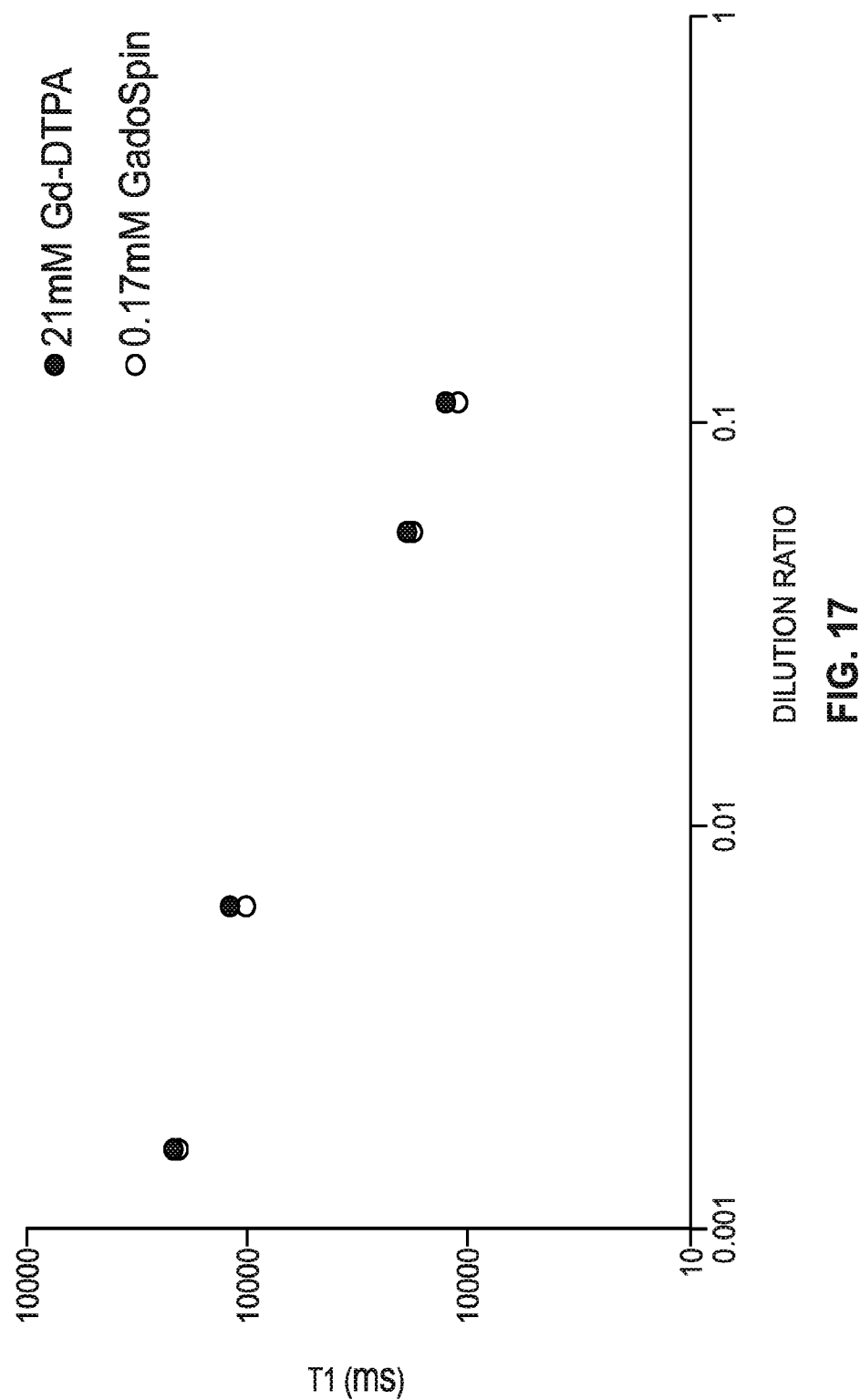

POSTERIOR LATERAL CHOROIDAL ARTERIAL COMPLEX

Gd-DTPA CLUSTER ANALYSIS

Gd-DTPA CLUSTER ANALYSIS

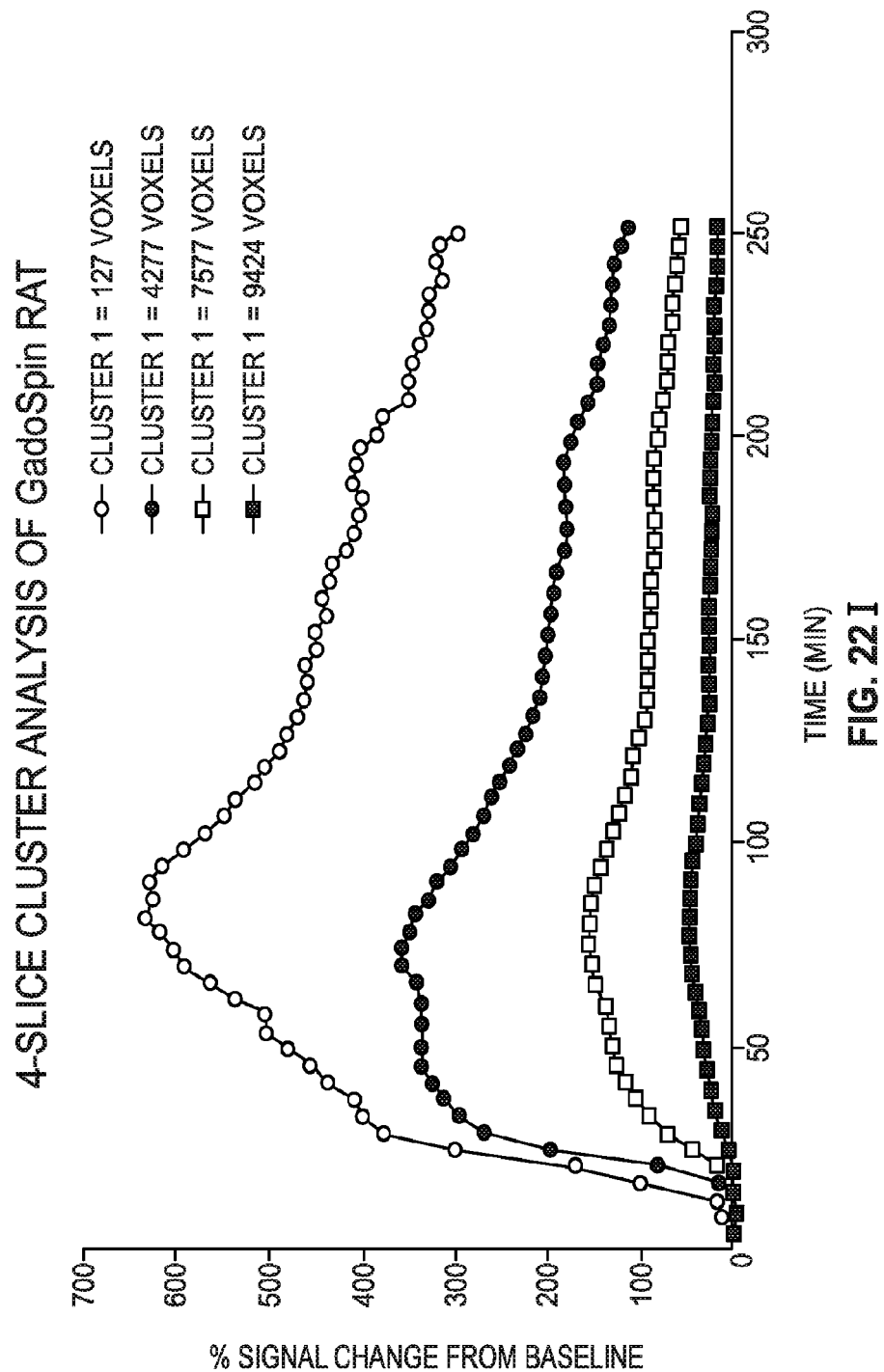

RAT LUMBAR INTRATHECAL TRACER INJECTION
SMALL M.W. TRACER (TR-d3)

RAT LUMBAR INTRATHECAL TRACER INJECTION
LARGE M.W. TRACER (FITC-d500)

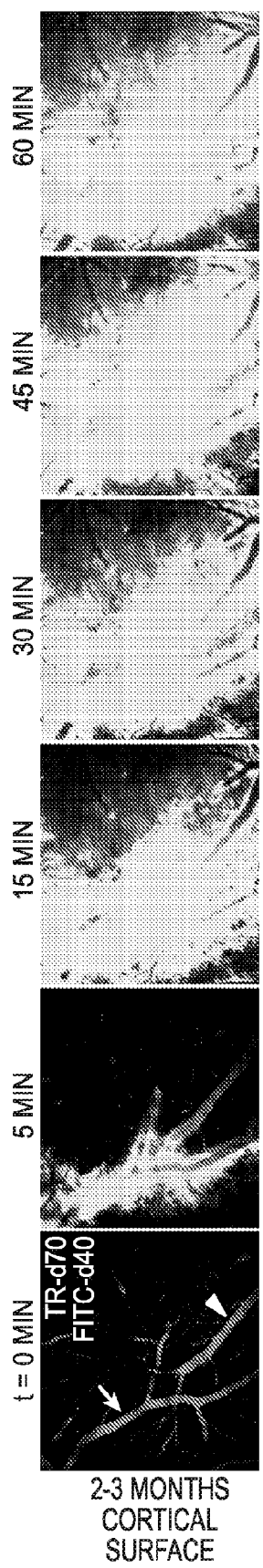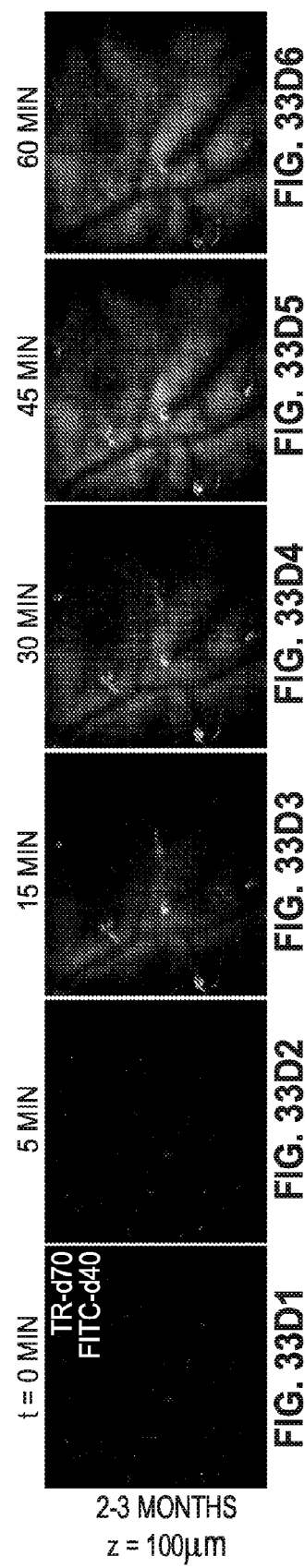

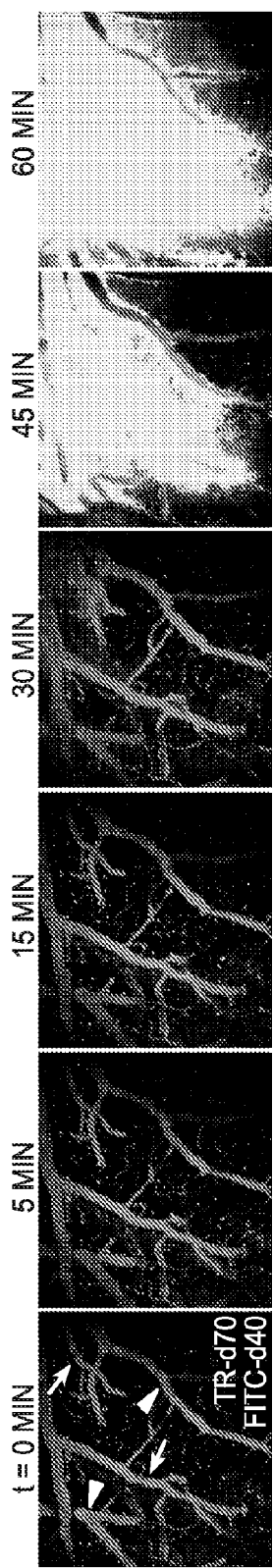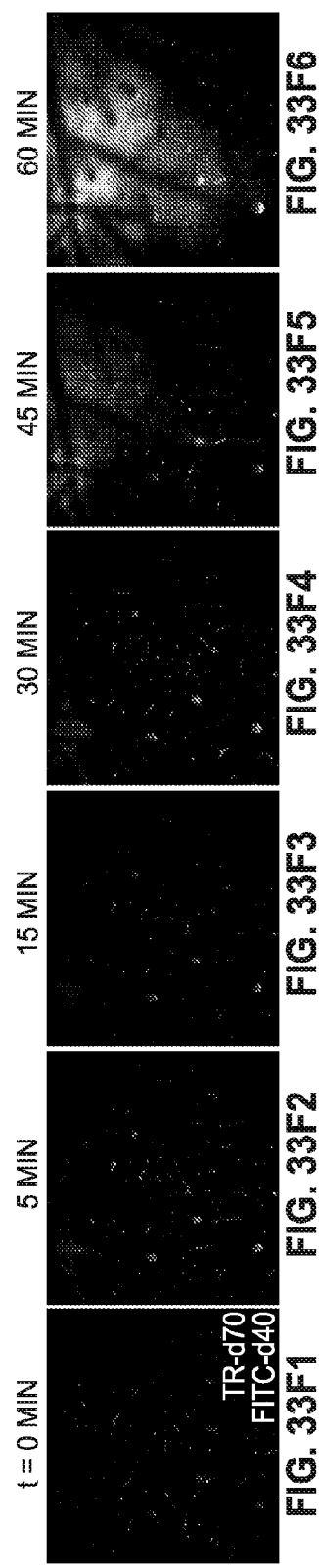

2-3 MONTHS 2-3 MONTHS

Figure 37A:
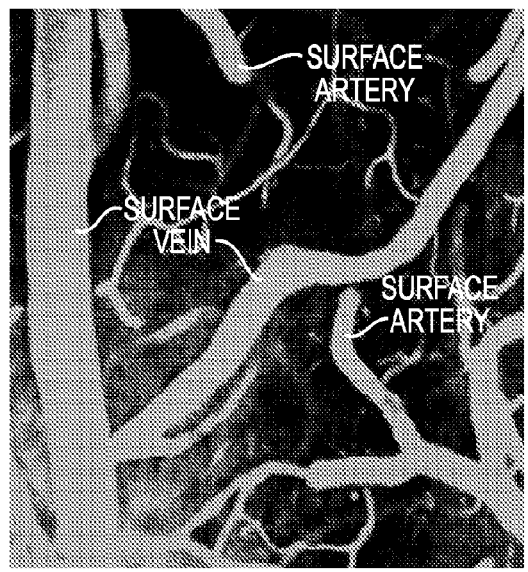
Figure 37B:
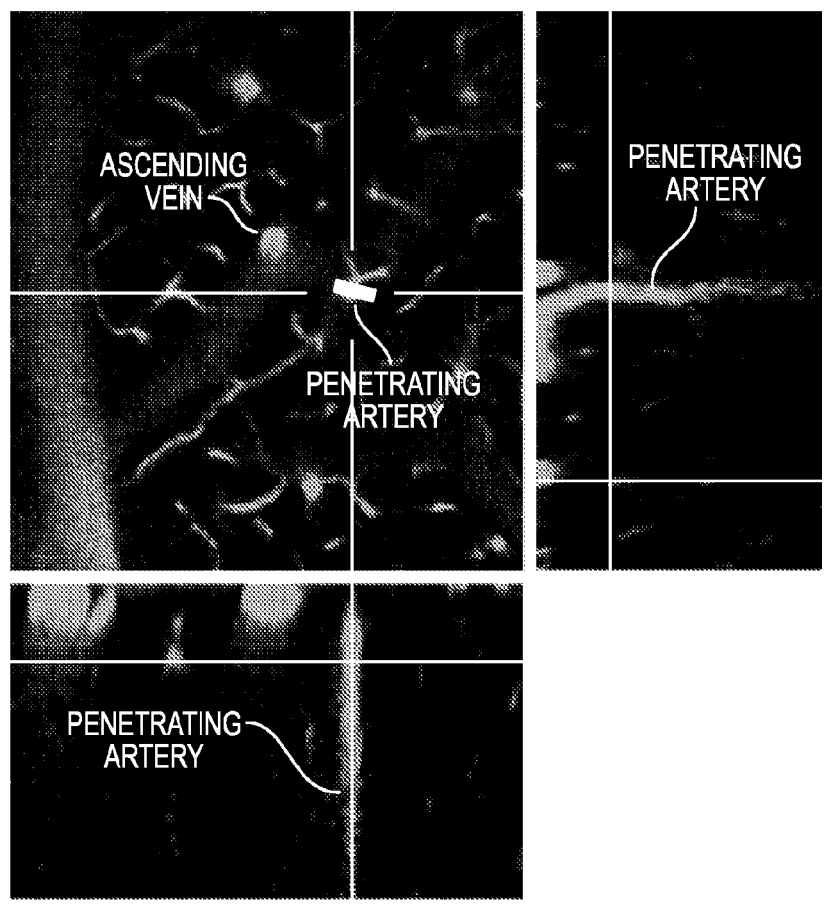
Figure 38A:
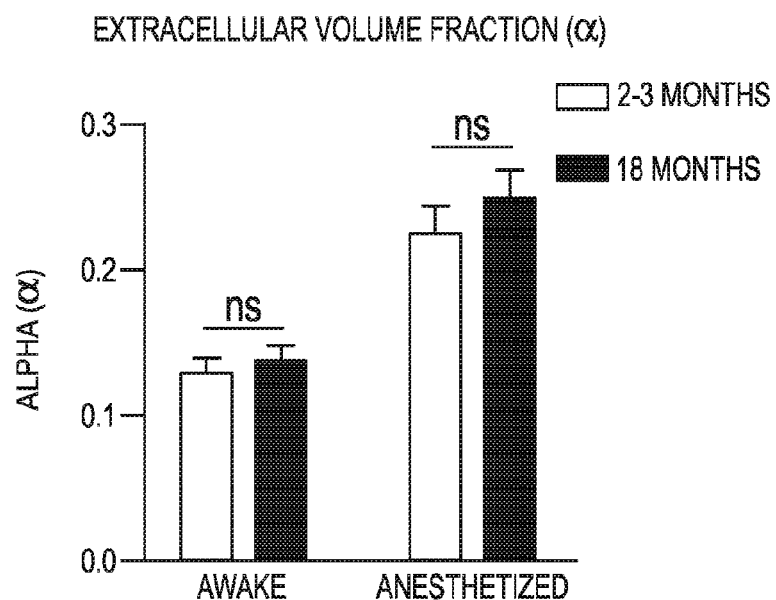
Figure 38B:
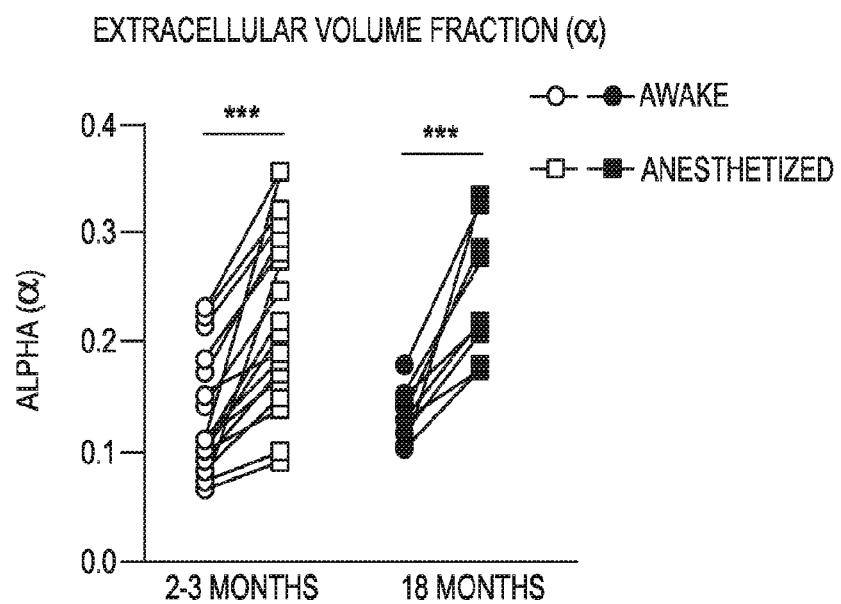
Figure 38C:
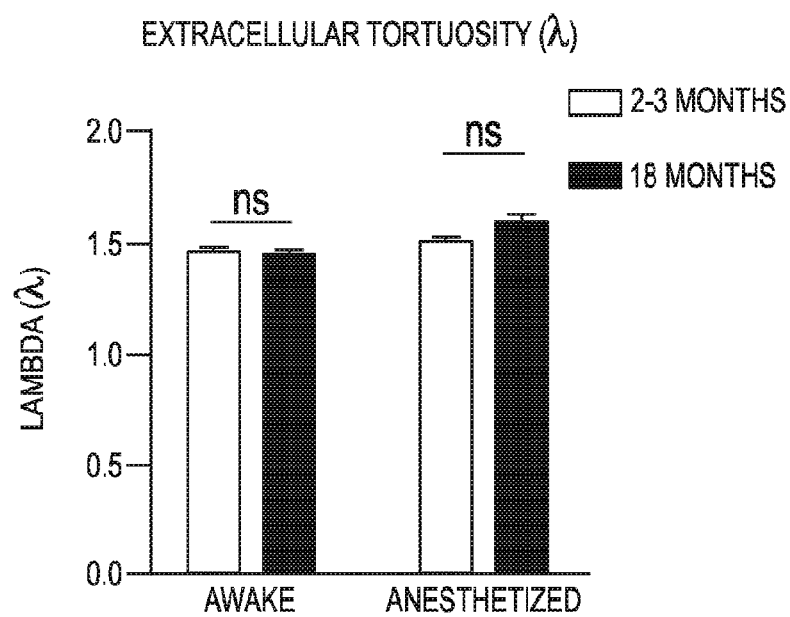
Figure 38D:
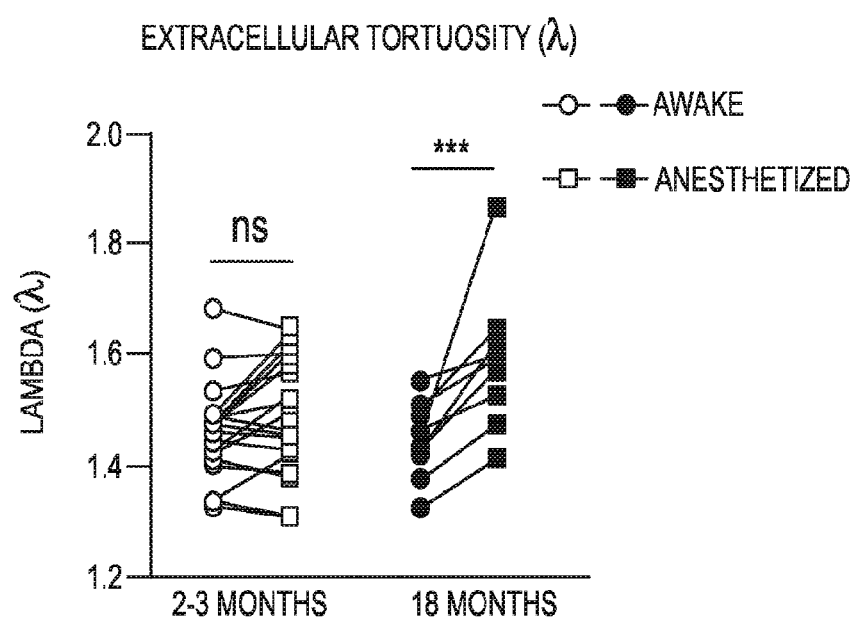
Figure 39A:
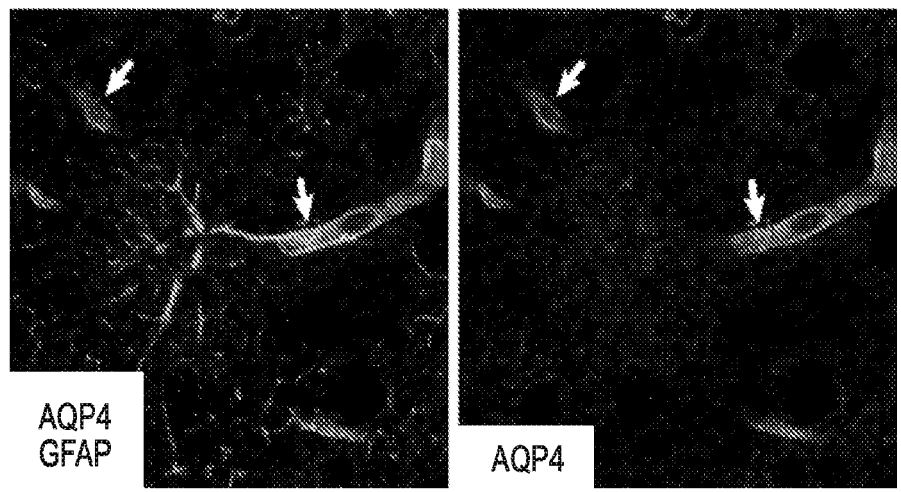
Figure 39B:
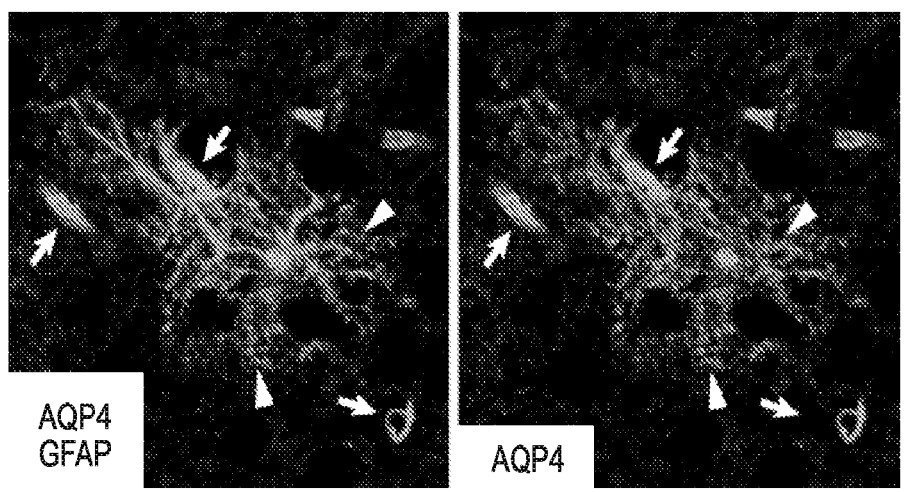
Figure 39C:
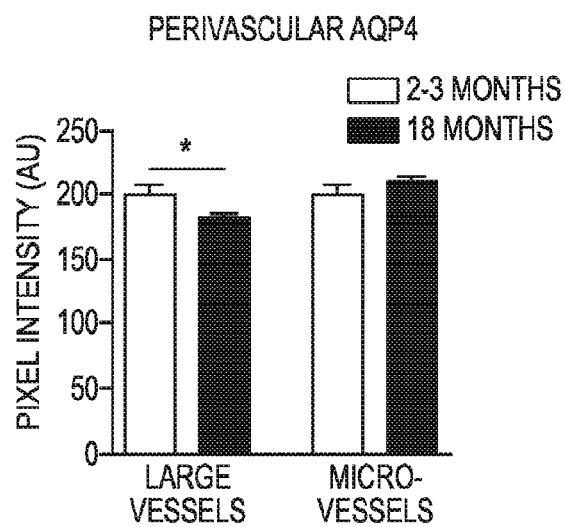
Figure 39D:
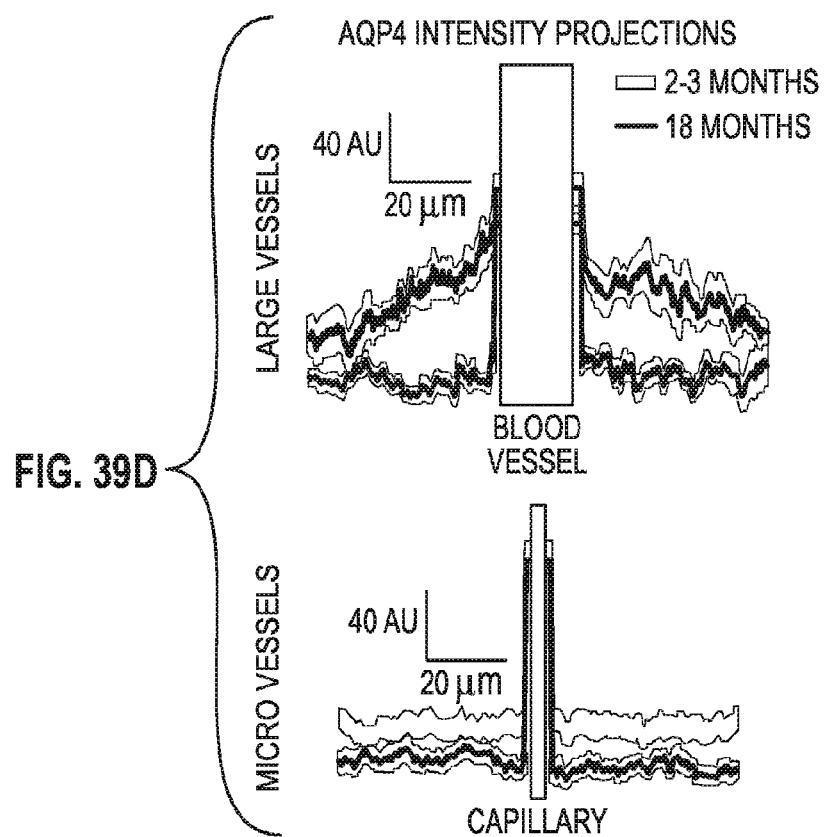
Figure 39E:
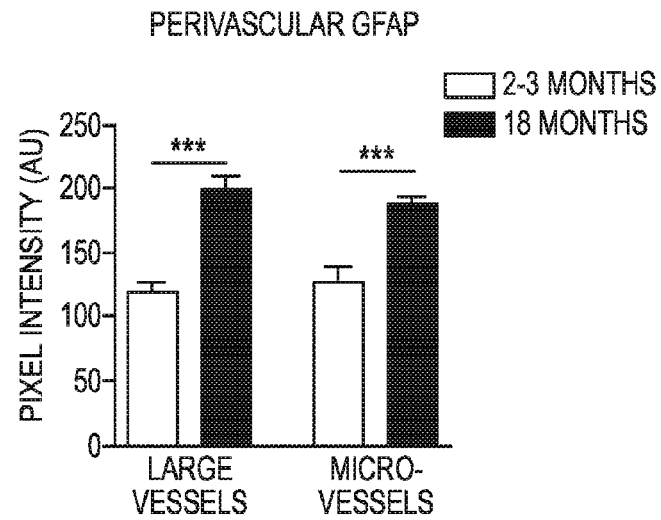
Figure 39F:
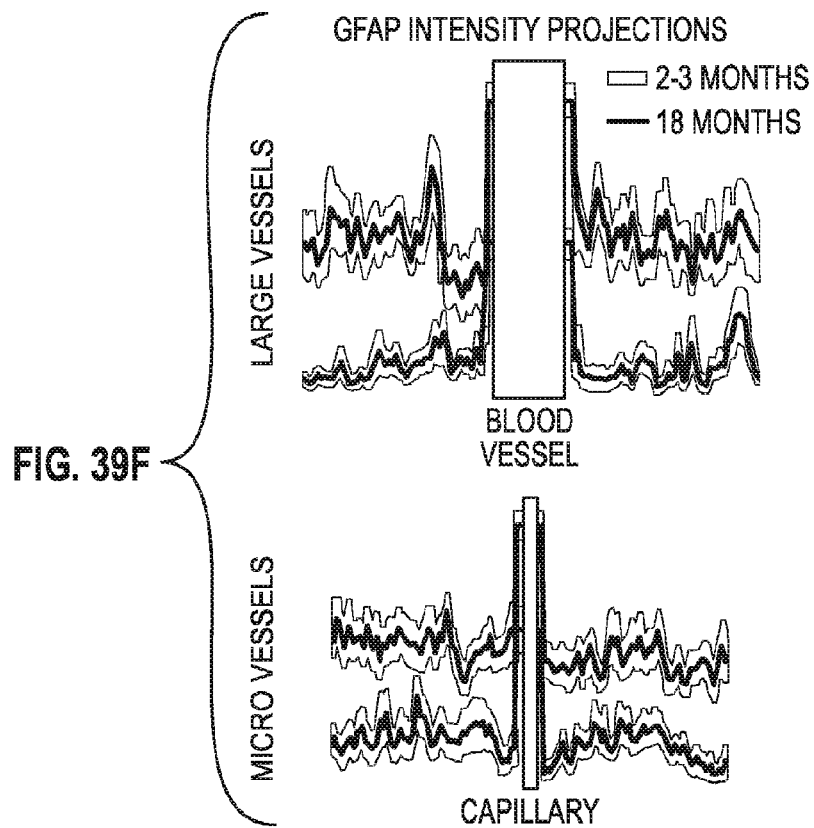

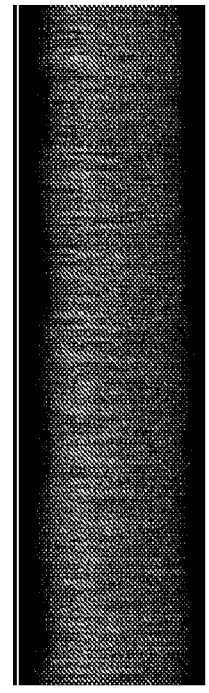
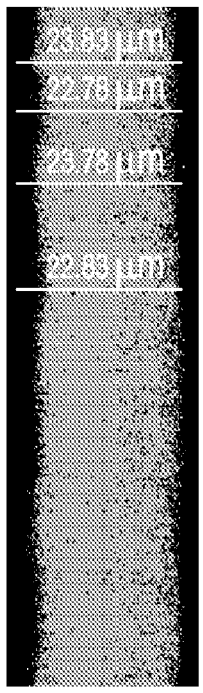
FIG. 37C
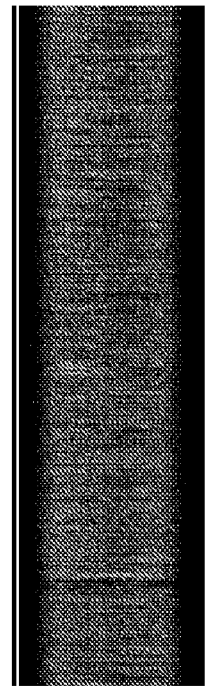
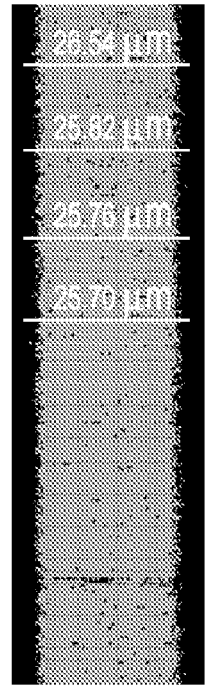
FIG. 37D
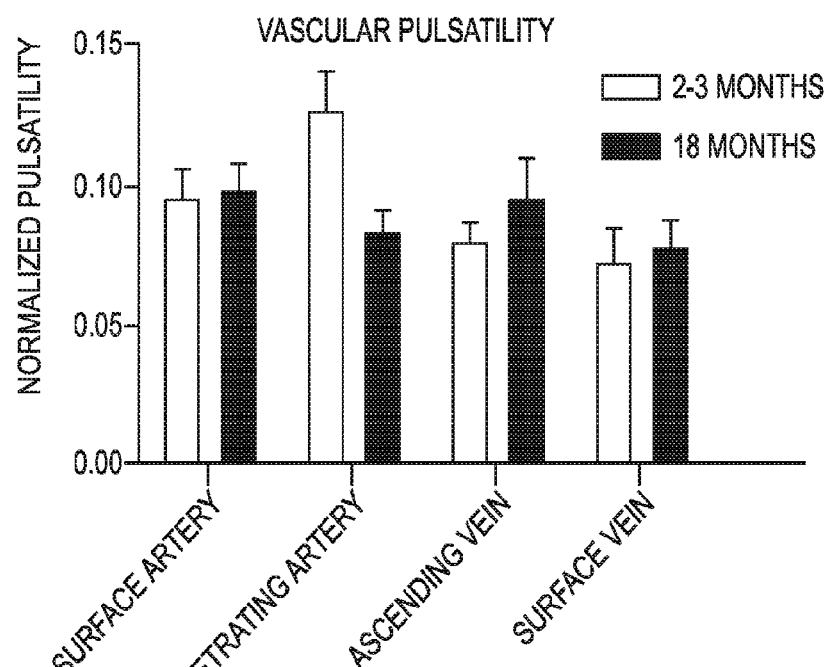
FIG. 37E

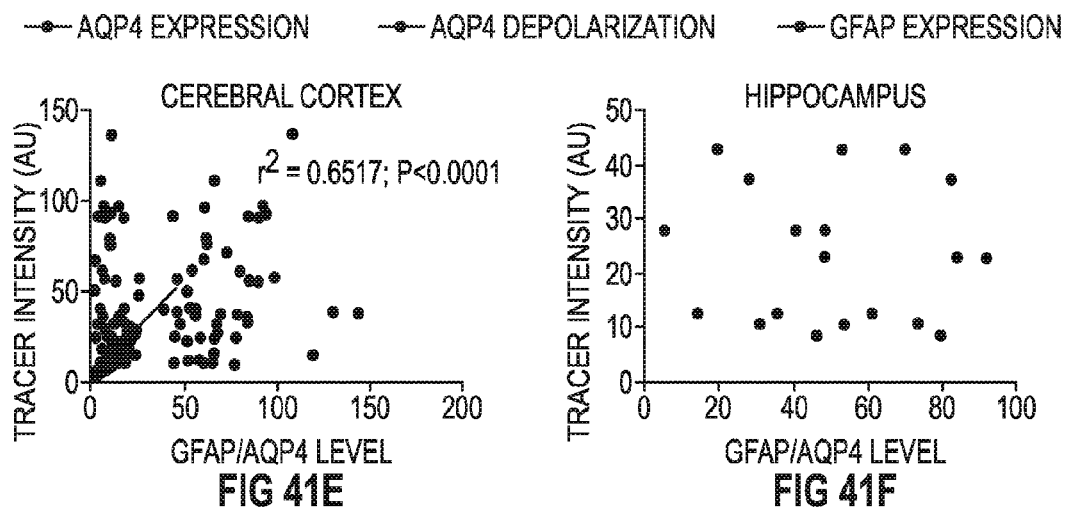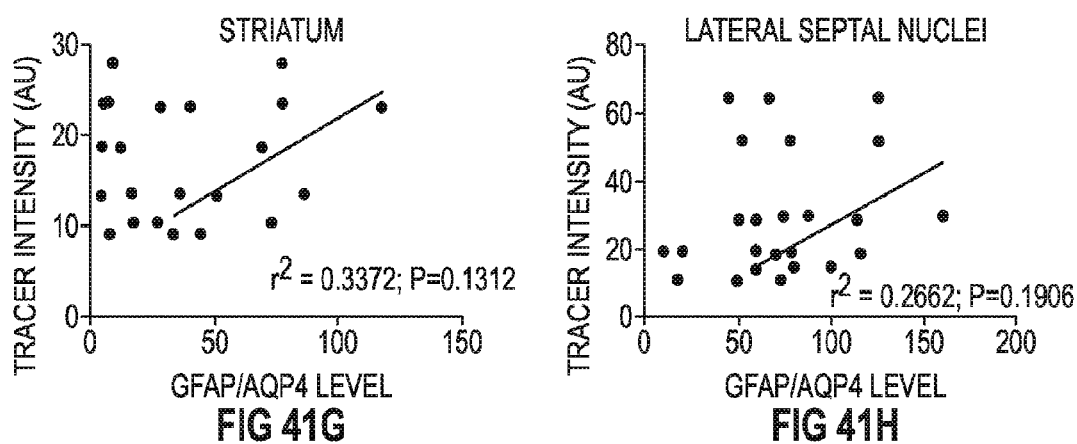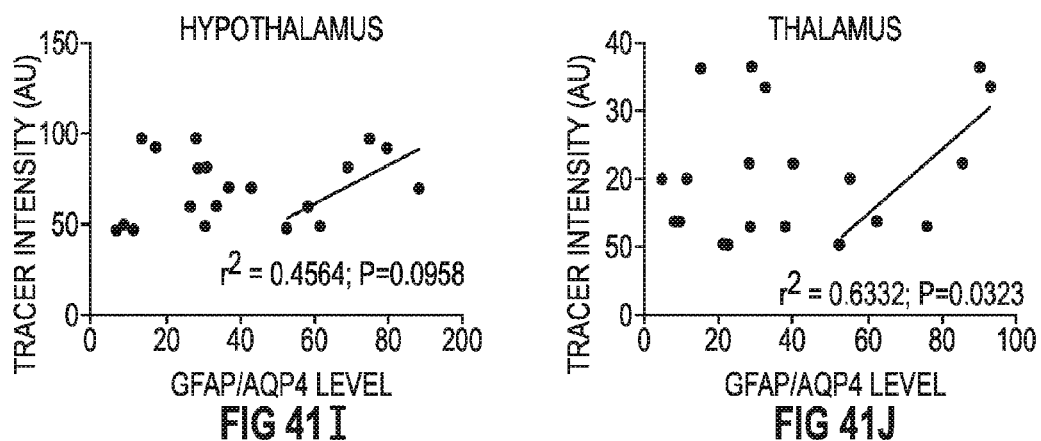

Figure 43E:
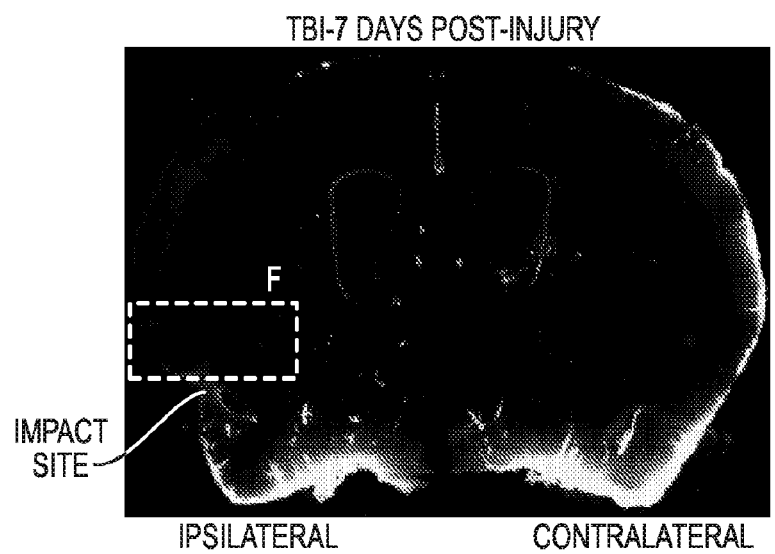
Figure 43F:
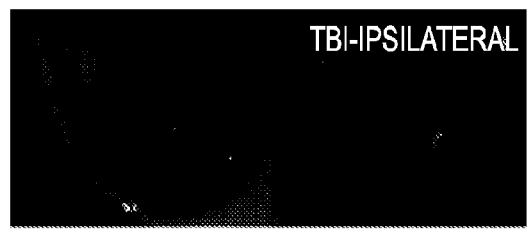
Figure 43G:
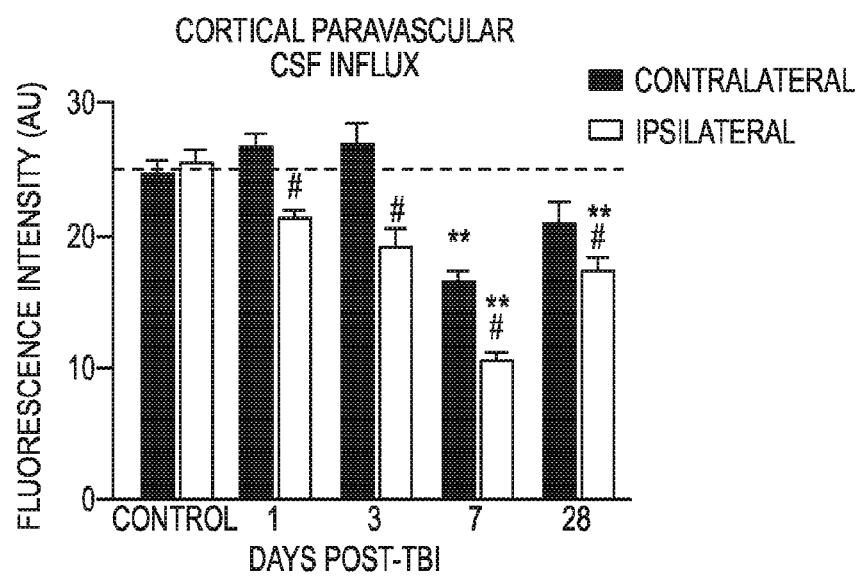

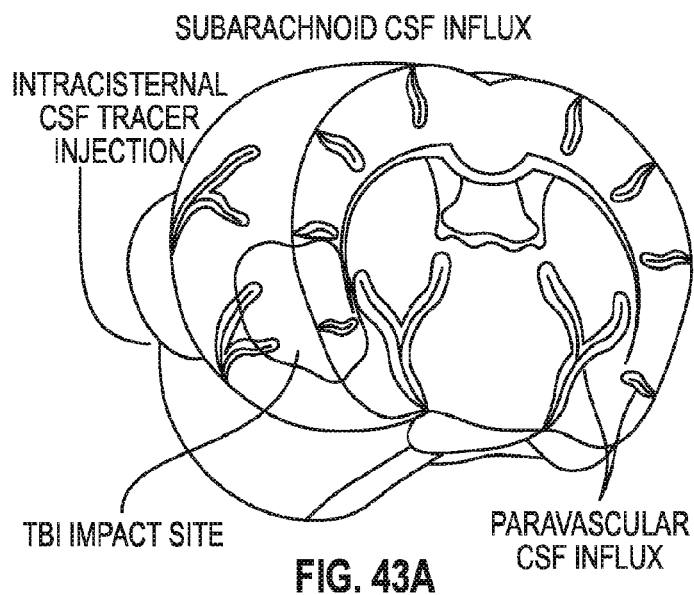
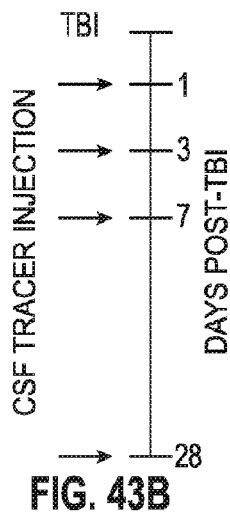
FIG. 43A
FIG. 43B
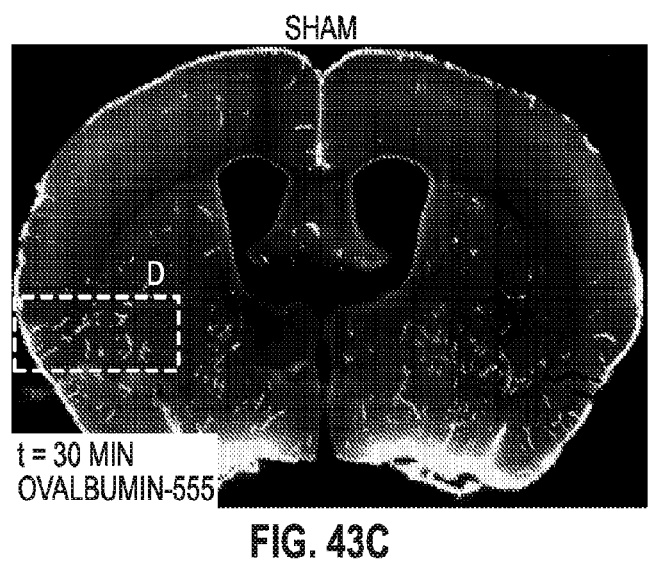
FIG. 43C
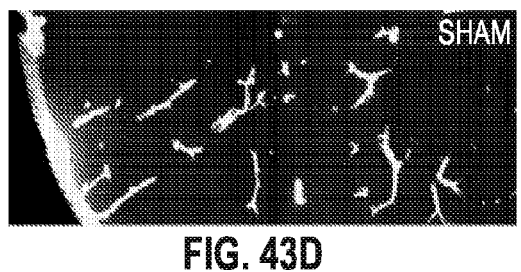
FIG. 43D

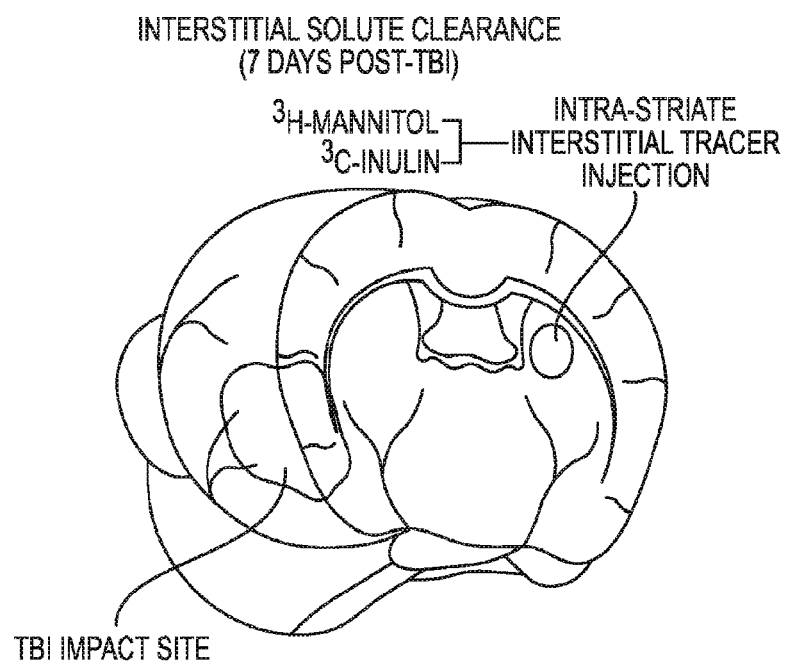
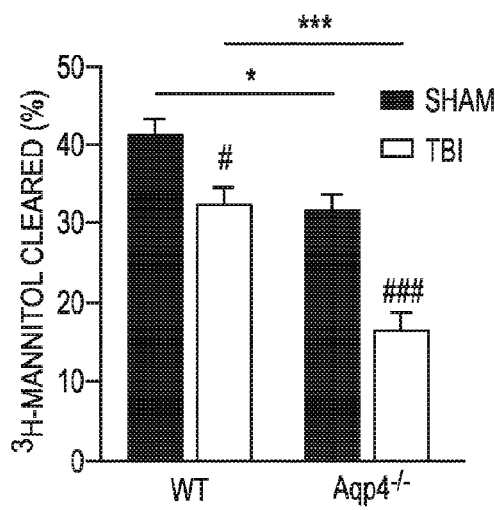
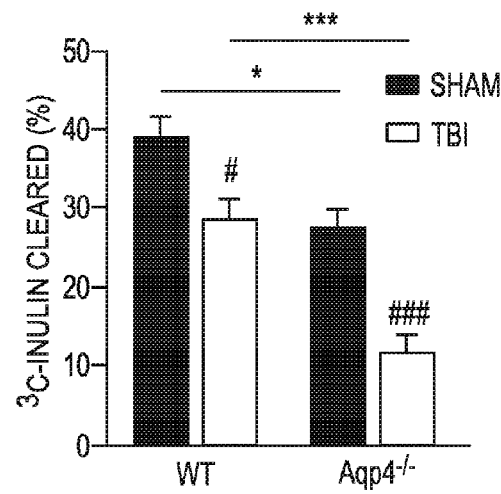
FIG. 43H
FIG. 43I
FIG. 43J

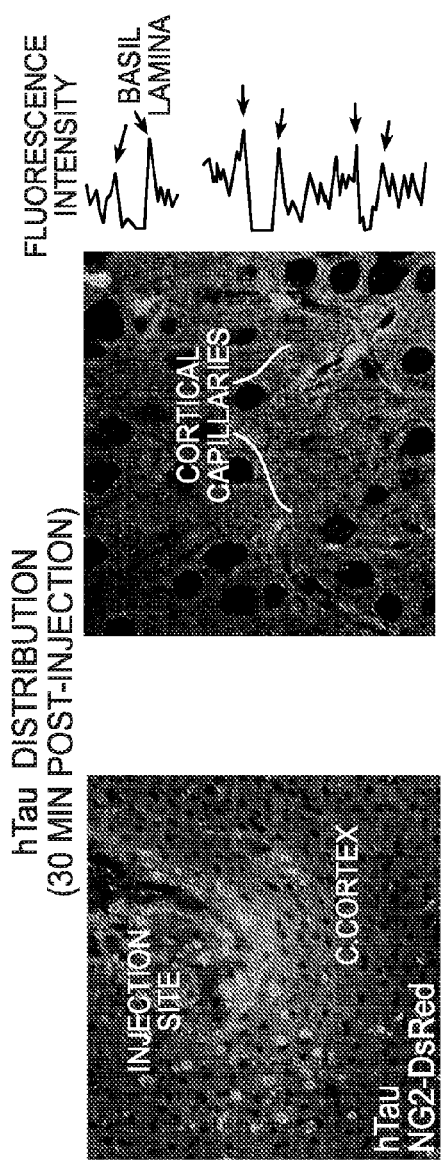
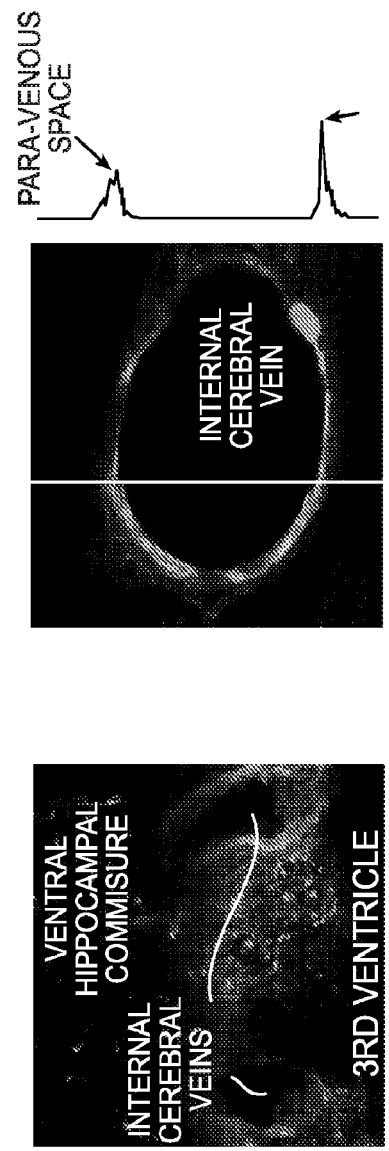
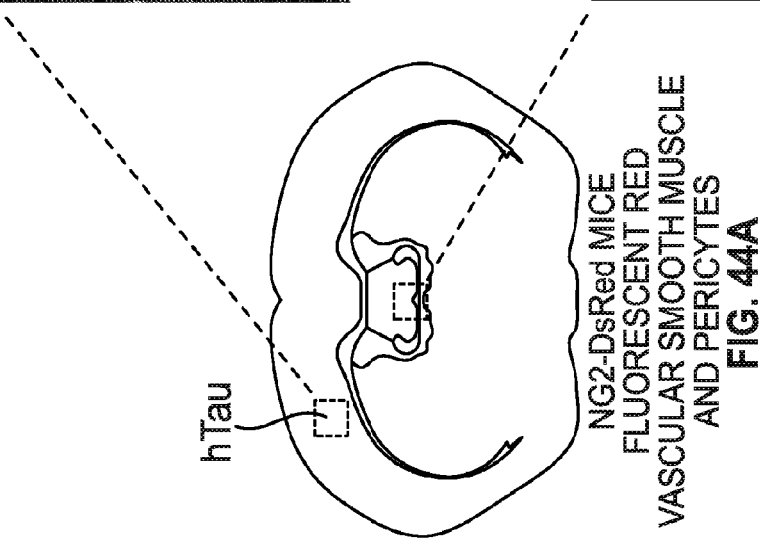
hTau DISTRIBUTION (30 MIN POST-INJECTION)
FIG. 44B — hTau NG2-DsRed, INJECTION SITE, CORTEX
FIG. 44C — CORTICAL CAPILLARIES; FLUORESCENCE INTENSITY, BASIL LAMINA
FIG. 44D — INTERNAL CEREBRAL VEINS, VENTRAL HIPPOCAMPAL COMMISURE, 3RD VENTRICLE
FIG. 44E — INTERNAL CEREBRAL VEIN; PARA-VENOUS SPACE
FIG. 44A — NG2-DsRed MICE FLUORESCENT RED VASCULAR SMOOTH MUSCLE AND PERICYTES

METHODS FOR EVALUATING BRAIN-WIDE PARAVASCULAR PATHWAY FOR WASTE CLEARANCE FUNCTION AND METHODS FOR TREATING NEURODEGENERATIVE DISORDERS BASED THEREON

CROSS-REFERENCE TO RELATED APPLICATIONS

This application is a national stage (371) application of International Patent Application No. PCT/US2014/017606 filed Feb. 21, 2014, which claims priority to and the benefit of U.S. provisional patent application Ser. No. 61/767,546, entitled Methods For Evaluating Brain-Wide Paravascular Pathway For Waste Clearance Function and Methods For Treating Neurodegenerative Disorders Based Thereon, filed Feb. 21, 2013, provisional patent application Ser. No. 61/862,321, entitled Methods For Evaluating Brain-Wide Paravascular Pathway For Waste Clearance Function and Methods For Treating Neurodegenerative Disorders Based Thereon, filed Aug. 5, 2013, and provisional patent application Ser. No. 61/942,447, entitled Methods For Evaluating Brain-Wide Paravascular Pathway For Waste Clearance Function and Methods For Treating Neurodegenerative Disorders Based Thereon, filed Feb. 20, 2014, each of which is incorporated herein by reference in its entirety.

STATEMENT REGARDING FEDERALLY SPONSORED RESEARCH OR DEVELOPMENT

The disclosed invention was made with government support under contract nos. NS078304, NS078167 and NS073373 from the National Institutes of Health. The government has rights in this invention.

1. TECHNICAL FIELD

The present invention relates to methods for measuring glio-vascular pathway function in the mammalian brain. The invention also relates to methods for measuring cerebrospinal fluid-interstitial fluid (CSF-ISF) exchange in the mammalian brain. The invention further relates to methods for treating diseases or disorders of the mammalian brain by promoting or impeding glio-vascular pathway function. The invention also relates to methods for promoting or augmenting cerebrospinal fluid secretion and flow in the mammalian brain.

2. BACKGROUND OF THE INVENTION

The lymphatic vasculature represents a second circulation, parallel to the blood vasculature, that accounts for the clearance of interstitial fluid (ISF) with its constituent proteins and other solutes not absorbed across postcapillary venules. In most vascularized tissues, the lymphatic system is critical to both hydrostatic and homeostatic maintenance. Yet, the brain does not have histologically identifiable lymphatic vessels and thus lacks the discrete pathways for interstitial solute and fluid clearance present in other peripheral tissues. This is surprising, because the high metabolic rate and exquisite sensitivity of neurons and glia to alterations in their extracellular environment suggest a need for rapid clearance of ISF and solutes.

The cerebrospinal fluid (CSF) of the central nervous system (CNS) has been thought to play a role in solute clearance from the brain. CSF formed in the choroid plexi flows through the cerebral ventricles and the subarachnoid space to its ultimate sites of reabsorption into the bloodstream via arachnoid villi of the dural sinuses, along cranial nerve sheaths or through the nasal lymphatics. Interstitial solutes have been thought to be cleared to the CSF by the convective bulk flow of ISF, which courses diffusely through brain tissue, rather than through an anatomically or functionally discrete structure.

Accumulation of toxic dysfunctional proteins in the mammalian central nervous system, including the brain and spinal cord, is associated with many neurodegenerative diseases, including Alzheimer's disease (AD), Parkinson's disease (PD), Huntington's disease (HD) and amyotrophic lateral sclerosis (ALS) in humans. However, the mechanism that leads to the accumulation of toxins in the aging mammalian brain is not completely known. In the case of Alzheimer's disease (AD) two hallmarks are senile plaques, which are extracellular deposits of amyloid β (also referred to herein as amyloid-β, amyloid beta or Aβ) toxins, and intracellular neurofibrillary tangles (hyperphosphorylated tau). The "amyloid cascade" hypothesis suggests that the cognitive decline and the distinct pathogenic features in AD are related to abnormal accumulation of these toxins (Selkoe, D. J. "Clearing the Brain's Amyloid Cobwebs." Neuron 32, no. 2 (2001): 177-80; Hardy, J. "A Hundred Years of Alzheimer's Disease Research." Neuron 52, no. 1 (2006): 3-13).

U.S. Pat. No. 6,689,085 (Rubenstein et al. Feb. 10, 2004) discloses a method and apparatus for treating adult-onset dementia of the Alzheimer's type. According to the method, a portion of the patient's cerebrospinal fluid (CSF) is removed, by transporting the fluid to another portion of the patient's body. Also disclosed in U.S. Pat. No. 6,689,085 is a shunt for removing CSF.

Citation or identification of any reference in Section 2, or in any other section of this application, shall not be considered an admission that such reference is available as prior art to the present invention.

3. SUMMARY OF THE INVENTION

A method is provided for measuring glio-vascular pathway (hereinafter "glymphatic system") function in the brain and/or spinal cord (collectively the "central nervous system" or "CNS") of a mammal comprising the steps of:
performing imaging of the central nervous system; and
measuring cerebrospinal fluid-interstitial fluid (hereinafter "CSF-ISF") exchange in the central nervous system, thereby measuring glymphatic system function in the central nervous system of the mammal.

In one embodiment of the method, the mammal is a human or a non-human primate. In another embodiment of the method, the mammal is a patient or a subject in need of treatment.

In another embodiment, the method further comprises the step of administering an imaging agent prior to the step of performing imaging of the central nervous system.

In another embodiment of the method, the imaging agent is administered intrathecally.

In another embodiment of the method, the step of administering intrathecally the imaging agent comprises the step of administering a lumbar or an intracisternal intrathecal injection of the imaging agent.

In another embodiment of the method, the imaging agent is a negative or positive (paramagnetic) MRI contrast agent, and the step of performing imaging of the central nervous system comprises the step of performing dynamic or contrast-enhanced magnetic resonance imaging (MRI) of the central nervous system.

In another embodiment of the method, at least two different—magnetic or MRI contrast agents are administered, the different—magnetic contrast agents being matched in terms of their effects on T1 (paramagnetic) or T2 (negative contrast agents) so that their kinetic characteristics in brain tissue can be compared.

In another embodiment of the method, the imaging agent is a positron-emitting radionuclide tracer, and the step of performing imaging of the brain and spinal cord comprises the step of performing positron emission tomography (PET) scanning of the central nervous system.

In another embodiment of the method, the step of measuring CSF-ISF exchange comprises measuring clearance of soluble amyloid β (also referred to herein as amyloid beta or Aβ), tau, a nanoparticle such as functionalized or therapeutic nanoparticle, a chemotherapy agent, a toxic product administered therapeutically, small interfering RNA (siRNA), alpha synuclein, a small molecule drug, a viral vector, an antibody-based therapeutic, a liposome or a therapeutic RNA construct.

In another embodiment of the method, the step of measuring CSF-ISF exchange comprises measuring clearance of a therapeutic agent.

In another embodiment of the method, the therapeutic agent is a chemotherapy agent, a functionalized nanoparticle or a toxic composition administered for a therapeutic use.

In another embodiment of the method, the step of measuring CSF-ISF exchange comprises analyzing influx kinetics, parenchymal distribution and/or clearance of the paramagnetic or negative contrast agent in the brain.

In another embodiment of the method, the step of measuring CSF-ISF exchange comprises measuring CSF-ISF exchange at the pituitary recess, the pineal gland recess, the cerebellum and/or the olfactory bulb.

In another embodiment of the method, the step of measuring CSF-ISF exchange comprises the step of performing parametric or non-parametric data analysis of signal changes.

In another embodiment of the method, the step of performing parametric or non-parametric data analysis of signal changes comprises the step of measuring T1 shortening or T2 changes, respectively.

In another embodiment of the method, the step of measuring CSF-ISF exchange comprises the step of calculating an influx kinetic parameter, wherein the influx kinetic parameter reflects a rate of CSF-ISF exchange.

In another embodiment of the method, the step of measuring CSF-ISF exchange comprises the single step of calculating a kinetic parameter from a static contrast-enhanced MRI or PET image, wherein the kinetic parameter reflects a rate of CSF-ISF exchange.

In another embodiment, the method further comprises the step of calculating a risk of developing a neurodegenerative disease in the mammal.

In another embodiment of the method, the neurodegenerative disease is Parkinson's disease (PD), Alzheimer's disease (AD), Alzheimer's disease with Lewy bodies, Lewy body dementia, or mixed dementia.

In another embodiment of the method, the mammal is suffering from traumatic brain injury, further comprising the step of calculating a risk of developing chronic traumatic encephalopathy (CTE).

A method is provided for treating onset of a neurodegenerative disease in the central nervous system of a mammal comprising the step of increasing glymphatic system clearance, whereby reactive gliosis is treated, ameliorated, prevented, decreased or reduced.

In one embodiment, the step of increasing glymphatic system clearance comprises the step of administering an agent to the mammal that increases or promotes glymphatic clearance; or pumping fluid through the central nervous system interstitium of the mammal, thereby decreasing, reducing, delaying onset of, or preventing amyloid β (Aβ), tau and/or alpha synuclein accumulation in the brain interstitium of the mammal. Pumping can be accomplished by any device or method known in the art, for example, by using a mechanical pump, an infusion pump, etc.

In one embodiment of the method, the reactive gliosis decreases or prevents interstitial waste clearance.

In another embodiment of the method, the mammal is a human or a non-human primate.

In another embodiment of the method, the mammal is a patient or a subject in need of treatment.

In another embodiment of the method, the neurodegenerative disease is Parkinson's disease (PD), Alzheimer's disease (AD), Alzheimer's disease with Lewy bodies, Lewy body dementia, mixed dementia, vascular dementia, frontotemporal dementia, chronic traumatic encephalopathy (CTE) or HIV associated dementia.

In another embodiment, the method further comprises the step of measuring glymphatic system function in the brain according to the method for measuring glymphatic system function in the central nervous system of a mammal disclosed herein.

In another embodiment of the method, the step of increasing glymphatic clearance comprises the step of administering an agent to the mammal that increases glymphatic clearance, e.g., a Stat-3 inhibitor or molecules known in the art to be bone morphogenetic protein (BMP) signaling axis molecules.

In other embodiments, the therapeutic agent that increases or promotes glymphatic clearance is an antagonist of AVP (vasopressin) such as tolvaptan, conivaptan, or VPA-985, an antagonist of atrial natriuretic peptide (ANP) such as anantin, an antagonist of Angiotensin II such as losartan, an antagonist of AT2R receptors such as PD123319, or an antagonist of AT1 receptors such as valsartan.

In another embodiment, the agent that increases glymphatic clearance is an agent for use in the treatment of insomnia or as an aid for sleep, including but not limited to:
Antihistamines (e.g., Over-the-Counter):
ALLEGRA® (Fexofenadine)
BENADRYL® (Diphenhydramine)
CLARITIN® or TAVIST® (loratadine)
CHLOR-TRIMETON® (chlorpheniramine maleate)
DIMETANE® (Brompheniramine, Phenylpropanolamine)
ZYRTEC® (Cetirizine)
Nonprescription Sleep Aids:
Unisom Nighttime Sleep-Aid
Dormin
Nytol
Simply Sleep
Sominex
Extra Strength Tylenol PM
Diphenhydramine hydrochloride
Excedrin P.M.
Benzodiazepines:
PROSUM® (estazolam)
DALMANE® (flurazepam)
DORAL® (quazepam)

RESTORIL® (temazepam)
HALCION® (triazolam)
VALIUM® (diazepam)
Non-Benzodiazepines:
Imidazopyridines: AMBIEN®, AMBIEN® CR, INTERMEZZO® (zolpidem) (class of its own)
SONATA® (pyrazolopyrimidine) (class of its own)
melatonin receptor stimulator:
ROZEREM® (ramelteon)
NOTEC® (chloral hydrate)
PRECEDEX® (dexmedetomidine hydrochloride)
LUNESTA® (eszopiclone)
Barbiturates:
NEMBUTAL® (phenobarbital)
MEBARAL® (mephobarbital)
Amytal Sodium (amobarbital sodium)
BUTISOL® (butabarbital sodium)
SECONAL® Sodium Pulvules (secobarbital sodium)

In another embodiment, the agent that increases glymphatic clearance is an agent that prevents AQP4 depolarization or loss of AQP4 polarization.

In another embodiment, the agent that prevents AQP4 depolarization or loss of AQP4 polarization is JNJ-17299425 or JNJ-17306861.

In another embodiment, the step of increasing glymphatic clearance comprises the step of pumping fluid through the central nervous system interstitium. Pumping can be accomplished by any device or method known in the art, for example, by using a mechanical pump, an infusion pump, etc.

A method is provided for treating reactive gliosis in the central nervous system of a mammal comprising the step of increasing glymphatic system clearance, whereby reactive gliosis is treated, ameliorated, prevented, decreased or reduced.

In one embodiment of the method, the mammal is a human or a non-human primate.

In another embodiment of the method, the mammal is a patient or a subject in need of treatment.

In another embodiment of the method, the reactive gliosis decreases aquaporin 4 (AQP4)-dependent bulk flow.

In another embodiment, the method further comprises the step of measuring glymphatic system function in the brain according to the method for measuring glymphatic system function in the central nervous system of a mammal disclosed herein.

In another embodiment of the method, the step of increasing glymphatic clearance comprises the step of administering an agent to the mammal that increases glymphatic clearance, e.g., a Stat-3 inhibitor or molecules known in the art to be bone morphogenetic protein (BMP) signaling axis molecules.

In other embodiments, the therapeutic agent that increases or promotes glymphatic clearance is an antagonist of AVP (vasopressin) such as tolvaptan, conivaptan, or VPA-985, an antagonist of atrial natriuretic peptide (ANP) such as anantin, an antagonist of Angiotensin II such as losartan, an antagonist of AT2R receptors such as PD123319, or an antagonist of AT1 receptors such as valsartan.

In another embodiment, the agent that increases glymphatic clearance is an agent that prevents AQP4 depolarization or loss of AQP4 polarization.

In another embodiment, the agent that prevents AQP4 depolarization or loss of AQP4 polarization is JNJ-17299425 or JNJ-17306861.

In another embodiment of the method, the step of increasing glymphatic clearance comprises the step of increasing glymphatic clearance comprises the step of pumping fluid through the central nervous system interstitium. Pumping can be accomplished by any device or method known in the art, for example, by using a mechanical pump, an infusion pump, etc.

A method is provided for promoting clearance of a waste product from the brain interstitium and/or spinal cord interstitium (or CNS interstitium) of a mammal comprising the step of administering an agent to the mammal that increases or promotes glymphatic clearance. In one embodiment of the method, the method comprises the step of administering an agent to the mammal that increases or promotes glymphatic clearance, e.g., a Stat-3 inhibitor or molecules known in the art to be bone morphogenetic protein (BMP) signaling axis molecules.

In other embodiments, the agent that increases or promotes glymphatic clearance is an antagonist of AVP (vasopressin) such as tolvaptan, conivaptan, or VPA-985, an antagonist of atrial natriuretic peptide (ANP) such as anantin, an antagonist of Angiotensin II such as losartan, an antagonist of AT2R receptors such as PD123319, or an antagonist of AT1 receptors such as valsartan.

In another embodiment, the agent that increases or promotes glymphatic clearance is an agent that prevents AQP4 depolarization or loss of AQP4 polarization.

In another embodiment, the agent that prevents AQP4 depolarization or loss of AQP4 polarization is JNJ-17299425 or JNJ-17306861.

In one embodiment of the method, the mammal is a human or a non-human primate. In another embodiment, the mammal is a patient or a subject in need of treatment.

In another embodiment of the method, the brain waste product is soluble amyloid β (Aβ), tau, or alpha synuclein.

In another embodiment, the method further comprises the step of measuring glymphatic system function in the brain according to the method for measuring glymphatic system function in the central nervous system of a mammal disclosed herein.

A method is provided for treating the central nervous system of a mammal comprising the step of increasing glymphatic clearance. In one embodiment, the step of increasing glymphatic clearance comprises the step of administering an agent to the mammal that increases or promotes glymphatic clearance; or pumping fluid through the central nervous system interstitium of the mammal. Pumping can be accomplished by any device or method known in the art, for example, by using a mechanical pump, an infusion pump, etc.

The method is used to slow, delay, reduce, decrease or prevent accumulation of a waste product in the central nervous system of the mammal. In one embodiment of the method, the mammal is a human or a non-human primate. In another embodiment of the method, the mammal is a patient or a subject in need of treatment.

In another embodiment of the method, the brain waste product is soluble amyloid β (Aβ), tau, or alpha synuclein.

In another embodiment, the method further comprises the step of measuring glymphatic system function in the brain according to the method for measuring glymphatic system function in the central nervous system of a mammal disclosed herein.

A method is provided for treating the central nervous system (brain and/or spinal cord) of a mammal comprising the step of administering an agent to the mammal that increases or promotes glymphatic clearance, thereby decreasing, delaying or preventing amyloid β (Aβ), tau and/or alpha synuclein accumulation, e.g., in the CNS interstitium of the mammal, comprising the step of administering an agent to the mammal that increases or promotes glymphatic clearance.

In one embodiment of the method, the brain of the mammal has been subjected to brain injury. In one embodiment, the brain injury is traumatic brain injury. In another embodiment, the brain injury is diffuse ischemic injury.

In another embodiment of the method, the mammal is a human or a non-human primate.

In another embodiment of the method, the mammal is a patient or a subject in need of treatment.

In another embodiment of the method, the patient or a subject in need of treatment is aged or elderly. In one embodiment, the aged or elderly patient or subject is a human greater than 50, 60, 70 80 or 90 years old.

In another embodiment of the method, the therapeutic agent is an adrenergic receptor antagonist.

In another embodiment, the method further comprises the step of measuring glymphatic system function in the brain according to the method for measuring glymphatic system function in the central nervous system of a mammal disclosed herein.

A method is provided for decreasing or impeding clearance of a therapeutic or modulatory agent from the CNS (brain and/or spinal cord) interstitium of a mammal comprising the step of decreasing or impeding glymphatic clearance.

In one embodiment of the method, the mammal is a human or a non-human primate.

In another embodiment of the method, the mammal is a patient or a subject in need of treatment.

In another embodiment of the method, the patient or a subject in need of treatment is aged or elderly. In one embodiment, the aged or elderly patient or subject is a human greater than 50, 60, 70 80 or 90 years old.

In another embodiment of the method, the step of decreasing or impeding glymphatic clearance comprises the step of administering an agent to the mammal that decreases or impedes glymphatic clearance.

In another embodiment of the method, the agent is bumetanide, small interfering RNA (siRNA) directed against AQP4, an agonist of AVP (vasopressin), an agonist of atrial natriuretic peptide (ANP), an agonist of Angiotensin II, an agonist of AT2R receptors, or an agonist of AT1 receptors.

In another embodiment of the method, the step of decreasing (or impeding) glymphatic clearance comprises the step of blocking or erecting a barrier to fluid flow through the central nervous system interstitium of the mammal.

In another embodiment, the method further comprises the step of measuring glymphatic system function in the brain according to the method for measuring glymphatic system function in the central nervous system of a mammal disclosed herein.

Also provided is an apparatus for restoring and/or augmenting reduced cerebrospinal fluid (CSF) secretion and/or reduced flow associated with cerebrospinal fluid (CSF)/interstitial fluid (ISF) exchange in the brain of a mammal. In a preferred embodiment, the mammal is a human. The apparatus comprises a mechanical pumping system (e.g., an infusion pump), thereby promoting faster CSF clearance in the brain. In one embodiment, the apparatus also comprises artificial ("mock") CSF and the pumping system pumps or infuses the artificial CSF in the brain.

In another embodiment of the apparatus, the apparatus restores and/or augments reduced cerebrospinal fluid (CSF) secretion and/or reduced flow associated with a neurodegenerative disease, including but not limited to Parkinson's disease (PD), Alzheimer's disease (AD), Alzheimer's disease with Lewy bodies, Lewy body dementia, and mixed dementia, or associated with traumatic brain injury or ischemic brain injury.

4. BRIEF DESCRIPTION OF THE DRAWINGS

The present invention is described herein with reference to the accompanying drawings, in which similar reference characters denote similar elements throughout the several views. It is to be understood that in some instances, various aspects of the invention may be shown exaggerated, enlarged, exploded, or incomplete to facilitate an understanding of the invention.

It is also to be understood that in some instances, the color-coding of data, including the coding of cluster analysis data, which has been carried out according to methods well known in the art, has been converted to gray-scale in the drawings.

FIGS. 1A-O. Distribution of subarachnoid CSF into the brain parenchyma.

Color-coding has been converted to gray-scale. (A) The movement of ventricular and subarachnoid CSF into the brain parenchyma was evaluated after infusion of fluorescent tracer into the lateral ventricle (LV) or cisterna magna. (B to G) After 30 min of intraventricular infusion, small- (A594; molecular size, 759 daltons; red), moderate-(TR-d3; molecular size, 3 kD; blue), and large-molecular weight (FITC-d2000; molecular size, 2000 kD; green) tracer movement into the brain parenchyma was evaluated. 3V, third ventricle; 4V, fourth ventricle. (D and G) Absence of tracer in tissue remote from the periventricular space. Insets, 4',6-diamidino-2-phenylindole (DAPI) labeling in the same fields of view. (H to J) Small-molecular weight tracer permeation 30 min after intracisternal injection. Arrowheads, low-level paravascular accumulation. (K to M) Distribution of intracisternally injected TR-d3 (dark blue) and FITC-d2000 (green). Merge (light blue) indicates colocalization of TR-d3 and FITC-d2000. (N) Distributions of intracisternal fluorescent tracers, quantified as a percentage of total brain volume (integrated slice areas). A594 occupied the greatest proportion of brain tissue. TR-d3 exhibited an intermediate distribution, whereas FITC-d2000 was highly restricted (n=3, *P<0.05). (O) Accumulation of radiotracer within the brain after intracisternal injection of [$^3$H]mannitol (molecular size, 182 daltons) or [$^3$H]dextran-10 (molecular size, 10 kD). Compared to [$^3$H]mannitol, [$^3$H]dextran-10 accumulation in the brain was significantly slower (n=6 per time point, *P<0.0001). Scale bars, 100 mm.

FIGS. 2A-L. In vivo two-photon imaging of para-arterial CSF flux into the mouse cortex. Color-coding has been converted to gray-scale. The influx into the cerebral cortex of tracers injected intracisternally into the subarachnoid CSF was assessed in vivo by two-photon imaging through a closed cranial window. (A) Schematic of imaging setup. Imaging was conducted between 0 and 240 mm below the cortical surface at 1-min intervals. (B) The cerebral vasculature was visualized with intra-arterial CB-d10, and arteries (A) and veins (V) were identified morphologically. Immediately after intracisternal injection, CSF tracer moved along the outside of cerebral surface arteries, but not veins. Red circles, arterioles; blue circles, venules. (C to E) Over time, tracer moved rapidly into the brain along penetrating arterioles, but not venules. The small-molecular weight tracer (TR-d3, dark blue) moved readily into the interstitium, whereas the large-molecular weight tracer (FITC-d2000, green) was confined to the paravascular space. Merge (light blue) indicates colocalization of TR-d3 and FITC-d2000. (F to H) Along the cortical surface arteries, the large-molecular weight tracer (FITC-d2000) was present in the paravascular space (PVS) immediately surrounding the arterial vascular smooth muscle cells (VSM). The bloodstream (BS) is defined by intravenously injected TR-d70. Low-level labeling of the basement membrane (BM) shows that a small proportion of CSF tracer moves along the basement membrane. (I and J) Intracisternally injected large-molecular weight tracer (FITC-d2000) entered the brain along paravascular spaces surrounding penetrating arterioles (TR-d70). (K and L) Glial fibrillary acidic protein (GFAP)-positive astrocytes in transgenic mice expressing a GFAP-GFP (green fluorescent protein) reporter. The paravascular space containing TR-d2000 is bounded by perivascular astrocytic endfeet (white). Scale bars, 100 mm [(B) to (E)], 20 mm [(F) to (I)], and 5 mm [(J) to (L)].

FIGS. 3A-H. CSF enters and is cleared from the brain interstitium along paravascular pathways. Color-coding has been converted to gray-scale. To evaluate the pathways of subarachnoid CSF flux into the brain parenchyma, fluorescent tracer was injected intracisternally into Tie2-GFP:NG2-DsRed double reporter mice, allowing arteries and veins to be directly distinguished. (A and B) Intracisternally injected OA-647 enters (green arrows depict tracer entry) the cerebral cortex along penetrating arterioles (Tie2-GFP+/NG2-DsRed+ vessels, empty arrowheads), not along ascending veins (Tie2-GFP+/NG2-DsRed− vessels, filled arrowheads). (C) CSF tracer moves along both paravascular space (PVS) and the basement membrane (BM) between the vascular endothelial and the smooth muscle cell layers. Tracer movement along capillaries proceeds along the basal lamina. (D) Large amounts of tracer are observed in the basal ganglia and thalamus, entering along large ventral perforating arteries. (E) Detailed tracer distribution around lenticulostriate artery. Plot shows intensity projection along white line. Green, tracer; gray, endothelial GFP; red, vascular smooth muscle. (F to H) At longer time points (>1 hour compared to 0 to 30 min for tracer influx), OA-647 (molecular size, 45 kD) entered the interstitial space and accumulated primarily along capillaries (F) and parenchymal venules (G). Accumulation was greatest along medial interior cerebral veins and ventral-lateral caudal rhinal veins (H). Orange arrows in (G) to (H) depict the observed route of interstitial tracer clearance. Scale bars, 100 mm [(A) and (D)], 50 mm (H), 20 mm [(B), (F), and (G)], and 4 mm [(C) and (E)].

FIGS. 4A-I. Paravascular aquaporin 4 (AQP4) facilitates CSF flux through the brain interstitium. Color-coding has been converted to gray-scale. (A) AQP4 (purple) is specifically expressed in brain astrocytes (white), where localization is highly polarized to perivascular endfeet (arrowheads). (B and C) AQP4-positive perivascular astrocytic endfeet immediately surround the para-arterial CSF influx pathway. Plots depict fluorescence intensity projections from (B) and (C), indicated by white rectangles. Tracer (green) is localized within the paravascular space (PVS), between the vascular smooth muscle (red) and the astrocytic endfeet (purple). (D) Tracer movement along the capillary basal lamina (green) is bounded by peri-vascular AQP4-positive endfeet (purple). (E and F) The contribution of AQP4-mediated fluid flux to the movement of subarachnoid CSF into and through the brain parenchyma was evaluated ex vivo. When tracer labeling was quantified, the movement of intracisternally injected tracer into the brain was significantly reduced in Aqp4-null mice compared to wild-type (WT) controls 30 min after injection (n=4 to 5 per time point, *P<0.05). (G) The influx of small-(TR-d3) (dark blue) and large-molecular weight (FITC-d2000) (green) intracisternal tracers into the cortex was evaluated in vivo. The cerebral vasculature was visualized with intra-arterial CB-d10 (inset). Merge (light blue) indicates colocalization of TR-d3 and FITC-d2000. (H) The movement of large-molecular weight tracer (green) along para-arterial spaces [as measured by the mean fluorescence intensity in green circle region of interests (ROIs)] was not significantly altered in Aqp4-null versus WT control animals. (I) The movement of small-molecular weight tracer into the interstitium surrounding penetrating arterioles (as measured by the mean fluorescence intensity in the blue donut ROIs) was abolished in Aqp4-null compared to WT controls (n=6 per group, *P<0.01), demonstrating that Aqp4 gene deletion affects the movement of intracisternally injected tracer through the cortical parenchyma. AU, arbitrary units. Scale bars, 100 mm (G), 40 mm (A), 20 mm (D), and 10 mm [(B) and (C)].

Figure 5A:
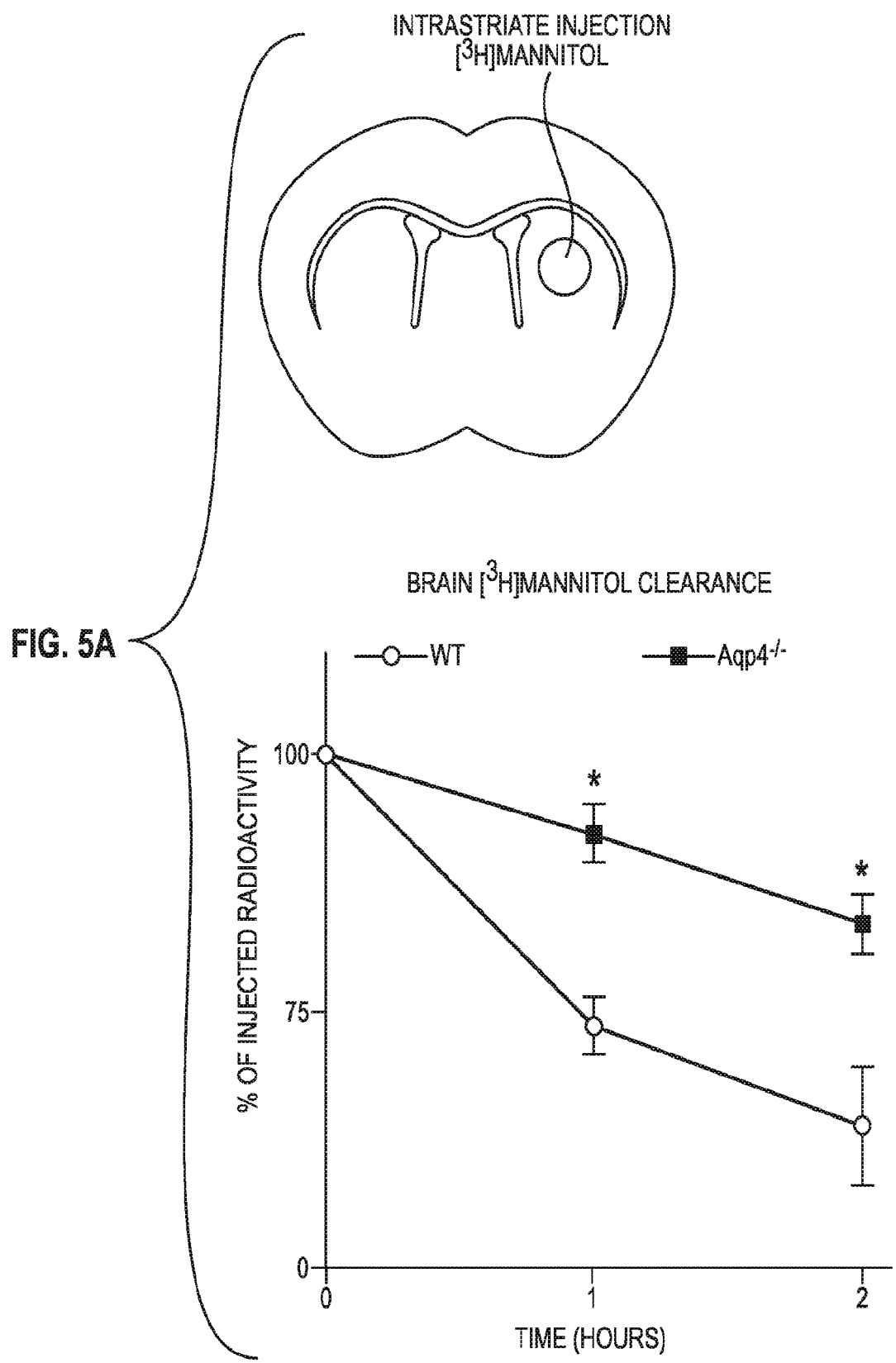
Figure 5B:
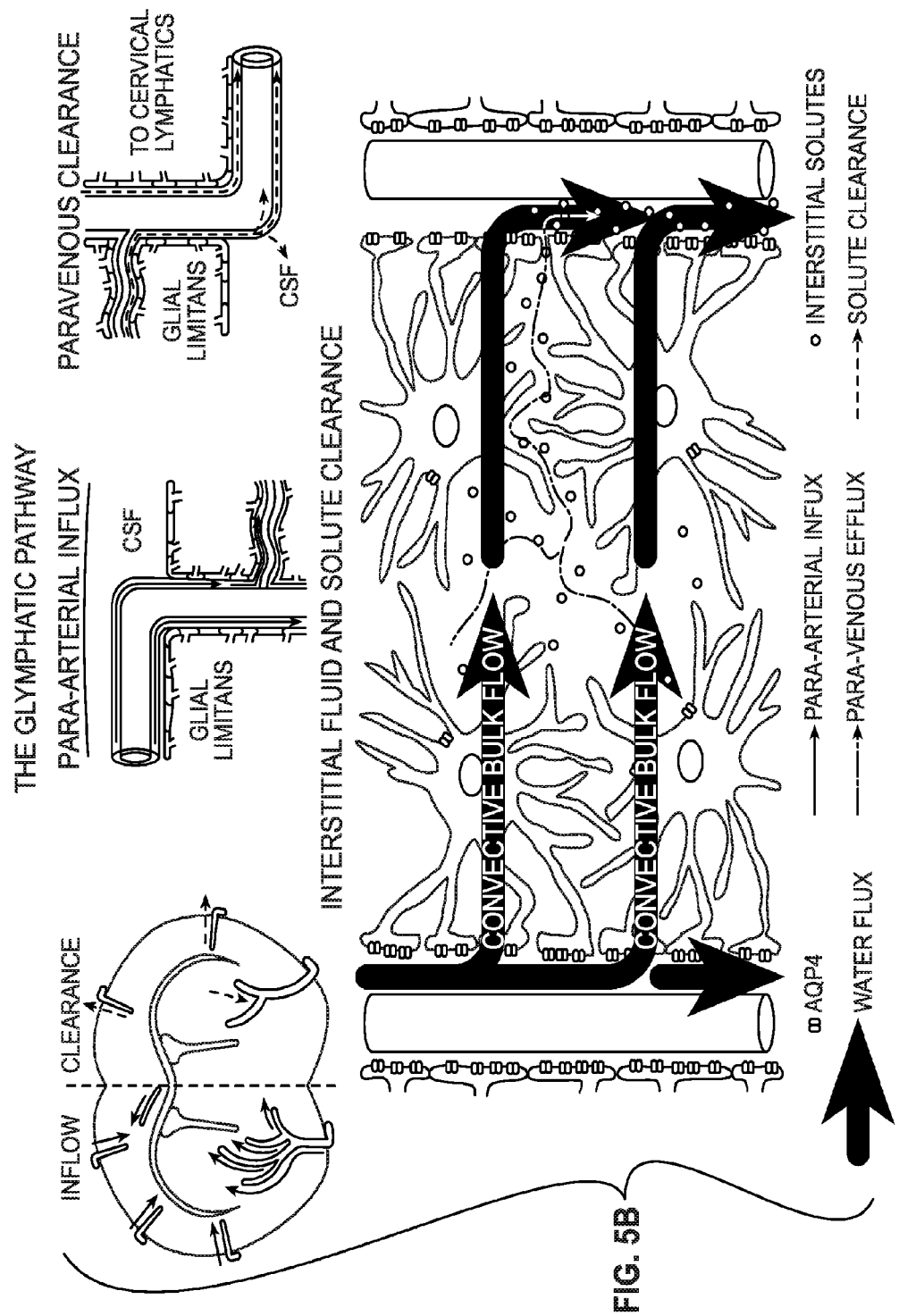

FIGS. 5A-B. The glymphatic system supports interstitial solute and fluid clearance from the brain. (A) To evaluate the role of the clearance of interstitial solutes, the elimination of intrastriate [$^3$H]mannitol from the brain was measured (for details, see FIG. 14A). Over the first 2 hours after injection, the clearance of intrastriate [$^3$H]mannitol from Aqp4-null mouse brains was significantly reduced (*P<0.01, n=4 per time point) compared to WT controls. (B) Schematic depiction of the glymphatic pathway. In this brain-wide pathway, CSF enters the brain along para-arterial routes, whereas ISF is cleared from the brain along paravenous routes. Convective bulk ISF flow between these influx and clearance routes is facilitated by AQP4-dependent astroglial water flux and drives the clearance of interstitial solutes and fluid from the brain parenchyma. From here, solutes and fluid may be dispersed into the subarachnoid CSF, enter the bloodstream across the postcapillary vasculature, or follow the walls of the draining veins to reach the cervical lymphatics.

FIGS. 6A-E. Interstitial Aβ is cleared along paravascular pathways. To evaluate whether interstitial soluble amyloid Aβ is cleared along the same pathways as other tracers, fluorescent or radiolabeled amyloid $\beta_{1-40}$ was injected into the mouse striatum. (A) Fifteen minutes, 30 min, or 1 hour after $^{125}$I-amyloid $\beta_{1-40}$ injection, whole-brain radiation was measured, as detailed in FIGS. 14A-B. At t=60 min in WT animals, I-amyloid $\beta_{1-40}$ was cleared more rapidly than [$^3$H]mannitol or [$^3$H]dextran-10. I-Amyloid $\beta_{1-40}$ clearance in Aqp4-null mice was significantly reduced (*P<0.05, n=4 to 6 per time point). (B to D) One hour after injection with HyLyte-555-amyloid $\beta_{1-40}$ into Tie2-GFP mice, tracer accumulated along capillaries (D, arrows) and large draining veins (B and C). Image in (C) depicts (B) without the endothelial GFP fluorescence signal. (E) To evaluate whether soluble Aβ within the CSF could recycle through the brain parenchyma, $^{125}$I-amyloid $\beta_{1-40}$ was injected intracisternally, and radiotracer influx into the brain was evaluated (as in FIGS. 8) 15, 30, and 45 min after injection. $^{125}$I-Amyloid $\beta_{1-40}$ entered the brain in a manner comparable to [$^3$H]dextran-10, and compared to WT controls, $^{125}$I-amyloid $\beta_{1-40}$ influx was significantly reduced in Aqp4-null mice (*P<0.05, n=4 to 6 per time point). Scale bar, 50 mm.

Figure 7:
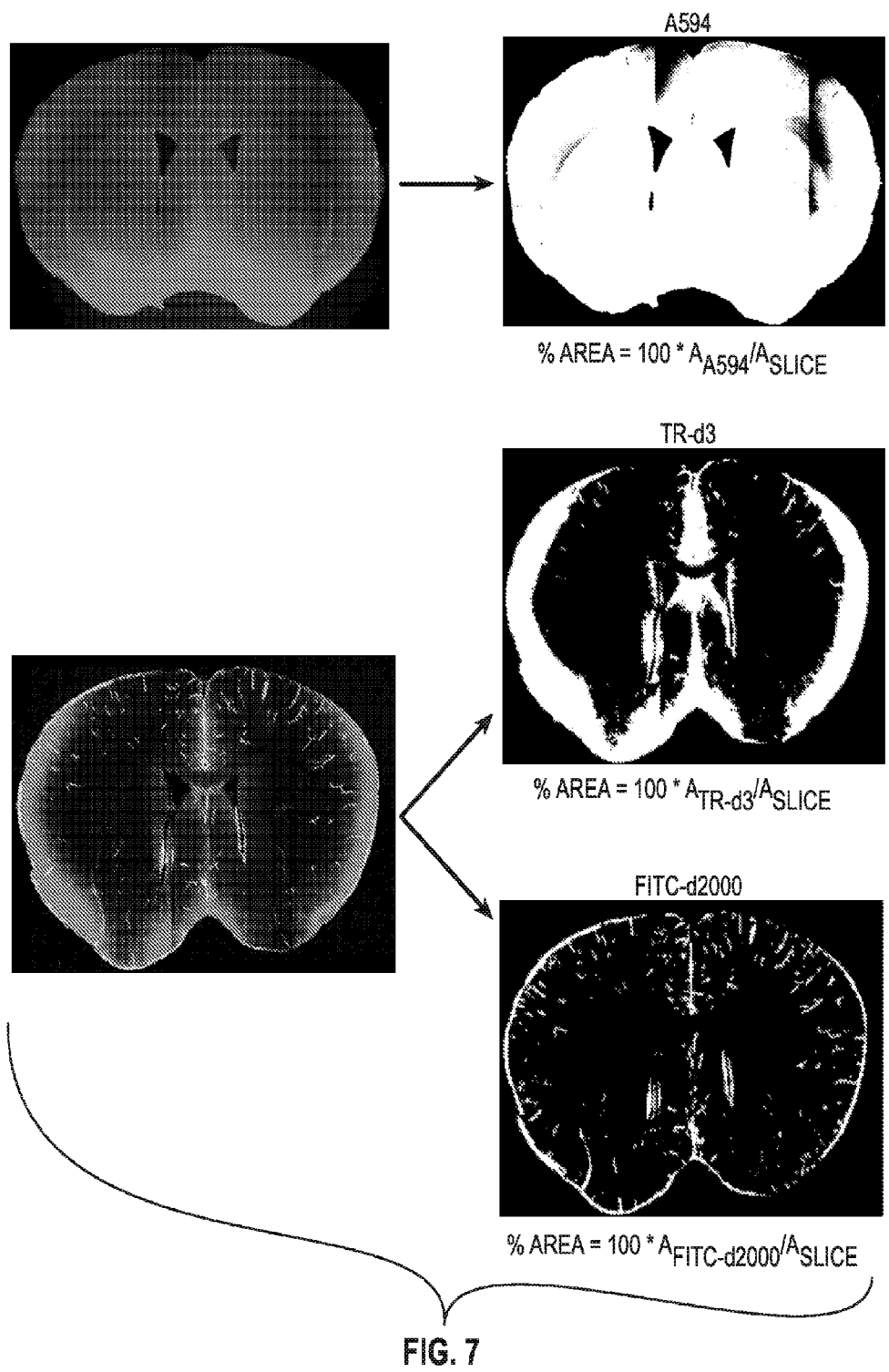

FIG. 7. Quantification of fluorescent CSF tracer distribution within the brain parenchyma. After injection of intracisternal A594, TR-d3 and FITC-d2000 injections, animals were perfusion fixed and 100-μm vibratome sections cut. Slices were imaged by epifluorescence microscopy at 4× and montages generated. To evaluate tracer coverage, the color channels were separated, the images background subtracted, uniformly thresholded and the thresholded area was calculated and expressed as a percentage of overall slice area.

Figure 8:
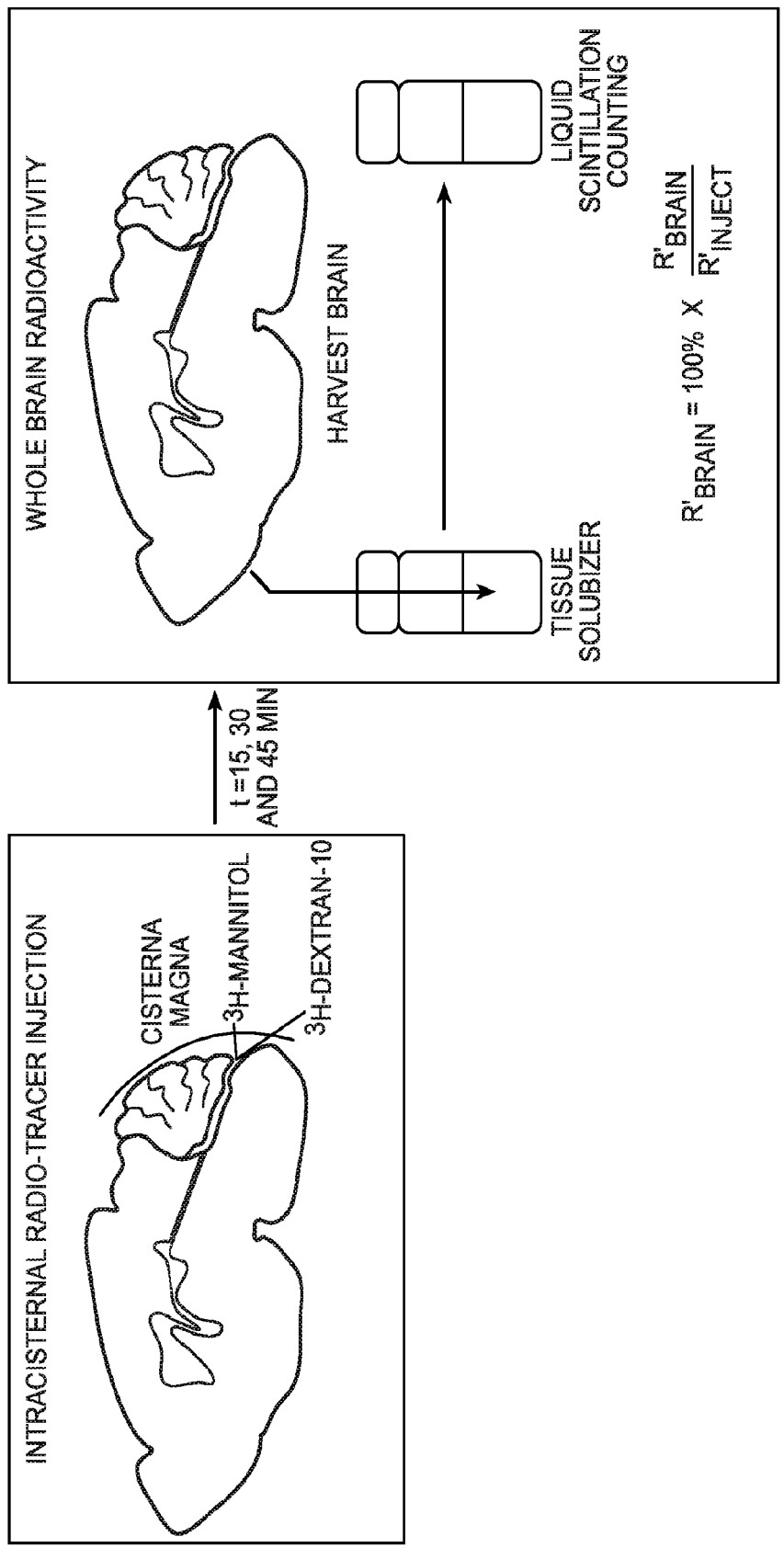

FIG. 8. Measurement of subarachnoid CSF entry into the brain parenchyma. Schematic diagram depicting the measurement of subarachnoid CSF entry into the brain parenchyma. $^3$H-Mannitol, $^3$H-Dextran-10 or $^{125}$I-A$\beta_{1-40}$ was injected intracisternally. To quantify radiotracer accumulation within the brain parenchyma, the brain was harvested 15, 30 or 45 min after radio-tracer injection. Brains were solubilized in Soluene, and then total brain radioactivity was measured by liquid scintillation counting. The proportional brain radioactivity (R'Brain) was calculated based upon the total measured brain radioactivity (RBrain) and the total injected radioactivity (RInject). During harvest, the dura was removed from the brain. Thus the brain homogenate does not include radio-tracer remaining in the subarachnoid CSF compartment.

FIGS. 9A-D. In vivo imaging of para-arterial influx of small- and large-molecular weight tracers. Color-coding has been converted to gray-scale. The movement of two dextrans of differing molecular weight (TR-d3 and FITC-d2000) along para-arterial pathways and into the cortical interstitium was imaged in anesthetized mice by in vivo 2-photon laser scanning microscopy within a closed cranial window. (A) The cerebral vasculature was visualized with intra-arterial Cascade Blue-dextran-10 (CB-d10) and penetrating arterioles (A) and veins (V) were identified morphologically (red and blue circles, respectively). (B-D) The movement of small and large molecular weight tracer along para-arterial and paravenous pathways was evaluated by measuring the mean fluorescence intensity within circular ROIs centered on penetrating vessels. The movement of tracer into the surrounding interstitium was defined by measuring mean fluorescence intensity in donut-shaped ROIs centered upon penetrating vessels (red and blue dashed donuts). (C) Small molecular weight tracer moved readily from the para-arterial space (red solid line) into the para-arterial (red dashed line) and paravenous (blue dashed line) interstitium. The lack of a statistically-significant difference (P=0.056, n=6 each group) between the curves indicates that this tracer enjoys relatively unrestricted movement outward from the para-arterial space. (D) Large molecular weight tracer moved readily into the cortex along penetrating arterioles (solid red line) but not along penetrating venules (solid blue line; *P<0.01, n=6 each group). Tracer intensity measured in the tissue surrounding penetrating arterioles and veins (dashed red and blue line, respectively) remained at the same low levels observed for paravenous spaces. Thus, large molecular weight tracer remains confined primarily to para-arterial spaces and does not readily enter the brain interstitium. Scale bars: 100 µm.

FIGS. 10A-E. CSF does not enter the brain parenchyma along paravenous pathways. To evaluate para-arterial versus paravenous subarachnoid CSF tracer influx, OA-647 was injected intracisternally into Tie2-GFP:NG2-DsRed double reporter mice. (A) In these mice, the endothelium of all blood vessels is labeled with GFP while vascular smooth muscle cells and pericytes are labeled with DsRed. Thus arteries and arterioles (empty arrowheads) are easily distinguished by the presence of distinct circumferential DsRed labeling, while veins (filled arrowheads) lack such labeling. The arterial specificity of NG2-DsRed labeling is seen when brain slices from NG2-DsRed mice are labeled with the endothelial marker CD-31 (right). (B) In the cerebral cortex, intracisternal tracer enters the brain along DsRed+ penetrating arterioles but not along DsRed− veins. Distal venous labeling is seen at times, but typically originates from a para-arteriolar inflow path via the intervening capillary bed. (C-E) Large vessels along the ventral brain surface exhibit the same pattern. Paravascular spaces surrounding large perforating arteries (empty arrowheads, D) move large fluxes of CSF tracer into the parenchyma, while tracer does not substantially penetrate into the parenchyma along basal draining veins (filled arrow heads, E). Scale bars: 100 µm (B, C), 50 µm (A), 20 µm (D-E).

FIGS. 11A-E. Intracisternally and intraparenchymally injected tracer shares the same paravenous drainage pathway. Tie2-GFP:NG2-DsRed double reporter mice were injected intra-parenchymally with OA-647. (A-B) Intracortically-injected tracer accumulated around the microvasculature, and moved outward from the injection site most rapidly along para-capillary and paravenous (arrowheads) pathways. (C-D) Intra-striate tracer similarly accumulated around capillaries and venules. Tracer that was injected into gray matter was excluded from white matter bundles (asterisks, D). (E) Intra-parenchymal tracer was cleared from the brain primarily along the internal cerebral and caudal rhinal veins, although lesser clearance along cortical ascending veins and venules was also observed. Scale bars: 50 µm (B, D-E), 20 µm (A, C).

FIGS. 12A-E. Visualization of paravascular accumulation of tracer and the Virchow-Robin space in wild-type and Aqp4-null mice. (A-B) Intracisternally injected FITC-d40 was visualized by DAB immunohistochemistry. 5 minutes after injection, reaction product is evident along penetrating cortical vessels (arrows in inset) of wild type animals (A). Labeling intensity around vessels is much weaker in Aqp4-null animals (B). Insets show labeling in parietal cortex at high magnification. (C-D) Electron micrographs showing the electron dense DAB reaction product in the proximal paravascular space (Virchow-Robin space, VRS) surrounding penetrating cortical arterioles. Compared to wild type animals (C), the VRS in Aqp4-null animals (D) appears ultrastructurally intact. (E) VRS of an uninjected Aqp4-null animal visualized ~1000 µm below the cortical surface. Inset shows width of VRS around penetrating vessels (n=10 for wild type animals, n=11 for Aqp4-null animals; values are mean±SEM). Endo, endothelial cell; VSM, vascular smooth muscle cell. Scale bars: 500 µm (insets in A and B), 1 µm (C-E).

FIGS. 13A-D. Differential expression of AQP4 in periarterial versus perivenous astrocytes. (A-B) Immunofluorescence labeling for AQP4 in the cortex of NG2-DsRed mice. Penetrating arteries are readily distinguished by intense, circumferential DsRed labeling of the vascular smooth muscle (A, empty arrowhead) while ascending veins exhibit irregular DsRed labeling (B, solid arrowhead). (C) Quantification of AQP4 immunoreactivity in perivascular endfeet, normalized to background AQP4 intensity. Periarterial endfeet expressed significantly less AQP4 than did pericapillary or perivenous endfeet (*P<0.01, ANOVA; n=24 arteries, 19 veins and 43 capillaries from 3 animals). (D) When AQP4 immunoreactivity was measured within 20 µm of the vessel wall (excluding the endfeet), periarterial AQP4 intensity was significantly reduced compared to levels around capillaries levels (*P<0.05, t-test). This was largely driven by a subpopulation of penetrating arteries (~40% of overall group) that exhibited a marked absence of AQP4 immunoreactivity labeling for up to 50 µm surrounding the vessel (seen in A).

Figure 14A:
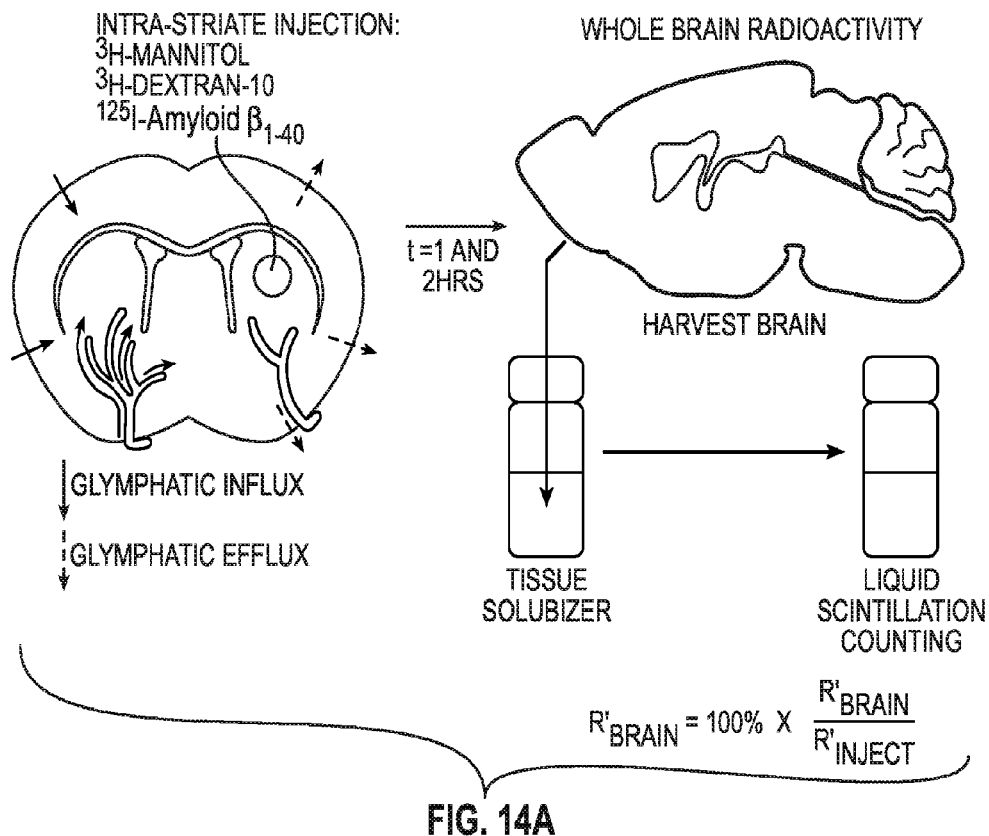
Figure 14B:
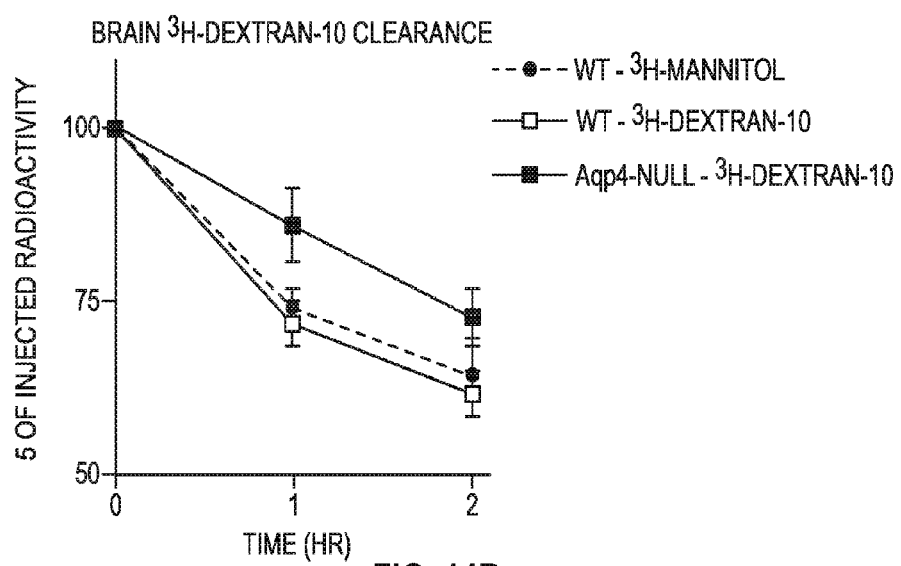

FIGS. 14A-B. Measurement of interstitial solute clearance from the brain. (A) Schematic diagram depicting the measurement of interstitial solute clearance from the brain parenchyma. $^3$H-mannitol, $^3$H-dextran-10 or $^{125}$I-amyloid β$_{1-40}$ was injected into the striatum. To quantify radio-tracer clearance from the parenchyma, the brain was harvested at t=1 or 2 hrs following radio-tracer injection. Brains were solubilized, then total brain radioactivity was measured by liquid scintillation counting. The remaining brain radioactivity (R'Brain) was calculated based upon the total measured brain radioactivity (RBrain) and the total injected radioactivity (RInject). When the brain was harvested, the dura was removed. Thus the measured RBrain value does not include radio-tracer present within the subarachnoid space. (B) The effect of Aqp4 gene deletion upon the clearance of intra-parenchymally injected $^3$H-dextran-10 from the brain. In wild type animals, both $^3$H-mannitol and $^3$H-dextran-10 were cleared from the brain at identical rates. This is consistent with the observation that bulk flow [in contrast to diffusion(9)]-mediated transport is independent of molecular weight(4). Aqp4 gene deletion had an effect upon the efflux of $^3$H-dextran-10 similar to that of $^3$H-mannitol (FIG. 5B), markedly reducing the rate of their clearance from the brain parenchyma (*P<0.01, n=4 per time point).

Figure 15A:
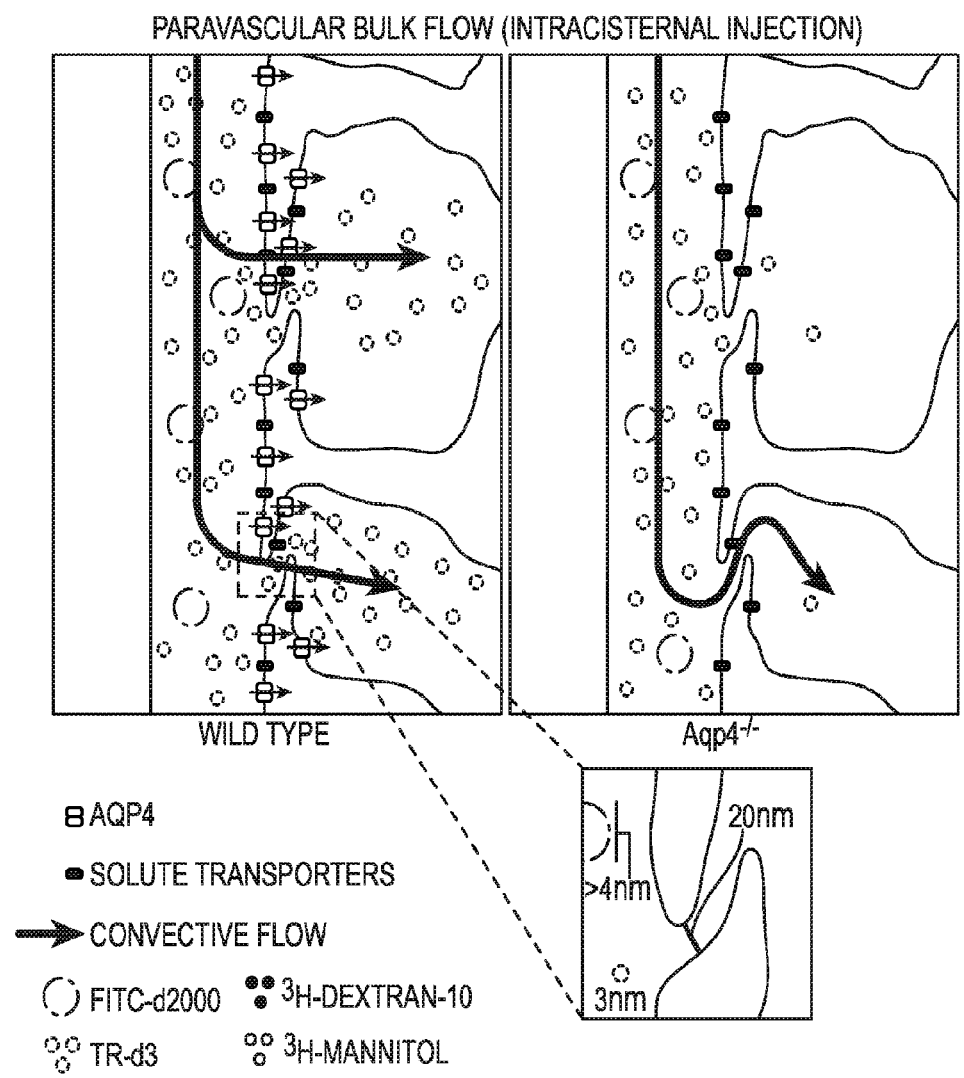
Figure 15B:
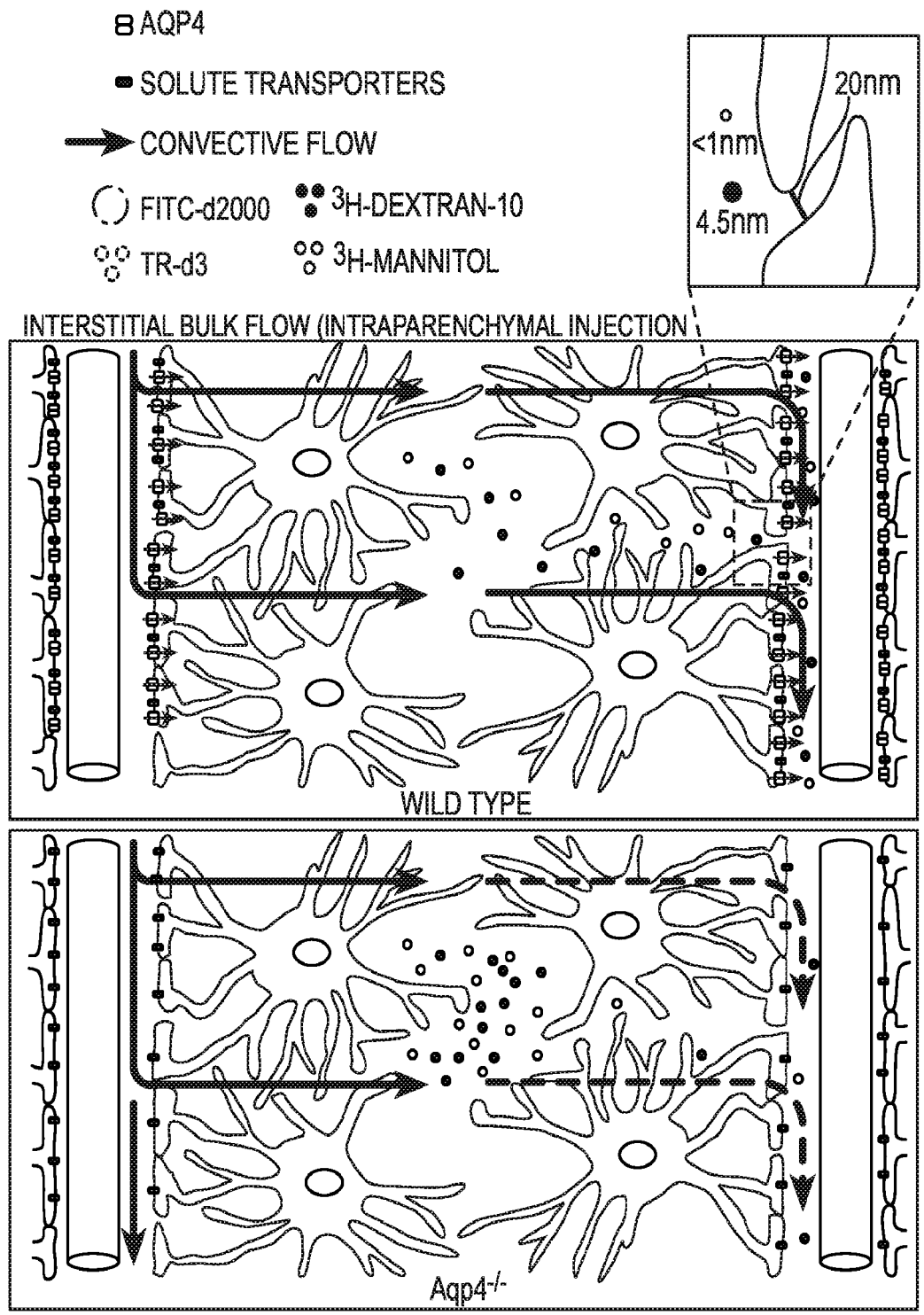

FIGS. 15A-B. Schematic diagram of paravascular and interstitial bulk flow pathways. (A) Schematic depicting the proposed role of periarterial astroglial endfoot AQP4 in facilitating bulk water flow between the para-arterial influx pathway and the interstitial compartment. Because of high AQP4 expression, water passes freely across the perivascular endfoot. Small solutes, including the fluorescent tracer TR-d3 (MW 3 kD), follow the resulting osmotic gradient into the interstitium through intercellular clefts between overlapping endfoot processes. Large solutes, including FITC-d2000 (MW 2000 kD), cannot pass this cleft and are retained in the paravascular space. In Aqp4-null mice, water flux between the paravascular space and the interstitium is reduced, as is accompanying solute movement into the interstitium. Inset depicts physical dimensions of TR-d3, FITC-d2000 [dH, hydration diameter (9) and the inter-endfoot cleft (17). (B) Detailed schematic depicting the proposed role of astroglial AQP4 in maintaining convective ISF bulk flow and interstitial solute clearance. Para-arterial and paravenous AQP4 permits the free movement of water between the para-arterial influx and paravenous clearance pathway. This convective water flux sweeps interstitial solutes and tracers (such as $^3$H-mannitol and $^3$H-dextran-10) along its path. In Aqp4-null mice, water flux between the paravascular spaces and the interstitium are reduced, resulting in the failure of interstitial solute clearance. Inset depicts the physical dimensions of $^3$H-mannitol, $^3$H-dextran-10 and the inter-endfoot cleft.

Figure 16:
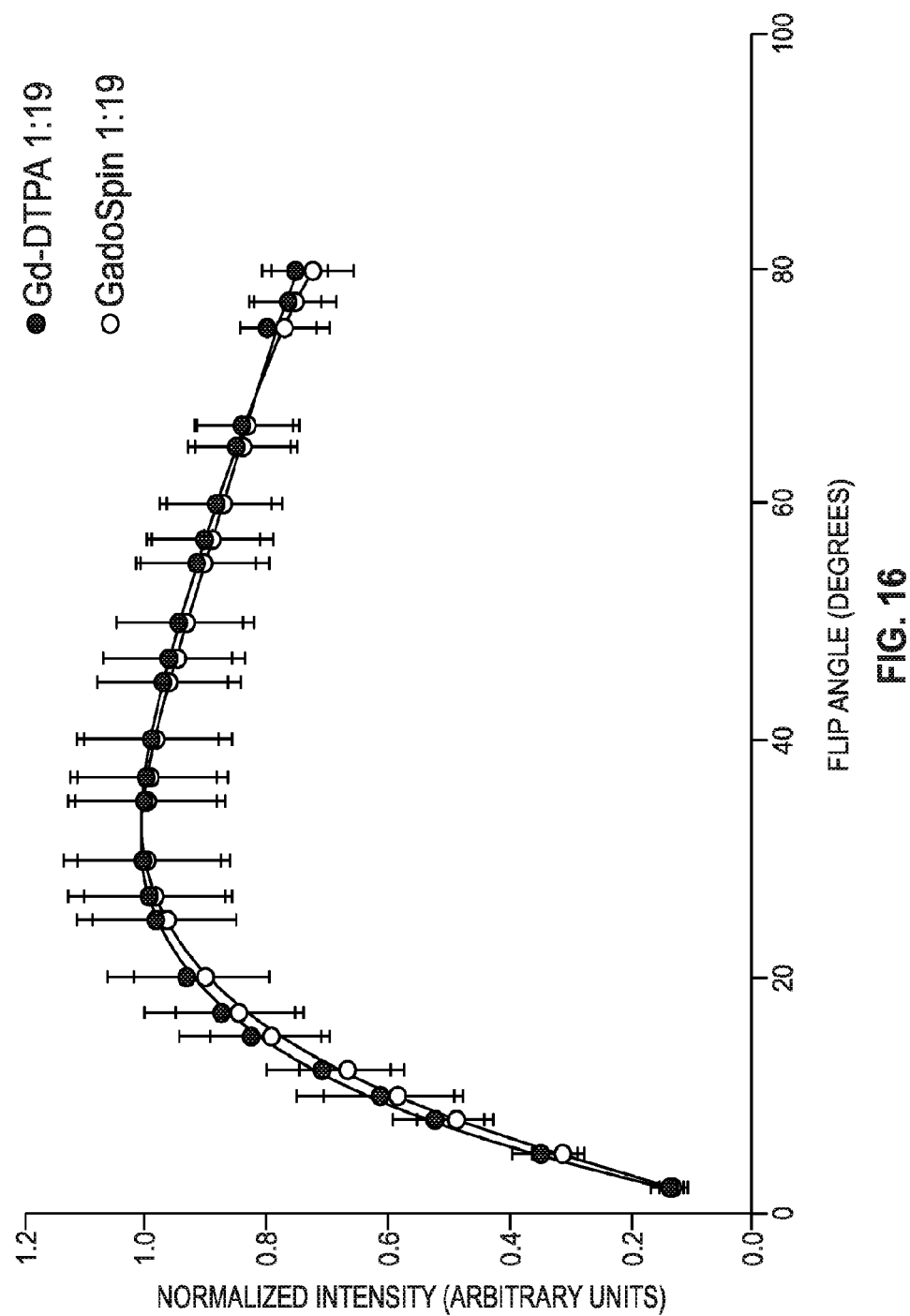

FIG. 16. Normalized signal intensities (mean±SD) are plotted as a function of flip angles in FLASH MRI sequence taken at dilution ratio of 1:19, defined by volume ratio between paramagnetic contrast agents (21 mM diethylenetriaminepentacetate (GD-DTPA) and 0.17 mM GadoSpin™) and 0.9% NaCl, taken at 37° C. Normalization is achieved by dividing intensity by its maximal value across the flip angles.

FIG. 17. Longitudinal relaxation times (T1) are plotted as a function of dilution ratios, defined by volume ratio between 0.9% NaCl and paramagnetic contrast agents, in logarithmic scales taken at 37° C.

FIGS. 18A-J. Paravascular influx of paramagnetic contrast. (A) 3D visualization of key anatomical structures in the rat brain prior to administration of contrast. Color-coding has been converted to gray-scale. The anatomical structures include the pituitary (light blue), hippocampus (green), superior colliculus (orange), inferior colliculus (dark blue) and pineal gland (yellow). The olfactory artery (OA), azygos of the anterior cerebral artery (azACA), azygos pericallosal artery (AzPA), the middle internal frontal artery (IFA) and the posterior lateral choroidal arterial complex were visualized. (B) A two-dimensional T1-weighted MRI with the color-coded anatomical structures displayed. (C-E) The time series demonstrate early influx of the small molecular weight paramagnetic contrast agent Gd-DTPA (MW 938 D). The time at which the intrathecally infused Gd-DTPA appears in the cisterna magna is defined as '0' min (C) and the earliest part of the influx process is demonstrated in the subsequent time frames (D, E); and shows that Gd-DTPA enters the brain along paravascular pathways. (F-H) The dynamic time series of early influx of the large molecular weight paramagnetic contrast agent GadoSpin™ (MW 200 kD) also shows that transport into the brain is paravascular. Note that it is evident that even though the two paramagnetic contrast agents differ in molecular weight, they pass through paravascular conduits at similar rates; supporting that CSF bulk flow governs this process. (I,J) Paravascular transport of the paramagnetic contrast agent is demonstrated particularly clearly at the level of the Circle of Willis along the internal carotid (IC) artery, posterior communicating (Pcom) arteries and lateral orbitofrontal artery.

Figure 19:
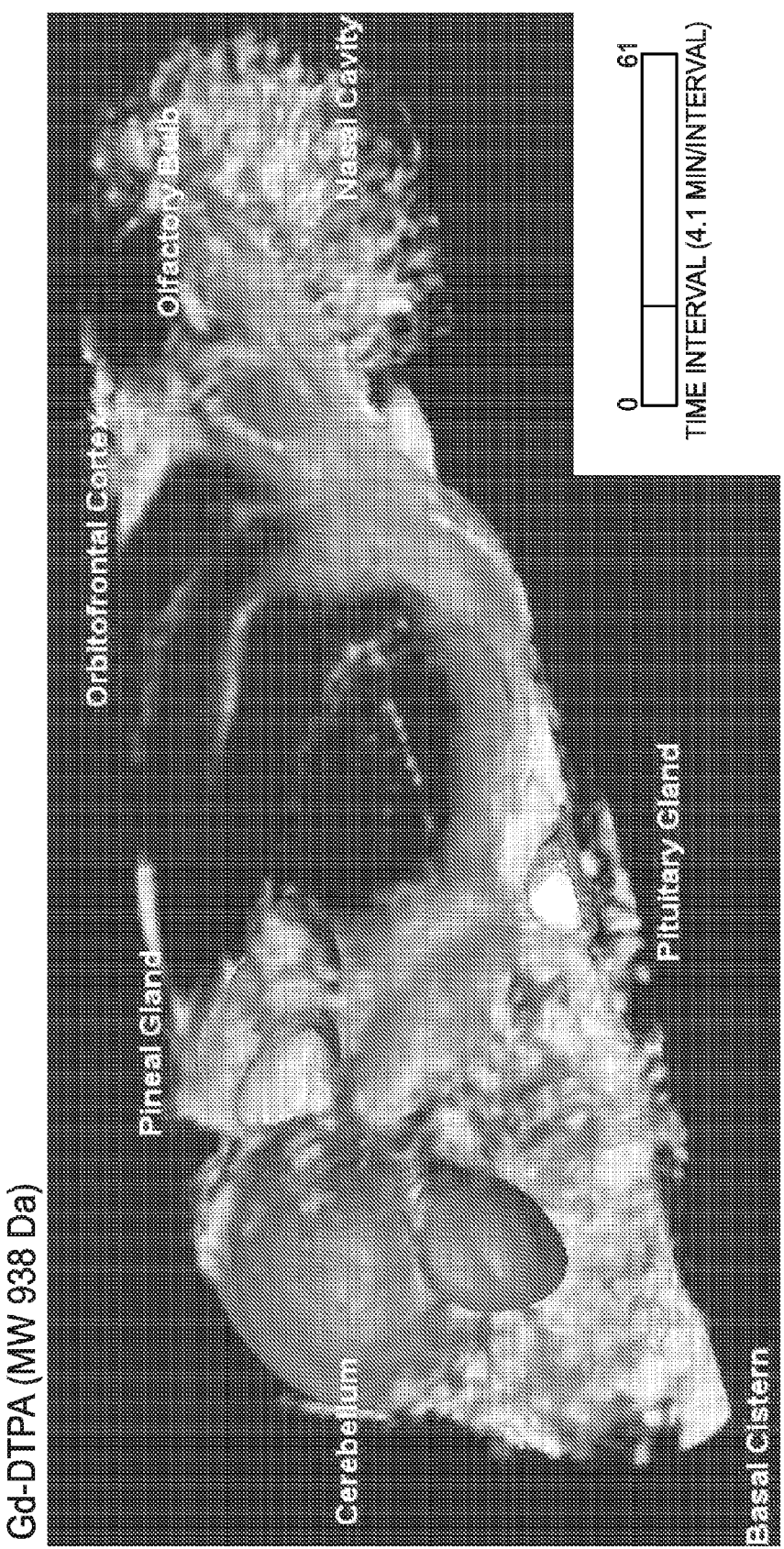

FIG. 19. Still image taken from a dynamic display (movie) of Gd-DTPA administered into the basal cistern and moving through the 'glymphatic' pathway'. Color-coding has been converted to gray-scale. Gd-DTPA paramagnetic contrast was represented in the movie by green/blue color and each time-frame represented 4.1/min. Key anatomical structures of the rat brain were displayed in 3D including the cerebellum (brown), pineal gland (yellow) superior colliculus (orange), inferior colliculus (red), pituitary gland (white) and large basal arteries (red) (color coding in movie, not shown in this still image). Gd-DTPA was observed to move from the basal cistern along para-vascular pathways associated with the large vessels and then enter the brain parenchyma and also exit from the brain and into the nasal cavity via the cribriform plate. The movement of Gd-DTPA was captured over ~4 hrs. The contrast had still not cleared and was evident at the pineal recess, olfactory bulb and at the basal cistern at the end of the 4 hour period.

Figure 20:
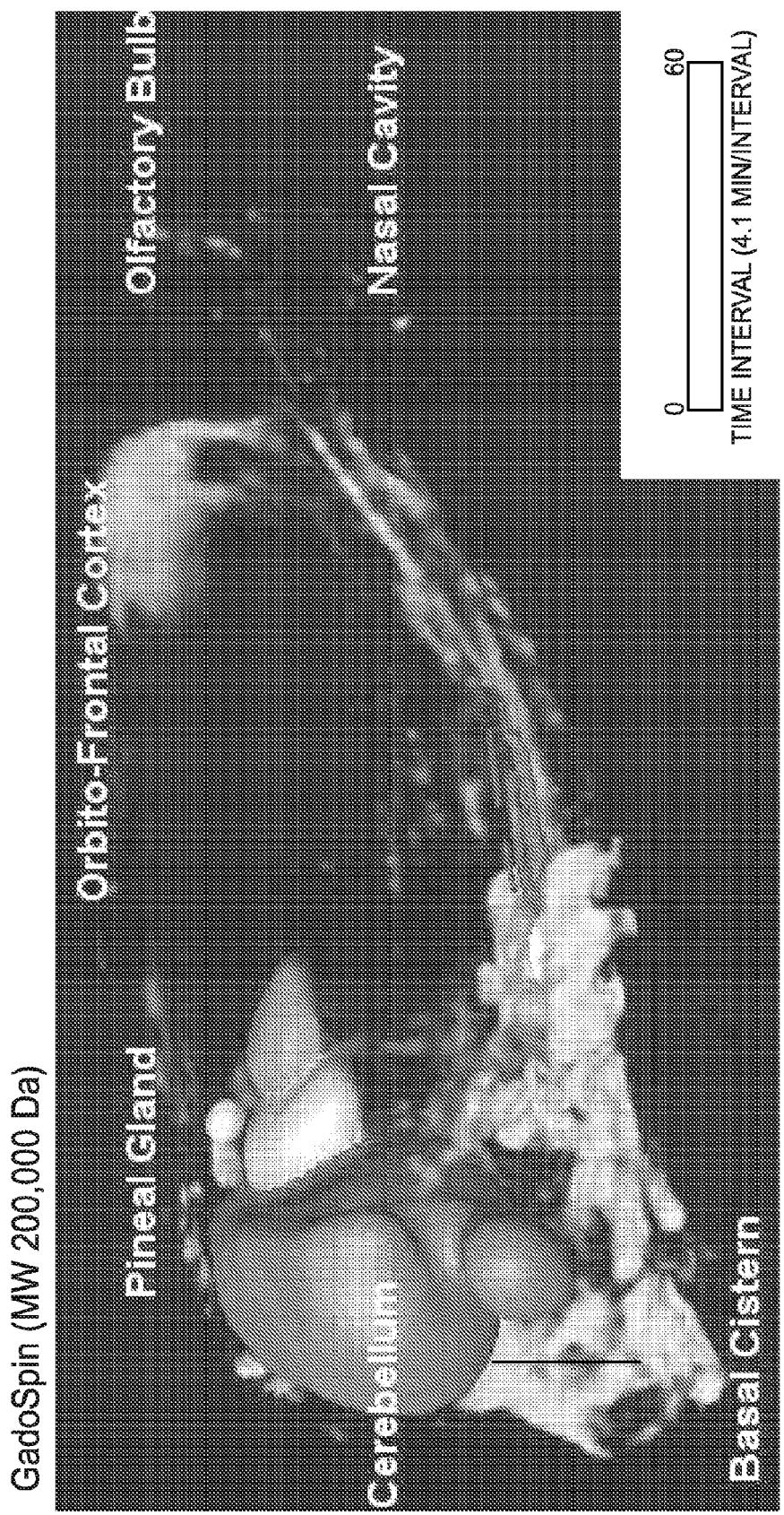

FIG. 20. Still image taken from a dynamic display (movie) of GadoSpin™ administered into the basal cistern and moving through the 'glymphatic' pathway'. Color-coding has been converted to gray-scale. GadoSpin™ paramagnetic contrast was represented in the movie by green/blue color and each time-frame represented 4.1/min. Key anatomical structures of the rat brain were displayed in 3D including the cerebellum (brown), pineal gland (yellow) superior colliculus (orange), inferior colliculus (red), pituitary gland (white) and large basal arteries (red) (color coding in movie, not shown in this still image). Similar to Gd-DTPA, GadoSpin™ also entered the most proximal part of the glymphatic pathway along para-vascular conduits. However, in contrast to the smaller contrast molecule Gd-DTPA (MW 938 Da), which more easily gains access to the brain interstitial space, the larger GadoSpin™ molecule (MW 200,000 Da), preferentially remained in the paravascular compartment.

FIGS. 21A-F. Gd-DTPA and GadoSpin™ transport along glymphatic pathways. Color-coding has been converted to gray-scale. The average time-activity curves (TACs) for Gd-DTPA (blue filled circles) and GadoSpin™ (red filled circles) are shown for the pituitary recess (A), pineal recess (B), Cerebellum (C), Olfactory Blub (D), Aqueduct (E) and Pontine Nucleus (F). The location of each of the regions of interest is shown on the sagittal brain icon displayed in the upper right corner of each of the graphs. It is evident that contrast uptake in the pituitary recess and pineal recess are largely similar for Gd-DTPA and GadoSpin™ (A, B). This confirms that within the proximal portions of the glymphatic pathway, paramagnetic contrast agent transport is largely independent of molecular size. It is also clear that tissue uptake of Gd-DTPA is significantly higher than observed for GadoSpin™ in the cerebellum (C), aqueduct (E) and pontine nucleus (F). This confirms that the movement of contrast agent from the subarachnoid/proximal paravascular pathway into and through the brain interstitium is indeed dependent upon molecular size. Data are presented as mean±SEM.

FIGS. 22A-J. Cluster-based spatial distribution of Gd-DTPA and GadoSpin™ in the rat brain. (A) T1-weighted sagittal midline section at the level of the aqueduct (Aq) with anatomical landmarks displayed prior to administration of GadoSpin™: AzACA=azygos of the anterior cerebral artery; BC=basal cistern; BA=basal artery; Cb=cerebellum; GA=vein of Galen; IFA=middle internal frontal artery; Ob=olfactory bulb; OA=olfactory artery Pin=pineal gland; Pit=pituitary gland. (B) Cluster analysis in GadoSpin™ rat. Color-coding of cluster analysis data is shown in gray-scale. The para-vascular cluster is overlaid on the corresponding MRI, demonstrating that the red and orange clusters match the spatial location of the basal cistern, pineal recess and pituitary recess and tissue in the immediate vicinity of the major arteries. (C) Distribution of blue and green clusters from the same GadoSpin™ rat demonstrating the more parenchymal location of these clusters. (D) All clusters displayed simultaneously and overlaid on the MRI; the red and orange clusters in the para-vascular conduits are classified as 'zone 1', the green cluster as 'zone 2' and the blue cluster as 'zone 3'. (E) T1-weighted MRI at the level of the aqueduct (Aq) with anatomical landmarks displayed from a rat prior to administration of Gd-DTPA. (F) Para-vascular, zone 1 cluster displayed from the Gd-DTPA rat. (G) Green and blue cluster distribution in the Gd-DTPA rat. (H) All four clusters displayed; the red, green and blue clusters are classified as zone 1, 2 and 3, respectively. The time-activity-curves (TACs) for each of the four clusters for a GadoSpin™ rat (I) and a Gd-DTPA rat (J) are displayed in addition to the total number of voxels of each the clusters.

FIGS. 23A-I. Fluorescence-based imaging of paravascular CSF-ISF exchange. Small (Texas Red-dextran3, TR-d3; MW 3 kD) and large (FITC-d500; MW 500 kD) molecular weight fluorescent tracers were injected intrathecally and imaged ex vivo by conventional and laser scanning confocal fluorescence microscopy. (A, F, H) Whole-slice montage showing paravascular (arrowheads) CSF tracer influx into the brain at 30 min (A), 60 min (F) and 180 min (H) after injection. (B) Coronal slice counter-labeled with vascular endothelial marker isolectin B4 (IB4) 30 min post-injection. (C-D) High power confocal imaging shows that CSF tracer enters the brain along penetrating arteries (arrowheads) but not along draining veins (E). Large molecular weight FITC-d500 remains confined to the paravascular spaces while small molecular weight TR-d3 moves readily into and through the surrounding interstitium. (F) 60 min after injection, small molecular weight TR-d3 is localized diffusely throughout the brain interstitium, while large molecular weight FITC-d500 is apparent along terminal capillary bed (G). Inset depicts z-projection of image stack demonstrating extent of capillary labeling with FITC-d500. (H) At 180 min post-injection, parenchymal tracer levels are reduced compared to 30 and 60 min post-injection, while intrathecal tracer persists along para-venous clearance pathways (I).

Figure 24:

FIG. 24. Brain-wide glymphatic pathways of CSF-ISF exchange assessed by contrast-enhanced MRI in the rat. Color-coding has been converted to gray-scale. Brain-wide glymphatic pathways of CSF-ISF exchange assessed by contrast-enhanced MRI in the rat. After injection into the subarachnoid space of the cisterna magna, contrast agent follows specific paravascular pathways (yellow arrows) to enter the brain parenchyma and exchange with the interstitial compartments (orange arrows and fields). Acquisition of dynamic image series identified key CSF influx nodes at the pineal (Pin) and pituitary (Pit) recesses and allowed simple kinetic parameters to be derived that deflect the extent and rate of glymphatic CSF-ISF exchange throughout the whole brain. Cb: cerebellum; Ob: olfactory bulb; BA: basilar artery; OA: olfactory artery.

FIGS. 25A-H. Evaluating intracisternal CSF tracer influx and clearance in mouse and rat. Color-coding has been converted to gray-scale. Representative anterior (A-B) and posterior (C-D) coronal slices from mouse (A, C) and rat (B, D) brains following intracisternal injection of Texas Red-conjugated dextran (TR-d3, MW 3 kD; t=30 min post-injection) show similar tracer distributions between species. (E-H) Tissue fluorescence was evaluated in different brain regions: cortex (blue), white matter (grey), hippocampus (magenta), and subcortical structures (red) of the anterior (E-F) and posterior (G-H) brain. (F, H) Quantification of mean fluorescence intensity within each region (*$P<0.05$ cortex vs. subcortical structures; ##$P<0.01$ vs. cortex; 2-way ANOVA; n=3-4 per time point).

FIGS. 26A-F. Effect of molecular weight on tracer influx into the brain after lumbar intrathecal injection. (A-B) Coronal brain slices show penetration of large molecular weight FITC-conjugated dextran (FITC-d500, MW 500 kD) and small molecular weight Texas Red-conjugated dextran (TR-d3, MW 3 kD) 120 min after lumbar intrathecal co-injection. FITC-d500 is largely confined to paravascular spaces (B, arrows), while TR-d3 moves readily though the brain parenchyma from paravascular spaces (A, arrows) or from the pial surface (arrowheads). (C-F) Quantification of fluorescent tracer influx into anterior (C-D) and posterior (E-F) brain after lumbar intrathecal injection, anatomically subdivided into cortex, white matter, subcortical structures, and hippocampus. (*$P<0.05$, *$P<0.01$ cortex vs. subcortical structures; ##$P<0.01$ cortex vs. white matter; $^{554}P<0.05$, $^{554\dagger}P<0.01$ cortex vs. hippocampus; 2-way ANOVA; n=3-4 per time point).

FIGS. 27A-L. CSF tracer localization after intracisternal and lumbar intrathecal injection. (A-F) Localization of FITC-conjugated dextran (FITC-d500, MW 500 kD) and Texas Red-conjugated dextran (TR-d3, MW 3 kD) 30 min after intracisternal injection. Large molecular weight FITC-d500 remained restricted to paravascular spaces (arrows) surrounding penetrating arteries (A-B) and extending to the level of the terminal capillary beds (C-F, arrows). Small molecular weight TR-d3 moved quickly into the brain interstitium and was taken up by subpopulations of neurons (arrowheads). (G-L) 120 min after lumbar intrathecal injection of tracers, large molecular weight FITC-d500 accumulated in perivascular spaces (arrows), but not as uniformly as observed after intracisternal injection. Small molecular weight TR-d3 moved readily throughout the brain parenchyma. GFAP: glial fibrillary acidic protein (astrocytic marker); IB4: isolectin B4 (vascular endothelial marker).

Figure 28:
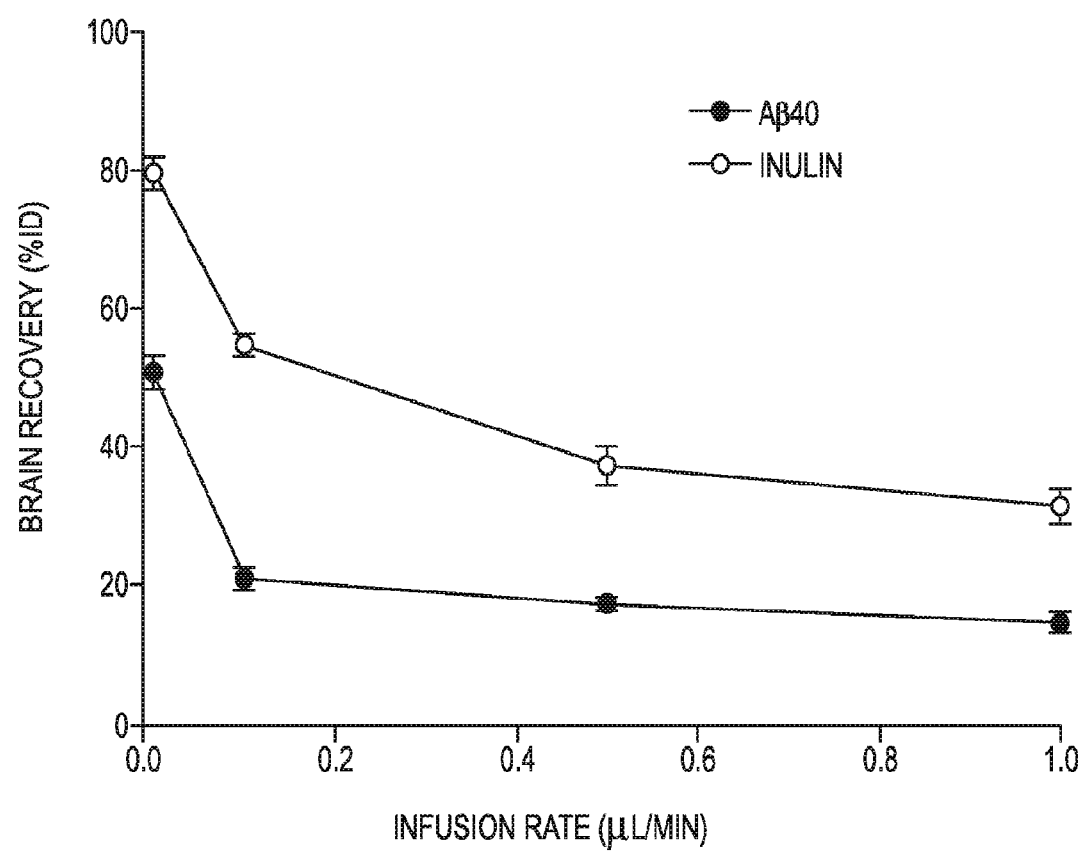

FIG. 28. Brain clearance of Aβ40 and inulin increased with CSF infusion rate.

Figure 29A:
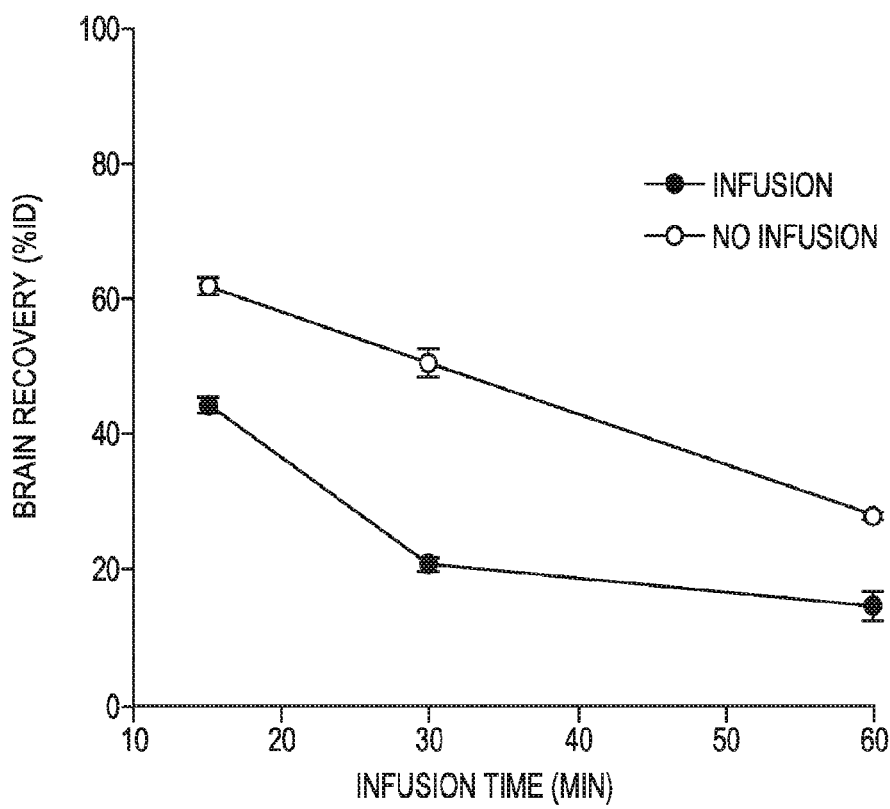
Figure 29B:
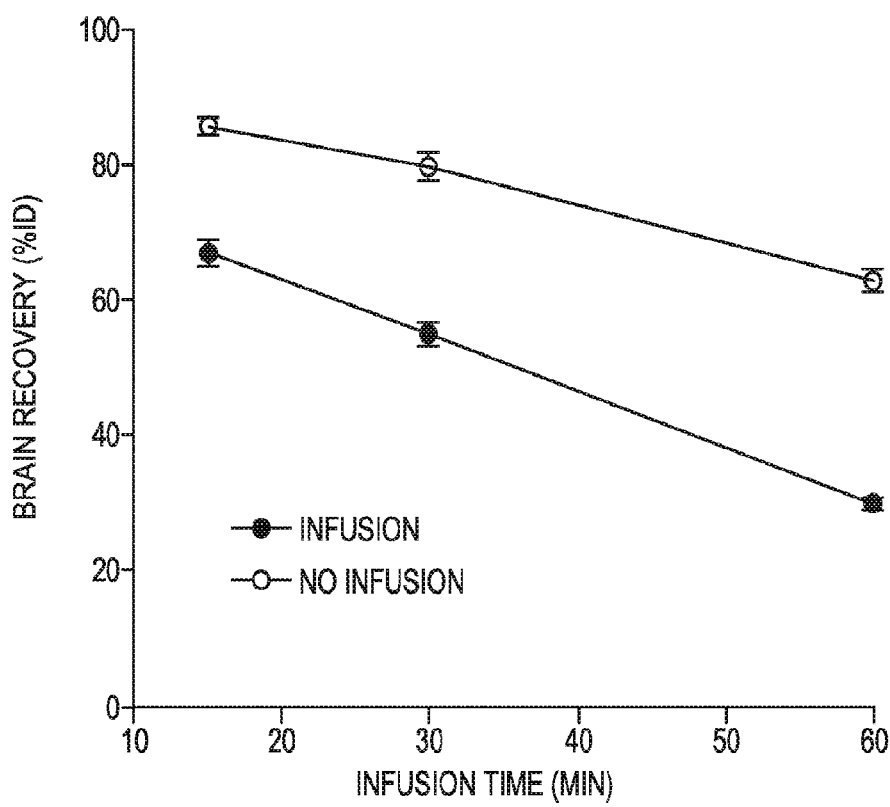

FIGS. 29A-B. Brain clearance of Aβ40 (A) and inulin (B) increased with CSF infusion duration.

Figure 30A:
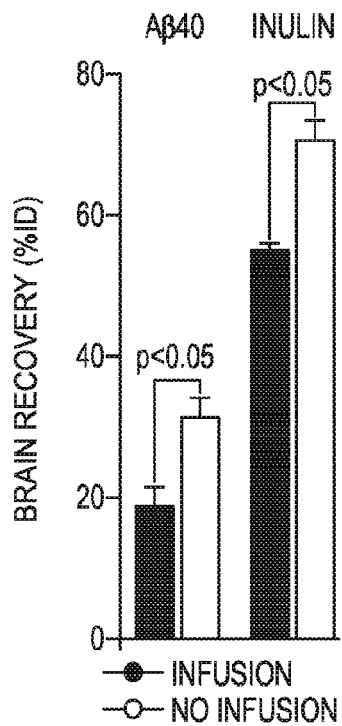
Figure 30B:
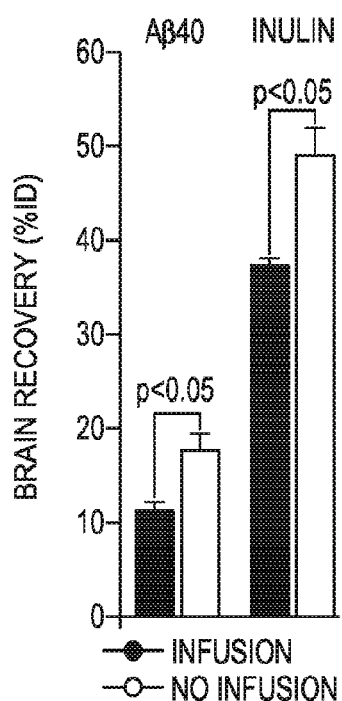

FIGS. 30A-B. Brain clearance of Aβ40 and inulin from the frontal cortex at 30 minutes (A) and 60 minutes (B) after CSF infusion.

Figure 31A:
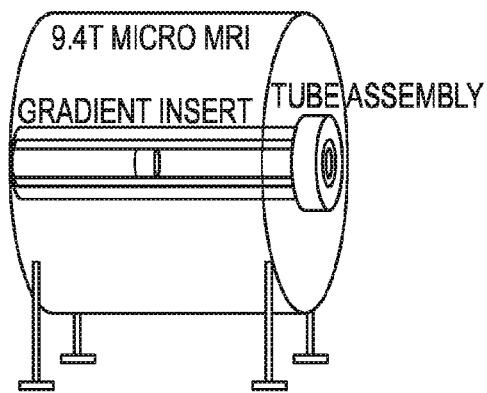
Figure 31B:
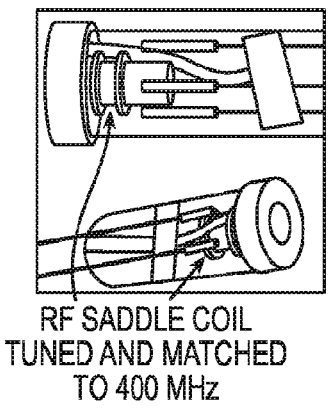
Figure 31C:
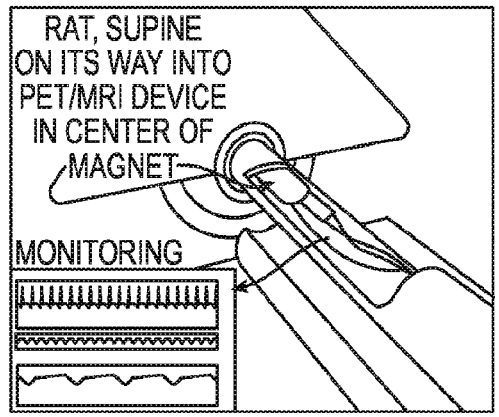

FIGS. 31A-C. Experimental set-up. A. Diagram of 9.4T micro MRI tube assembly with gradient insert. B. RF saddle coil, tuned and matched to 400 Mhz. C. Rat, supine on its way into PET/MRI device in center of magnet. Monitoring trace shown beneath.

FIGS. 32A-F. Intrathecal $^{18}$FDG is superior to DTPA for assessing brain-wide glymphatic transport. (A) Brain images from a rat receiving intrathecal Gd-DTPA-$^{18}$FDG during PET-MRI dynamic imaging. Distribution of Gd-DTPA shown on the T-weighted MRI highlights high signal intensity in the basal cisterns, cerebellum and pons. (B) Time activity curves (TAC) of signal changes in response to Gd-DTPA in pons, cerebellum and cortex over time. (C) Corresponding $^{18}$FDG distribution pattern from rat shown in A; demonstrating widespread distribution of $^{18}$FDG activity in the entire brain which is reflected in the corresponding TACs (D). (E) Rat receiving intrathecal $^{18}$F and corresponding TACs (F) demonstrating that $^{18}$F uptake is confined to pons with very limited uptake in cortex and cerebellum over time. The differences in TACs from the three intrathecal molecules suggest that glymphatic transport of $^{18}$FDG is rapid in comparison to Gd-DTPA and $^{18}$F. In graphs B, D and F, Pons=upper plot, Cerebellum=middle plot, Cortex=lower plot.

FIGS. 33A-F. Impairment of glymphatic paravascular CSF influx in the aging brain. (A) Paravascular CSF influx was evaluated by in vivo 2-photon microscopy in the anesthetized mouse cortex. The cerebral vasculature was defined by intra-arterial Texas Red dextran (70 kD, TR-d70) and cortical arteries (arrows) and veins (arrowheads) were defined morphologically. 10 µl Fluorescent CSF tracer (FITC-conjugated dextran, 40 kD; FITC-d40) was injected intracisternally while paravascular tracer influx was visualized via a closed cranial window preparation. (B) Quantification of paravascular CSF influx into the cortex 100 µm below the cortical surface shows that compared to the young (2-3 month old) brain, paravascular CSF influx into the aged (12 months) cortex is significantly slowed (*$P<0.05$, 12 month vs. 2-3 month, 2-way repeated measures ANOVA; n=4 per group). (C-D) Representative serial imaging of CSF tracer as it enters the cortex initially along cerebral surface arteries (C1-C6), then along penetrating arterioles as it moves into the surrounding interstitium imaged here at 100 µm below the cortical surface (D1-D6). (E-F) Representative serial imaging of CSF tracer entry into the cortex of aged mice (12 months) shows slowed movement of CSF tracer first along the paravascular spaces of the cerebral surface vasculature (E1-E6) as well as its movement into the cortical interstitium (F1-F6).

FIGS. 34A-E. Impairment of brain-wide glymphatic pathway function in the aging brain. Glymphatic pathway function was evaluated in the anesthetized mouse brain by ex vivo fluorescence imaging. (A) Two different fluorescent CSF tracers (Texas Red-conjugated dextran, MW 3 kD, TR-d3; ovalbumin-conjugated ALEXA 647, MW 45 kD, OA-647) were co-injected into the cisterna magna. 30 min later, animals were perfusion fixed, the brains sliced on a vibratome, and coronal sections imaged by 2-channel conventional fluorescence microscopy. (B) Quantification of CSF tracer influx revealed an age-related impairment of glymphatic pathway function, as influx of both low molecular weight TR-d3 and high molecular weight OA-647 were significantly impaired in the old (18 months) compared to the young (2-3 months) mouse brain (*$P<0.05$, ***$P<0.001$ vs. 2-3 months; ANOVA; n=5-8 per group). CSF tracer influx into the middle-aged (10-12 months) brain was intermediate between that of the young and old brains. (C-E) Representative images showing differences in fluorescent CSF tracer influx between the 2-3 month (C), 10-12 month (D), and 18 month (E) brain show marked impairment of tracer influx with progressing age, particularly with increasing distance from the pial surface.

FIGS. 35A-J. Region-specific age-related impairment of glymphatic pathway function. Glymphatic pathway function was evaluated in the anesthetized mouse brain by ex vivo whole slice fluorescence imaging of CSF tracer influx. Small (Texas Red-conjugated dextran, MW 3 kD, TR-d3) and large molecular weight (ovalbumin-conjugated ALEXA 647, MW 45 kD, OA-647) tracers were injected into the cisterna magna, and the animals were perfusion fixed 30 min later. Fluorescent CSF tracer influx was evaluated in sagittal (A, C) and coronal (B, D) slices counterstained with the nuclear stain DAPI. Assessment of CSF tracer influx across the whole brain revealed differences in CSF influx between regions within the young brain, in addition to distinct susceptibilities to age-related glymphatic pathway failure between regions in the aged brain. (E-J) Both the anterior (E) and posterior (H) brain were divided into gross regions of interest and OA-647 influx was evaluated on a regional basis. In general, glymphatic pathway function was most dramatically impaired in the aged (18 months) cortex compared to the young (2-3 months) cortex, with greater attenuation observed in the posterior cortex (I) compared to the anterior cortex (F) (*$P<0.05$, $P<0.01$, *$P<0.001$ vs. 2-3 months, ANOVA; n=4 per group). In comparison, glymphatic CSF influx into subcortical regions was comparatively small compared to that observed in the cortex, while age-related impairment within these subcortical regions was similarly muted (G, J).

Figure 36A:
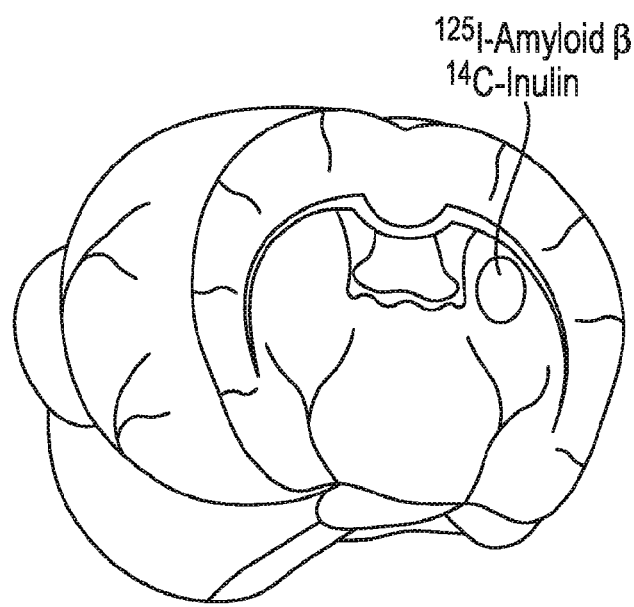
Figure 36B:
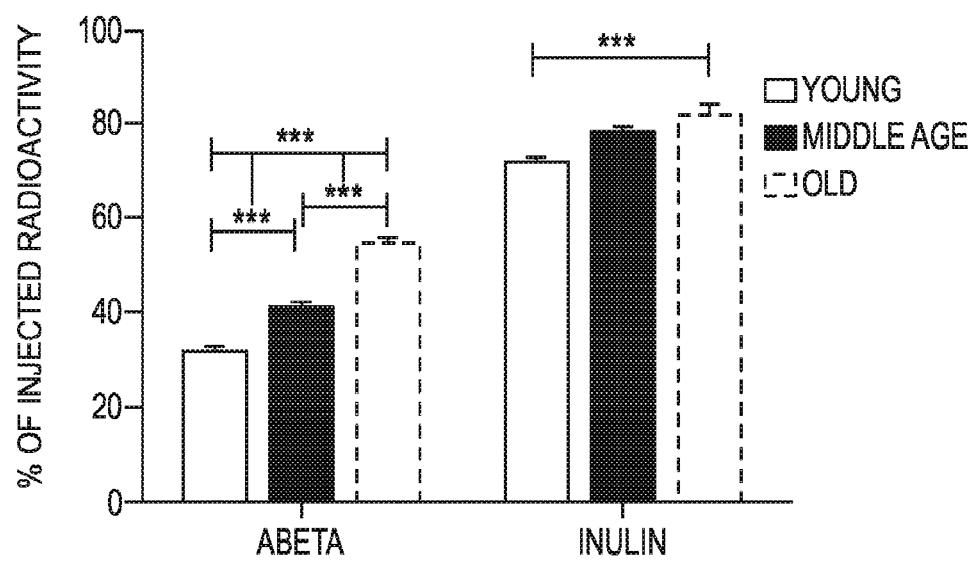

FIGS. 36A-B. Impairment of interstitial amyloid β clearance in the aged brain. The clearance of interstitial solutes from the aging brain was evaluated by a radio-tracer clearance assay. (A) Trace amounts of radio-labeled $^{125}$I-Amyloid $β_{1-40}$ and $^{14}$C-Inulin were co-injected into the caudate nucleus of young (2-3 months), middle aged (10-12 months) and old (18 months) anesthetized mice. 1 hr later, the animals were sacrificed, the brains harvested, and the residual radioactivity within the brain tissue was quantified by gamma particle counting and liquid scintillation counting. (B) In the old brain, the clearance of both $^{125}$I-Amyloid $β_{1-40}$ and $^{14}$C-Inulin were significantly slowed compared to the clearance in the young brain (***$P<0.001$ vs. young, ANOVA; n=8 per group). The clearance of $^{125}$I-Amyloid $β_{1-40}$ and $^{14}$C-Inulin from the middle aged brain was intermediate between that of the young and the old brain.

FIGS. 37A-E. Reduction of cerebral arterial pulsation in the aging brain. Cerebral vascular pulsatility was evaluated in anesthetized mice by in vivo 2-photon microscopy. (A-B) The cerebral vasculature was visualized by intra-arterial injection of fluorescent Texas Red-conjugated dextran (70 kD). Cerebral surface arteries and veins (A), and penetrating arteries and ascending veins (B) were identified morphologically. Insets in (B) show orthogonal XZ and YZ projections of the XYZ volume imaged for the experiment. (C-D) Cerebral surface arteries and veins, penetrating arteries and ascending veins were identified and imaged by high-frequency linescanning. The resulting X-t (time) plot were thresholded to improve contrast, allowing changes in vessel diameter resulting from each cardiac cycle to be measured. Changes in vascular diameter were integrated about the average vessel diameter over a 3 s interval to define a parameter termed vascular Pulsatility'. (E) Pulsatility measured in penetrating arteries was reduced in the aged (18 months) compared to the young (2-3 months) brain (n=2-4 per group). No obvious differences were observed in other elements of the cerebrovascular tree.

FIGS. 38A-D. Aging does not alter cortical extracellular volume fraction but does alter tortuosity. Diffusion parameters (extracellular volume fraction, alpha; tortuosity, lambda) were evaluated by in vivo tetramethyl ammonia electrophysiology in the waking and anesthetized cortex in vivo (see also Xie et al. Science 2013). (A-B) No differences in extracellular volume fraction were observed between old (18 months) and young (2-3 month) brains (A); while the marked enlargement of the extracellular space in the sleeping versus the waking brain were preserved unaltered in the aged brain (B) (*$P<0.001$, awake vs. asleep, 2-way ANOVA, n=9-20 per group). (C-D) While no overall differences in either waking or sleeping tortuosity in the old versus the young cortex were noted (C), a change in the sleep-wake relationship in tortuosity values was observed in the aging brain (D). In the young brain, tortuosity values did not differ between the waking and the sleeping state. In contrast, in the aged brain, the onset of sleep was accompanied by a significant increase in extracellular tortuosity (*$P<0.001$ awake vs. asleep, 2-way ANOVA, n=9-20 per group).

FIGS. 39A-F. Altered perivascular AQP4 expression in the aged brain. Changes in cortical AQP4 and GFAP expression were evaluated by immunofluorescence double labeling followed by laser scanning confocal microscopy. (A-B) Representative images show that in the young brain (2-3 months), AQP4 expression is restricted almost exclusively to perivascular astrocytic endfeet (arrows). In the aging cortex (18 months), AQP4 localization shifts to include fine astrocytic processes (arrowheads) that are not strictly perivascular. (C) Quantification of AQP4 expression in endfoot domains shows that in the aged brain, a slight reduction in perivascular AQP4 expression is observed surrounding large cerebral vessels, but not surrounding cerebral capillaries (*$P<0.05$, 18 months vs. 2-3 months, t-test; n=4 per group). (D) In contrast, the localization of AQP4 shifts dramatically in the aged brain. In the young brain, AQP4 polarization is very pronounced, with low levels of AQP4 expression save only in perivascular endfeet. In the aged brain, global AQP4 expression increases slightly, while regions immediately surrounding large cerebral vessels exhibit strongly increased AQP4. Thus, in the aged brain, AQP4 surrounding large cerebral vessels loses its strict perivascular polarization, while microvascular polarization remains largely intact. (E) Such specificity is not observed for the marker of reactive astrogliosis, GFAP. In the aged brain, perivascular GFAP expression was significantly elevated both surrounding large cerebral vessels and cerebral microvessels (***$P<0.001$, 18 months vs. 2-3 months, t-test; n=4 per group). (F) Similarly, when GFAP expression is evaluated spatially, increased GFAP expression is observed globally throughout the cortex, and differences in GFAP expression are not observed between large vessels and microvessels.

Figure 40A:
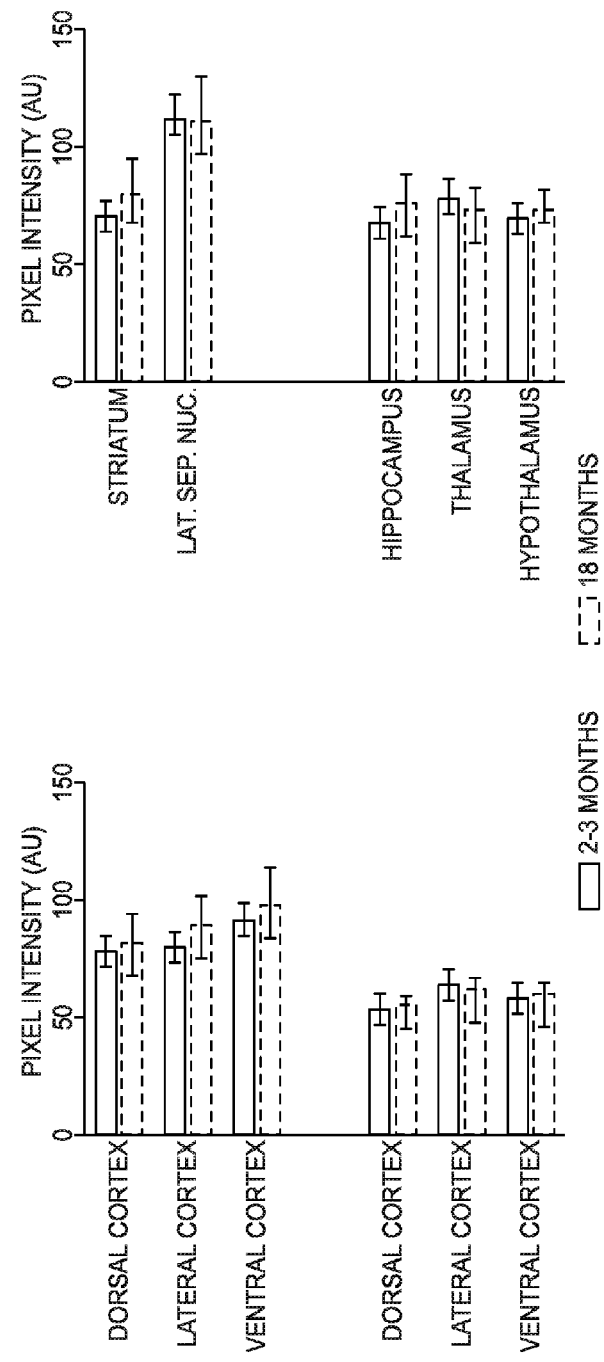
Figure 40B:
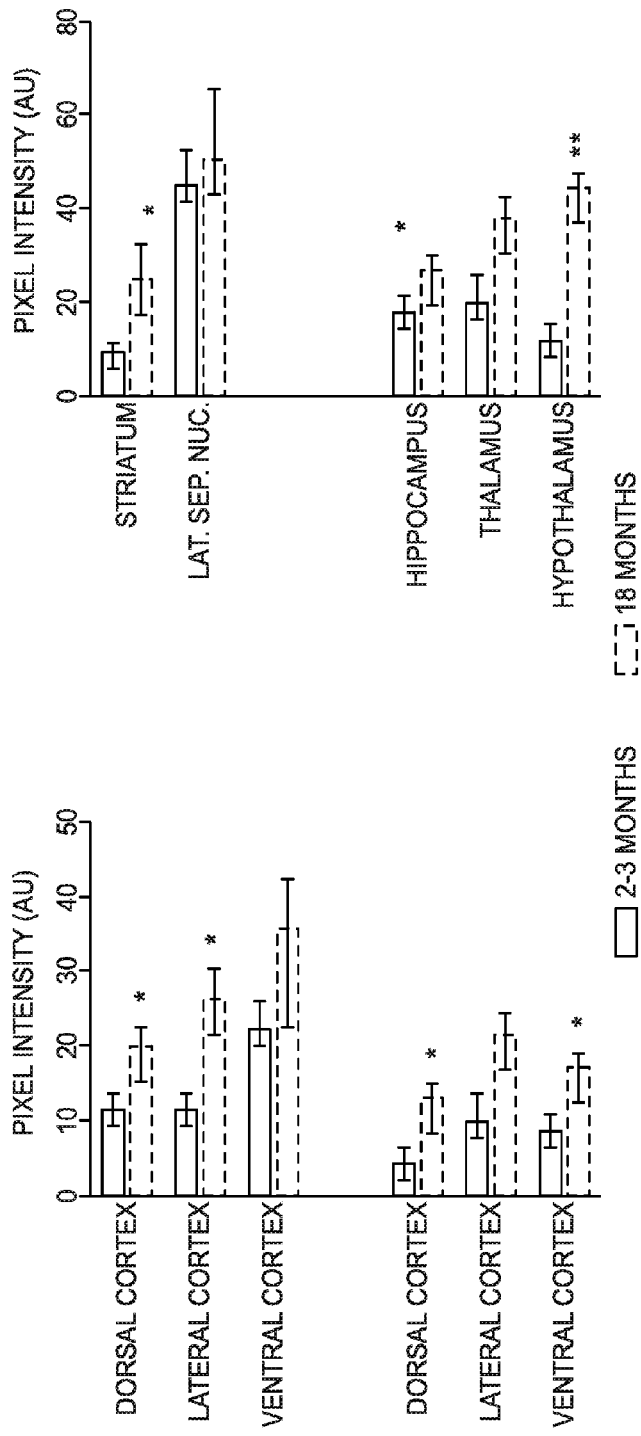
Figure 40C:
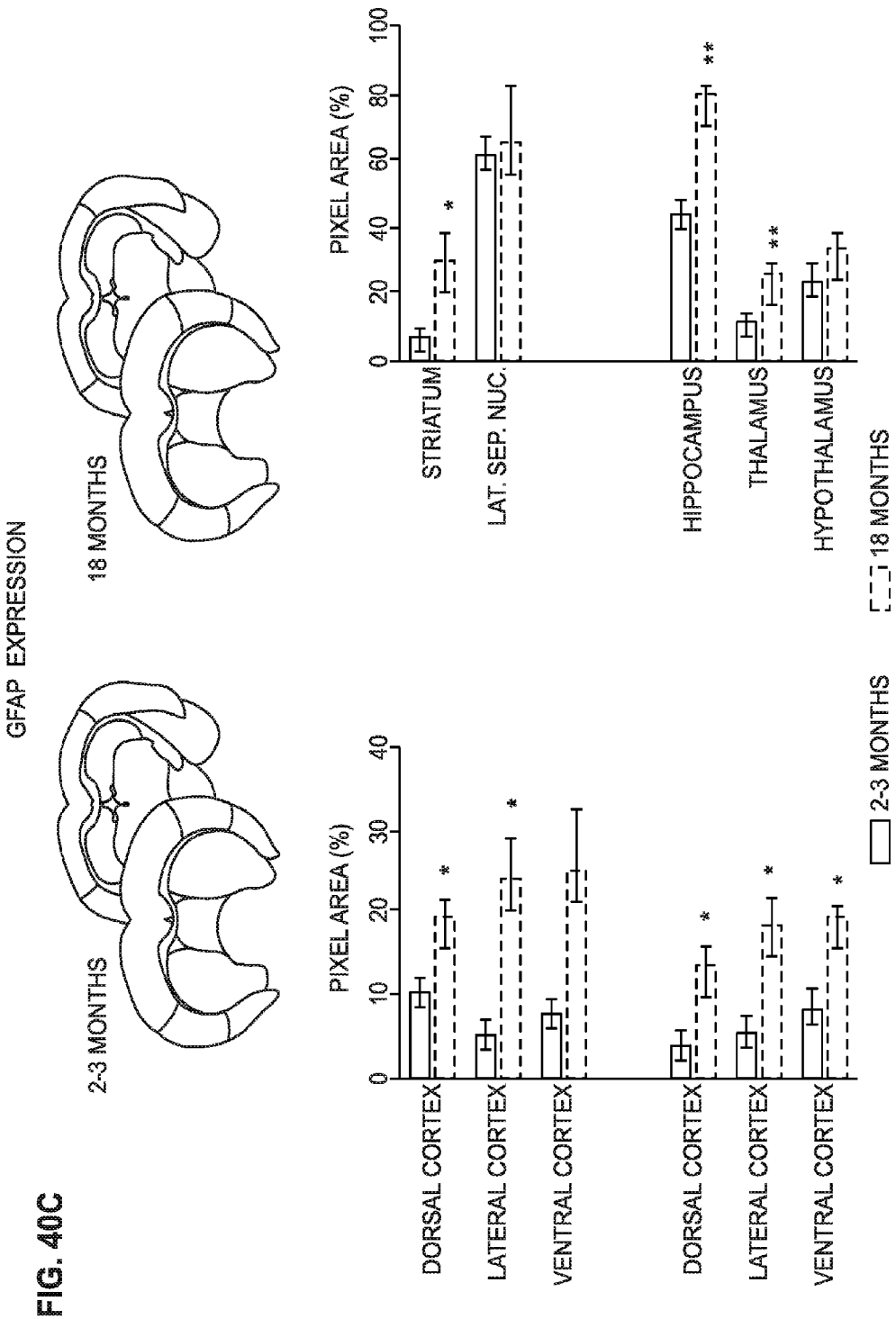
Figure 41A:
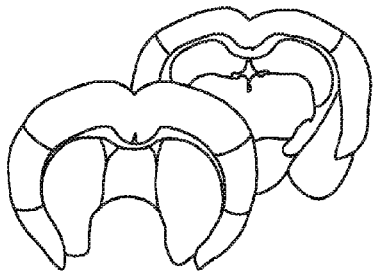
Figure 41B:
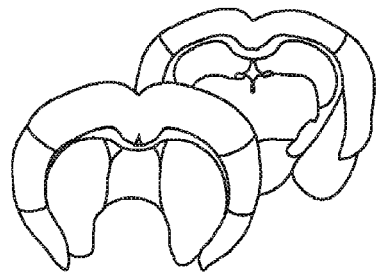
Figure 41C:
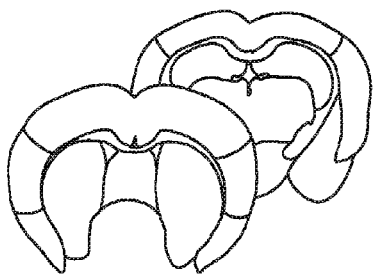
Figure 41D:
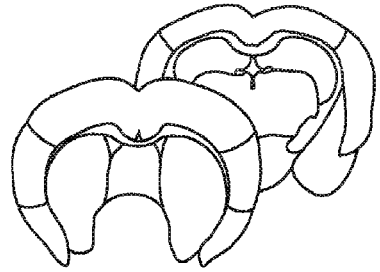
Figure 42A:
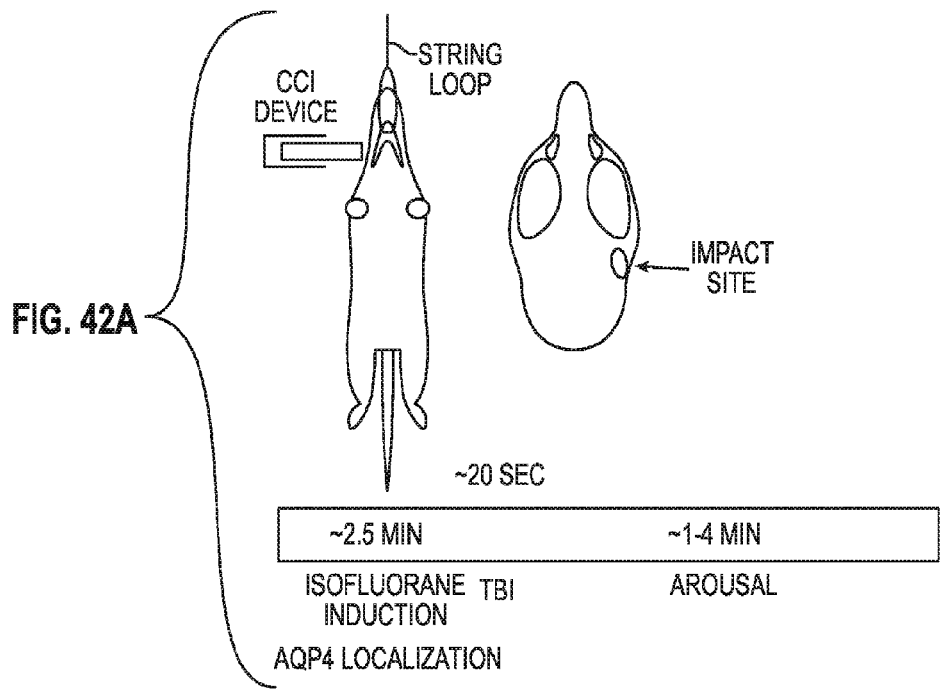
Figure 42B:
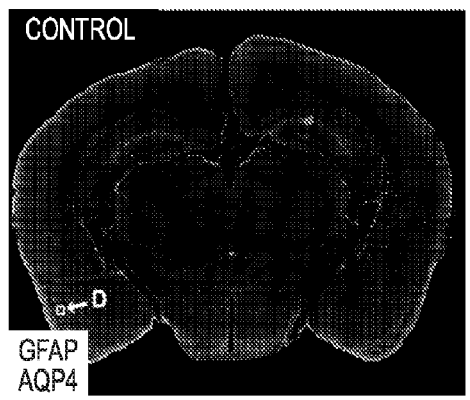
Figure 42C:
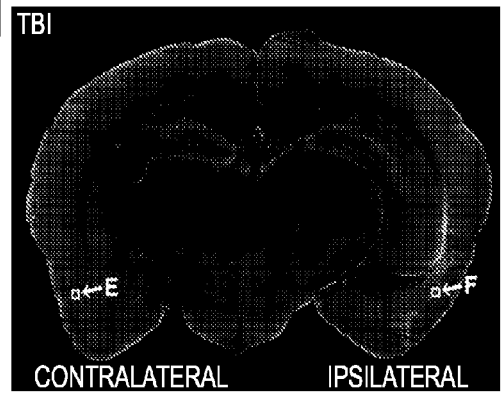
Figure 42D:
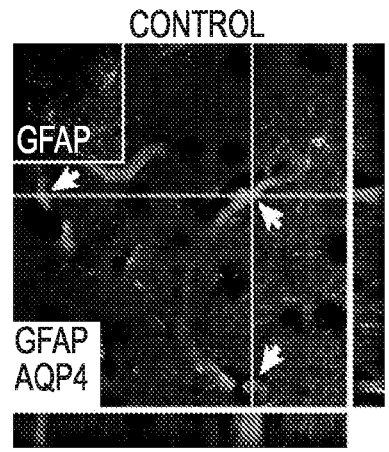
Figure 42E:
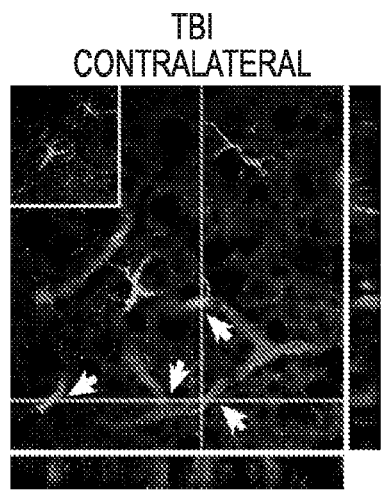
Figure 42F:
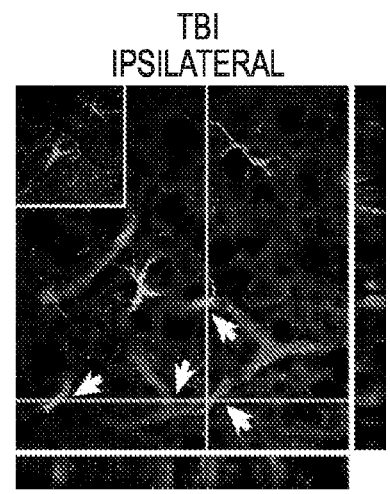

FIGS. 40A-C. Regional differences in AQP4 expression and polarization. Changes in AQP4 expression (A), AQP4 polarization (B) and GFAP expression (C) were evaluated throughout defined regions of interest within the anterior and posterior brain slices by immunofluorescence double labeling, laser scanning confocal microscopy, and an image analysis approach defined previously (Wang et al. *J Neurosci* 2012; Ren et al. *J Cereb Blood Flow Metab* 2013). (A) Color intensity maps depict regional mean AQP4 immunofluorescence intensity for the 2-3 month and 18 month brain. When AQP4 expression is quantified in each region, no signifcant changes in AQP4 expression are noted between the young and old brain. (B) AQP4 "depolarization" is defined as the tissue area with AQP4 immunofluorescence that is equal to or greater than perivascular AQP4 immunoreactivity (more detailed description provided in Ren et al. *J Cereb Blood Flow Metab* 2013). Thus higher values reflect loss of perivascular AQP4 polarization, or AQP4 "depolarization". As shown in color intensity maps, marked loss of AQP4 polarization occured in the aged brain. Significant loss of polarization wsa evident throughout the cortex and subcortical structures (*$P<0.05$, **$P<0.01$ vs. 2-3 month; 2-way ANOVA; n=4 per group). (C) GFAP expression was evaluated based upon the area covereage of GFAP-positive astrocytic processes. Color intensity maps show an increase in GFAP coverage in the aged brain. These changes were most pronounced in the cortex, but were also observed in subcortical structures (*$P<0.05$, **$P<0.01$ vs. 2-3 month; 2-way ANOVA; n=4 per group).

FIGS. 41A-J. AQP4 polarization is a key determinant of cortical glymphatic pathway function. The interrelationship between reactive astrogliosis (GFAP expression), AQP4 expression, AQP4 polarization and glymphatic pathway function (influx of intracisternally injected CSF tracer) were evaluated thoughout different anterior and posterior brain regions. Animals were injected intracisternally with ovalbumin-conjugated ALEXA-647 (OA-647, MW 45 kD). 30 min later, animals were fixed, and brains sliced. Anterior and posterior brain slices were labeled by immunofluoresence double-labeling for AQP4 and GFAP. OA-647 influx (A), AQP4 expression (B), AQP4 depolarization (C) and GFAP expression (D) were evaluated in different regions of interest throughout the anterior and posterior brain. (A-D) Color intensity maps depict the relative increase (red values) versus decrease (blue values) in glymphatic OA-647 influx, AQP4 expression, AQP4 depolarization, and GFAP expression between 2-3 months of age and 18 months of age. This is a graphical representation of data presented in columnar form in FIGS. 40A-C above. (E-I) The relationship between AQP4 expression, AQP4 depolarization, and GFAP expression were evaluated within each region were evaluated pooling 2-3 month and 18 month values, then subjecting paired OA-647/AQP4 expression, OA-647/AQP4 depolarization, and OA-647/GFAP expression values to linear regression analysis. The strongest associations are depicted in each figure with trendlines, and the corresponding $r^2$ and P values (for non-zero slopes) are provided. (E) In the cortex, changes in AQP4 polarization were most strongly associated with glymphatic pathway function, with loss of AQP4 polarization corresponding strongly to impaired glymphatic CSF tracer influx. (F) Within the hippocampus, no strong associations between glymphatic pathway function, AQP4 expression, AQP4 polarization or GFAP expression were evident. (G-J) Within the striatum, lateral septal nuclei, thalamus and hypothalamus, AQP4 expression (not polarization) was most strongly associated with glymphatic pathway function. Interestingly, this was a positive correlation, with increasing AQP4 expression associated with increased glymphic CSF influx within these regions. These data demonstrate that perivascular AQP4 polarization is key determinant of paravascular CSF influx in the cerebral cortex, while in subcortical tissues global AQP4 expression may be a more important determinant of glymphatic pathway function.

FIGS. 42A-F. Traumatic brain injury (TBI) causes loss of polarized localization of AQP4 perivascular astrocytic endfeet. (A) Schematic depicting mouse model of moderate TBI. Mouse is briefly anesthetized with isofluorane, suspended by its incisors from a string, and calibrated temporal impact is delivered by a pneumatic controlled cortical impactor device. The animal falls to an underlying pad and rapidly awakens from anesthesia. (B-F) 28 days after TBI, AQP4 localization and GFAP expression are evaluated by immunofluorescence double-labeling and laser scanning confocal microscopy. As shown in the whole-slice montage (B-C) a region of persistent reactive astrogliosis remains in the ipsilateral temporal cortex 28 days after TBI. Evaluating AQP4 localization under high objective power, no obvious change in AQP4 polarization is apparent when control cortex (D) is compared to the contralateral cortex after TBI (E) as AQP4 localization remains restricted primarily to perivascular astrocytic endfeet (arrows). In the ipsilateral cortex (F), GFAP-positive reactive astrocytes exhibit profound loss of AQP4 polarization, with AQP4 expression being evenly distributed between fine processes and those surrounding cerebral vessels (arrows). These findings demonstrate that TBI results in the chronic loss of perivascular AQP4 polarization.

FIGS. 43A-J. Glymphatic clearance of interstitial solutes is chronically impaired after TBI. (A) Paravascular CSF-ISF exchange was evaluated by intracisternal injection of CSF tracer (Ovalbumin-conjugated ALEXA-555) 1, 3, 7 and 28 days after TBI. (B-F) Ex vivo whole-slice fluorescence imaging shows paravascular CSF influx evaluated 30 min post-injection was dramatically reduced 7 days after TBI. Interestingly, reduced glymphatic influx was observed bilaterally despite the unilateral traumatic injury. Quantification of tracer influx into the cortex (G) show that the effect of TBI upon CSF influx peaks at 7 days post-injury, however a significant impairment of glymphatic function remains 28 days after injury ($*P<0.05$, $**P<0.01$ vs. control; $^{\#}P<0.05$ vs. contralateral structure; 2-way ANOVA, n=5-12 animals per group). Although impaired CSF influx is observed bilaterally in the cortex, the impairment is greatest in the ipsilateral cortex. (H) The effect of TBI upon interstitial solute clearance from the cortex was evaluated 7 days post-injury. The clearance of radio-labeled $^3$H-mannitol (MW 182 Da) (I) and $^{14}$C-inulin (MW-5 kDa) (J) was measured 60 min after infusion into contralateral frontal cortex. In wild type mice, TBI significantly slowed the clearance of both $^3$H-mannitol and $^{14}$C-inulin ($^{\#}P<0.05$, $^{\#\#\#\#}P<0.001$ vs sham; 2-way ANOVA, n=6 animals per group). Clearance studies conducted in Aqp4$^{-/-}$ mice demonstrated that impairment of solute clearance after TBI was exacerbated by Aqp4 gene deletion ($*P<0.05$, $***P<0.001$ vs. WT; 2-way ANOVA, n=6 animals per group). These data demonstrate that glymphatic pathway function, including interstitial solute clearance, is profoundly and chronically impaired after TBI.

FIGS. 44A-E. Interstitial tau cleared from the brain along paravascular pathways. (A) Recombinant human monomeric tau (hTau) was injected into the cortex of NG2-DsRed transgenic mice, which express DsRed fluorescent protein in cerebral vascular smooth muscle and pericytes. (B-E) Movement of interstitial hTau through the brain was evaluated 30 min post-injection by immunofluorescence followed by laser scanning confocal microscopy. hTau moved diffusely from the injection site (B), accumulating along the capillary basal lamina (C). Projections of fluorescence intensity depict hTau accumulations in these spaces relative to surrounding interstitial compartments. (D-E) 30 min post-injection, hTau moved rapidly through the brain interstitium to reach paravascular spaces surrounding the large-caliber internal cerebral veins in the roof of the 3$^{rd}$ ventricle. These data demonstrate that soluble interstitial tau is cleared from the brain along paravascular pathways of the brain-wide glymphatic system.

Figure 45A:
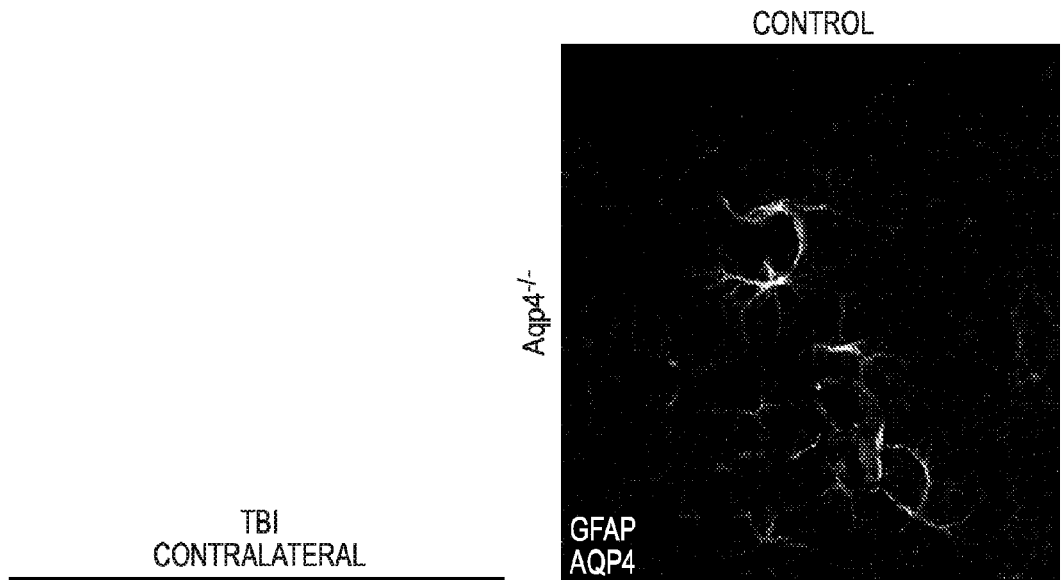
Figure 45B:
Figure 45C:
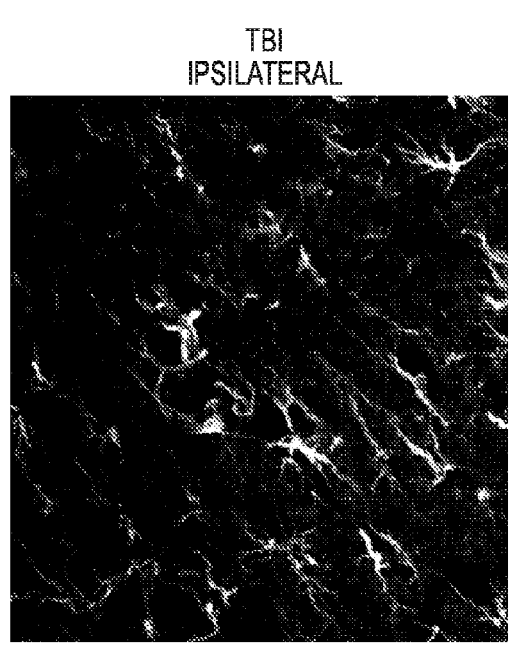

FIGS. 45A-C. AQP4 immunoreactivity is absent in Aqp4$^{-/-}$ mice. To ensure the specificity of the anti-AQP4 primary antibody utilized in the present study, we conducted immunolabeling of control and TBI-treated brains from Aqp4$^{-/-}$ mice perfused 7 days after injury. Although GFAP expression was readily detectable control (A), contralateral TBI (B) and ipsilateral TBI (C) cortex, no AQP4 immunoreactivity was detectable.

Figure 46A:
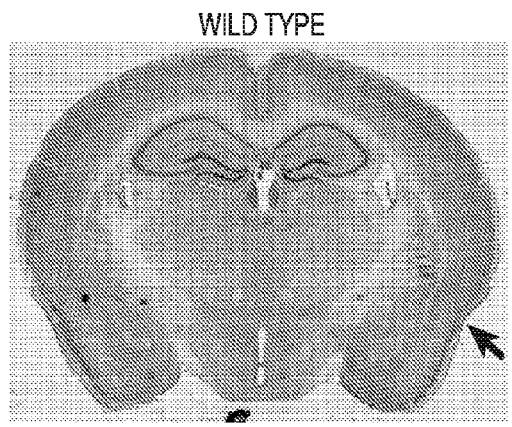
Figure 46B:
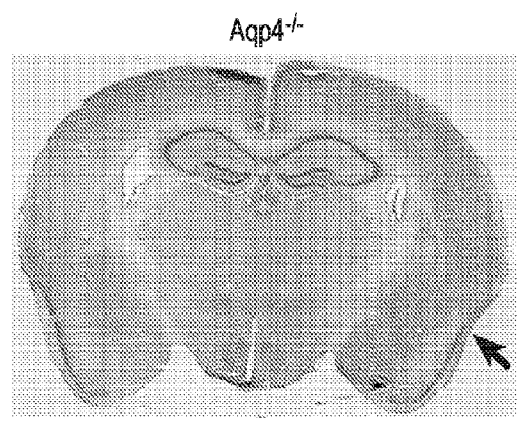
Figure 46C:
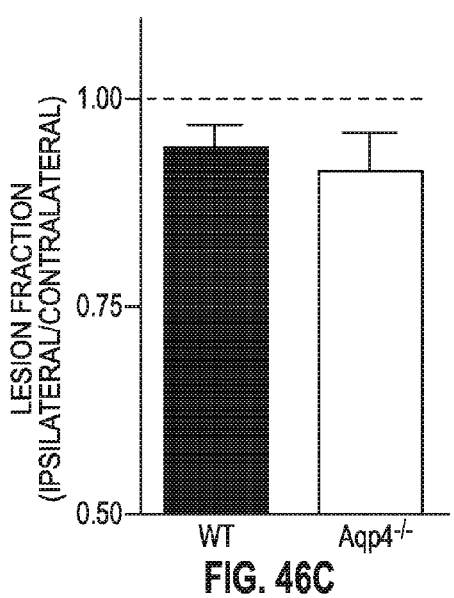
Figure 47A:
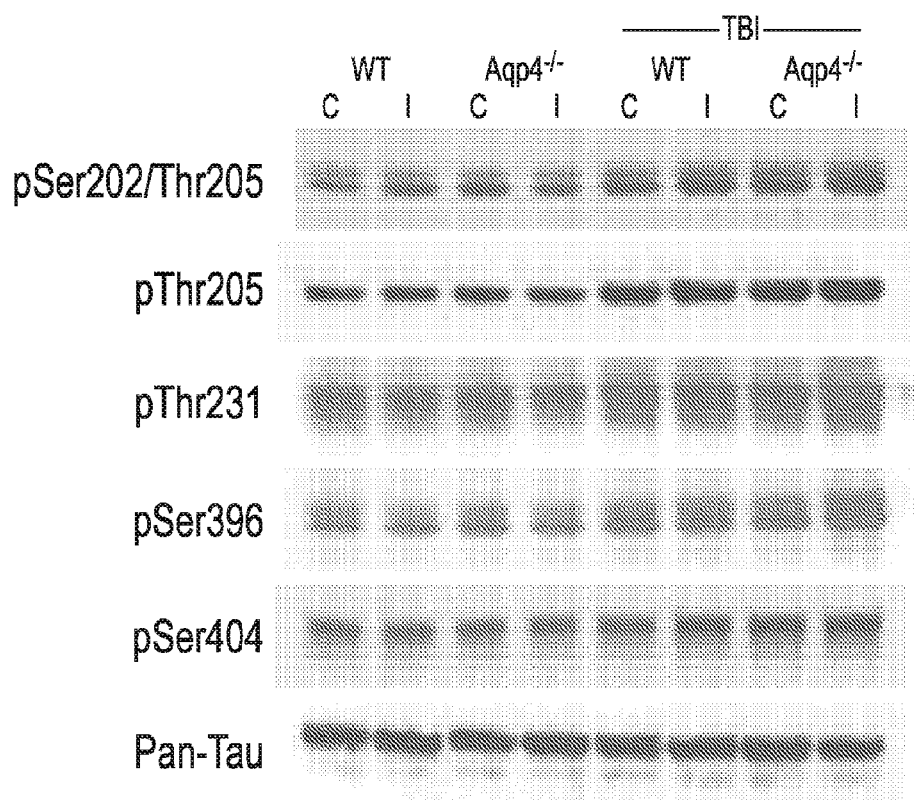
Figure 47B:
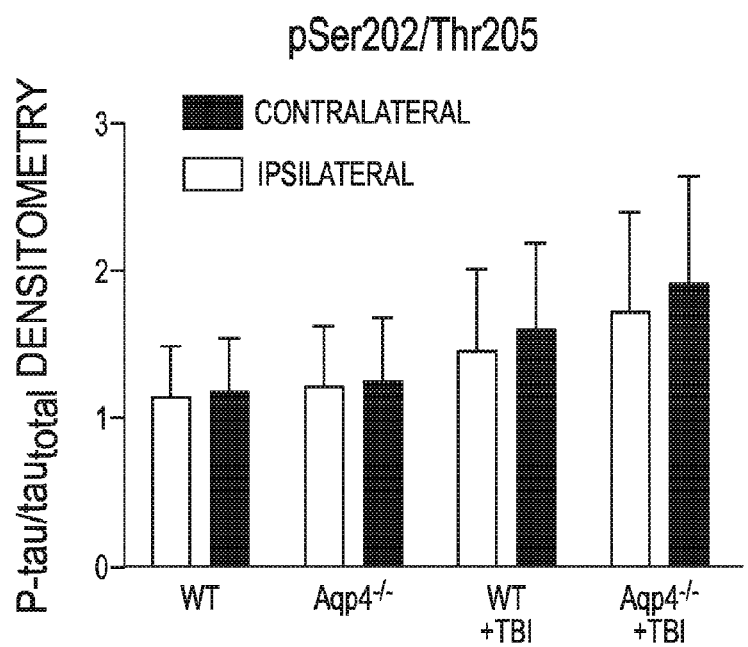
Figure 47C:
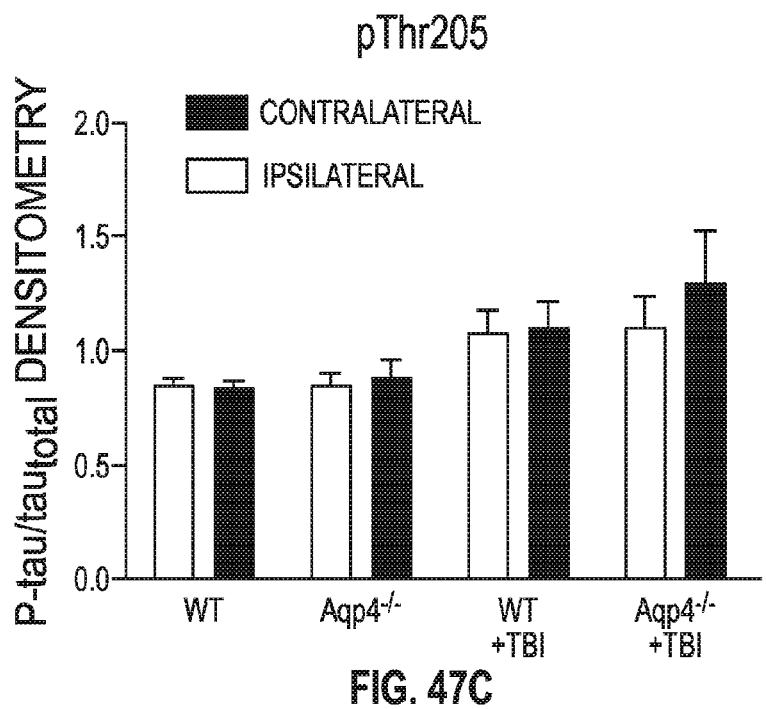
Figure 47D:
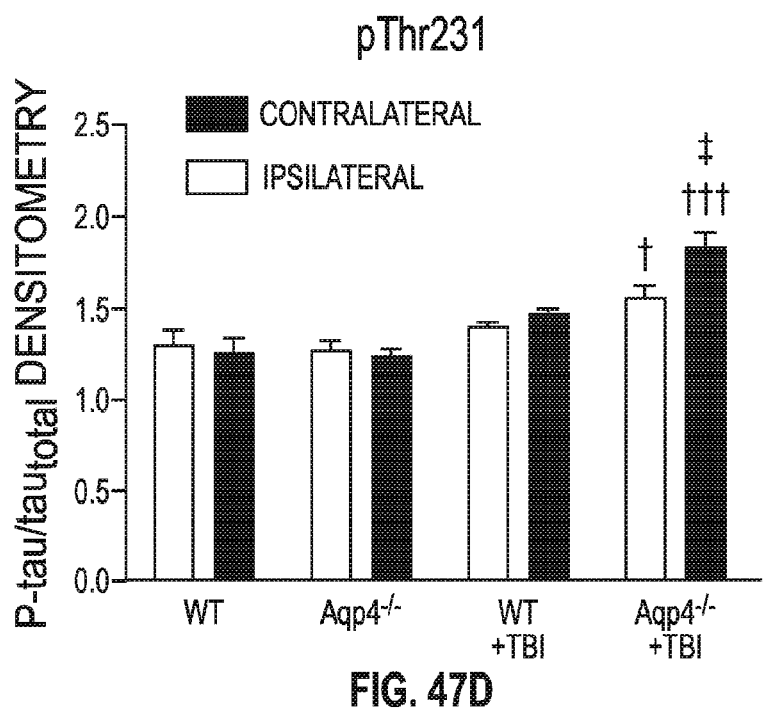
Figure 47E:
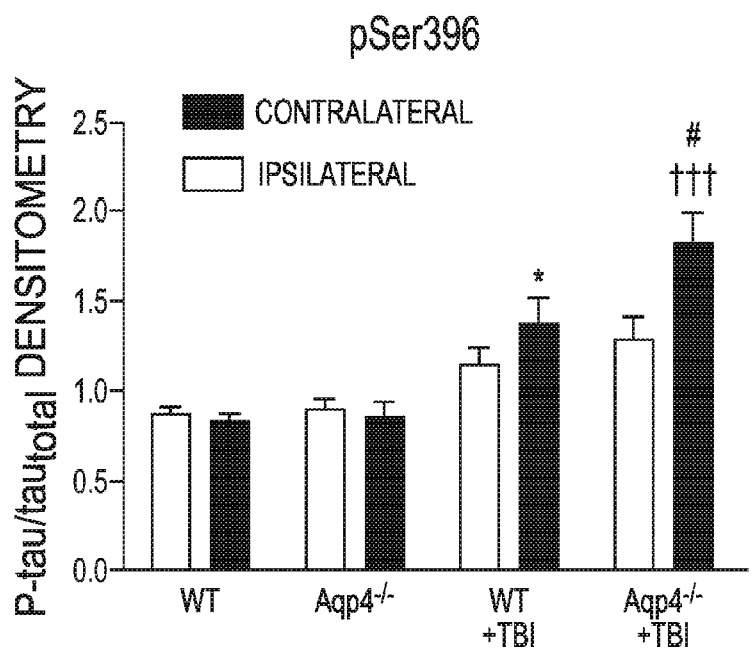
Figure 47F:
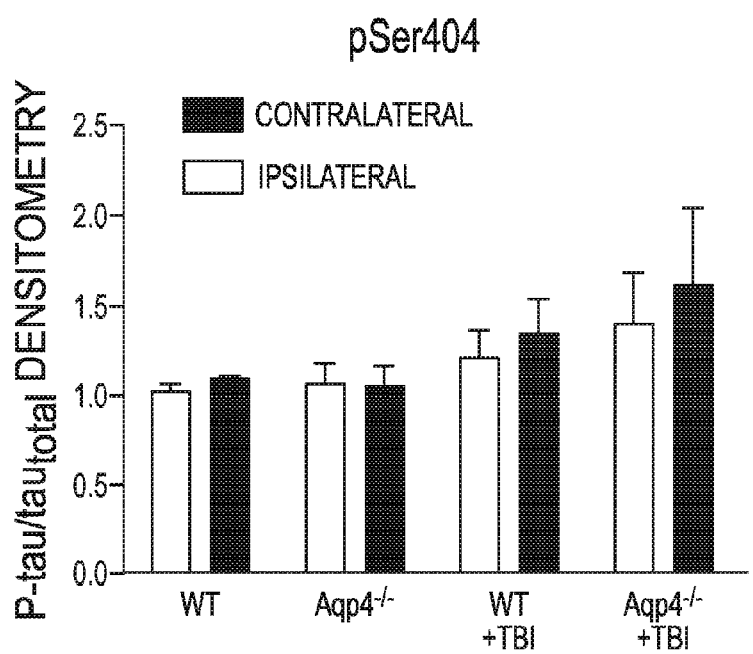
Figure 48A:
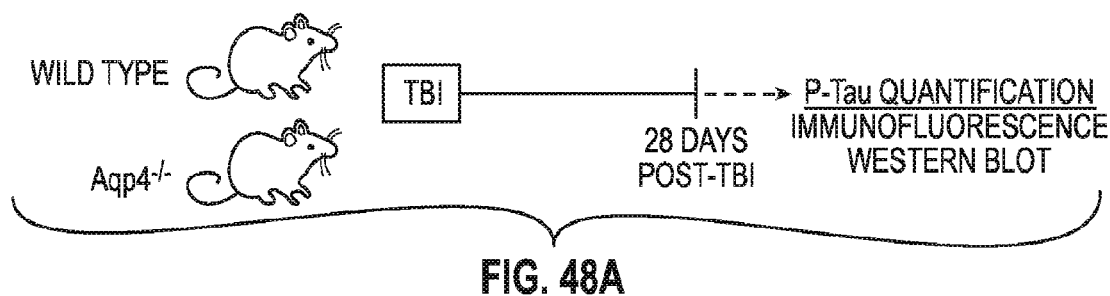
Figure 48B:
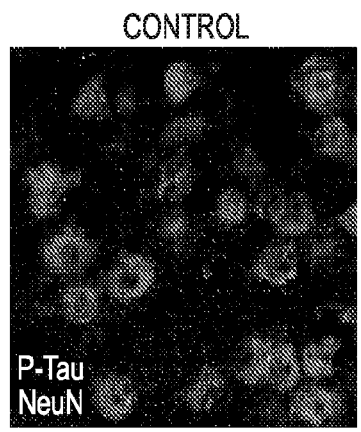
Figure 48C:
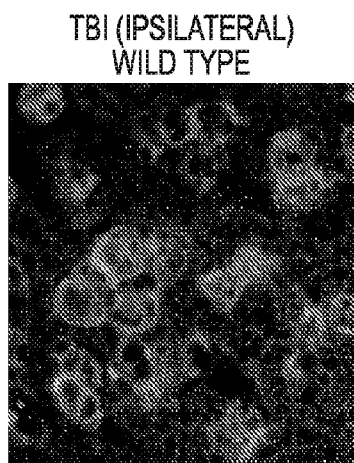
Figure 48D:
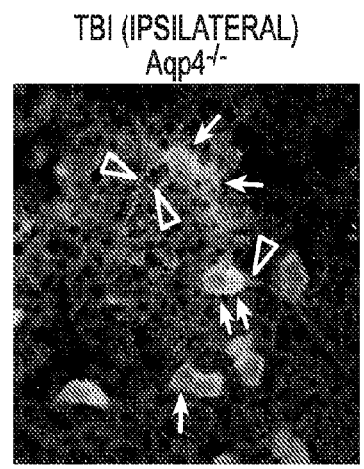
Figure 48E:
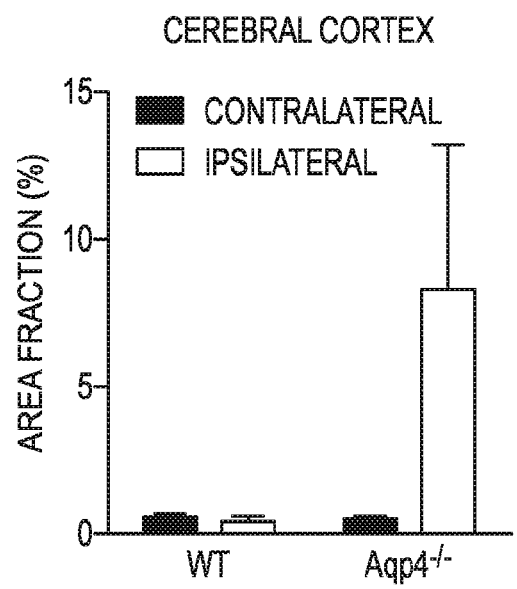
Figure 48F:
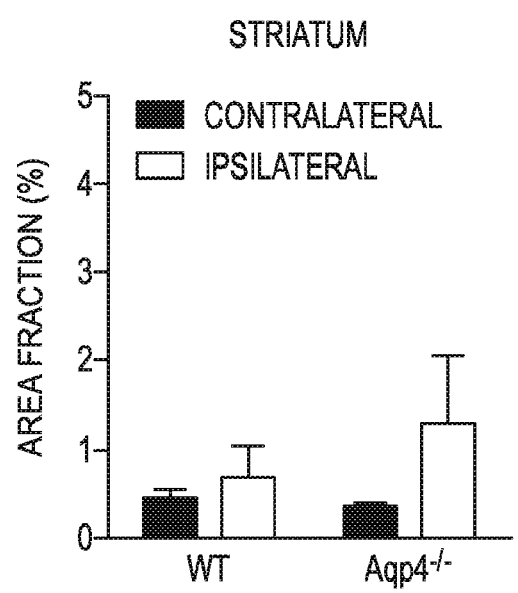
Figure 49A:
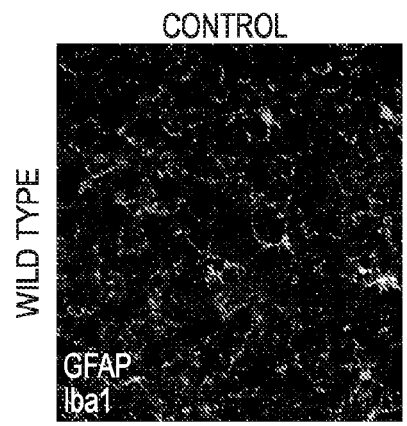
Figure 49B:
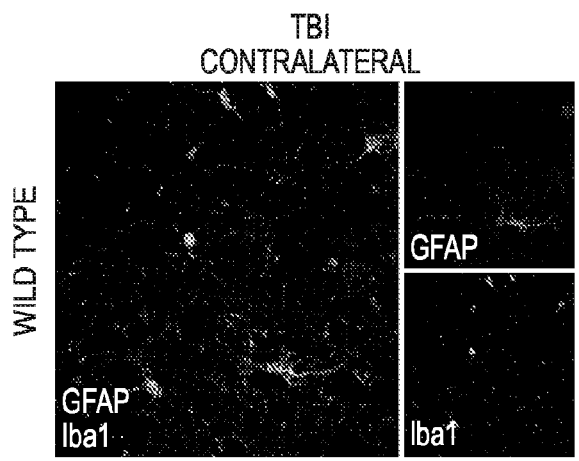
Figure 49C:
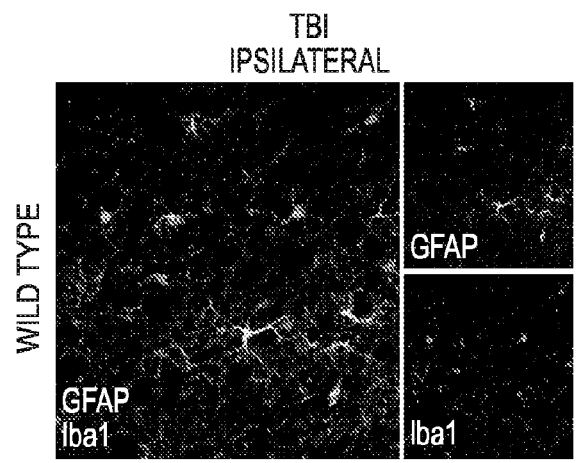
Figure 49D:
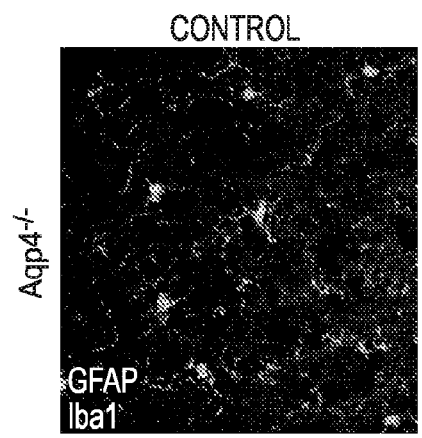
Figure 49E:
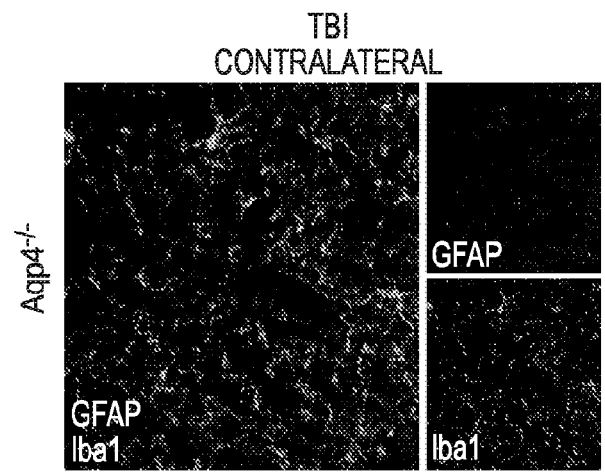
Figure 49F:
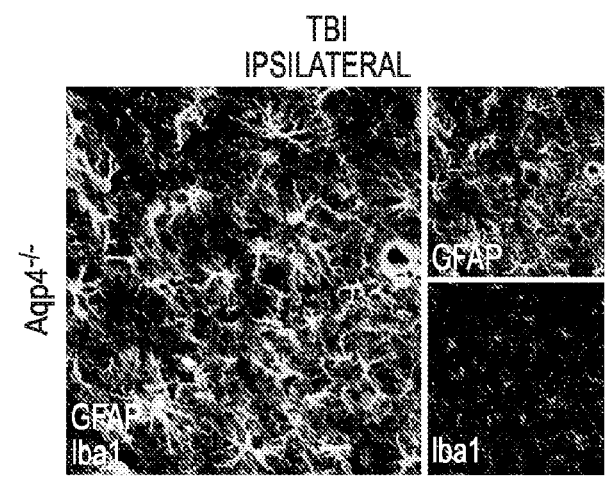
Figure 49G:
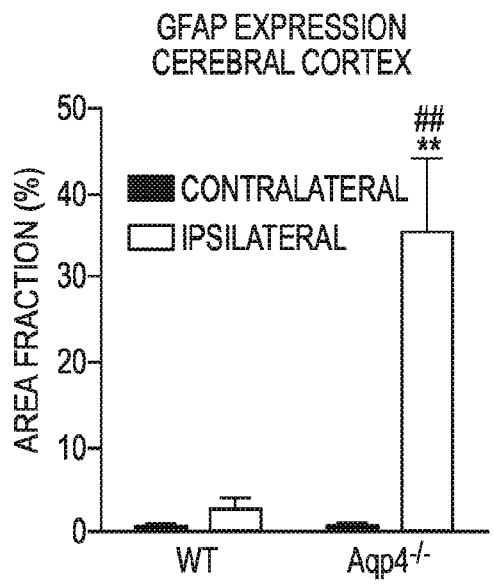
Figure 49H:
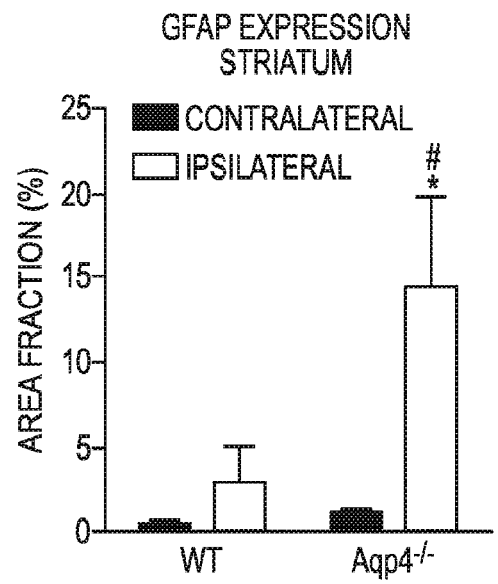
Figure 49I:
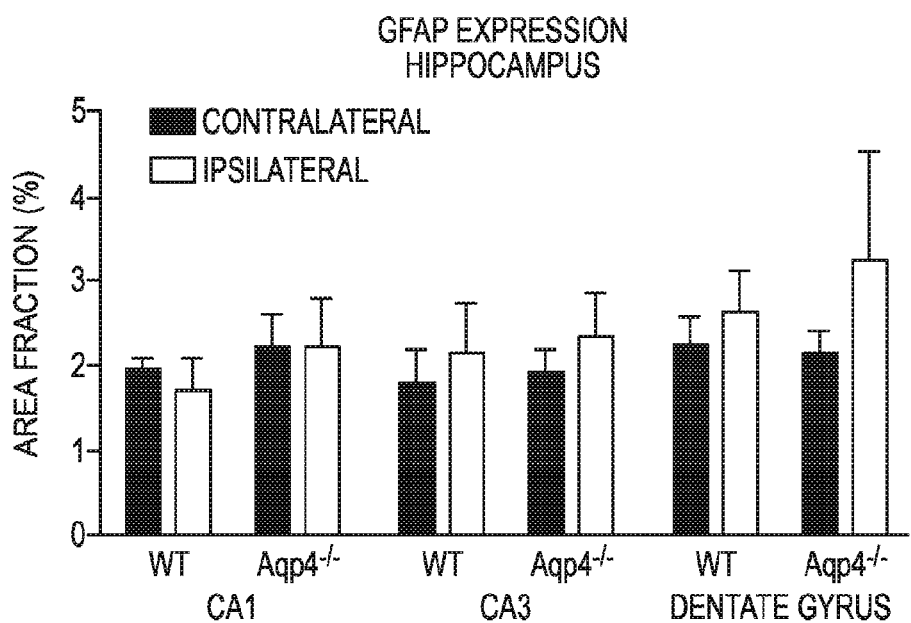
Figure 49J:
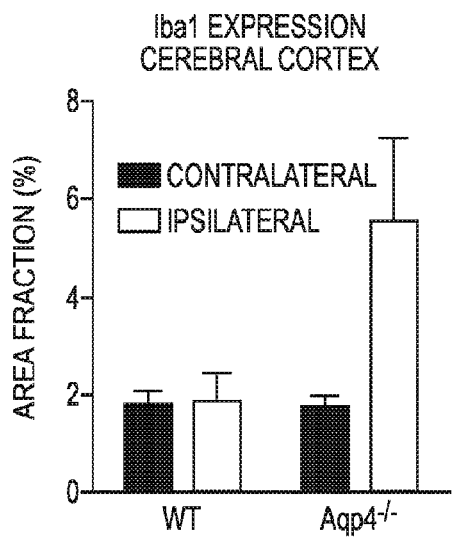
Figure 49K:
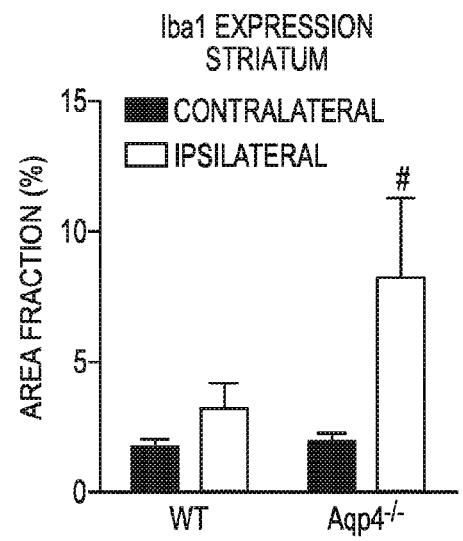
Figure 49L:
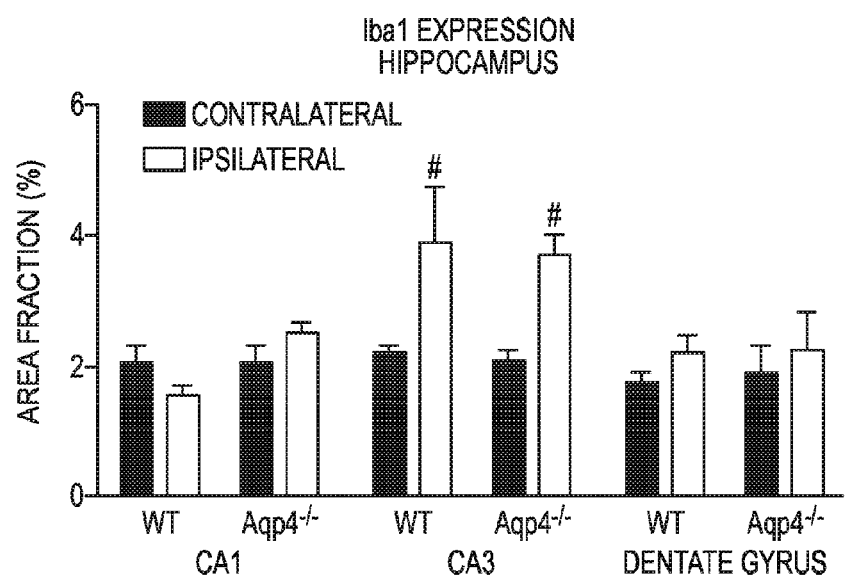
Figure 50A:
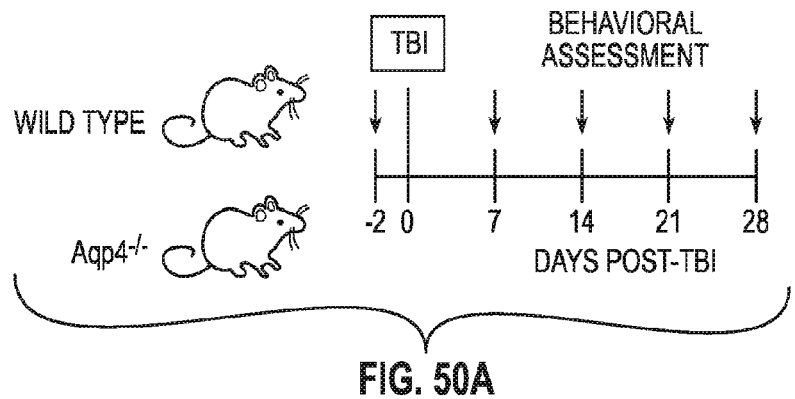
Figure 50B:
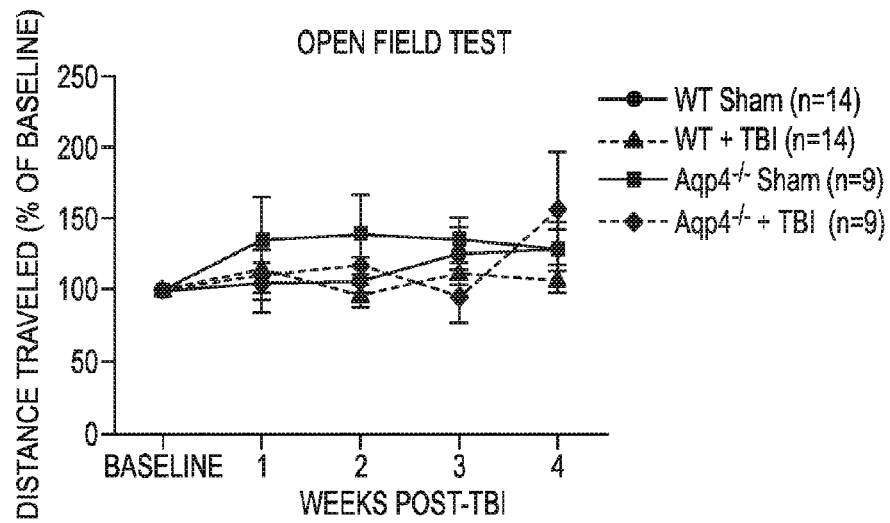
Figure 50C:
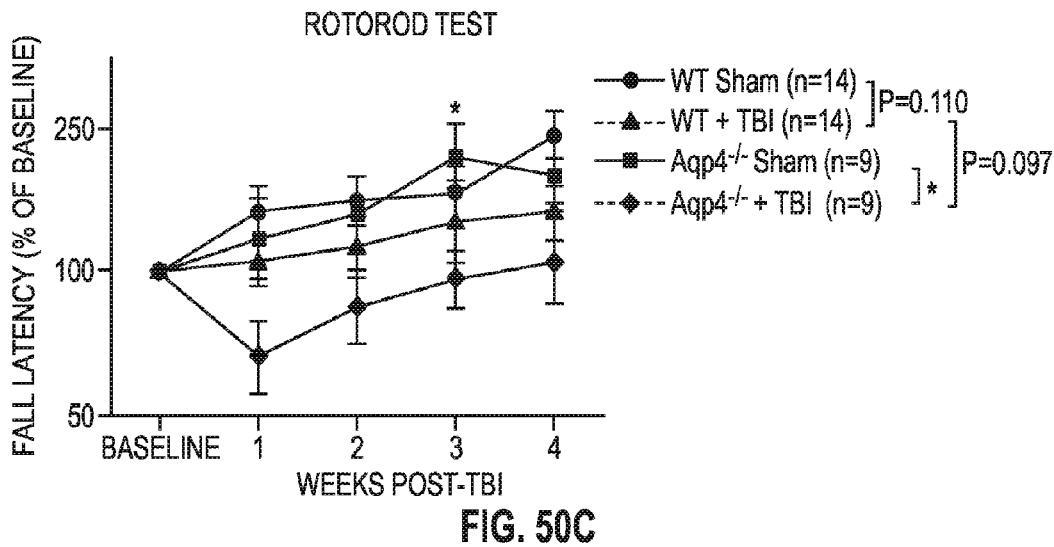
Figure 50D:
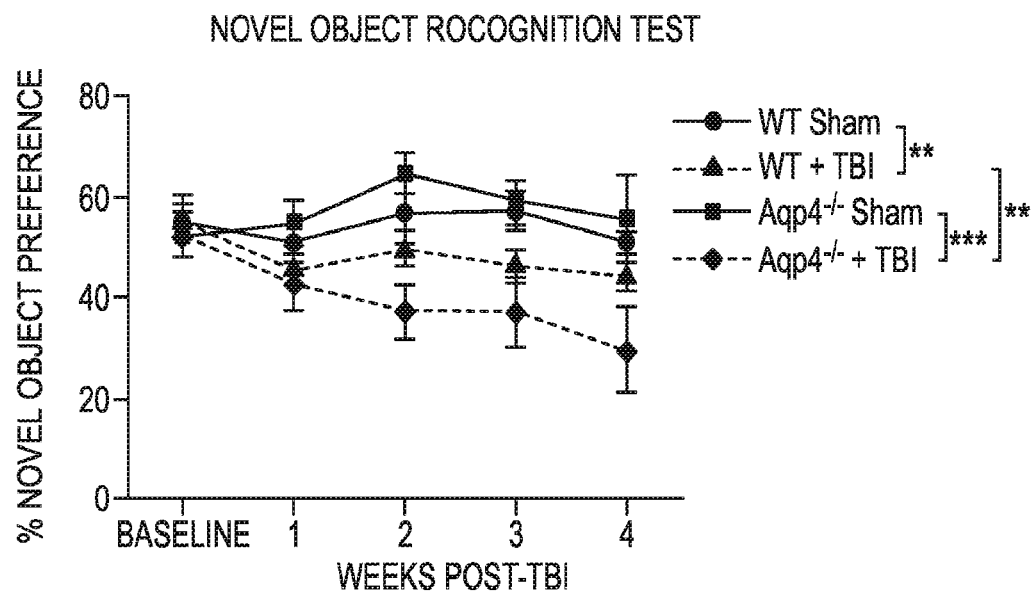
Figure 50E:
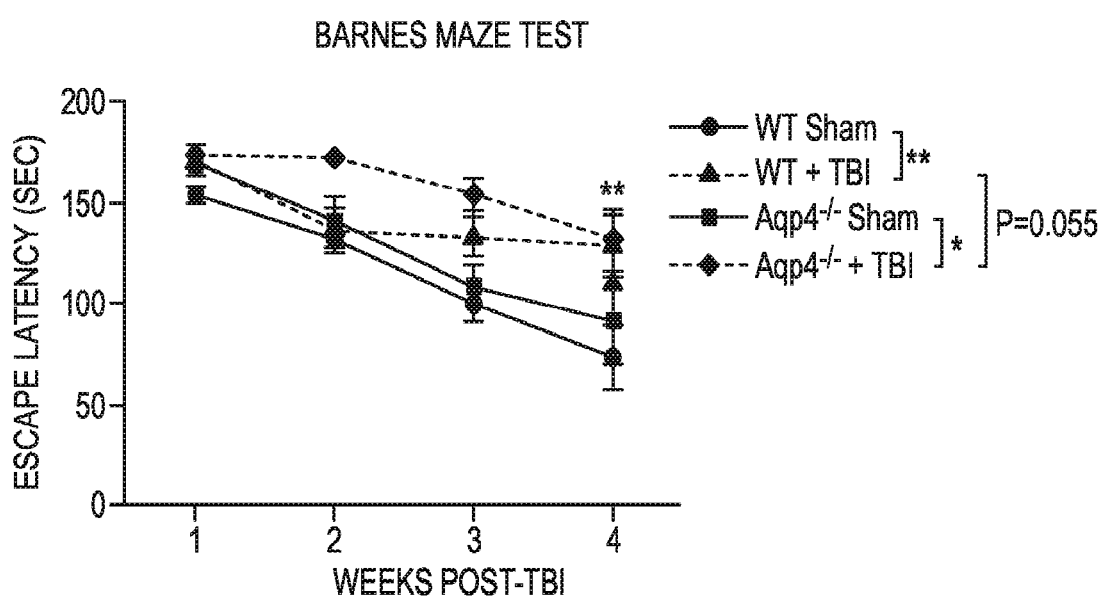
Figure 51A:
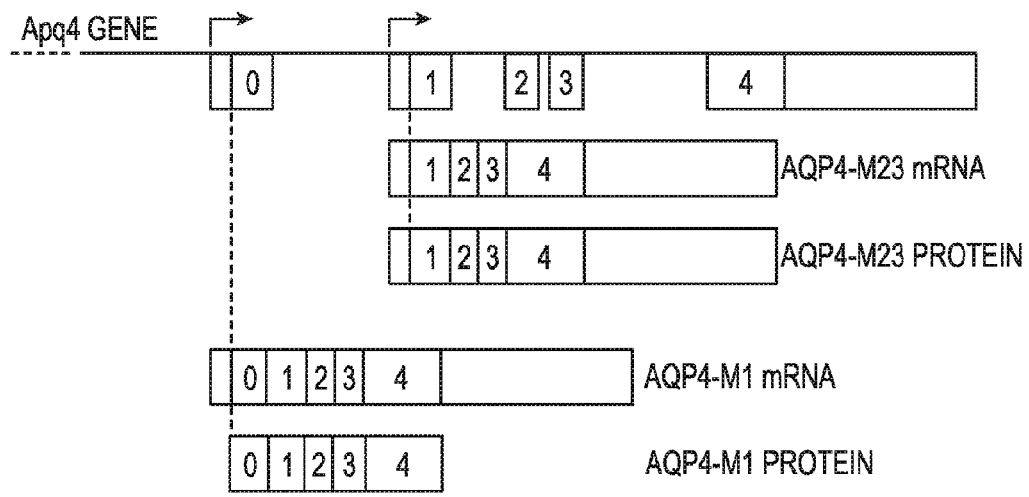
Figure 51B:
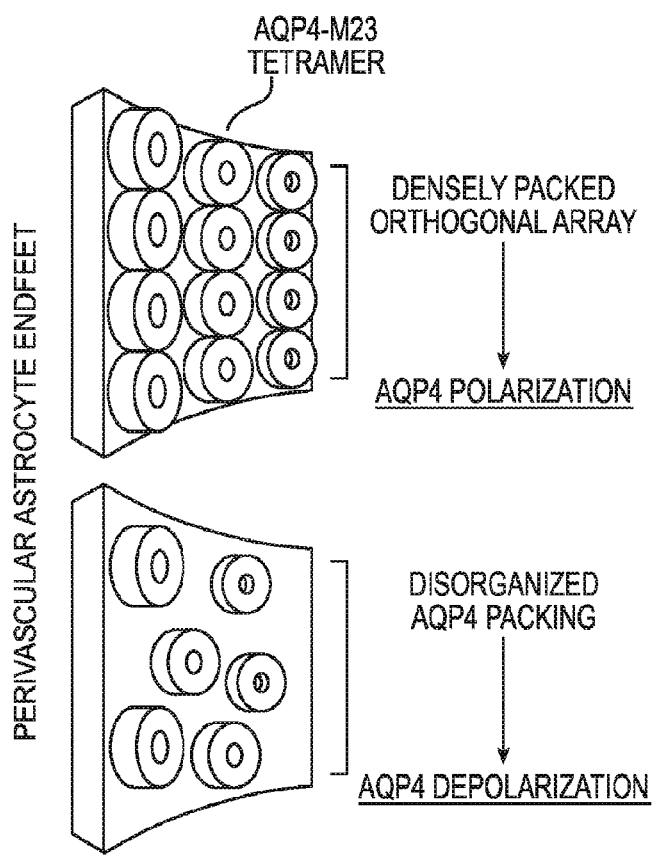
Figure 51C:
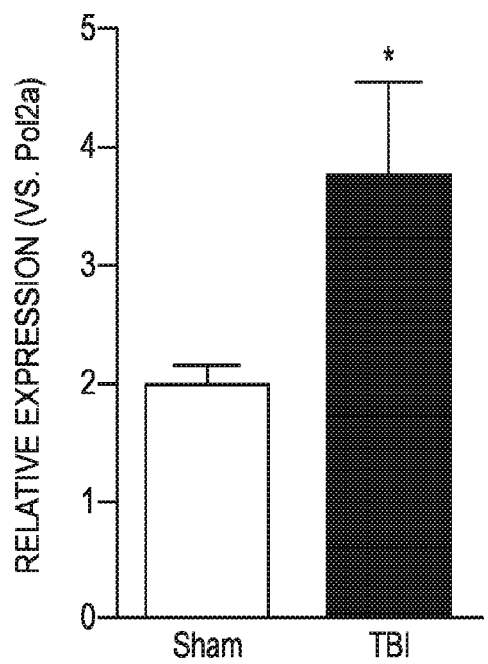
Figure 51D:
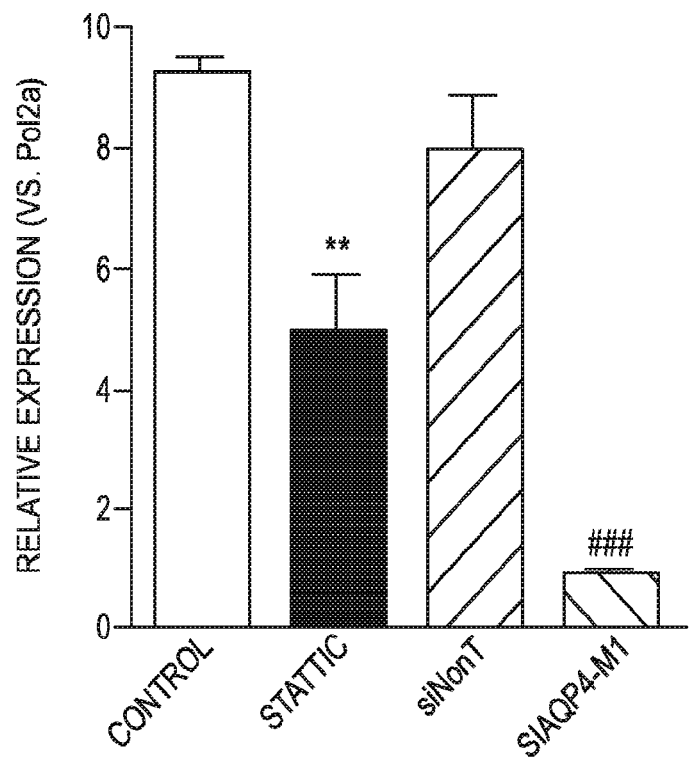
Figure 52A:
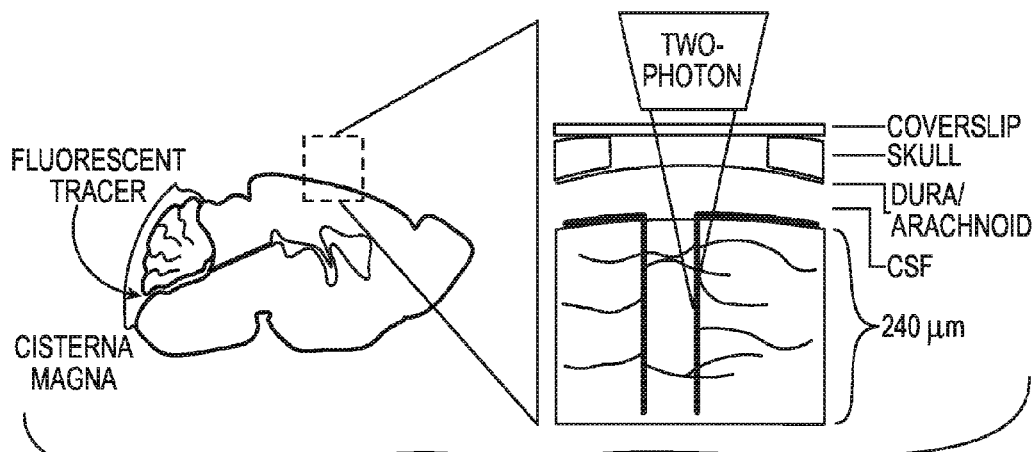
Figure 52B:
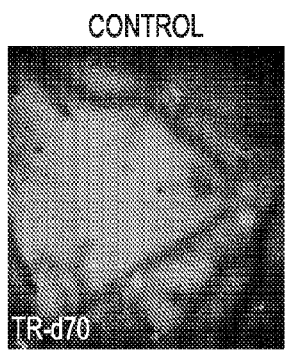
Figure 52C:
Figure 52D:
Figure 52E:
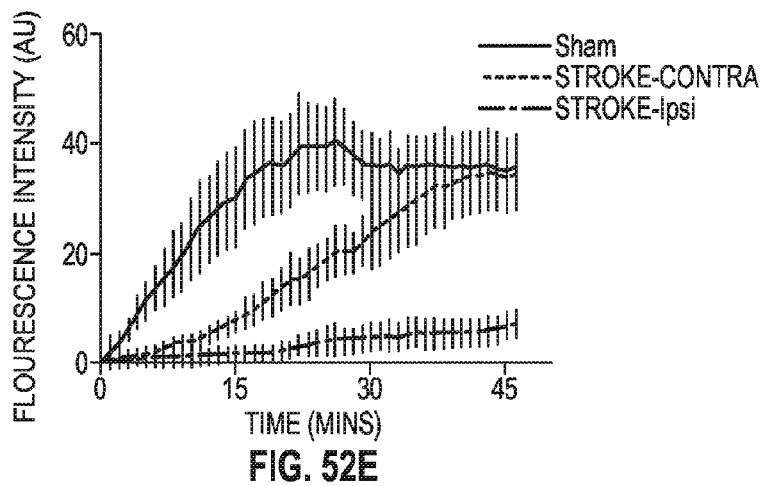

FIGS. 46A-C. Aqp4 gene deletion does not alter TBI lesion volume. The effect of Aqp4 gene deletion upon traumatic lesion volume was evaluated in brains harvested 28 days after TBI. (A-B) Brains were serially sliced and brain structure was evaluated by H & E staining. Red arrow indicates site of traumatic impact and area of greatest cortical damage. Ipsilateral and contralateral cortical areas were measured for each slice, then integrated through serial slices to derive a cortical volume. Cortical volume expressed as a ratio to the contralateral volume (C). No significant difference was observed in ipsilateral lesion volume between wild type and Aqp4$^{-/-}$ mice.

FIGS. 47A-F. Aqp4 gene deletion exacerbates development of tauopathy after TBI. The effect of impairing glymphatic pathway function by Aqp4 gene deletion upon the development of tauopathy after TBI was evaluated. (A) Wild type and Aqp4$^{-/-}$ brains were harvested 28 days post-injury and probed for the presence of phosphorylated tau (P-tau) epitopes. Representative blots are presented showing effect of mouse genotype (wild type vs. Aqp4$^{-/-}$), injury status (sham vs. TBI) and hemisphere (contralateral (C) vs. ipsilateral (I)) upon labeling by various P-tau monoclonal antibodies targeting different tau phosphorylation epitopes. Total tau was also measured (Pan-tau) and all P-tau levels were normalized to P-tau levels within each biological sample. (B-F) Across all epitopes, TBI tended to increase P-tau labeling, particularly on the ipsilateral side. Similarly, labeling tended to be stronger in Aqp4$^{-/-}$ mice after TBI compared to wild type mice after TBI. Specifically, antibodies recognizing the pThr231 and pSer396 P-tau epitopes registered significant increases in P-tau labeling in Aqp4$^{-/-}$ mice compared to wild type animals ($^{\dagger}P<0.05$, $^{\dagger\dagger\dagger}P<0.001$ vs. Aqp4$^{-/-}$ sham; $^{\ddagger}P<0.05$ vs. wild type TBI; $*P<0.05$ vs. wild type sham; $^{\#}P<0.05$ vs. contralateral structure; 1-way ANOVA; n=4 animals per group). These data demonstrate that when glymphatic pathway function is impaired beyond what is seen with TBI alone, chronic tau aggregation is promoted.

FIGS. 48A-F. Impairment of glymphatic pathway function promotes tau aggregation after TBI. (A) The effect of impairment of glymphatic pathway function by Aqp4 gene deletion upon the development of tauopathy after TBI was evaluated. Wild type and Aqp4$^{-/-}$ mice were subjected to TBI and the accumulation of phosphorylated tau (P-tau) was evaluated by immunofluorescence and Western blot (presented in FIGS. 47A-F) 28 days post-injury. (B-D) Double labeling with the AT8 P-tau antibody (specific for pSer202/pThr205 epitopes) and the neuronal marker NeuN showed that in the wild type cortex, P-tau immunoreactivity was not observed. In the Aqp4$^{-/-}$ cortex, marked P-tau labeling was observed, both within neuronal soma (arrows) and in surrounding neurites (arrowheads). (E-F) Quantification of P-tau staining revealed that 28 days after TBI, P-tau immunoreactivity was evident within the ipsilateral cortex, and to a lesser extent the underlying striatum, of Aqp4$^{-/-}$ mice. These data demonstrate that impairment of glymphatic pathway function after TBI promotes tau aggregation and the deposition of P-tau both within neurons and extra-neurally.

FIGS. 49A-L. Impaired glymphatic pathway function sustains neuroinflammation after TBI. The effect of Aqp4 gene deletion upon the persistence of neuroinflammation after TBI was evaluated. (A-F) Wild type and Aqp4$^{-/-}$ mice were subjected to TBI and reactive astrogliosis (GFAP expression) and microgliosis (Iba1 expression) was evaluated by immunofluorescence 28 days post-injury. Markedly elevated GFAP- and Iba1-immunoreactivity was observed solely in the ipsilateral cortex of Aqp4$^{-/-}$ mice after TBI. (G-H) Quantification of GFAP labeling demonstrated significantly increased reactive astrogliosis in the cortex and underlying striatum of Aqp4$^{-/-}$ but not wild type mice (*P<0.05, **P<0.01 vs. wild type; #P<0.05, ##P<0.01 vs. contralateral structure; 2-way ANOVA; n=4 animals per group). (I) No differences in GFAP immunoreactivity were observed in the hippocampus. (J-K) Quantification of Iba1 labeling showed that microglial activation persisted in the ipsilateral cortex and striatum of Aqp4$^{-/-}$ mice, but had resolved in wild type mice within 28 days post-injury (#P<0.05 vs. contralateral structure; 2-way ANOVA; n=4 animals per group). (L) Increased Iba1 labeling was observed in the CA3 region of the hippocampus in both wild type and Aqp4$^{-/-}$ mice (#P<0.05 vs. contralateral structure; 2-way ANOVA; n=4 animals per group).

FIGS. 50A-E. Aqp4 gene deletion exacerbates post-traumatic cognitive impairment. (A) The effect of impairing the glymphatic pathway upon post-traumatic cognitive deficits was evaluated in wild type and Aqp4$^{-/-}$ mice subjected to TBI. Animals underwent baseline behavioral testing 2 days prior to injury, then weekly after TBI. (B) Gross motor behavior was assessed by the open field test. TBI did not alter performance in the open field test in either wild type of Aqp4$^{-/-}$ mice. (C) Motor coordination and learning was evaluated by the rotarod test. While TBI did not significantly impair rotarod performance in wild type animals, in Aqp4$^{-/-}$ mice TBI significantly impaired test performance (*P<0.05 Aqp4$^{-/-}$ sham vs. Aqp4$^{-/-}$ TBI; 2-way repeated measures ANOVA, n=9-14 animals per group). Cognitive function was evaluated with the novel object recognition test (D) and the Barnes maze test (E). In both tests, TBI impaired cognitive performance among both wild type and Aqp4$^{-/-}$ mice (*P<0.05, P<0.01, *P<0.001 TBI vs. Sham; 2-way repeated-measures ANOVA, n=9-14 animals per group). Post-traumatic cognitive impairment was exacerbated in Aqp4$^{-/-}$ mice compared to wild type animals (**P<0.01 wild type TBI vs. Aqp4$^{-/-}$ TBI; 2-way repeated measures ANOVA; n=9-14 per group).

FIGS. 51A-D. AQP4-M1 variant as a determinant of perivascular AQP4 polarization. (A) The Aqp4 gene has two transcription initiation site, with transcription initiated at each site resulting in two AQP4 mRNA variants: AQP4-M1 which includes Exons 0-4 of the Aqp4 gene and AQP4-M23 which lacks Exon 0. (B) AQP4-M23 (the predominant form in the CNS under physiological conditions) permits perivascular AQP4 packing while AQP4-M1 prevents it; thus increasing AQP4-M1 expression impairs AQP4 polarization (Crane et el. *J Biol Chem* 2009; Furman et al. *Proc Nat Acad Sci* 2003). (C) The expression of AQP4-M1 was evaluated by real-time quantitative PCR (qPCR) in the mouse ipsilateral cortex 3 days after TBI using PCR primers specifically targeting Exon 0 of the AQP4-M1 transcript. Compared to AQP4-M1 expression in the control (sham) cortex, TBI increased AQP4-M1 expression by approximately two-fold (*P<0.05, t-test; n=5 per group). (D) Using an siRNA-based approach targeting Exon 0 of the AQP4-M1 variant, the expression of AQP4-M1 could be efficiently knocked down in cultured primary mouse cortical astrocytes. Three siRNA duplexes were designed to target Exon 0 of the AQP4-M1 transcript, and primary mouse astrocytes were transfected with these siRNA duplexes for six days. After siRNA treatment, AQP4-M1 expression was evaluated by qPCR, showing efficient knockdown of AQP4-M1 by siRNA targeting of Exon 0 (####P<0.001, siAQP4-M1 vs. Control, 1-way ANOVA; n=3). In silico screening of the Aqp4 gene promoter revealed two binding sites for the transcription factor signal transducer and activator of transcription (STAT)-3 upstream of the AQP4-M1 transcription initiation site. Thus, we tested whether inhibition of STAT3 signaling in primary mouse cortical astrocytes could reduce AQP4-M1 expression. Treatment of primary astrocytes with the STAT3-specific inhibitor STATTIC significantly reduced AQP4-M1 expression (**P<0.01 STATTIC vs. control, 1-way ANOVA; n=3). These data demonstrate that AQP4-M1 expression is increased after TBI while AQP4-M1 expression can be reduced either by siRNA targeting of the AQP4-M1 transcript or by STAT3 inhibition in astrocytes. These findings are consistent with the notion that the loss of AQP4 polarization after brain injury could be prevented through these approaches.

FIGS. 52A-E. Glymphatic pathway function is impaired after diffuse ischemic injury. Using a mouse model of multiple microinfarcts (M. Wang et al., Cognitive Deficits and Delayed Neuronal Loss in a Mouse Model of Multiple Microinfarcts, J. Neuroscience, 12 Dec. 2012, 32(50): 17948-17960), the effect of diffuse ischemic injury was evaluated by in vivo 2-photon imaging. (A) Animals were subjected to diffuse ischemic injury. 3 days later, glymphatic pathway function was evaluated by imaging the influx of intracisternally-injected fluorescent CSF tracer (Texas Red-conjugated dextran, MW 70 kD) into the cerebral cortex via a closed cranial window. (B-D) Representative 2-photon images acquired 100 μm below the cortical surface show fluorescent CSF tracer movement into the cortical parenchyma 20 min after intracisternal injection. (E) Quantification of fluorescence intensity 3 days post-injury 100 μm below the cortical surface by serial 2-photon imaging shows that in control animals, CSF tracer rapidly enters the cortex, peaking within 20 min of injection. In the ipsilateral cortex, CSF tracer influx is virtually abolished, while even in the contralateral cortex, CSF tracer influx is markedly impaired. These data demonstrate that diffuse ischemic injury, which causes loss of perivascular AQP4 polarization (Wang et al. *J Neurosci* 2012), also dramatically impairs glymphatic pathway function.

Figure 53A:
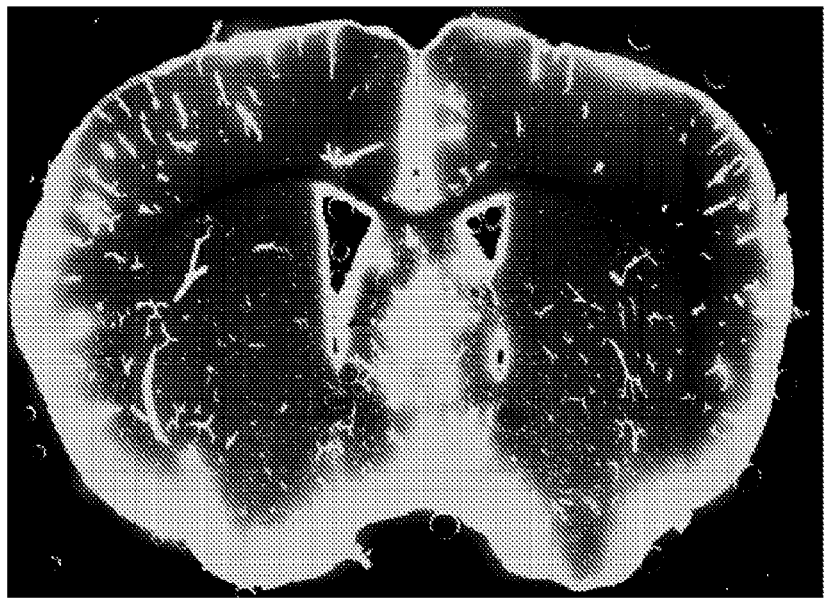
Figure 53B:

FIGS. 53A-B. Using a mouse model of multiple microinfarcts, the effect of diffuse ischemic injury was evaluated by whole-slice fluorescence imaging. (A) In the control brain, CSF tracer moves rapidly into the brain parenchyma along paravascular spaces. (B) After diffuse ischemic injury CSF influx into the brain is dramatically reduced. Ipsilaterally, CSF movement into the parenchyma is virtually abolished. In the contralateral hemisphere, although paravascular CSF influx is present, its rate and extent of exchange with the surrounding interstitial space is dramatically reduced. See Example 6.6 for details.

Figure 54:
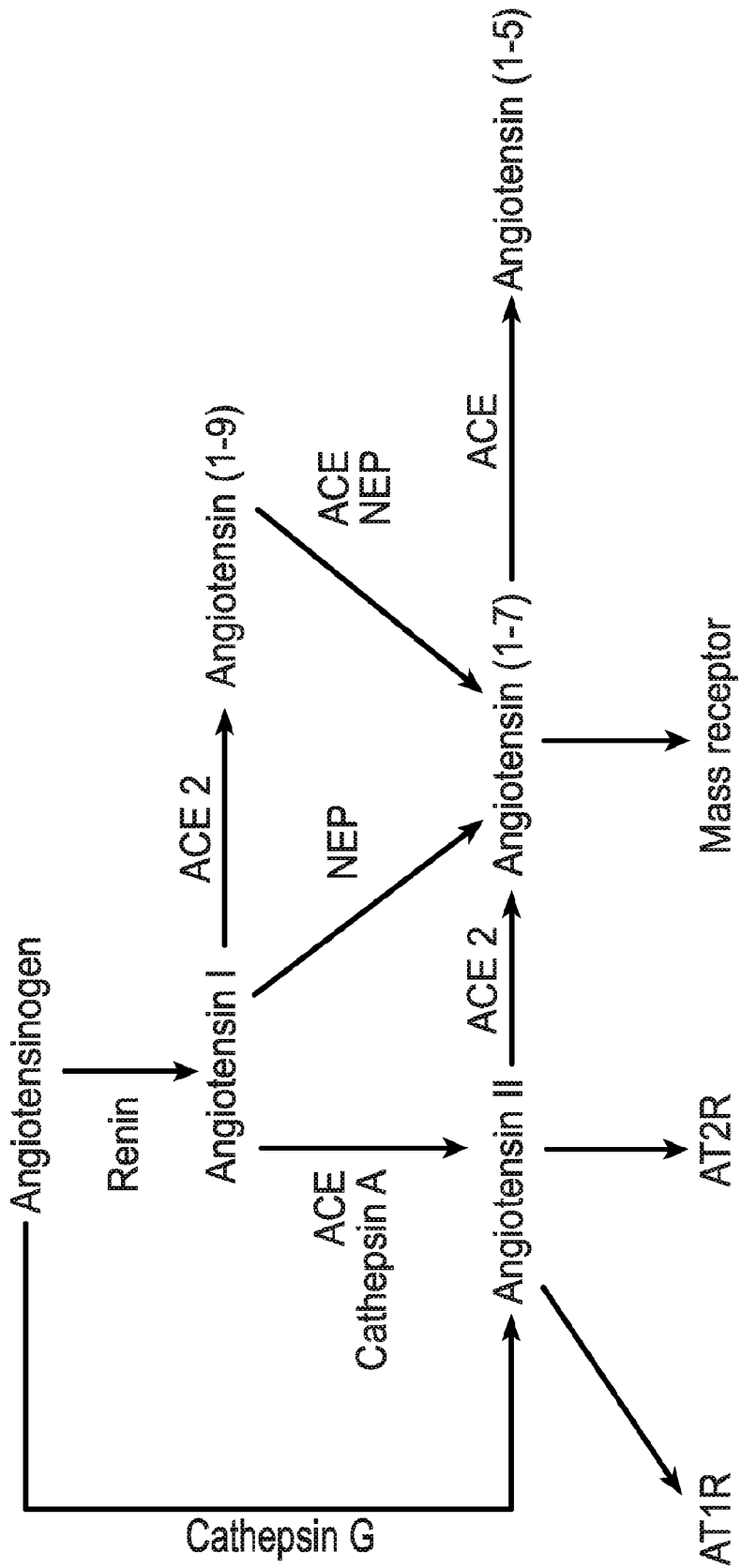

FIG. 54. Cascade for the production of angiotensin and active metabolites. ACE is angiotensin-converting enzyme. NEP is neprilysin. AT1R and AT2R are angiotensin receptor 1 and 2 respectively.

Figure 55A:
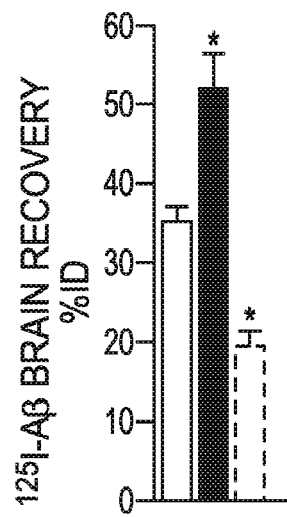
Figure 55B:
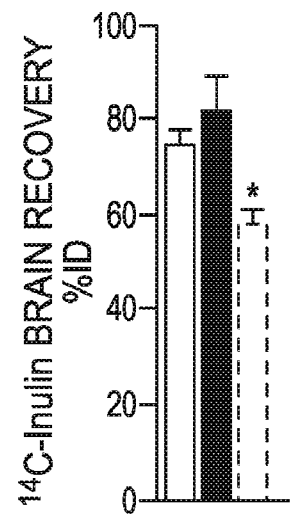

FIGS. 55A-B. Brain clearance of Aβ (A) and inulin (B) were reduced with angiotensin II (1 μM) and increased with losartan (1 μM; an inhibitor of AT1R). Bar 1 (first, going from left to right) in each graph(control), bar 2 in each graph (angiotensin II) and bar 3 in each graph (losartan) *P<0.05 compared to controls.

Figure 56A:
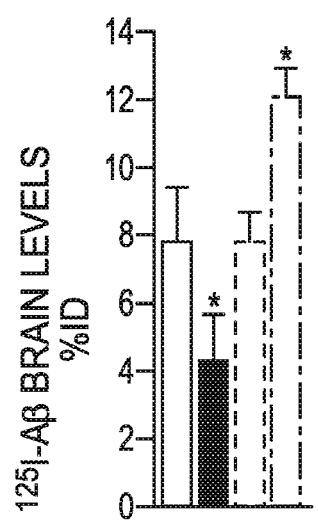
Figure 56B:
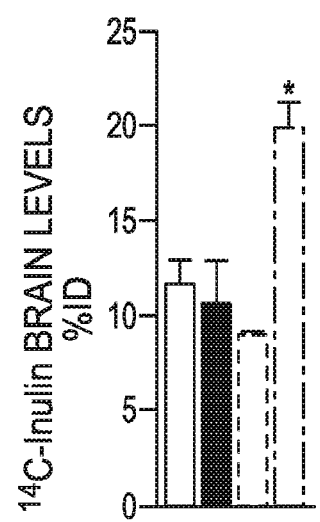

FIGS. 56A-B. Brain influx of Aβ (A) and inulin (B) in the presence of angiotensin II (1 μM, bar 2 in each graph), losartan (1 μM) injected into the cisterna magna (bar 3 in each graph) and losartan (I mg) injected intraperitoneally (IP)) (fourth bar in each graph) Bar 1 (first, going from left to right) in each graph (control).

Figure 57:
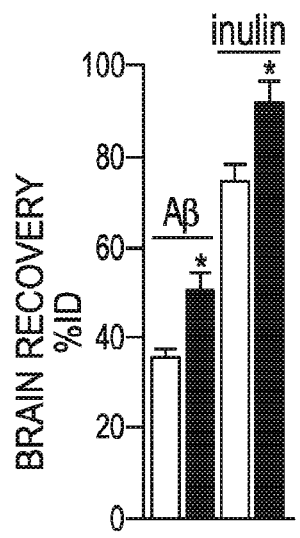

FIG. 57. Brain clearance of Aβ and inulin were reduced with vasopressin (1 μM). Bar 1 (left) in each set of bar graphs (control). Bar 2 (right) in each set of bar graphs (vasopressin)

Figure 58:
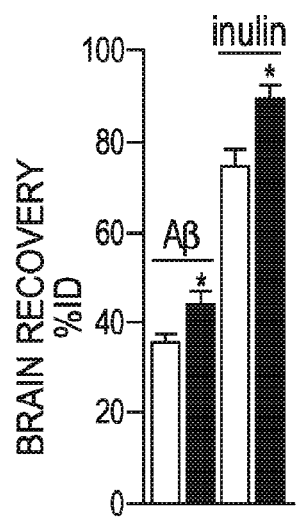

FIG. 58. Brain clearance of Aβ and inulin were reduced with atrial natriuretic peptide (ANP) (1 μM). Bar 1 (left) in each set of bar graphs (control). Bar 2 (right) in each set of bar graphs (atrial natriuretic peptide, ANP)

Figure 59:
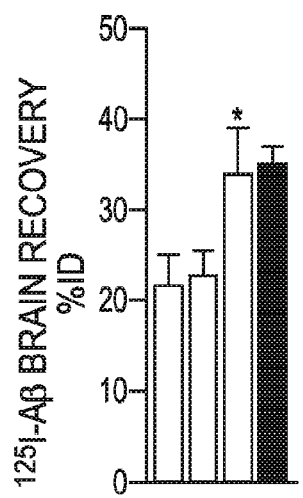

FIG. 59. Brain clearance of Aβ was increased with angiotensin (1-7) in a dose-dependent manner. Dose of angiotensin (1-7), from left to right, 1 μM (bar 1), 0.1 μM (bar 2) and 0.01 μM (bar 3). Bar 4 (control). *P<0.05 compared to highest dose.

Figure 60:
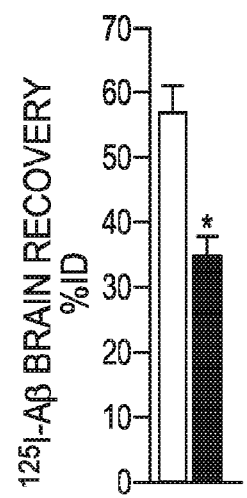

FIG. 60. Brain clearance of Aβ is increased with angiotensin (1-7) in a dose-dependent manner at 15 minutes. at 1 nM (left column) and at 10 nM (right column).*P<0.05 comparing the two doses FIG. 61. Brain clearance of Aβ and inulin were reduced in the presence of A779 (an inhibitor of angiotensin (1-7), which blocked the effects of angiotensin (1-7). These values are not significantly different from controls FIG. 62. Dose-dependent effect on Aβ and inulin clearance FIG. 63. Dose-dependent effect on Aβ and inulin influx.

Figure 64:
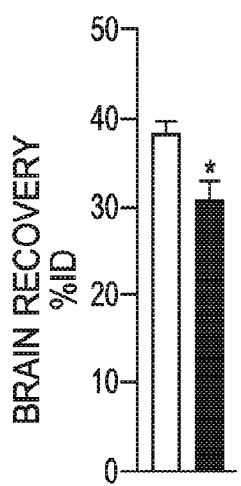

FIG. 64. Brain clearance of Aβ from the cortex was reduced with CSF drainage from the cisterna magna. Bar 1, left (CSF drainage) Bar 2, right (control).

Figure 65:
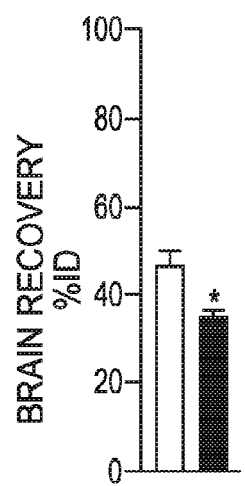

FIG. 65. Brain clearance of Aβ was reduced with sleep deprivation. Bar 1, left (sleep deprivation). Bar 2, right (control). N=3.

5. DETAILED DESCRIPTION OF THE INVENTION

For clarity of disclosure, and not by way of limitation, the detailed description of the invention is divided into the subsections set forth below.

5.1. Methods for Measuring Glio-vascular Pathway (Glymphatic System) Function in the Brain A method is provided for measuring glio-vascular pathway (also referred to herein as "glymphatic system") function in the brain and/or spinal cord (or collectively, the central nervous system or "CNS") of a mammal. In one embodiment, the method comprises the steps of:

performing imaging of the central nervous system; and measuring CSF-ISF exchange in the central nervous system, thereby measuring glymphatic function in the central nervous system of the mammal.

In one embodiment of the method, the mammal is a human or a non-human primate. In another embodiment of the method, the mammal is a patient or a subject in need of treatment. In other embodiments, the mammal can be a domestic animal (e.g., cat, dog, pig, sheep, cow, horse, and goat) or an exotic mammal (e.g., zoo mammal).

In one embodiment, the method further comprises the step of administering an imaging agent (also referred to herein as a tracer) or a contrast agent prior to the step of performing imaging of the central nervous system.

The method can be used to track, with imaging, the exchange between CSF and ISF compartments. The imaging technique preferably tracks this exchange process separately from other exchanges outside of the brain and spinal cord. Therefore, the imaging agent or tracer is preferably not present in the peripheral (systemic) compartment of the body.

In a preferred embodiment, the imaging agent is administered intrathecally. In another embodiment of the method, the step of administering intrathecally the imaging agent comprises the step of administering a lumbar or intracisternal intrathecal injection of the imaging agent. Intrathecal administration of imaging agents is well known in the art.

In another embodiment of the method, the imaging (or contrast) agent can be administered intra-nasally or ocularly (e.g., via the eyes applied as eye drops).

In other embodiment, an imaging (or contrast) agent can be co-administered with a drug infused either intraparenchymally or intraventricularly. Such methods of co-administration are well known in the art.

In another embodiment of the method, the step of performing imaging of the central nervous system comprises the step of performing dynamic or contrast-enhanced magnetic resonance imaging (MRI) of the central nervous system. The imaging agent can be a negative or positive (paramagnetic) contrast agent. MRI methods for imaging the brains and spinal cords of mammals, including those of humans and non-human primates, are well known in the art.

In another embodiment of the method, the imaging agent is a positron-emitting radionuclide tracer, and the step of performing imaging of the central nervous system comprises the step of performing positron emission tomography (PET) scanning of the brain and/or the spinal cord to follow the CSF-ISF exchange of the tracer. Suitable PET scanning protocols for imaging the mammalian brain and spinal cord are well known in the art. The PET scanning protocol can track the tracer movement under optimized scanning conditions, which can be optimized using routine methods in the art.

In a specific embodiment of the method, in which PET scanning is used as the imaging method, the initial bed position used for the subject or patient during the PET scanning can be adjusted such that the injection site is just out of view. This maximizes the ability to see tracer movement. The injection site is preferably shielded after the injection to reduce the random background emission.

In another embodiment of the method, the step of performing imaging of the central nervous system comprises administering at least two different magnetic contrast agents. The different magnetic contrast agents can be matched in terms of their effects on T1 (paramagnetic) or T2 (negative contrast agents) so that their kinetic characteristics in central nervous system tissue can be compared. In a specific embodiment, the kinetic characteristics are compared or analyzed using the methods disclosed in the examples below, e.g., Examples 1-3.

In another embodiment, the step of measuring CSF-ISF exchange comprises measuring or monitoring the clearance of soluble amyloid β (Aβ), tau, a nanoparticle such as a functionalized or therapeutic nanoparticle, a chemotherapy agent, a toxic product administered therapeutically, small interfering RNA (siRNA), alpha synuclein, a small molecule drug, a viral vector, an antibody-based therapeutic, a liposome or a therapeutic RNA construct, to name but a few. In certain embodiments, the analysis techniques disclosed in the examples below, e.g., Examples 1-3, can be used.

In another embodiment, the step of measuring CSF-ISF exchange comprises analyzing influx kinetics, parenchymal distribution and/or clearance of the paramagnetic or negative contrast agent in the central nervous system. In certain embodiments, the analysis techniques disclosed in the examples below, e.g., Examples 1-3, can be used.

In another embodiment of the method, the step of measuring CSF-ISF exchange comprises measuring CSF-ISF exchange at the pituitary recess, the pineal gland recess, the cerebellum and/or the olfactory bulb.

In another embodiment of the method, the step of measuring CSF-ISF exchange comprises the step of performing parametric or non-parametric data analysis of signal changes. Such data analysis can be carried out as disclosed in the examples below, e.g., Examples 1-3.

In another embodiment of the method, the step of performing parametric or non-parametric data analysis of signal changes comprises the step of measuring T1 shortening or T2 changes, respectively. Example 2 discloses methods for measuring T1 shortening and/or T2 changes.

In another embodiment of the method, the step of measuring CSF-ISF exchange comprises the step of calculating an influx kinetic parameter, wherein the influx kinetic parameter reflects a rate of CSF-ISF exchange.

In another embodiment of the method, the step of measuring CSF-ISF exchange comprises the single step of calculating a kinetic parameter from a static contrast-enhanced MRI or PET image, wherein the kinetic parameter reflects a rate of CSF-ISF exchange.

In another embodiment, the method further comprises the step of calculating a risk of developing a neurodegenerative disease in the mammal. The neurodegenerative disease can be, e.g., Parkinson's disease (PD), Alzheimer disease (AD), Alzheimer's disease with Lewy bodies, Lewy body dementia, mixed dementia, vascular dementia, frontotemporal dementia or chronic traumatic encephalopathy.

Methods for calculating a risk of developing a neurodegenerative disease are well known in the art. For example, diagnostic tests known in the art such as for APOE4 allele carrier status or CSF biomarker status (e.g., amyloid β, tau, alpha synuclein) can be used.

In another embodiment of the method, the mammal is suffering from traumatic brain injury. In this case, the method can further comprise the step of calculating a risk of developing chronic traumatic encephalopathy (CTE), using methods well known in the art.

In a specific embodiment of the method (also described in Example 2), an intrathecal catheter for administering (e.g., injecting) at least one contrast agent is inserted in the mammalian patient (or subject) using suitable surgical methods known in the art. Preferably, lumbar intrathecal insertion of the catheter and injection of the contrast agent is used. In certain embodiments, other routes of administration, such as intracisternal, ventricular or intraparenchymal insertion and injection, can be used. Following the surgery, the patient can be positioned in a head fixation device for MRI imaging. Non-invasive, MRI compatible monitors (e.g., pulse-oximetry, respiratory rate and rectal temperature probes) can be positioned for continuous monitoring of vital signs while the subject undergoes MRI imaging. During imaging, body temperature is preferably monitored closely and maintained, e.g., using a computer assisted air heating system. The intrathecal catheter can be connected to a line (e.g., PE 20) filled with two paramagnetic MR contrast agents diluted in physiological saline and attached to a syringe and microinfusion pump. Hydration and supplemental anesthesia can be carried out according to methods known in the art.

To visualize the glymphatic pathways by contrast-enhanced MRI (T1 shortening effects the initial concentrations at which the two different paramagnetic contrast agents can be matched so that decreasing concentrations produced over time in brain tissue far from the injection site are comparable. The T1 effects induced by the two paramagnetic contrast agents are preferably matched, since after they are injected into the cisterna magna they will travel through the brain-wide glymphatic pathways and become progressively diluted over time.

MRI imaging can be performed using an MRI instrument interfaced with a controlling device, such as a control console controlled by Paravision 5.0 software (Bruker Bio Spin, Billerica, Mass.). A surface radio-frequency coil can be used as a receiver and a volume coil can be used as a transmitter. Following localizer anatomical scout scans, a 3D T1-weighted FLASH sequence (TR=15 msec, TE=3.4 ms, Flip angle 15°, NA=1, FOV=3.0×3.0×3.2 cm, scanning time=4 minutes 5 sec, acquisition matrix size of 256×128×128 interpolated to 256×256×256 yielding an image resolution of 0.12×0.12×0.13 mm) is acquired in the sagittal or coronal plane.

Image intensity can be normalized over the time series using methods known in the art. The scanning protocol can consist, for example, of three baseline scans followed by intrathecal paramagnetic contrast delivery of the two contrast agents via the indwelling catheter while MRI acquisitions continue. Paramagnetic contrast agent can be delivered intrathecally at suitable infusion rates and suitable times as determined using methods known in the art. After completion of the intrathecal infusion, the 3D MRI acquisitions can be continued for a desired length of time as determined by art known methods.

General MRI image processing procedures can be carried out, e.g., head motion correction, intensity normalization, smoothing and voxel-by-voxel conversion to % of baseline signal, using methods known in the art. The acquired T1-weighted MRI images can be exported as DICOM files and converted to 3D NIfti image format.

Scan-to-scan misregistration caused by head movement can be corrected by rigid-body alignment of each scan to the time-averaged (mean) image.

Image intensity can be normalized over the time-series by dividing voxel intensity by the mean intensity of the reference phantom using the following expression: img_normalized=img_original/phantom1000; followed by 0.1 mm full width at half maximum isotropic Gaussian smoothing.

All time-series images can then be subtracted and divided by the baseline average image using the following expression: $(P(l,j,k)=(l(l,j,k)-base(l,j,k))/base(l,j,k)*100)$ to ensure that voxel intensity represents percentage change relative to the average baseline images.

The signal changes measured on the T1-weighted MRIs over time in pre-selected anatomical areas can be used to obtain the time 'activity' curves (TACs) of regional tissue uptake of the paramagnetic contrast agents. The T1-weighted averaged baseline images as well as the contrast-enhanced T1-weighted MRIs can be used to anatomically guide placement of the regions-of-interest (ROIs). From near-midline sagittal MRIs, ROIs can be drawn on four sagittal slices in each hemisphere and the signals from each of the anatomical ROIs can be averaged using PMOD software (PMOD Version 3.307, PMOD Technologies, Ltd, Zurich, Switzerland). The ROIs can include, for example, the pituitary recess, pineal recess, olfactory bulb, cerebellum, pontine nucleus and/or aqueduct. The TACs for each ROI can be extracted via the PKMod module. The area under the curve (AUC) for each ROI's TAC can be calculated using the 'trapezoidal rule' (see Example 2 for further details). The calculated AUCs can be normalized by dividing each subject's AUC by the number of the corresponding time intervals used for that particular study referred to as 'mean Area Under the Curve (mAUC)' calculated as: (mAUC=AUC/(n−1)). Furthermore, to minimize potential differences in the amount of paramagnetic contrast delivered to each subject or patient within a group, the mAUC of the pituitary recess (which represent the major input and source of contrast) can be used to normalize the other regions mAUCs. Subsequently, the mean mAUC-ratios can be compared between groups or subjects for each anatomical location using a two-sided independent t-test.

Cluster analysis can be performed to analyze non-parametric segmentation to group voxels in the MRI images on the basis of similar kinetics can be performed using a k-means cluster algorithm (PMOD Version 3.307, PMOD Technologies, Ltd, Zurich, Switzerland) on four sagittal slices at the level of the aqueduct from each of the 4D T1-weighted MRIs. A volume-of-interest mask containing the brain only can be created for the cluster analysis. The number of clusters (K) used was determined by the K which was able to segment out voxels adjacent to the large vessels such as basilar artery (including pituitary recess) and olfactory artery complex. This was done on an interactive, per animal basis. Each analysis was performed using a 50% percentile threshold (i.e. only 50% of the pixels with the highest signal changes (sum of squared TAC values were used). The number of clusters which provided the most ideal visualization of para-vascular inflow conduits was 4 clusters. The four clusters were examined visually and co-registered with the corresponding contrast-enhanced and anatomical MRIs to verify the positions of the clusters in relation to the large vessels. The number of voxels and TACs for each cluster was extracted for further processing.

Statistical analyses can be performed using methods known in the art, e.g., using a statistical software package such as SAS version 9.2 (SAS Institute Inc, USA) and XLSTAT Version 2011 (Addinsoft, N.Y., USA) with $p\text{-value} < 0.05$ described as significantly different. All data can be presented as mean±SD. Differences in regional tissue uptake (e.g., as represented by the average ratio between the mean 'Area Under Curve' (mAUC) of the anatomical region of interest and the average mAUC of the pituitary recess) can be compared using a two-sided t-test for independent groups.

In one embodiment, the following parameters can be derived from K-means cluster analysis: 1) total number of voxels in each of the three anatomical zones, 2) the time-weighted cluster number of each zone (#voxels*AUC) and 3) ratios of zone 2's and 3's total time-weighted cluster number to that of zone 1's time-weighted cluster number. Differences in average values of each of these parameters can be derived from cluster analysis between comparison groups or subjects using a two-sided t-test for independent groups.

5.2. Methods for Treating Onset of a Neurodegenerative Disease

A method is provided for treating onset of a neurodegenerative disease in the brain and/or spinal cord (or CNS) of a mammal comprising the step of increasing glymphatic system clearance.

In one embodiment of the method, reactive gliosis is reduced, thereby delaying or preventing onset of the neurodegenerative disease. Reactive gliosis decreases or prevents interstitial waste clearance. Reactive gliosis is known in the art to be associated with neurodegenerative diseases such as Alzheimer's disease. Increasing gliosis is also observed in the aging mammalian brain. Reactive gliosis is also associated with certain autoimmune inflammatory disorders, notably multiple sclerosis. It has also been observed in the CNS of individuals suffering from amyotrophic lateral sclerosis (ALS). Increasing glymphatic system clearance of waste products from the CNS can be used, in certain embodiments, to delay, prevent, decrease or reduce reactive gliosis and its neurodegenerative consequences.

Reactive gliosis decreases Aqp4-dependent bulk flow and reduces the volume of the extracellular space, impeding ISF solute clearance, including waste products, from the brain and spinal cord.

Neurodegenerative diseases can be, e.g., Parkinson's disease (PD), Alzheimer disease (AD), Alzheimer's disease with Lewy bodies, Lewy body dementia, mixed dementia, vascular dementia, frontotemporal dementia or chronic traumatic encephalopathy.

In one embodiment of the method, the mammal is a human or a non-human primate. In other embodiments, the mammal can be a domestic animal (e.g., cat, dog, pig, sheep, cow, horse, goat) or an exotic mammal (e.g., zoo mammal). The mammal can be a patient or a subject in need of treatment.

In one embodiment, the method further comprises measuring glymphatic system function in the central nervous system according to the methods disclosed in Section 5.1 and in the examples below, e.g., Examples 1-3.

In another embodiment of the method, reactive gliosis is reduced, delayed or prevented. In another embodiment, In one embodiment, the method comprises the step of administering a therapeutic agent to the mammal that increases or promotes glymphatic system clearance (also referred to herein as "glymphatic clearance").

Increasing glymphatic clearance, can, as discussed above, reduce, delay the onset of, or prevent reactive gliosis. Thus, a method is also provided for treating reactive gliosis in the central nervous system of a mammal comprising the step of increasing glymphatic system clearance, whereby reactive gliosis is decreased, prevented, reduced or its onset delayed.

In one embodiment, the method comprises the step of administering a therapeutic agent to the mammal that increases or promotes glymphatic clearance. In a specific embodiment, the agent is a Stat-3 inhibitor or molecules known in the art to be bone morphogenetic protein (BMP) signaling axis molecules.

In other embodiments, the therapeutic agent that increases or promotes glymphatic clearance is an antagonist of AVP (vasopressin) such as tolvaptan, conivaptan, or VPA-985, an antagonist of atrial natriuretic peptide (ANP) such as anantin, an antagonist of Angiotensin II such as losartan, an antagonist of AT2R receptors such as PD123319, or an antagonist of AT1 receptors such as valsartan.

In another embodiment, the method comprises the step of pumping fluid through the central nervous system interstitium of the mammal to increase of promote glymphatic clearance. Pumping can be accomplished by any device or method known in the art, for example, by using a mechanical pump, an infusion pump, etc.

5.3. Methods for Promoting Clearance of a Brain Waste Product from Brain Interstitium A method is provided for promoting clearance of a waste product (e.g., a brain, spinal cord or CNS waste product) from the brain interstitium and/or spinal cord interstitium of a mammal comprising the step of administering an agent to the mammal that increases or promotes glymphatic clearance, whereby clearance of the waste product from the brain interstitium and/or spinal cord interstitium is promoted. The agent can be, for example, a diuretic.

In one embodiment of the method, the method comprises the step of administering an agent to the mammal that increases or promotes glymphatic clearance, e.g., a Stat-3 inhibitor or molecules known in the art to be bone morphogenetic protein (BMP) signaling axis molecules.

In other embodiments, the agent that increases or promotes glymphatic clearance is an antagonist of AVP (vasopressin) such as tolvaptan, conivaptan, or VPA-985, an antagonist of atrial natriuretic peptide (ANP) such as anantin, an antagonist of Angiotensin II such as losartan, an antagonist of AT2R receptors such as PD123319, or an antagonist of AT1 receptors such as valsartan.

In another embodiment, the agent that increases or promotes glymphatic clearance is an agent that prevents AQP4 depolarization or loss of AQP4 polarization.

In another embodiment, the agent that prevents AQP4 depolarization or loss of AQP4 polarization is JNJ-17299425 or JNJ-17306861.

In one embodiment of the method, the mammal is a human or a non-human primate. In other embodiments, the mammal can be a domestic animal (e.g., cat, dog, pig, sheep, cow, horse, goat) or an exotic mammal (e.g., zoo mammal). The mammal can be, for example, a patient or a subject in need of treatment.

In one embodiment, the method further comprises measuring glymphatic system function in the brain according to the methods disclosed in Section 5.1 and in the examples below, e.g., Examples 1-3.

In another embodiment of the method, the brain, spinal cord or CNS waste product is amyloid β (Aβ) (e.g., soluble Aβ, tau or alpha synuclein. The method is also suitable for promoting clearance of virtually any brain waste product known in the art. In one embodiment, the method comprises the step of administering a therapeutic agent to the mammal that increases or promotes glymphatic clearance.

Also provided is an apparatus for restoring and/or augmenting reduced cerebrospinal fluid (CSF) secretion and/or reduced flow associated with cerebrospinal fluid (CSF)/interstitial fluid (ISF) exchange in the brain of a mammal. In a preferred embodiment, the mammal is a human. The apparatus comprises a mechanical pumping system (e.g., an infusion pump), thereby promoting faster CSF clearance in the brain. In one embodiment, the apparatus also comprises artificial ("mock") CSF and the pumping system pumps or infuses the artificial CSF in the brain. See Section 6.4 (Example 4).

In another embodiment of the apparatus, the apparatus restores and/or augments reduced cerebrospinal fluid (CSF) secretion and/or reduced flow associated with a neurodegenerative disease, including but not limited to Parkinson's disease (PD), Alzheimer's disease (AD), Alzheimer's disease with Lewy bodies, Lewy body dementia, and mixed dementia, or associated with traumatic brain injury or ischemic (e.g., diffuse ischemic) brain injury.

5.4. Methods for Slowing, Delaying or Preventing Accumulation of a Brain Waste Product A method is provided for slowing, delaying or preventing accumulation of a waste product in the central nervous system of a mammal comprising the step of increasing glymphatic clearance, thereby increasing the clearance of the waste product from the central nervous system.

In one embodiment, the method comprises the step of administering a therapeutic agent to the mammal that increases or promotes glymphatic clearance.

In a specific embodiment, an adrenergic receptor antagonist is the therapeutic agent. Adrenergic receptor antagonists are well known in the art. A surgical implantation of ventriculo-peritoneal shunt can also be used in conjunction with a therapeutic agent, to increase or promote glymphatic clearance.

In one embodiment of the method, the method comprises the step of administering an agent to the mammal that increases or promotes glymphatic clearance, e.g., a Stat-3 inhibitor or molecules known in the art to be bone morphogenetic protein (BMP) signaling axis molecules.

In other embodiments, the agent that increases or promotes glymphatic clearance is an antagonist of AVP (vasopressin) such as tolvaptan, conivaptan, or VPA-985, an antagonist of atrial natriuretic peptide (ANP) such as anantin, an antagonist of Angiotensin II such as losartan, an antagonist of AT2R receptors such as PD123319, or an antagonist of AT1 receptors such as valsartan.

In another embodiment, the agent that increases or promotes glymphatic clearance is an agent that prevents AQP4 depolarization or loss of AQP4 polarization.

In another embodiment, the agent that prevents AQP4 depolarization or loss of AQP4 polarization is JNJ-17299425 or JNJ-17306861.

In another embodiment, the method comprises the step of pumping fluid through the central nervous system interstitium of the mammal to increase of promote glymphatic clearance. Pumping can be accomplished by any device or method known in the art, for example, by using a mechanical pump, an infusion pump, etc.

In one embodiment of the method, the mammal is a human or a non-human primate. In other embodiments, the mammal can be a domestic animal (e.g., cat, dog, pig, sheep, cow, horse, goat) or an exotic mammal (e.g., zoo mammal). The mammal can be, for example, a patient or a subject in need of treatment.

In one embodiment, the method further comprises measuring glymphatic system function in the brain according to the methods disclosed in Section 5.1 and in the examples below, e.g., Examples 1-3.

In another embodiment of the method, the brain waste product is amyloid β (Aβ) (e.g., soluble Aβ) tau, or alpha synuclein. The method is also suitable for slowing, delaying or preventing accumulation of virtually any brain waste product known in the art.

In a specific embodiment, a method is provided for decreasing, reducing, delaying onset of, or preventing amyloid β (Aβ), tau and/or alpha synuclein accumulation in brain interstitium of a mammal. The method comprises the step of administering an agent to the mammal that increases or promotes glymphatic clearance.

5.5. Methods for Decreasing or Impeding Clearance of a Therapeutic or Modulatory Agent from the Brain Interstitium of a Mammal A method is provided for decreasing or impeding clearance of a therapeutic or modulatory agent from the brain interstitium of a mammal. Such a method can be used to clearance of a therapeutic drug or compound, e.g., in the treatment of brain tumors.

The therapeutic or modulatory agent can be any known in the art, e.g., therapeutic or functionalized nanoparticle, chemotherapy agent, antineoplastic agent, immune modulator, antibody based therapeutic, viral vector, liposome or RNA-based therapeutic construct.

In one embodiment, the method comprises the step of decreasing (or impeding) glymphatic clearance.

In another embodiment, the method further comprises measuring glymphatic system function in the brain according to the methods disclosed in Section 5.1 and in the examples below, e.g., Examples 1-3.

In another embodiment of the method, the step of decreasing (or impeding) glymphatic clearance comprises the step of administering an agent to the mammal that decreases or impedes glymphatic clearance. In certain embodiments, the agent can be bumetanide, small interfering RNA (siRNA) directed against AQP4, an agonist of AVP (vasopressin), an agonist of atrial natriuretic peptide (ANP), an agonist of Angiotensin II, an agonist of AT2R receptors, or an agonist of AT1 receptors.

In another embodiment of the method, the step of decreasing (or impeding) glymphatic clearance comprises the step of blocking or erecting a barrier to fluid flow through the central nervous system interstitium of the mammal.

5.6. Therapeutic Uses of Methods

The methods disclosed herein for determining patterns of parenchymal fluid flow can be employed for a number of therapeutic approaches. First, improving the efficiency of bulk flow in the brain can permit the improved clearance of brain waste products such as soluble Aβ, tau or alpha synuclein, potentially accelerating either their degradation or their re-uptake into the systemic circulation.

Conversely, impeding solute clearance can slow the removal of therapeutic agents, such as antineoplastic agents and immune modulators, from the brain, e.g., for the treatment of brain cancers or tumors.

Bulk flow can also facilitate immune surveillance of the brain parenchyma without compromising CNS immune privilege. Both lymphocytes and antigen-presenting cells in the subarachnoid CSF may detect interstitial antigens delivered to the CSF by paravenous bulk outflow. Paravascular routes can also serve as pathways for migrating cells and their guidance molecules, thus representing a potential avenue for monitoring tumor cell migration. Additionally, paravascular routes can be conduits for cell migration and monitored for such migration.

The following examples are offered by way of illustration and not by way of limitation.

6. EXAMPLES

6.1. Example 1

A Paravascular Pathway Facilitates CSF Flow Through the Brain Parenchyma and the Clearance of Interstitial Solutes Including Amyloid β

Because the brain lacks a lymphatic circulation, it must clear extracellular proteins by an alternative mechanism. The cerebrospinal fluid (CSF) functions as a sink for brain extracellular solutes, but it is not clear how solutes from the brain interstitium move from the parenchyma to the CSF. This example demonstrates that a substantial portion of subarachnoid CSF cycles through the brain interstitial space. On the basis of in vivo two-photon imaging of small fluorescent tracers, this example demonstrates that CSF enters the parenchyma along paravascular spaces that surround penetrating arteries and that brain interstitial fluid is cleared along paravenous drainage pathways. Animals lacking the water channel aquaporin-4 (AQP4) in astrocytes exhibit slowed CSF influx through this system and a ~70% reduction in interstitial solute clearance, suggesting that the bulk fluid flow between these anatomical influx and efflux routes is supported by astrocytic water transport. Fluorescent-tagged amyloid β, a peptide thought to be pathogenic in Alzheimer's disease, was transported along this route, and deletion of the Aqp4 gene suppressed the clearance of soluble amyloid β, suggesting that this pathway removes amyloid β from the central nervous system. Clearance through paravenous flow can also regulate extracellular levels of proteins involved with neurodegenerative conditions, its impairment contributing to the mis-accumulation of soluble proteins.

Introduction

The lymphatic vasculature represents a second circulation, parallel to the blood vasculature, that accounts for the clearance of interstitial fluid (ISF) with its constituent proteins and other solutes not absorbed across postcapillary venules (1, 2). In most vascularized tissues, the lymphatic system is critical to both hydrostatic and homeostatic maintenance. Yet, the brain does not have histologically identifiable lymphatic vessels and thus lacks the discrete pathways for interstitial solute and fluid clearance present in other peripheral tissues (3-5). This is surprising, because the high metabolic rate and exquisite sensitivity of neurons and glia to alterations in their extracellular environment suggest a need for rapid clearance of ISF and solutes.

The cerebrospinal fluid (CSF) of the central nervous system (CNS) has been thought to play a role in solute clearance from the brain (6). CSF formed in the choroid plexi flows through the cerebral ventricles and the subarachnoid space to its ultimate sites of reabsorption into the bloodstream via arachnoid villi of the dural sinuses, along cranial nerve sheaths or through the nasal lymphatics (3, 7, 8). Interstitial solutes have been thought to be cleared to the CSF by the convective bulk flow of ISF, which courses diffusely through brain tissue, rather than through an anatomically or functionally discrete structure (3, 4, 9). Here, in vivo two-photon imaging and other techniques have been used to investigate the flow of subarachnoid CSF into and through the brain interstitium.

Materials and Methods

Animals

All experiments were approved by the University Committee on Animal Resources of the University of Rochester Medical Center. Unless otherwise noted, 8-12 week old male C57BL/6 mice (Charles River) were used in experiments.

To visualize perivascular astrocytic endfeet, FVB/N-Tg (GFAPGFP)14Mes/J (GFAP-GFP, JAX) mice were used. These mice overexpress green fluorescent protein under the control of the astrocytespecific GFAP promoter.

NG2-DsRed and Tie2-GFP:NG2-DsRed were used to identify arteries/arterioles versus veins/venules by endogenous fluorescence: Arteries and arterioles express endothelial GFP and vascular smooth muscle DsRed, and veins and venules express endothelial GFP but lack vascular smooth muscle DsRed.

To define the paravascular route of CSF tracer influx and efflux, a transgenic double reporter mouse was generated. Tg(TIE2GFP)287Sato/J (Tie2-GFP, JAX) were crossed with NG2DsRedBAC(54) (NG2-DsRed, JAX). Tie2-GFP mice overexpress green fluorescent protein under the endothelium-specific Tie2 promoter, while NG2-DsRed mice express the red fluorescent protein DsRed under the control of the NG2 promoter. Although the NG2-DsRed mice were initially generated to study NG2-positive glial cells, adult animals also express DsRed in brain pericytes and vascular smooth muscle cells. In Tie2-GFP:NG2-DsRed animals, all blood vessels are labeled with GFP (in the endothelial cell layer). Capillaries (FIG. 3F), veins (FIG. 3H) and venules (FIG. 3G) express low levels of punctuate DsRed (in pericytes and disperse vascular smooth muscle cells), while arteries (FIGS. 3D-E) and arterioles (FIGS. 3A-C) exhibit a dense circumferential pattern of DsRed labeling. This allows arteries and arterioles to be readily distinguished from veins and venules (FIG. 3A, FIGS. 10A-E) without the need of additional histochemical labeling.

Aqp4−/− (Aqp4-null) mice were generated as described (53). These animals are global Aqp4 gene knockouts backcrossed onto a C57BL/6 background.

Anesthesia

In all experiments, animals were anesthetized with a combination of ketamine (0.12 mg/g intraperitoneally) and xylazine (0.01 mg/g intraperitoneally).

Statistics

In all figures, data are presented as means±SEM. All statistics were performed with the software Prism (GraphPad). A P value of <0.05 was considered significant. The statistical treatment of each data set is described below.

CSF Tracers

All fluorescent CSF tracers were constituted in artificial CSF at a concentration of 0.5%. This includes ALEXA-594 hydrazide (A594), FITC-dextran 2000 (FITC-d2000), Texas Red-dextran 3 (TR-d3), Texas Red-dextran 2000 (TR-d2000), ovalbumin-conjugated ALEXA-647 (OA-647) (all from Invitrogen). HiLyte555-conjugated amyloid $\beta_{1-40}$ (Anaspec) was constituted in artificial CSF at a concentration of 0.1%. Radio-labeled $^3$H-mannitol (15-30 Ci/mmol, Perkin Elmer) was dissolved in artificial CSF at a 0.1 µCi/µl. Radio-labeled $^3$H-dextran 10 (100-500 mCi/g, American Radiolabeled Chemicals) was dissolved in artificial CSF at 0.01 µCi/µl. Radio-labeled $^{125}$I-amyloid $\beta_{1-40}$ (2200 Ci/mmol, Perkin Elmer) was dissolved in artificial CSF at 0.005 µCi/µl (2.3 nmol/L).

Ventriculo-cisternal Perfusion

Anesthetized mice were fixed in a stereotaxic frame and a 33GA steel needle was stereotactically inserted via a small burr hole into the right lateral ventricle (0.95 mm lateral, 2.35 mm ventral and 0.22 mm caudal to bregma). A second 30GA needle was inserted into the cisterna magna. Closed ventriculo-cisternal perfusion was conducted by infusing tracer dissolved in artificial CSF into the lateral ventricle and withdrawing CSF from the cisterna magna at an equal rate of 200 nl/min with a coupled syringe pump (Micro4, WPI).

For evaluating the distribution of tracer into the brain parenchyma, animals were trans-cardially perfused with 4% paraformaldehyde (PFA), post-fixed overnight, and 100 µm slices were cut on a vibratome and mounted with PROLONG Anti-Fade Gold with DAPI (Invitrogen). Tracer penetration from the ventricular compartment was imaged ex vivo by epifluorescence microscopy or laser scanning confocal microscopy.

Intracisternal Tracer Injection

Anesthetized mice were fixed in a stereotaxic frame and a 30GA needle was inserted into the cisterna magna. For intracisternal injections, 10 µl of CSF tracer was injected at a rate of 2 µl/min over 5 minutes with a syringe pump (Harvard Apparatus).

To visualize tracer movement from the subarachnoid space of the cisterna magna into the brain parenchyma, animals were perfusion fixed between 30 minutes and 6 hours after intracisternal tracer injection. 100 µm vibratome slices were cut and mounted as above and tracer movement was imaged ex vivo by epifluorescence microscopy or laser scanning confocal microscopy.

To evaluate the absolute proportion of subarachnoid CSF that enters the brain (FIG. 8), either radio-labeled $^3$H-mannitol (1.0 µCi in 10 µl) or $^3$H-dextran-10 (0.1 µCi in 10 µl) was first injected intracisternally into anesthetized animals. After 15, 30 or 45 minutes, animals were rapidly decapitated, the skull opened, the dura removed and the brain harvested. The brain was solubilized in 2 ml Soluene (Sigma) at 45° C. overnight. 10 ml Hionic Fluor liquid scintillation cocktail (Perkin Elmer) was added and radioactivity was measured in a Multipurpose Scintillation Counter (Beckman Coulter). Brain radioactivity was normalized to total radioactivity detected in a 10 µl aliquot put directly into a scintillation vial immediately before intracisternal radio-tracer injection and expressed as the % of total injected radioactivity. $^3$H-mannitol and $^3$H-dextran accumulation in the brain was compared by 2-way ANOVA with Bonferroni's post-hoc test. Approximate maximal $^3$H-mannitol influx was determined by fitting the accumulation curve to a one-phase association function, then determining the plateau value for the best fit curve (39.96±5.55%, $R^2$=0.3597).

Ex Vivo Fluorescence Imaging

Tracer penetration into the brain was evaluated ex vivo by epifluorescence microscopy. Multi-channel whole-slice montages were acquired with the Virtual Slice module of StereoInvestigator Software (Microbrightfield). This included separate DAPI, Green and Red emission channels. Exposure levels were determined based upon un-injected control slices, then maintained constant throughout the study.

To quantify tracer movement into fixed slices, slice images were analyzed in ImageJ software (NIH, FIG. 7). For each slice, color channels were split and a wholeslice region of interest (ROI) was defined based upon the DAPI channel. The color channels corresponding to each tracer were background subtracted based upon an ROI outside of the slice area. The mean slice fluorescence intensity was calculated, then the slice was uniformly thresholded at a pixel intensity of 75 (out of 255) and the thresholded area expressed as a % of overall slice area. Approximately 10-14 slices per animal were imaged in this manner, and mean fluorescence intensity and tracer coverage between slices was averaged within each animal to generate a single biological replicate. The effect of tracer size upon fluorescence intensity or tracer distribution was evaluated by one-way ANOVA with Tukey's post-hoc test to determine differences between individual tracers. The effect of Aqp4 gene deletion upon tracer influx into the brain was evaluated by 2-way ANOVA with Bonferroni's post-hoc test to determine differences at individual time points.

Tracer movement into and through fixed vibratome slices was additionally imaged at high power by laser scanning confocal microscopy (FV500, Olympus) with FluoView (Olympus) software. Images were processed with ImageJ Software (NIH) with the UCSD plugin set.

In Vivo 2-photon Laser Scanning Microscopy

For in vivo imaging, anesthetized animals were intubated and artificially ventilated with room air using a small animal ventilator (CWE) at ~100 breaths/min and tidal volume of 0.3-0.4 ml. Body temperature was kept at 37° C. with a temperature-controlled warming pad. A craniotomy (3 mm in diameter) was made over the cortex 1 mm lateral and 0.5 mm posterior to bregma. The dura was left intact and the craniotomy was covered with aCSF and sealed with a glass coverslip. The femoral artery was cannulated for mean arterial blood pressure monitoring and the measurement of arterial blood gas values. Only mice with blood gases within the physiological range (pO2=80-150 mmHg, pH 7.25-7.5) were included in the present study. To visualize the vasculature, 0.1 ml BBBimpermeable Cascade Blue-dextran 10 (MW 10 kD) or Texas Red-dextran 70 (MW 70 kD; both 1% in saline, Invitrogen) was injected intra-arterially immediately before imaging.

A Mai Tai laser (SpectraPhysics) attached to a confocal scanning system (Fluoview 300, Olympus) and an upright microscope (IX51W, Olympus) was used for in vivo imaging as described (55). A 20λ (0.9 NA) water immersion lens was used to image the cortex, from the surface to a depth of ~250 μm. Excitation wavelength was 800 for Cascade Blue and 870 nm for GFP, FITC and Texas Red. For GFP, FITC and Texas Red, emission was collected at 575-645 nm. The cerebral vasculature was first imaged with 512×512 pixel frames from the surface to a depth of 240 μm with 5 μm z-steps. After intracisternal injection of CSF tracer, tracer movement into the cortex was conducted with dual-channel (FITC and Texas Red) 512×512 pixel image acquisition. The cortex was repeatedly scanned from the surface to 240 μm below the surface with 20 μm z-steps at 1 minute intervals for the duration of the experiment. Image analysis was conducted in with ImageJ software (NIH) with the UCSD plugin set. After imaging, penetrating arterioles were distinguished from penetrating venules on the basis of morphology: surface arteries passing superficially to surface veins and exhibiting less branching at superficial cortical depths. Imaging planes 100-120 μm below the cortical surface were selected for the analysis of intracisternal tracer penetration. To define para-vascular tracer movement, a circular ROI 25 pixels in diameter was defined surrounding three penetrating arterioles and ascending venules. To define tracer movement into para-vascular brain tissue, donut-shaped ROIs were defined that had an external diameter of 150 pixels and an internal diameter of 50 pixels (thus excluding the paravascular ROI). These were centered upon the penetrating arterioles and ascending venules. Mean pixel intensity within these ROIs was measured at each time point. Within each animal at each time point para-arteriolar and paravenous ROIs were separately averaged to generate values for a single biological replicate. When tracer movement along penetrating arterioles or ascending veins, or into para-arteriolar and paravenous brain tissue was compared, a 2-way ANOVA was used followed by Bonferroni's post-hoc test. The same test was used to evaluate the effect of Aqp4 gene deletion on tracer movement along paravascular spaces or into paravascular brain tissue.

Intraparenchymal Tracer Injection

To evaluate the pathways and rates of interstitial fluid and solute clearance from the brain, fluorescent and radio-labeled tracers were injected stereotactically into the brain parenchyma. Anesthetized animals were fixed in a stereotaxic frame and a 33GA needle was inserted via a small burr hole into the brain at the following coordinates: intracortical injections (0.22 mm caudal, 2.0 mm lateral, 1.75 mm ventral to bregma), intra-striate injections (0.22 mm caudal, 2.5 mm lateral, 3.5 mm ventral to bregma), intrathalamic injections (1.82 mm caudal, 1.25 mm lateral, 3.75 mm ventral to bregma). After needle insertion, 30 minutes was allowed to elapse to allow the needle track to swell closed. 1.0 μl of tracer (dissolved in artificial CSF) was injected at a rate of 17 nl/min.

When the distribution of intra-parenchymal fluorescent tracer (OA-647) was evaluated, animals were perfusion-fixed for 1-3 h after injection and vibratome slices were imaged by laser scanning confocal microscopy. To define the pathways of HiLyte-555-amyloid $β_{1-40}$ clearance from the brain after intra-striate injection, fixed vibratome sections were imaged by laser scanning confocal microscopy.

When the absolute rate of interstitial solute clearance from the brain was evaluated, $^3$H-mannitol, $^3$H-dextran-10 or $^{125}$I-amyloid $β_{1-40}$ was injected into the striatum (FIGS. 14A-B). 15 min, 30 min, 1 h or 2h later, the animal was rapidly decapitated and the brain harvested. The brain was solubilized as above, and the radioactivity present in the brain was measured by liquid scintillation spectrometry. All radioactivity values were normalized to 1 μl injection standards taken immediately prior to each intra-parenchymal injection. The effect of Aqp4 gene deletion upon $^3$H-mannitol, $^3$H-dextran-10 or $^{125}$I amyloid $β_{1-40}$ clearance from the brain was evaluated with a 2-way ANOVA and Bonferroni's post-hoc test to determine differences at individual time points.

Immunofluorescence

Free-floating immunofluorescence was conducted on 100 μm PFA-fixed vibratome slices. Slices were blocked for 1 h at room temperature with 3% normal donkey serum (Jackson Immunoresearch), incubated with primary antibody overnight at 4° C. and incubated with secondary antibody for 2 hours at room temperature. Primary antibodies included rat anti-CD31 (an endothelial marker; 1:200, Abcam), mouse anti-GFAP (an astrocytic marker; 1:500, Millipore) and rabbit anti-AQP4 (1:500, Millipore). Secondary antibodies included Cy2-conjugated donkey anti-rat, Cy5-conjugated donkey antimouse and Cy3-conjugated donkey anti-rabbit (Jackson Immunoresearch).

Preembedding Light and Electron Microscopic Cytochemistry

Wild type and Aqp4-null mice were injected with FITC-d40 and fixed after 5 minutes by transcardiac perfusion with 4% formaldehyde and 0.1% glutaraldehyde in 0.1M phosphate buffer (pH 7.4). Brains were post-fixed overnight and cut in 100 μm coronal sections by a vibratome. Free-floating sections were incubated with HRP-conjugated anti-fluorescein antibodies (Abcam, Cat: AB6656, 5 μg/ml) for 24 h (4° C.) and then subjected to the diaminobenzidine (DAB)-peroxidase procedure to visualize the fluorescein tracer, as described (56). Light microscopy images of the sections were acquired before areas of the parietal cortex were dissected and embedded in Durcupan (56). Ultrathin sections (~90 nm) were cut on a Reichert ultramicrotome. Finally, the sections were counterstained and examined in a FEI Tecnai 12 transmission electron microscope. Digital images were recorded at a nominal magnification of ×26000.

Electron Microscopic Morphological Analysis

Wild type (n=3) and Aqp4-null mice (n=4) were fixed by transcardiac perfusion with 2.5% glutaraldehyde and 1% formaldehyde in 0.1M phosphate buffer (pH 7.4, 9 ml/min for 25 min). Brains were post-fixed overnight before 300-500 μm coronal sections were dissected and embedded in Durcupan (55). Ultrathin sections were cut, counterstained, and examined as described above. Digital images of penetrating vessels were recorded at a nominal magnification of ×4200. Maximal width of the Virchow-Robin space was measured around penetrating vessels at a minimum depth 80

μm from the pial surface (range: 166-415 μm and 83-366 μm for wild type and Aqp4-null mice, respectively).

Results

Ventricular CSF Minimally Enters the Brain Parenchyma

It was first evaluated whether CSF enters the brain from the ventricular compartment by infusing fluorescent tracers of differing molecular weights into the lateral ventricle of anesthetized mice (FIG. 1A). After 30 min of continuous infusion, the movement of tracers was assessed [Alexa Fluor 594 hydrazide (A594): molecular size, 759 daltons; Texas Red-dextran-3 (TR-d3): molecular size, 3 kD; fluorescein isothiocyanate-dextran-2000 (FITC-d2000): molecular size, 2000 kD] into the brain parenchyma ex vivo by fluorescence imaging of fixed vibratome slices. Small amounts of A594 and TR-d3 crossed the ependyma of the lateral and third ventricles (FIGS. 1B, C, E, and F). However, the tracer was not observed at sites remote from the immediate periventricular region (FIGS. 1D and G).

Subarachnoid CSF Rapidly Enters the Brain Parenchyma

It was next evaluated whether CSF from the subarachnoid compartment enters the brain parenchyma by injecting both fluorescent and radio-labeled tracers into the cisterna magna (FIG. 1A). Thirty minutes after injection, fluorescent tracer distribution differed radically from the pattern observed after the tracers were injected into the ventricles (FIGS. 1H and K, compare to FIGS. 1B and E). Large-molecular weight FITC-d2000 (molecular size, 2000 kD) entered the brain along paravascular spaces, was confined there, and did not enter the surrounding interstitial space (FIGS. 1K and L). TR-d3 (molecular size, 3 kD) concentrated in the paravascular spaces but also entered the interstitium both from the paravascular space (FIGS. 1K and L) and from the pial surface (FIG. 1M). TR-d3 was more widely distributed than FITC-d2000, which is mainly localized paravascularly. The lower-molecular weight A594 (molecular size, 759 daltons) moved quickly throughout the brain interstitium, and only small amounts concentrated within paravascular spaces (FIGS. 1H and J). Both A594 and TR-d3 moved slowly and uniformly into the brain from the pial surface (FIGS. 1H, K, and M). Parenchymal distribution of tracers of different molecular weights was then quantified by image analysis (FIG. 7). Whereas A594 permeated virtually the entire brain volume within 30 min of injection, penetration of the higher-molecular weight tracers proved more restricted (FIG. 1N).

These findings were confirmed intracisternal radiotracer injection. Within 45 min of injection, ~40% of injected [$^3$H]mannitol (molecular size, 182 daltons; FIG. 8) was detectable in the brain (FIG. 1O). A larger tracer ([$^3$H] dextran-10; molecular size, 10 kD) accumulated in the brain more slowly (FIG. 1O). Because water has a 10-fold lower molecular weight than mannitol, the CSF flux reflected by [$^3$H]mannitol accumulation (~40% of total subarachnoid CSF) likely underestimates the true movement of CSF into the brain parenchyma. Previous studies that have evaluated the penetration of subarachnoid CSF into the brain have used tracers such as inulin (molecular size, ~5 kD), albumin (molecular size, 66 kD), and dextrans (molecular size, 3 to 2000 kD) (10, 11). The findings in this example show that higher-molecular weight tracers are preferentially excluded from the brain parenchyma, suggesting that previous studies may have systematically underestimated "retrograde" subarachnoid CSF flow into the brain by basing their analyses on larger tracers.

In Vivo Imaging Reveals Paravascular CSF Influx

Figure 2B:
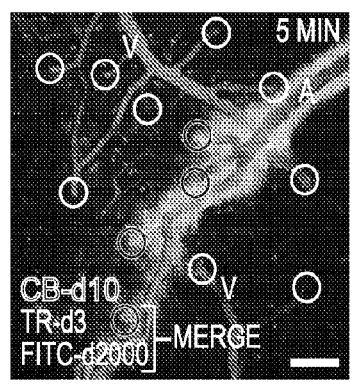
Figure 2C:
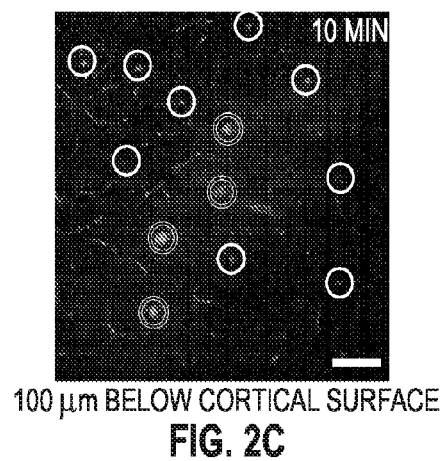
Figure 2D:
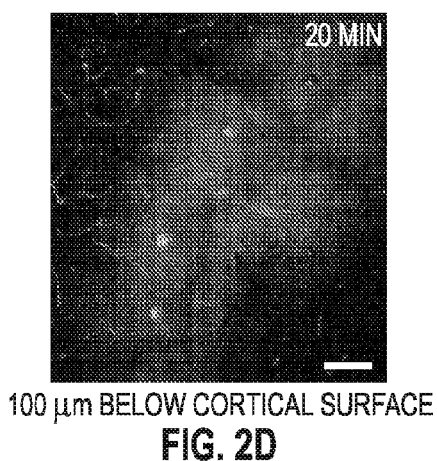
Figure 2E:
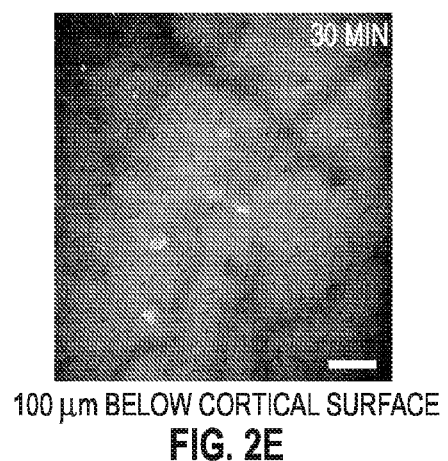
Figure 2F:
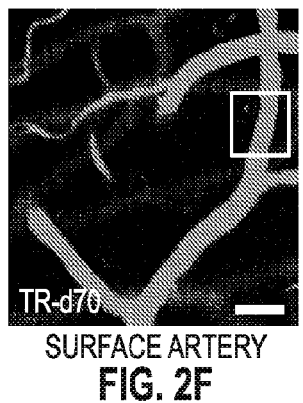
Figure 2G:
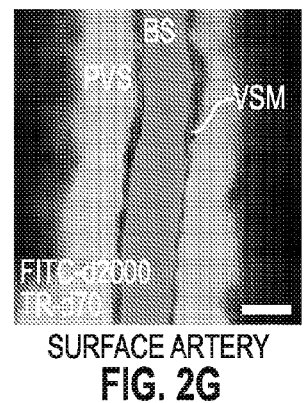
Figure 2H:
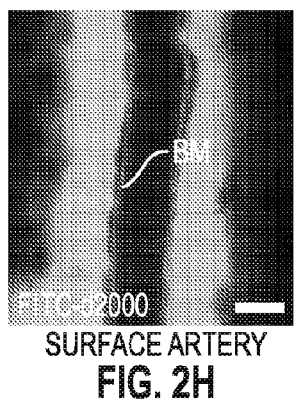
Figure 2I:
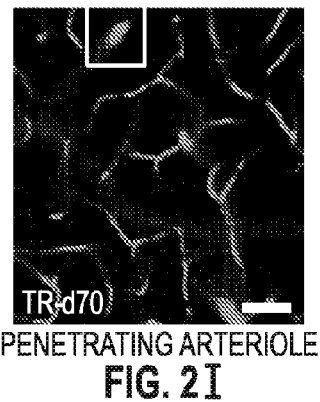
Figure 2J:
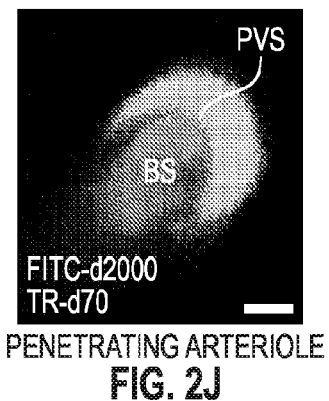

Two-photon laser scanning microscopy was next used to visualize in real time the routes and kinetics of subarachnoid CSF influx into the brain parenchyma. By imaging through a closed cranial window in anesthetized mice (FIG. 2A), the movement of intracisternally injected fluorescent dextrans into the cerebral cortex was visualized. The cerebral vasculature was labeled with blood-brain barrier (BBB)-impermeant fluorescent dextran (CB-dl 0) (intravenously), and penetrating arteries and veins were identified morphologically (FIG. 2B).

Figure 2K:
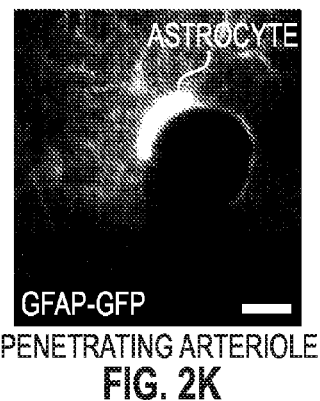
Figure 2L:
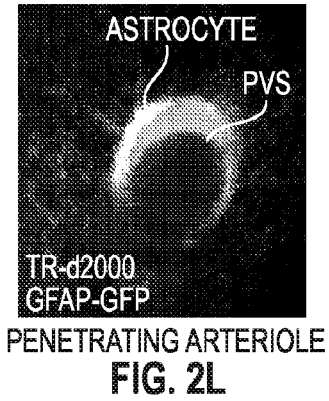
Figure 4A:
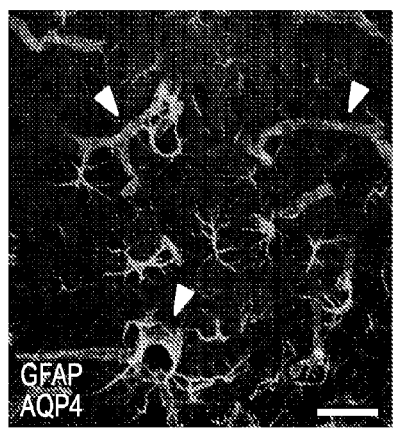
Figure 4B:
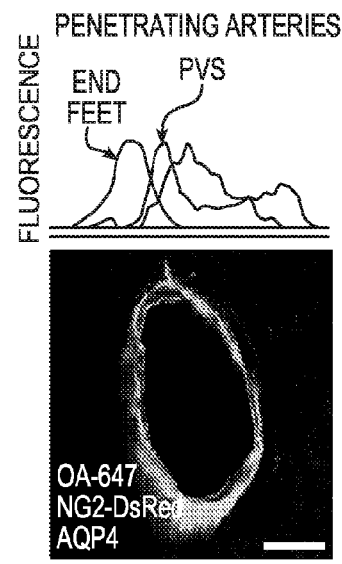
Figure 4C:
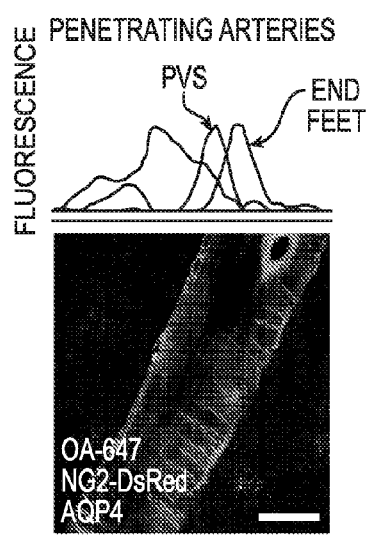
Figure 4D:
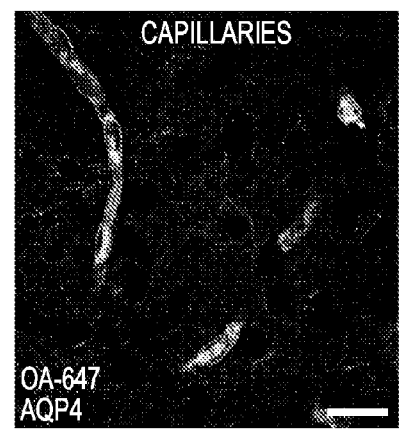

After injection, the tracers rapidly entered the brain along the outside of cortical surface arteries and penetrating arterioles (FIGS. 2B and C and FIGS. 9A-D) through a pathway immediately surrounding the vascular smooth muscle cells (FIGS. 2F to J, and FIGS. 3C and E) and bounded by perivascular astrocytic endfeet (FIGS. 2K and L, and FIGS. 4B to D). This para-arterial CSF movement was seen as FITC-d40 (molecular size, 40 kD) influx more than ~35 min after intracisternal injection at the cortical surface, 60 and 120 mm below the cortical surface. Rapid tracer movement along the margins of surface arteries, rather than through the subarachnoid CSF, is consistent with the presence of paravascular sheaths surrounding cerebral surface arteries, as described by Weller (12). These paravascular spaces are continuous with the subarachnoid space yet provide distinct channels for the rapid para-arterial bulk flow of CSF into the parenchyma, driven by arterial pulsation (13-15).

Figure 9A:
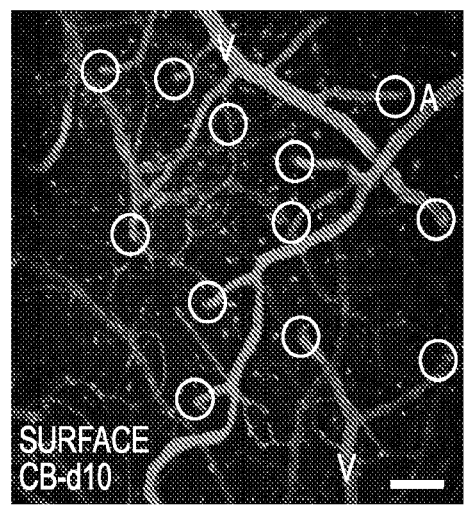
Figure 9B:
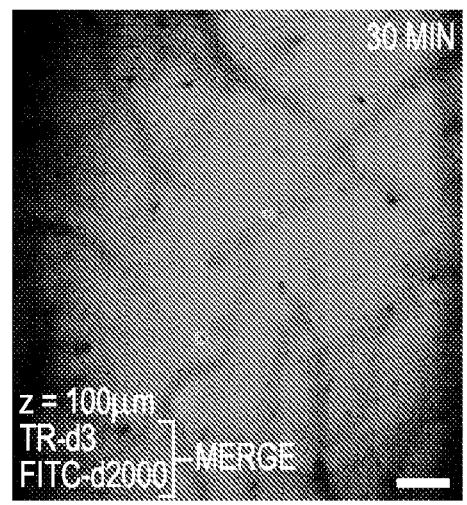
Figure 9C:
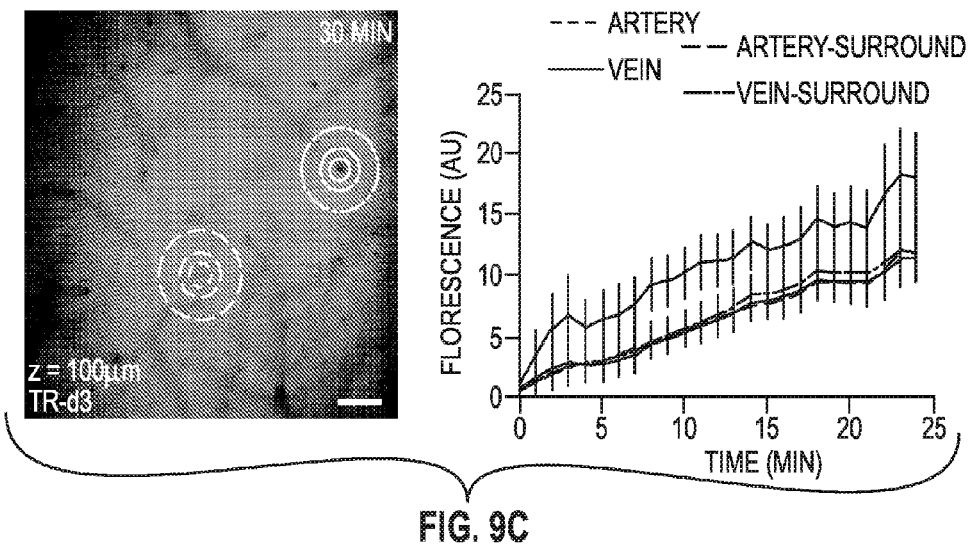
Figure 9D:
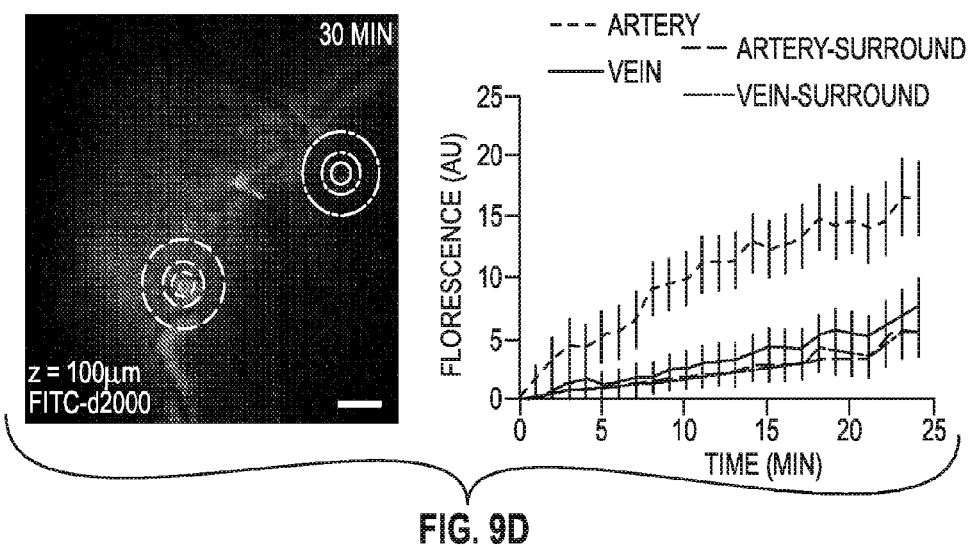

When TR-d3 (molecular size, 3 kD) and FITC-d2000 (molecular size, 2000 kD) were injected, both rapidly entered the paravascular spaces along penetrating cortical arteries, despite large differences in their respective molecular weights (FIGS. 9C and D). This suggested that their transit occurs via bulk CSF flow through the paravascular spaces (4, 16). In contrast, movement from the paravascular spaces into the surrounding tissue differed between FITC-d2000 and TR-d3. TR-d3 readily entered the interstitium, whereas the larger FITC-d2000 remained confined to the paravascular space (FIG. 2C to E, and FIGS. 9B to D). A recent study demonstrated that astrocytic endfeet cover most of the surface area of the murine cerebral microcirculation so that access to the parenchyma is provided only by ~20-nm clefts between overlapping endfeet (17). This suggests that perivascular astrocytic endfeet may serve a sieving function, thereby accounting for the size dependence of paravascular solute entry into the interstitium. Although water and small solutes may freely enter the brain interstitium from the paravascular spaces by bulk flow, large-molecular weight solutes [FITC-d2000; diameter of hydration (dH)>32 nm (9)] are excluded, whereas smaller solutes [for example, ovalbumin and TR-d3; dH=2 to 3 nm and 6.1 nm, respectively (9)] pass the endfeet in a size- and structure-dependent manner (FIG. 2E and FIGS. 9B to D).

Paravascular CSF Influx and Clearance Occur Throughout the Brain

Figure 3A:
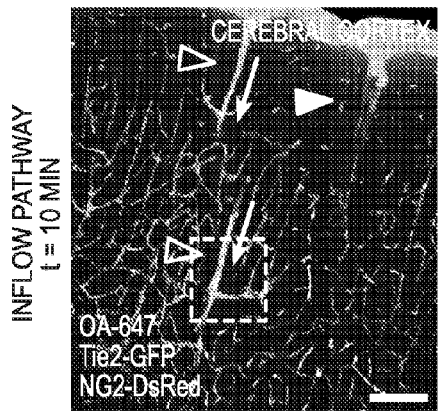
Figure 3B:
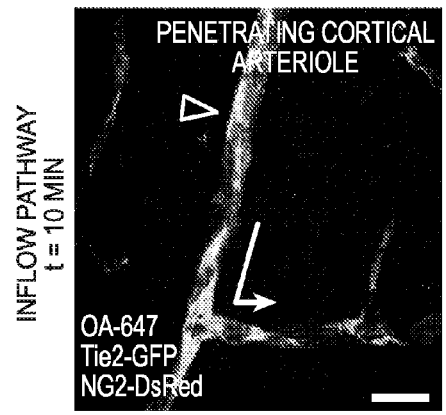
Figure 3C:
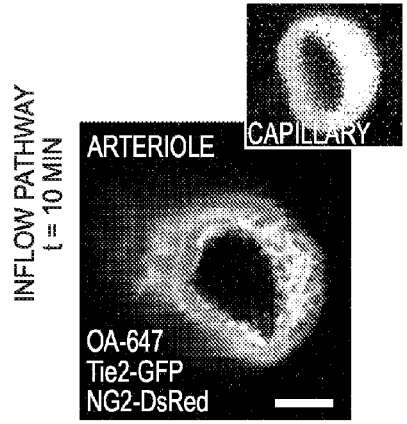
Figure 3D:
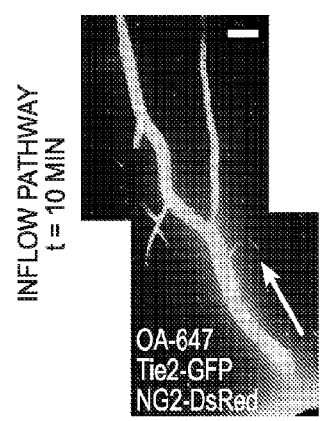
Figure 3E:
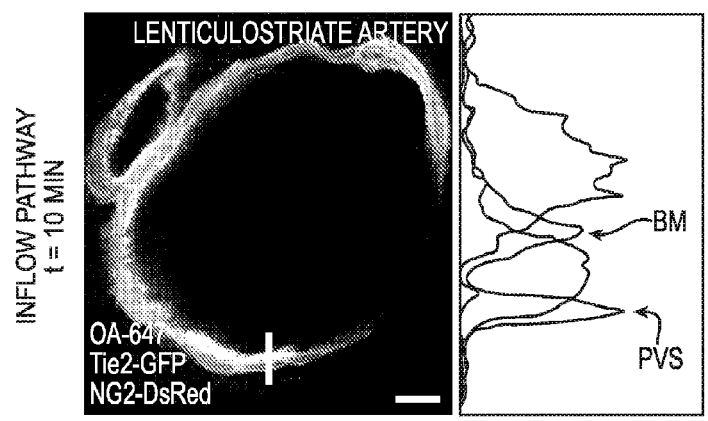
Figure 3F:
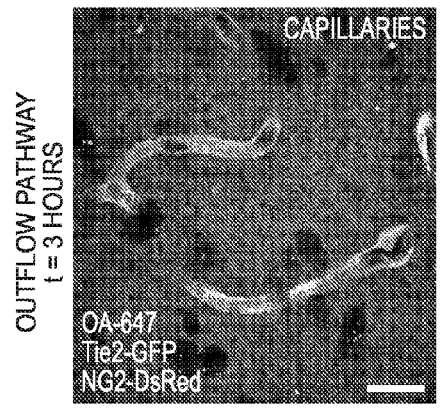
Figure 3G:
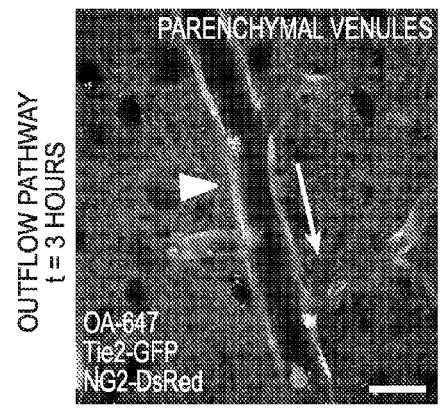
Figure 3H:
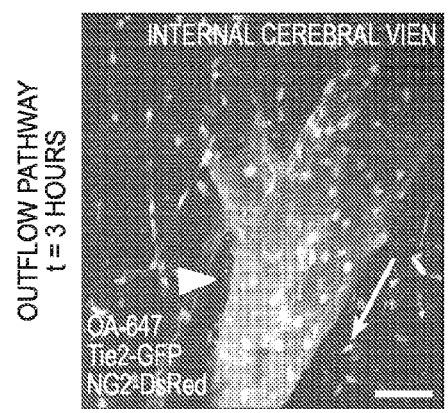
Figure 10A:
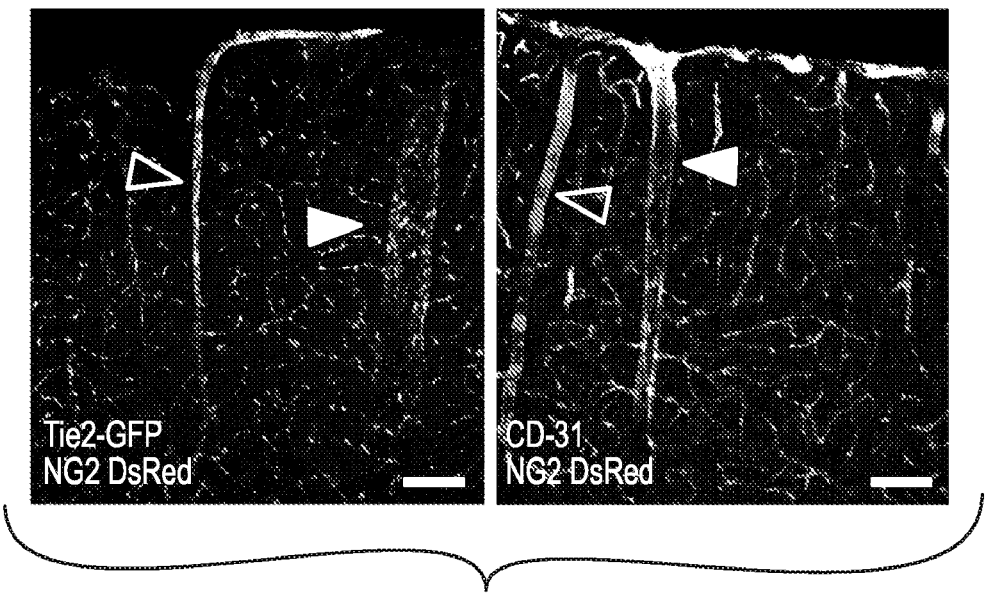
Figure 10B:
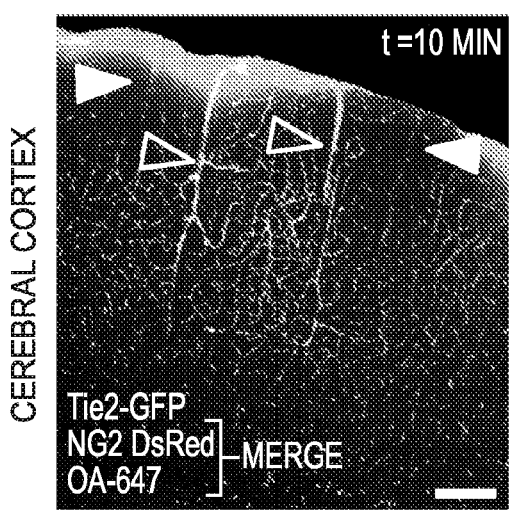
Figure 10C:
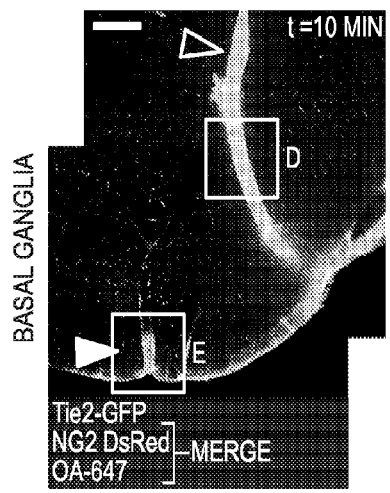
Figure 10D:
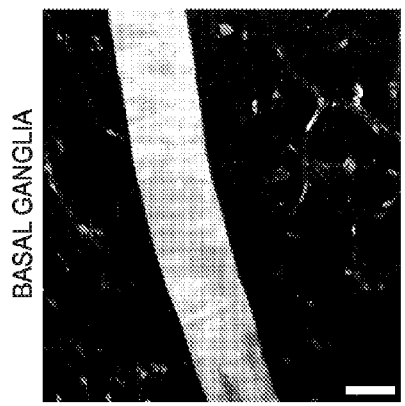
Figure 10E:
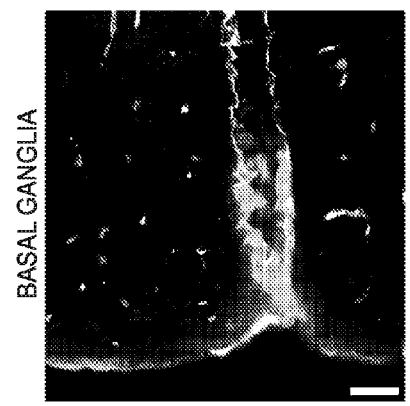

In vivo imaging demonstrated para-arterial influx of subarachnoid CSF into the cortex. However, because two-photon imaging cannot image tracer fluxes through deeper brain structures, an ex vivo approach was next used to map paravascular CSF influx and clearance throughout the brain. The distribution of the moderate molecular weight tracer ovalbumin-conjugated Alexa Fluor 647 (OA-647; molecular size, 45 kD) was analyzed in fixed vibratome sections of the Tie2-GFP:NG2-DsRed double-transgenic reporter mouse, in which arteries could be easily distinguished from veins (FIG. 10A). Immediately after intracisternal injection, the tracer moved rapidly inward along penetrating arteries and arterioles to reach the terminal capillary beds throughout the brain (FIG. 3A), with the largest influxes occurring along large ventral perforating arteries of the basal ganglia and thalamus (FIG. 3D and FIGS. 100 to E). The tracer was not observed around veins at early time points (<10 min after injection). At longer time points (>1 hour), tracers that had been injected intracisternally accumulated along capillaries and parenchymal venules (FIGS. 3F and G). The tracer exited the brain primarily along two paravenous routes: the medial internal cerebral veins and the lateral-ventral caudal rhinal veins (FIG. 3H). Intraparenchymal tracer injected directly into the cortex, striatum, or thalamus was cleared along the same common anatomical pathways, traveling either posterior-medially toward the internal cerebral veins or posterior-lateral-ventrally along the external capsule until its exit from the parenchyma along the caudal rhinal veins (FIGS. 11A to E). These results demonstrated that ISF and CSF that is moving through the brain parenchyma are cleared along the same paravenous drainage pathways.

Figure 4E:
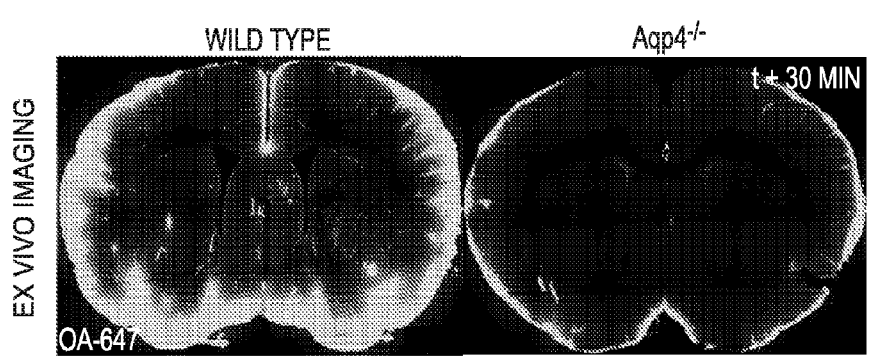
Figure 4F:
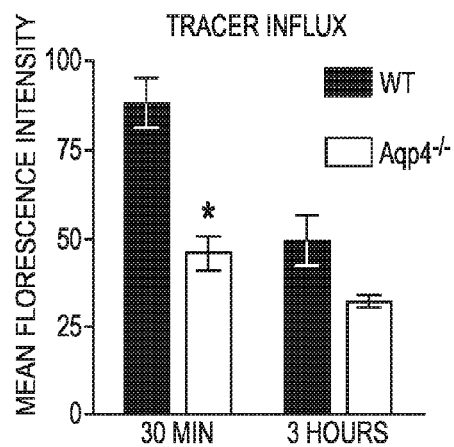
Figure 4G:
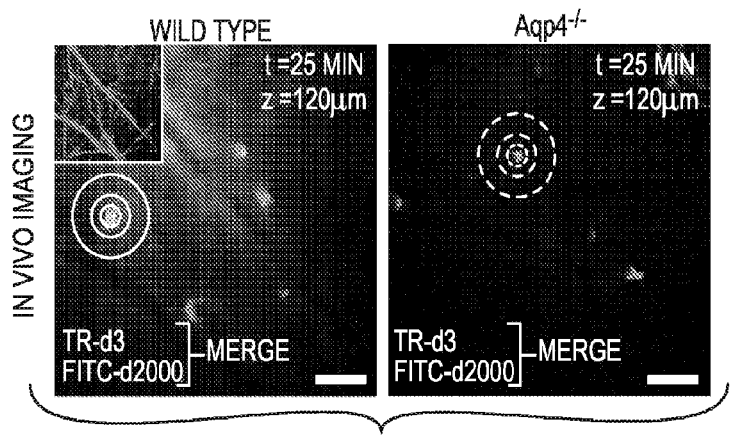
Figure 4H:
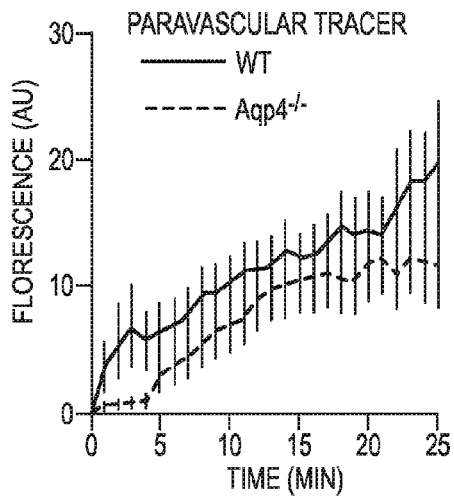
Figure 4I:
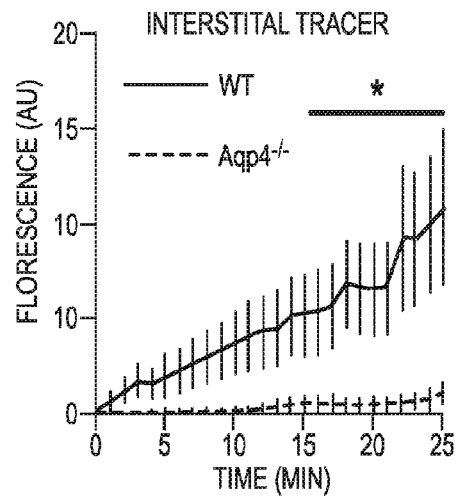
Figure 12A:
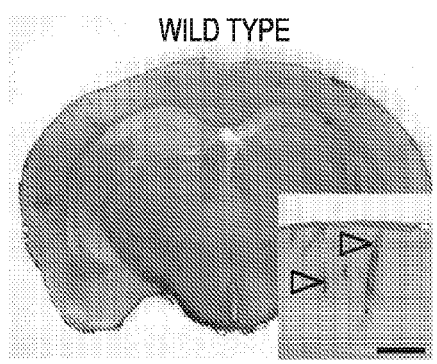
Figure 12B:
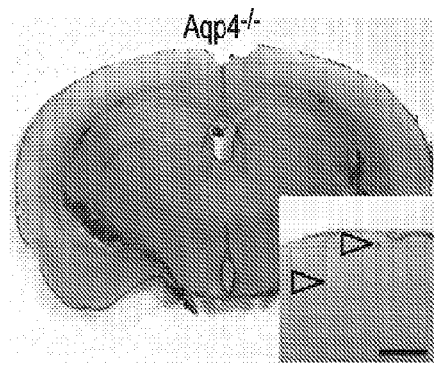
Figure 12C:
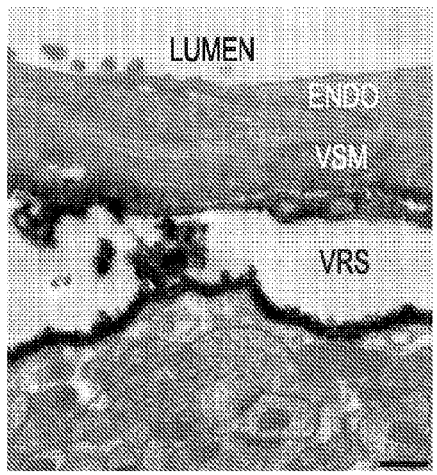
Figure 12D:
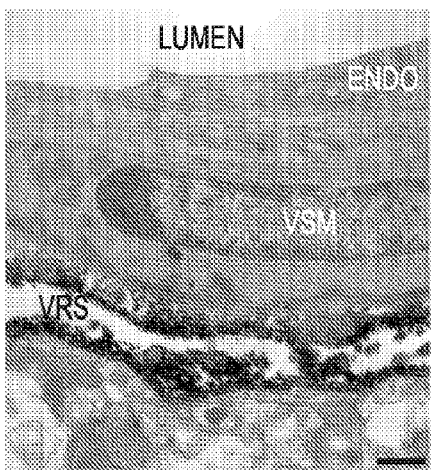
Figure 12E:
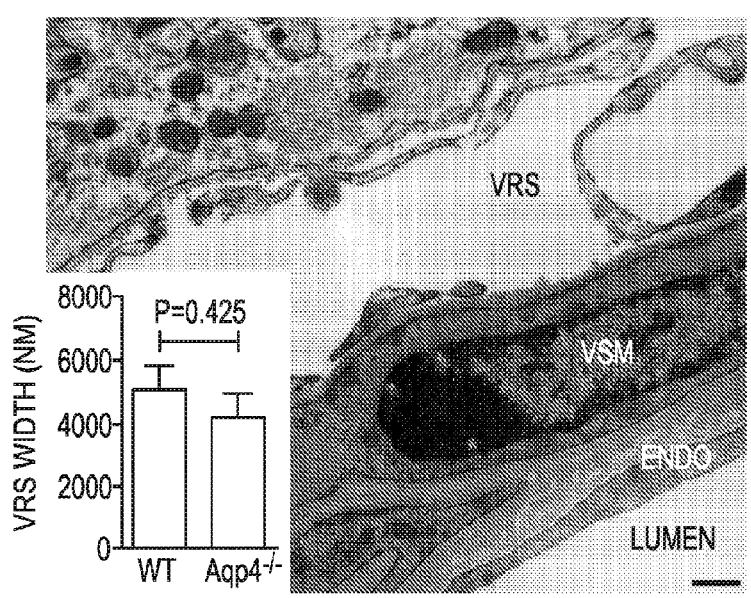

Astroglial water transport supports CSF flux into the parenchyma The localization of astroglial aquaporin-4 (AQP4) water channel is highly polarized to perivascular endfeet (FIG. 4A) that bound the para-arterial CSF influx and the paravenous ISF clearance pathways (FIGS. 4B to D). These astrocytic water channels provide low-resistance pathways for fluid movement between these paravascular spaces and the interstitium, linking paravascular and interstitial bulk flow and maintaining convective currents (3, 9) that drive the clearance of interstitial solutes from the brain parenchyma. To investigate this, it was determined whether increasing parenchymal resistance to fluid flux by the global knockout of the Aqp4 gene altered CSF flux through the interstitium. When CSF tracer influx was imaged ex vivo, tracer movement into the brain parenchyma was markedly reduced in Aqp4-null compared to wild-type control mice (FIGS. 4E and F, and FIGS. 12A and B). In vivo imaging confirmed these findings. After intra-cisternal injection, FITC-d2000 movement along the para-arteriolar inflow path was not significantly slowed in Aqp4-null mice (FIGS. 4G and H), demonstrating that bulk flow through the proximal segment of the para-arterial influx pathway (the Virchow-Robin space) was not compromised by Aqp4 deletion. In contrast, TR-d3 movement from the paravascular space into the surrounding interstitium was effectively abolished in Aqp4-null mice (FIGS. 4G and I). It was confirmed that in Aqp4-null mice, the paravascular spaces surrounding penetrating cortical arterioles were ultrastructurally normal through the depth of the cortex (FIGS. 12C to E) and that intracisternally injected FITC-d40 was detectable within the paravascular space of Aqp4-null as well as in that of wild-type mice by electron microscopy (FIGS. 12C and D).

Figure 13C:
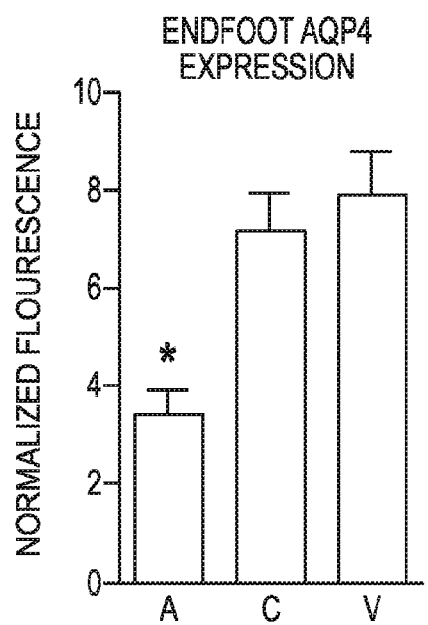
Figure 13D:
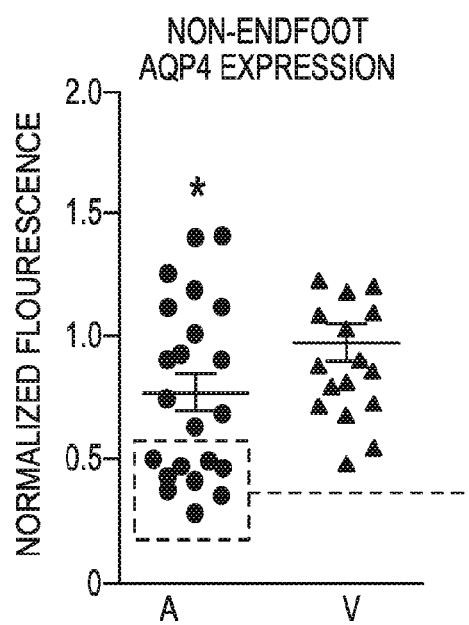

Differences in AQP4 expression may contribute to the polarization of bulk flow along these para-arterial CSF influx and paravenous ISF clearance pathways AQP4 immunoreactivity in NG2-DsRed animals (in which veins and arteries can be distinguished) was therefore assessed to define the relative amount of AQP4 expression in periarterial, perivenous, and pericapillary endfeet. Whereas perivenous and pericapillary endfeet did not differ in AQP4 expression, periarterial endfeet exhibited significantly less AQP4 immunoreactivity (FIGS. 13A to C). When non-endfoot AQP4 expression around arteries and veins was compared to expression around capillaries, reduced periarterial expression was clear (FIGS. 13A, B and D). This effect was largely due to a subpopulation of penetrating arteries that exhibited sharply diminished AQP4 immunoreactivity (FIGS. 13A and D).

Astroglial Water Transport Facilitates Bulk ISF Solute Clearance from the Parenchyma These data demonstrate that astroglial water flux facilitates the movement of subarachnoid CSF into and through the brain interstitium. One possible function for this transparenchymal CSF flux is the clearance of fluid and solutes from the brain interstitium.

This was tested by examining the effect of Aqp4 gene deletion upon the clearance of radiolabeled [$^3$H]mannitol from the brain parenchyma (FIG. 14A). In Aqp4-null mice, [$^3$H]mannitol clearance from the brain interstitium was reduced by ~70% compared to that of wild-type animals (FIG. 5A). In wild-type mice, the rate of clearance for [$^3$H]dextran-10 (with a 55-fold larger molecular size than mannitol) was identical to that of [$^3$H]mannitol (FIG. 14B), confirming that bulk ISF flow rather than diffusion is responsible for the clearance of these interstitial-delivered tracers (4, 9). The clearance of [$^3$H]dextran-10 was also significantly reduced in Aqp4-null mice (FIG. 14B). The present example demonstrates that astroglial AQP4 supports the bulk ISF flow that drives the clearance of interstitial solutes from the brain parenchyma. AQP4 facilitates the paravascular clearance of interstitial amyloid β Soluble amyloid β (Aβ) is present in the interstitium of the healthy young brain, yet interstitial Aβ levels are correlated with amyloid plaque burden (18).

Figure 6A:
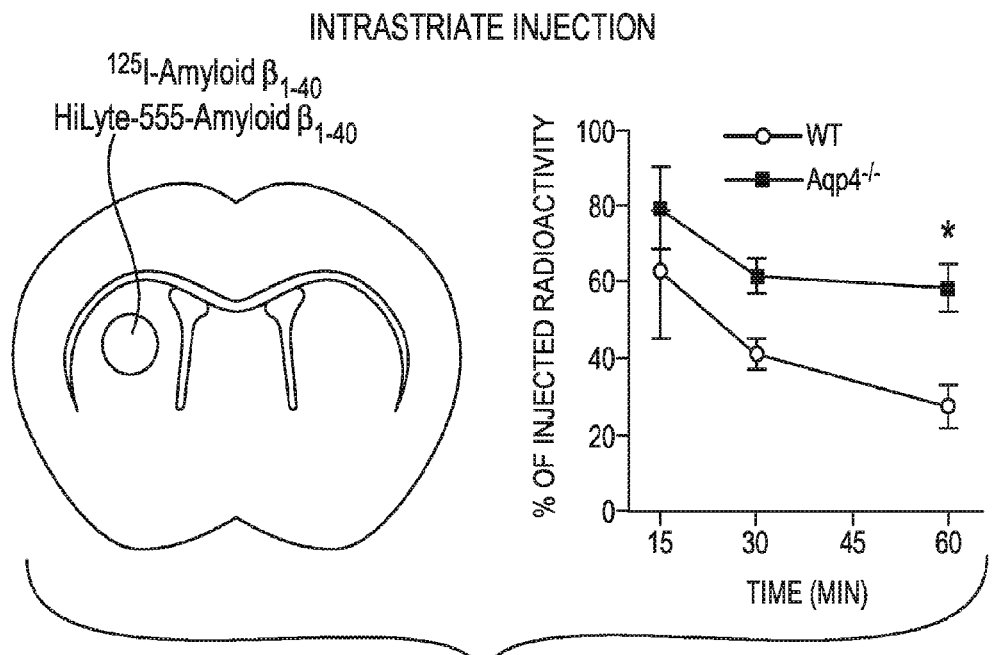
Figure 6B:
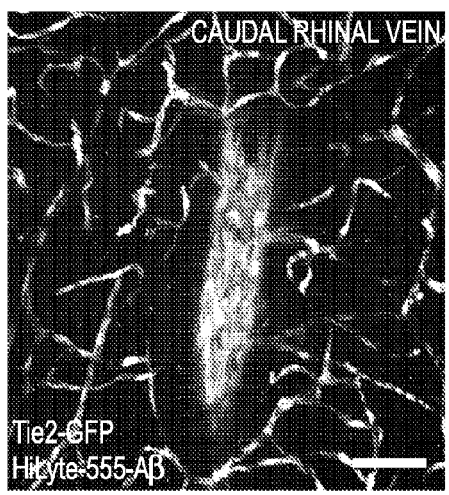
Figure 6C:
Figure 6D:

It was evaluated whether AQP4-dependent ISF bulk flow contributes to the clearance of soluble Aβ from the brain. After intrastriatal injection of $^{125}$I-amyloid β1-40, the compound was rapidly cleared from the brain (FIG. 6A). In agreement with the receptor-mediated efflux of Aβ across the BBB (19), the rate of $^{125}$I-amyloid $\beta_{1\text{-}40}$ clearance from the brain exceeded that of either [$^3$H]mannitol or [$^3$H] dextran-10, which lacks specific efflux receptors (FIG. 14A-B). In Aqp4-null mice, the rate of $^{125}$I-amyloid $\beta_{1\text{-}40}$ clearance was reduced by ~55% (FIG. 6A) compared to that of wild-type controls. This suggests that a large proportion of soluble Aβ is removed by bulk flow along the gliovascular clearance system rather than locally across the BBB. In support of this conclusion, fluorescent-tagged Aβ was observed to move rapidly along the vasculature when injected in the striatum, accumulating along the microvasculature and large-caliber internal cerebral and caudal rhinal veins (FIGS. 6B to D).

Soluble Aβ is also present in the CSF, from which it may be cleared by transport across the choroid plexus (20), as well as by bulk CSF turnover (21). It was thus asked whether soluble $A\beta_{1\text{-}40}$ within the CSF compartment recirculates through the brain parenchyma. After intracisternal $^{125}$I-amyloid $\beta_{1\text{-}40}$ injection, brain $^{125}$I-amyloid $\beta_{1\text{-}40}$ levels increased in a manner comparable to [$^3$H]dextran-10 (FIG. 6E, compare to FIG. 1O). In the Aqp4-null mouse, bulk influx of $^{125}$I-amyloid $\beta_{1\text{-}40}$ was significantly reduced compared to wild types (FIG. 6E). These data suggest that although interstitial soluble Aβ is cleared along the gliovascular pathway, a portion of Aβ within the CSF compartment may recirculate through the brain along this same route.

FIG. 7 shows quantification of fluorescent CSF tracer distribution within the brain parenchyma. After injection of intracisternal A594, TR-d3 and FITC-d2000 injections, animals were perfusion fixed and 100-μm vibratome sections cut. Slices were imaged by epifluorescence microscopy at 4× and montages generated. To evaluate tracer coverage, the color channels were separated, the images background subtracted, uniformly thresholded and the thresholded area was calculated and expressed as a percentage of overall slice area.

FIG. 8 shows measurement of subarachnoid CSF entry into the brain parenchyma. Schematic diagram depicting the measurement of subarachnoid CSF entry into the brain parenchyma. $^3$H-Mannitol, $^3$H-Dextran-10 or $^{125}$I-A$\beta_{1-40}$ was injected intracisternally. To quantify radiotracer accumulation within the brain parenchyma, the brain was harvested 15, 30 or 45 min after radio-tracer injection. Brains were solubilized in Soluene, and then total brain radioactivity was measured by liquid scintillation counting. The proportional brain radioactivity (R'Brain) was calculated based upon the total measured brain radioactivity (RBrain) and the total injected radioactivity (RInject). During harvest, the dura was removed from the brain. Thus the brain homogenate does not include radio-tracer remaining in the subarachnoid CSF compartment.

FIGS. 9A-D show in vivo imaging of para-arterial influx of small- and large-molecular weight tracers. The movement of two dextrans of differing molecular weight (TR-d3 and FITC-d2000) along para-arterial pathways and into the cortical interstitium was imaged in anesthetized mice by in vivo 2-photon laser scanning microscopy within a closed cranial window. (A) The cerebral vasculature was visualized with intra-arterial Cascade Blue-dextran-10 (CB-d10) and penetrating arterioles (A) and veins (V) were identified morphologically (red and blue circles, respectively). (B-D) The movement of small and large molecular weight tracer along para-arterial and paravenous pathways was evaluated by measuring the mean fluorescence intensity within circular ROIs centered on penetrating vessels. The movement of tracer into the surrounding interstitium was defined by measuring mean fluorescence intensity in donut-shaped ROIs centered upon penetrating vessels (red and blue dashed donuts). (C) Small molecular weight tracer moved readily from the para-arterial space (red solid line) into the para-arterial (red dashed line) and paravenous (blue dashed line) interstitium. The lack of a statistically-significant difference (P=0.056, n=6 each group) between the curves indicates that this tracer enjoys relatively unrestricted movement outward from the para-arterial space. (D) Large molecular weight tracer moved readily into the cortex along penetrating arterioles (solid red line) but not along penetrating venules (solid blue line; *P<0.01, n=6 each group). Tracer intensity measured in the tissue surrounding penetrating arterioles and veins (dashed red and blue line, respectively) remained at the same low levels observed for paravenous spaces. Thus, large molecular weight tracer remains confined primarily to para-arterial spaces and does not readily enter the brain interstitium. Scale bars: 100 μm.

FIGS. 10A-E show that CSF does not enter the brain parenchyma along paravenous pathways. To evaluate para-arterial versus paravenous subarachnoid CSF tracer influx, OA-647 was injected intracisternally into Tie2-GFP:NG2-DsRed double reporter mice. (A) In these mice, the endothelium of all blood vessels is labeled with GFP while vascular smooth muscle cells and pericytes are labeled with DsRed. Thus arteries and arterioles (empty arrowheads) are easily distinguished by the presence of distinct circumferential DsRed labeling, while veins (filled arrowheads) lack such labeling. The arterial specificity of NG2-DsRed labeling is seen when brain slices from NG2-DsRed mice are labeled with the endothelial marker CD-31 (right). (B) In the cerebral cortex, intracisternal tracer enters the brain along DsRed+ penetrating arterioles but not along DsRed-veins. Distal venous labeling is seen at times, but typically originates from a para-arteriolar inflow path via the intervening capillary bed. (C-E) Large vessels along the ventral brain surface exhibit the same pattern. Paravascular spaces surrounding large perforating arteries (empty arrowheads, D) move large fluxes of CSF tracer into the parenchyma, while tracer does not substantially penetrate into the parenchyma along basal draining veins (filled arrow heads, E). Scale bars: 100 μm (B, C), 50 μm (A), 20 μm (D-E).

FIGS. 11A-E show that intracisternally and intraparenchymally injected tracer shares the same paravenous drainage pathway. Tie2-GFP:NG2-DsRed double reporter mice were injected intra-parenchymally with OA-647. (A-B) Intracortically-injected tracer accumulated around the microvasculature, and moved outward from the injection site most rapidly along para-capillary and paravenous (arrowheads) pathways. (C-D) Intra-striate tracer similarly accumulated around capillaries and venules. Tracer that was injected into gray matter was excluded from white matter bundles (asterisks, D). (E) Intra-parenchymal tracer was cleared from the brain primarily along the internal cerebral and caudal rhinal veins, although lesser clearance along cortical ascending veins and venules was also observed. Scale bars: 50 μm (B, D-E), 20 μm (A, C).

FIGS. 12A-E shows visualization of paravascular accumulation of tracer and the Virchow-Robin space in wild-type and Aqp4-null mice. (A-B) Intracisternally injected FITC-d40 was visualized by DAB immunohistochemistry. 5 minutes after injection, reaction product is evident along penetrating cortical vessels (arrows in inset) of wild type animals (A). Labeling intensity around vessels is much weaker in Aqp4-null animals (B). Insets show labeling in parietal cortex at high magnification. (C-D) Electron micrographs showing the electron dense DAB reaction product in the proximal paravascular space (Virchow-Robin space, VRS) surrounding penetrating cortical arterioles. Compared to wild type animals (C), the VRS in Aqp4-null animals (D) appears ultrastructurally intact. (E) VRS of an uninjected Aqp4-null animal visualized ~1000 μm below the cortical surface. Inset shows width of VRS around penetrating vessels (n=10 for wild type animals, n=11 for Aqp4-null animals; values are mean±SEM). Endo, endothelial cell; VSM, vascular smooth muscle cell. Scale bars: 500 μm (insets in A and B), 1 μm (C-E).

FIGS. 13A-D shows differential expression of AQP4 in periarterial versus perivenous astrocytes. (A-B) Immunofluorescence labeling for AQP4 in the cortex of NG2-DsRed mice. Penetrating arteries are readily distinguished by intense, circumferential DsRed labeling of the vascular smooth muscle (A, empty arrowhead) while ascending veins exhibit irregular DsRed labeling (B, solid arrowhead). (C) Quantification of AQP4 immunoreactivity in perivascular endfeet, normalized to background AQP4 intensity. Periarterial endfeet expressed significantly less AQP4 than did pericapillary or perivenous endfeet (*P<0.01, ANOVA; n=24 arteries, 19 veins and 43 capillaries from 3 animals). (D) When AQP4 immunoreactivity was measured within 20 μm of the vessel wall (excluding the endfeet), periarterial AQP4 intensity was significantly reduced compared to levels around capillaries levels (*P<0.05, t-test). This was largely driven by a subpopulation of penetrating arteries (~40% of overall group) that exhibited a marked absence of AQP4 immunoreactivity labeling for up to 50 μm surrounding the vessel (seen in A).

FIGS. 14A-B shows measurement of interstitial solute clearance from the brain. (A) Schematic diagram depicting the measurement of interstitial solute clearance from the brain parenchyma. $^3$H-mannitol, $^3$H-dextran-10 or $^{125}$I-amyloid $\beta_{1-40}$ was injected into the striatum. To quantify radiotracer clearance from the parenchyma, the brain was harvested at t=1 or 2 hrs following radio-tracer injection. Brains were solubilized, then total brain radioactivity was measured by liquid scintillation counting. The remaining brain radioactivity (R'Brain) was calculated based upon the total measured brain radioactivity (RBrain) and the total injected radioactivity (RInject). When the brain was harvested, the dura was removed. Thus the measured RBrain value does not include radio-tracer present within the subarachnoid space. (B) The effect of Aqp4 gene deletion upon the clearance of intra-parenchymally injected $^3$H-dextran-10 from the brain. In wild type animals, both $^3$H-mannitol and $^3$H-dextran-10 were cleared from the brain at identical rates. This is consistent with the observation that bulk flow [in contrast to diffusion(9)]-mediated transport is independent of molecular weight(4). Aqp4 gene deletion had an effect upon the efflux of $^3$H-dextran-10 similar to that of $^3$H-mannitol (FIG. 14B), markedly reducing the rate of their clearance from the brain parenchyma (*P<0.01, n=4 per time point).

FIGS. 15A-B are schematic diagrams of paravascular and interstitial bulk flow pathways. (A) Schematic depicting the proposed role of periarterial astroglial endfoot AQP4 in facilitating bulk water flow between the para-arterial influx pathway and the interstitial compartment. Because of high AQP4 expression, water passes freely across the perivascular endfoot. Small solutes, including the fluorescent tracer TR-d3 (MW 3 kD), follow the resulting osmotic gradient into the interstitium through intercellular clefts between overlapping endfoot processes. Large solutes, including FITC-d2000 (MW 2000 kD), cannot pass this cleft and are retained in the paravascular space. In Aqp4-null mice, water flux between the paravascular space and the interstitium is reduced, as is accompanying solute movement into the interstitium. Inset depicts physical dimensions of TR-d3, FITC-d2000 [dH, hydration diameter (9] and the inter-endfoot cleft (17). (B) Detailed schematic depicting the proposed role of astroglial AQP4 in maintaining convective ISF bulk flow and interstitial solute clearance. Para-arterial and paravenous AQP4 permits the free movement of water between the para-arterial influx and paravenous clearance pathway. This convective water flux sweeps interstitial solutes and tracers (such as $^3$H-mannitol and $^3$H-dextran-10) along its path. In Aqp4-null mice, water flux between the paravascular spaces and the interstitium are reduced, resulting in the failure of interstitial solute clearance. Inset depicts the physical dimensions of $^3$H-mannitol, $^3$H-dextran-10 and the inter-endfoot cleft.

Discussion

In this example, a brain-wide pathway is identified for fluid transport in mice, which includes the para-arterial influx of sub-arachnoid CSF into the brain interstitium, followed by the clearance of ISF along large-caliber draining veins. Interstitial bulk flow between these influx and efflux pathways depends upon trans-astrocytic water movement, and the continuous movement of fluid through this system is a critical contributor to the clearance of interstitial solutes, likely including soluble Aβ1-40, from the brain. In light of its dependence on glial water flux, and its subservience of a lymphatic function in interstitial solute clearance, this system has been named the "glymphatic" pathway (FIG. 5B and FIGS. 15A-B).

Figure 11A:
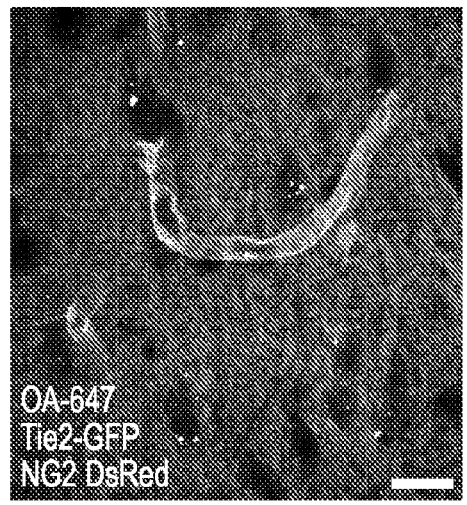
Figure 11B:
Figure 11C:
Figure 11D:
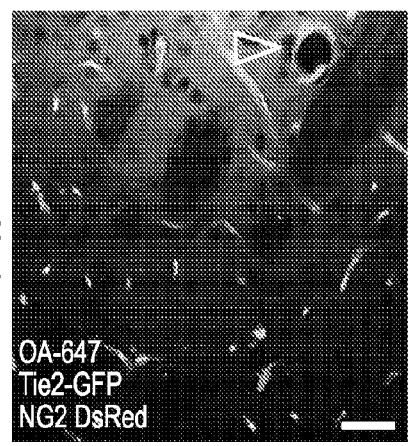
Figure 11E:

The relationship between the CSF compartment and the peripheral lymphatics is well established (8). In mammals, ~50% of radiolabeled albumin injected into the CSF drains to the cervical lymphatics via the cribriform plate, whereas the remainder is cleared to the bloodstream via arachnoid granulations of the dural sinuses (22-24). These recognized patterns of drainage initially led to the concept that CSF serves a "lymphatic" function through its exchange with brain ISF along paravascular spaces (6, 25). Consistent with our findings reported here, studies in the rat demonstrated that as much as 75% of tracer injected into the brain interstitium was cleared to the sub-arachnoid CSF, accounting for about 11% of total CSF production (26). In this example, the identification of paravenous pathways, particularly those surrounding the medial internal cerebral and caudal rhinal veins, as the primary route for clearance is in contrast to some studies identifying para-arterial sheaths as pathways for tracer clearance (26, 27). This para-arterial labeling after intraparenchymal injections is largely an artifact of high local intraparenchymal pressure from the injection and does not reflect the natural pathway for solute efflux. With intraparenchymal injections, para-arterial spaces accumulated tracer close to the injection site. If observations are limited to these sites, then it might mistakenly be concluded that tracer efflux is occurring primarily along para-arterial efflux pathways. However, at locations most remote from the injection site, tracer accumulation was greatest surrounding large-caliber draining veins (FIG. 3H and FIG. 11E).

These results confirm, in part, the basic observations of Rennels et al. (15, 28) in which horseradish peroxidase (molecular size, 40 kD) injected into subarachnoid space at the cisterna magna in the cat moved rapidly into the brain along para-arterial pathways. These findings were rebutted by Cserr and colleagues, who concluded that paravascular influx of subarachnoid CSF was "slow and variable in direction" (11, 29). The present findings, including in vivo two-photon imaging (FIGS. 2A-L and 9A-D), ex vivo analysis with double-transgenic reporter mice (FIGS. 1A-O, 3A-H, 10A-E and 11A-E), and quantitative radiotracer experiments (FIG. 1O), refute this conclusion. One possible reason for these discrepant findings is the previous studies' choice of larger-molecular weight tracers. In vivo (FIGS. 2B-E and 9A-D) and ex vivo imaging, as well as radiotracer influx data (FIG. 1O), demonstrate that tracer influx from the sub-arachnoid space into the brain parenchyma is dependent upon molecular weight. In previous studies evaluating the movement of subarachnoid CSF into the brain parenchyma, inulin (molecular size, ~5 kD), albumin (molecular size, 66 kD), and dextrans (usually 2000 kD) are typically used as CSF tracers (3, 10, 11, 29). On the basis of these findings, these studies underestimated the extent and rate of subarachnoid CSF influx into the brain interstitium. Other methodological differences appear to be at play as well. Pullen et al. used an open ventriculo-cisternal and cisterno-cisternal perfusion method that left the cisternal outflow tube open to the atmosphere for sample collection (29). Ichimura et al. pressure injected tracer directly into the paravascular and subarachnoid space at the site of observation (11). In experiments (data not shown), it was found that when the dura was pierced, as in the methodology used by Cserr and colleagues (11, 29), paravascular tracer flux was virtually abolished, suggesting that the maintenance of the hydraulic integrity of the subarachnoid and paravascular spaces is critical for maintaining paravascular bulk flow.

Role of AQP4 in Paravascular Pathway Function

These data suggest that AQP4-dependent astroglial water fluxes couple para-arterial CSF influx to paravenous ISF clearance within the brain. AQP4 has been implicated in water uptake into the brain tissue during the evolution of cytotoxic edema, as well as in water clearance after vasogenic edema (30, 31). These observations suggest that perivascular AQP4 facilitates the influx of subarachnoid CSF from para-arterial spaces into the brain interstitium, as well as the subsequent clearance of ISF via convective bulk flow (3, 4). Bulk flow CSF movement was observed along para-arterial pathways directly using in vivo two-photon imaging of intracisternally injected TR-d3 and FITC-d2000 Both of these agents moved rapidly along the wall of pial arteries to enter the Virchow-Robin spaces without mixing with CSF in the surrounding subarachnoid compartment (FIG. 2B). Consistent with ultrastructural analyses of leptomeningeal vessels conducted by Weller (12), this indicates that the paravascular space around surface arteries and the Virchow-Robin space into which these penetrate comprise a physically and functionally distinct subcompartment through which CSF rapidly enters the brain parenchyma by bulk flow. This CSF flux is likely driven by arterial pulsation (13-15): the directionality of CSF influx into para-arterial spaces perhaps reflecting the differing pulse pressures between para-arterial and paravenous pathways.

Perivascular astrocytic endfeet provide complete coverage of the cerebral microvasculature, with only 20-nm clefts between overlapping processes providing direct communication with the interstitium (17). This interposes a high-resistance barrier to fluid and solute flux between paravascular and interstitial compartments. AQP4, which occupies ~50% of the surface area of capillary-facing endfeet (32), constitutes a low-resistance pathway for water movement between these compartments. Transglial water movement, presumably driven by the hydrostatic pressure of para-arterial bulk flow, may drive solute flux from the paravascular space into the interstitium, either via specific astroglial solute transporters or through the intercellular cleft between endfeet. This role for AQP4 is supported by the effect of Aqp4 gene deletion on the movement of TR-d3 between the paravascular space and the surrounding interstitium. The sieving effect of the endfeet (restricting the movement of solutes as they approach a dH of 20 nm) may account for the influence of molecular weight on tracer penetration into the interstitium (FIGS. 15A-B).

As subarachnoid CSF enters the interstitium and mixes with ISF, both are cleared together with any associated solutes (including soluble Aβ) along specific paravenous pathways, including both the internal cerebral and the caudal rhinal veins. These veins drain directly into the great vein of Galen and the straight sinus (internal cerebral vein) and the transverse sinus (caudal rhinal vein) (33). As with the para-arterial influx route, AQP4 localized to astroglial endfeet around the microvasculature, and these large draining veins provide a low-resistance pathway for water and accompanying solute efflux into the paravenous compartment. This is consistent with the observation that in Aqp4-null animals, bulk flow-dependent clearance of interstitial solutes was reduced by ~70%. The relationship between these paravenous spaces and the dural sinuses can provide a low-pressure sink that, in combination with arterial pulsations within the subarachnoid space, results in an arterio-venous hydrostatic gradient that drives paravascular CSF bulk flow and ISF clearance. In this context, the higher expression of perivascular AQP4 surrounding veins compared to arteries may help to maintain low resistance clearance routes for ISF. This is supported by the observation that mice lacking the Aqp4 gene exhibit an enlarged extracellular space in the brain parenchyma compared to wild-type animals (34), which may represent a compensatory phenomenon to counteract the higher resistance toward parenchymal bulk ISF efflux in these mice. Mice with mislocalized or absent perivascular astrocytic AQP4, including a-syntrophin (35), mdx (36), and Aqp4 (37) knockout mice, show swollen endfeet and other pathological changes to perivascular astrocytes. These changes, related to the dysregulation of scaffolding at the perivascular endfoot, might account for the observed effects of Aqp4 gene deletion on interstitial bulk flow and solute clearance. Subsequent electron microscopic studies, however, reported no apparent ultrastructural changes in either the BBB or the perivascular astrocytic endfeet of Aqp4-null mice (38, 39), and the present analysis demonstrated that the paravascular space of Aqp4-null mice was structurally intact through the depth of the cortex (FIGS. 12A-E).

Although this example demonstrates that interstitial solutes are cleared by AQP4-dependent bulk flow along paravenous pathways, these pathways may not necessarily be the terminal route for solute clearance from the cranium. From previous studies, two routes for such terminal clearance appear most likely. First, the movement of solutes along the microvasculature and large draining veins of the brain provide ready access of solutes to specific transport mechanisms at the blood-brain barrier (BBB). A second possibility is that solutes draining along the internal cerebral and caudal rhinal veins to their associated sinuses are cleared to the bloodstream via arachnoid granulations (22-24), providing an exit route for interstitial solutes that do not interact with or have saturated specific transport pathways at the BBB.

The Paravascular Pathway and Disease

The finding that disruption of this pathway in Aqp4-null mice resulted in the failure of solute clearance is clinically relevant for neurodegenerative diseases in which the mis-accumulation of neurotoxic depositions contributes to disease development. Ball et al. have reported that intraparenchymally injected Aβ is cleared along paravascular pathways (40), whereas the failure of paravascular soluble Aβ clearance has been suggested to underlie the formation of extracellular Aβ aggregates and disease progression in Alzheimer's disease (41). In the present example, fluorescent-tagged soluble $Aβ_{1-40}$ injected into the brain parenchyma was cleared along the same paravascular pathways as other fluorescent tracers and the clearance of radiolabeled $Aβ_{1-40}$ from the interstitium was substantially reduced in Aqp4-null mice. This is significant because of the association of Alzheimer's disease with reactive gliosis and the increasing gliosis observed in the aging brain (42-44). Altered AQP4 expression and localization in reactive astrocytes under neuropathological conditions (45) may contribute to deranged interstitial bulk flow and a resulting failure in the clearance of neurotoxic solutes such as Aβ.

Soluble $Aβ_{1-40}$ was cleared from the brain interstitium more rapidly than a comparably sized dextran molecule, suggesting that interaction between specific BBB Aβ efflux receptors with bulk flow-dependent clearance (46, 47) may occur. The clearance of Aβ along specific anatomical paravascular pathways (including the deep venous system) raises the possibility that transendothelial Aβ efflux may not be uniform throughout the brain vasculature but may occur at certain specialized clearance vessels. Soluble Aβ moving along paravenous clearance pathways reenters the CSF compartment, either within the ventricles (internal cerebral veins) or in the subarachnoid space (caudal rhinal veins). The ventricular pathway provides a direct route to the choroid plexus, a structure that may contribute to Aβ clearance from the CSF compartment (48). Aβ sequestered from the aqueous phase into plaques (primarily Aβ1-42) would not be cleared by bulk flow either to remote sites of transendothelial or choroidal efflux, or by bulk clearance via the CSF.

These patterns of parenchymal fluid flow provide routes for a number of therapeutic approaches. First, improving the efficiency of AQP4-dependent bulk flow can permit the improved clearance of soluble Aβ, potentially accelerating either its degradation or its re-uptake into the systemic circulation. Conversely, impeding solute clearance can slow the removal of therapeutic agents, such as antineoplastic agents and immune modulators, from the brain. AQP4-dependent bulk flow can also facilitate immune surveillance of the brain parenchyma without compromising CNS immune privilege. Both lymphocytes and antigen-presenting cells in the subarachnoid CSF (49) may detect interstitial antigens delivered to the CSF by paravenous bulk outflow. Indeed, Aqp4-null mice exhibit reduced neuroinflammation after intracerebral lipopolysaccharide injection (50). This attenuation of the peripheral immune response may be a consequence of reduced antigen accumulation in the subarachnoid CSF compartment in Aqp4-null mice. These paravascular routes can also serve as pathways for migrating cells and their guidance molecules, thus representing a potential avenue for tumor cell migration (51). Additionally, paravascular routes can be conduits for cell migration, molecularly distinct and functionally overlapping with the perivascular niches for cell genesis and migration in the adult brain parenchyma (52).

Although this pathway is important to fluid and solute homeostasis in the rodent brain, it also of great importance for interstitial solute clearance in humans. One of the hallmarks of bulk flow, compared to simple diffusion, is the independence of solute movement from molecular size (4, 46), because all solutes are carried along with the moving medium at the same rate of fluid flow. In contrast, in simple diffusion, because of the dependence of diffusion rates on molecular size, larger solutes require longer times to clear from the brain parenchyma into the nearest CSF compartment (16, 46). Thus, whereas urea (molecular size, 60 daltons) requires 5.4 hours to diffuse 1 cm within the brain, albumin (molecular size, 66.5 kD) would require 109 hours. On the basis of these values, Cserr postulated that the larger the brain, the greater the dependence upon bulk flow for the efficient clearance of interstitial solutes, particularly for larger molecules such as peptides and proteins that cannot effectively clear via diffusion (16). Thus, in the human brain, paravascular pathways and AQP4-dependent bulk flow can be substantially more critical to brain function than in the rodent brain. To evaluate this possibility, less invasive approaches than those used in this example, for assessing interstitial solute movement in humans, such as magnetic resonance perfusion imaging, were used in Example 2.

REFERENCES CITED IN EXAMPLE 1

1. K. Aukland, R. K. Reed, Interstitial-lymphatic mechanisms in the control of extracellular fluid volume. Physiol. Rev. 73, 1-78 (1993).
2. G. W. Schmid-Schönbein, Microlymphatics and lymph flow. Physiol. Rev. 70, 987-1028 (1990).
3. N. J. Abbott, Evidence for bulk flow of brain interstitial fluid: Significance for physiology and pathology. Neurochem. Int. 45, 545-552 (2004).
4. H. F. Cserr, D. N. Cooper, P. K. Suri, C. S. Patlak, Efflux of radiolabeled polyethylene glycols and albumin from rat brain. Am. J. Physiol. 240, F319-F328 (1981).
5. H. F. Cserr, C. J. Harling-Berg, P. M. Knopf, Drainage of brain extracellular fluid into blood and deep cervical lymph and its immunological significance. Brain Pathol. 2, 269-276 (1992).
6. L. B. Flexner, Some problems of the origin, circulation and absorption of the cerebrospinal fluid. Q. Rev. Biol. 8, 397-422 (1933).
7. J. Praetorius, Water and solute secretion by the choroid plexus. Pflugers Arch. 454, 1-18 (2007).
8. L. Koh, A. Zakharov, M. Johnston, Integration of the subarachnoid space and lymphatics: Is it time to embrace a new concept of cerebrospinal fluid absorption? Cerebrospinal Fluid Res. 2, 6 (2005).
9. E. Syková, C. Nicholson, Diffusion in brain extracellular space. Physiol. Rev. 88, 1277-1340 (2008).
10. M. G. Proescholdt, B. Hutto, L. S. Brady, M. Herkenham, Studies of cerebrospinal fluid flow and penetration into brain following lateral ventricle and cisterna magna injections of the tracer [$^{14}$C]inulin in rat. Neuroscience 95, 577-592 (2000).
11. T. Ichimura, P. A. Fraser, H. F. Cserr, Distribution of extracellular tracers in perivascular spaces of the rat brain. Brain Res. 545, 103-113 (1991).
12. R. O. Weller, Microscopic morphology and histology of the human meninges. Morphologie 89, 22-34 (2005).
13. P. Hadaczek, Y. Yamashita, H. Mirek, L. Tamas, M. C. Bohn, C. Noble, J. W. Park, K. Bankiewicz, The "perivascular pump" driven by arterial pulsation is a powerful mechanism for the distribution of therapeutic molecules within the brain. Mol. Ther. 14, 69-78 (2006).
14. D. Schley, R. Carare-Nnadi, C. P. Please, V. H. Perry, R. O. Weller, Mechanisms to explain the reverse perivascular transport of solutes out of the brain. J. Theor. Biol. 238, 962-974 (2006).
15. M. L. Rennels, O. R. Blaumanis, P. A. Grady, Rapid solute transport throughout the brain via paravascular fluid pathways. Adv. Neurol. 52, 431-439 (1990).
16. H. F. Cserr, Physiology of the choroid plexus. Physiol. Rev. 51, 273-311 (1971).
17. T. M. Mathiisen, K. P. Lehre, N. C. Danbolt, O. P. Ottersen, The perivascular astroglial sheath provides a complete covering of the brain microvessels: An electron microscopic 3D reconstruction. Glia 58, 1094-1103 (2010).
18. A. W. Bero, P. Yan, J. H. Roh, J. R. Cirrito, F. R. Stewart, M. E. Raichle, J. M. Lee, D. M. Holtzman, Neuronal activity regulates the regional vulnerability to amyloid-β deposition. Nat. Neurosci. 14, 750-756 (2011).
19. B. V. Zlokovic, R. Deane, A. P. Sagare, R. D. Bell, E. A. Winkler, Low-density lipoprotein receptor-related protein-1: A serial clearance homeostatic mechanism controlling Alzheimer's amyloid β-peptide elimination from the brain. J. Neurochem. 115, 1077-1089 (2010).
20. J. S. Crossgrove, G. J. Li, W. Zheng, The choroid plexus removes b-amyloid from brain cerebrospinal fluid. Exp. Biol. Med. 230, 771-776 (2005).
21. J. M. Serot, J. Zmudka, P. Jouanny, A possible role for CSF turnover and choroid plexus in the pathogenesis of late onset Alzheimer's disease. J. Alzheimers Dis. 30, 17-26 (2012).
22. M. W. Bradbury, R. J. Westrop, Factors influencing exit of substances from cerebrospinal fluid into deep cervical lymph of the rabbit. J. Physiol. 339, 519-534 (1983).
23. M. Boulton, A. Young, J. Hay, D. Armstrong, M. Flessner, M. Schwartz, M. Johnston, Drainage of CSF through lymphatic pathways and arachnoid villi in sheep: Measurement of $^{125}$I-albumin clearance. Neuropathol. Appl. Neurobiol. 22, 325-333 (1996).
24. M. Johnston, A. Zakharov, C. Papaiconomou, G. Salmasi, D. Armstrong, Evidence of connections between cerebrospinal fluid and nasal lymphatic vessels in humans, non-human primates and other mammalian species. Cerebrospinal Fluid Res. 1, 2 (2004).
25. L. H. Weed, The absorption of cerebrospinal fluid into the venous system. Am. J. Anat. 31, 191-221 (1923).
26. I. Szentistványi, C. S. Patlak, R. A. Ellis, H. F. Cserr, Drainage of interstitial fluid from different regions of rat brain. Am. J. Physiol. 246, F835-F844 (1984).
27. R. O. Carare, M. Bernardes-Silva, T. A. Newman, A. M. Page, J. A. Nicoll, V. H. Perry, R. O. Weller, Solutes, but not cells, drain from the brain parenchyma along basement membranes of capillaries and arteries: Significance for cerebral amyloid angiopathy and neuroimmunology. Neuropathol. Appl. Neurobiol. 34, 131-144 (2008).
28. M. L. Rennels, T. F. Gregory, O. R. Blaumanis, K. Fujimoto, P. A. Grady, Evidence for a 'paravascular' fluid circulation in the mammalian central nervous system, provided by the rapid distribution of tracer protein throughout the brain from the subarachnoid space. Brain Res. 326, 47-63 (1985).
29. R. G. Pullen, M. DePasquale, H. F. Cserr, Bulk flow of cerebrospinal fluid into brain in response to acute hyperosmolality. Am. J. Physiol. 253, F538-F545 (1987).
30. M. C. Papadopoulos, A. S. Verkman, Aquaporin-4 and brain edema. Pediatr. Nephrol. 22, 778-784 (2007).
31. N. N. Haj-Yasein, G. F. Vindedal, M. Eilert-Olsen, G. A. Gundersen, Ø. Skare, P. Laake, A. Klungland, A. E. Thorén, J. M. Burkhardt, O. P. Ottersen, E. A. Nagelhus, Glial-conditional deletion of aquaporin-4 (Aqp4) reduces blood-brain water uptake and confers barrier function on perivascular astrocyte endfeet. Proc. Natl. Acad. Sci. U.S.A. 108, 17815-17820 (2011).
32. S. Nielsen, E. A. Nagelhus, M. Amiry-Moghaddam, C. Bourque, P. Agre, O. P. Ottersen, Specialized membrane domains for water transport in glial cells: High-resolution immunogold cytochemistry of aquaporin-4 in rat brain. J. Neurosci. 17, 171-180 (1997).
33. A. Dorr, J. G. Sled, N. Kabani, Three-dimensional cerebral vasculature of the CBA mouse brain: A magnetic resonance imaging and micro computed tomography study. Neuroimage 35, 1409-1423 (2007).
34. X. Yao, S. Hrabetová, C. Nicholson, G. T. Manley, Aquaporin-4-deficient mice have increased extracellular space without tortuosity change. J. Neurosci. 28, 5460-5464 (2008).
35. M. Amiry-Moghaddam, T. Otsuka, P. D. Hurn, R. J. Traystman, F. M. Haug, S. C. Froehner, M. E. Adams, J. D. Neely, P. Agre, O. P. Ottersen, A. Bhardwaj, An a-syntrophin-dependent pool of AQP4 in astroglial endfeet confers bidirectional water flow between blood and brain. Proc. Natl. Acad. Sci. U.S.A. 100, 2106-2111 (2003).
36. A. Frigeri, G. P. Nicchia, B. Nico, F. Quondamatteo, R. Herken, L. Roncali, M. Svelto, Aquaporin-4 deficiency in skeletal muscle and brain of dystrophic mdx mice. FASEB J. 15, 90-98 (2001).
37. J. Zhou, H. Kong, X. Hua, M. Xiao, J. Ding, G. Hu, Altered blood-brain barrier integrity in adult aquaporin-4 knockout mice. Neuroreport 19, 1-5 (2008).
38. M. Eilert-Olsen, N. N. Haj-Yasein, G. F. Vindedal, R. Enger, G. A. Gundersen, E. H. Hoddevik, P. H. Petersen, F. M. Haug, Ø. Skare, M. E. Adams, S. C. Froehner, J. M. Burkhardt, A. E. Thoren, E. A. Nagelhus, Deletion of aquaporin-4 changes the perivascular glial protein scaffold without disrupting the brain endothelial barrier. Glia 60, 432-440 (2012).
39. S. Saadoun, M. J. Tait, A. Reza, D. C. Davies, B. A. Bell, A. S. Verkman, M. C. Papadopoulos, AQP4 gene deletion in mice does not alter blood-brain barrier integrity or brain morphology. Neuroscience 161, 764-772 (2009).
40. K. K. Ball, N. F. Cruz, R. E. Mrak, G. A. Dienel, Trafficking of glucose, lactate, and amyloid-β from the inferior colliculus through perivascular routes. J. Cereb. Blood Flow Metab. 30, 162-176 (2010).
41. R. O. Weller, M. Subash, S. D. Preston, I. Mazanti, R. O. Carare, Perivascular drainage of amyloid-β peptides from the brain and its failure in cerebral amyloid angiopathy and Alzheimer's disease. Brain Pathol. 18, 253-266 (2008).
42. G. W. Ross, J. P. O'Callaghan, D. S. Sharp, H. Petrovitch, D. B. Miller, R. D. Abbott, J. Nelson, L. J. Launer, D. J. Foley, C. M. Burchfiel, J. Hardman, L. R. White, Quantification of regional glial fibrillary acidic protein levels in Alzheimer's disease. Acta Neurol. Scand. 107, 318-323 (2003).
43. J. P. O'Callaghan, D. B. Miller, The concentration of glial fibrillary acidic protein increases with age in the mouse and rat brain. Neurobiol. Aging 12, 171-174 (1991).
44. A. Verkhratsky, V. Parpura, Recent advances in (patho) physiology of astroglia. Acta Pharmacol. Sin. 31, 1044-1054 (2010).
45. M. E. Hamby, M. V. Sofroniew, Reactive astrocytes as therapeutic targets for CNS disorders. Neurotherapeutics 7, 494-506 (2010).
46. D. R. Groothuis, M. W. Vavra, K. E. Schlageter, E. W. Kang, A. C. Itskovich, S. Hertzler, C. V. Allen, H. L. Lipton, Efflux of drugs and solutes from brain: The interactive roles of diffusional trans-capillary transport, bulk flow and capillary transporters. J. Cereb. Blood Flow Metab. 27, 43-56 (2007).
47. R. Deane, R. D. Bell, A. Sagare, B. V. Zlokovic, Clearance of amyloid-β peptide across the blood-brain barrier: Implication for therapies in Alzheimer's disease. CNS Neurol. Disord. Drug Targets 8, 16-30 (2009).
48. X. Alvira-Botero, E. M. Carro, Clearance of amyCloid-b peptide across the choroid plexus in Alzheimer's disease. Curr. Aging Sci. 3, 219-229 (2010).
49. R. M. Ransohoff, P. Kivisakk, G. Kidd, Three or more routes for leukocyte migration into the central nervous system. Nat. Rev. Immunol. 3, 569-581 (2003).
50. L. Li, H. Zhang, M. Varrin-Doyer, S. S. Zamvil, A. S. Verkman, Proinflammatory role of aquaporin-4 in autoimmune neuroinflammation. FASEB J. 25, 1556-1566 (2011).
51. Y. Kienast, L. von Baumgarten, M. Fuhrmann, W. E. Klinkert, R. Goldbrunner, J. Herms, F. Winkler, Real-time imaging reveals the single steps of brain metastasis formation. Nat. Med. 16, 116-122 (2010).
52. S. A. Goldman, Z. Chen, Perivascular instruction of cell genesis and fate in the adult brain. Nat. Neurosci. 14, 1382-1389 (2011).
53. A. S. Thrane, P. M. Rappold, T. Fujita, A. Torres, L. K. Bekar, T. Takano, W. Peng, F. Wang, V. R. Thrane, R. Enger, N. N. Haj-Yasein, Ø. Skare, T. Nolen, A. Klungland, O. P. Ottersen, M. Nedergaard, E. A. Nagelhus, Critical role of aquaporin-4 (AQP4) in astrocytic Ca2+ signaling events elicited by cerebral edema. Proc. Natl. Acad. Sci. U.S.A. 108, 846-851 (2011).
54. X. Zhu, D. E. Bergles, A. Nishiyama, NG2 cells generate both oligodendrocytes and gray matter astrocytes. Development 135, 145-157 (2008).
55. T. Takano, G. F. Tian, W. Peng, N. Lou, W. Libionka, X. Han, M. Nedergaard, Astrocyte-mediated control of cerebral blood flow. Nat. Neurosci. 9, 260-267 (2006).

56. K. P. Lehre, L. M. Levy, O. P. Ottersen, J. Storm-Mathisen, N. C. Danbolt, Differential expression of two glial glutamate transporters in the rat brain: Quantitative and immunocytochemical observations. J. Neurosci. 15, 1835-1853 (1995).

6.2. Example 2

Brain-wide Paravascular Pathway for Waste Clearance Captured by Contrast-Enhanced MRI The glymphatic system, described above in Example 1, is a brain-wide paravascular pathway for cerebrospinal fluid (CSF) and interstitial fluid (ISF) exchange that facilitates efficient clearance of solutes and waste from the brain. CSF enters the brain along para-arterial channels to exchange with ISF, which is in turn cleared from the brain along para-venous pathways. Because soluble amyloid β clearance depends on glymphatic pathway function, failure of this clearance system may contribute to amyloid plaque deposition and Alzheimer's disease progression. This example demonstrates that glymphatic pathway function can be measured using a clinically relevant imaging technique. Dynamic contrast-enhanced MRI was used to visualize CSF-ISF exchange across the rat brain following intrathecal paramagnetic contrast agent administration. Features of glymphatic pathway function were characterized, including visualization of para-arterial CSF influx and molecular size-dependent CSF-ISF exchange. Whole-brain imaging allowed the identification of two key influx nodes, at the pituitary and pineal gland recesses, while dynamic MRI imaging permitted the definition of kinetic parameters to characterize glymphatic CSF-ISF exchange and solute clearance from the brain. The MRI approach demonstrated in this example can be used in a method for evaluating Alzheimer's disease susceptibility and progression in the live human brain.

Introduction

In the classical model, cerebrospinal fluid (CSF) is actively secreted by the choroid plexus of the cerebral ventricles, travels by bulk or pulsatile flow through the ventricular system, flowing from the fourth ventricle into the subarachnoid space through the foramina of Luschka and the foramen of Magendie. From the subarachnoid space, CSF is thought to be reabsorbed to the blood stream either via arachnoid granulations of the dural sinuses or by passing out of the cranial cavity along cranial nerve sheathes to be eliminated through the cervical lymphatics (1, 2). Fluid movement along this CSF column is commonly measured by magnetic resonance imaging (MRI). Phase contrast magnetic resonance imaging (MRI) allows the visualization of CSF flow dynamics and is used clinically in the evaluation of communicating versus non-communicating hydrocephalus, normal pressure hydrocephalus and arachnoid cysts (3). Contrast enhanced magnetic resonance cisternography can also be used to identify CSF leaks in the treatment of spontaneous intracranial hypotension or CSF rhinorrhea (4, 5).

Example 1 demonstrates that contrary to the textbook model of CSF secretion and reabsorption, a large proportion of subarachnoid CSF recirculates through the brain parenchyma along paravascular spaces and exchanges with the interstitial fluid (ISF). The flow of fluid along these paravascular routes and through the interstitium is supported by trans-glial water movement through astrocytic aquaporin-4 (AQP4) water channels and facilitates the efficient clearance of interstitial solutes, including soluble amyloid β, from the brain parenchyma. The description of this pathway in Example 1, termed the 'glymphatic' system, was based upon in vivo 2-photon and ex vivo fluorescence imaging. Analysis of ex vivo brain slices suggested that this pathway represented a brain-wide anatomical system to facilitate the efficient clearance of interstitial solutes and wastes, however the limitations of fluorescence-based imaging modalities prevented the direct assessment of brain-wide CSF-ISF flow dynamics in a three-dimensional (3D) manner.

In the present study, contrast enhanced MRI was used to visualize brain-wide subarachnoid CSF-ISF exchange in the live rat brain. The characteristics of the pathway described in the initial study (Example 1) were confirmed, including the bulk flow-dependent influx of subarachnoid CSF tracer along para-arterial routes and movement of tracer into and through the brain parenchyma. The inherent 3D nature of MRI was used in combination with various processing modalities including cluster analysis to map the CSF-ISF exchange pathway across the brain over time, to identify anatomical influx 'nodes' and clearance routes from the brain parenchyma. Kinetic parameters were defined that describe the influx and clearance of the paramagnetic contrast agents throughout the brain volume. In light of the key role that this pathway plays in soluble amyloid β clearance from the brain parenchyma as demonstrated in Example 1, this contrast-enhanced MRI quantification approach can provide the basis for a wholly new strategy to evaluating Alzheimer's disease (AD) susceptibility and disease progression.

Methods

Surgical Preparation

Female Sprague Dawley rats were used (Taconics, body weight: 220-280 g). For anesthesia, the animals were induced with 3% isoflurane in oxygen using an induction chamber and then received an intra-peritoneal injection of 40 mg/kg phenobarbital (Nembutal® Sodium solution, OVATION, Pharmaceuticals, Inc., Deerfield, Ill., USA). The animals were allowed to breathe spontaneously during the entire experiment. Non-invasive monitors (pulse-oximetry, respiratory rate and rectal temperature probe, SA Instruments, Inc., Stony Brook, N.Y.) were placed to assure adequate oxygenation ($O_2$-saturation>97%), ventilation (respiratory rate 50-65 breath per minute) and normal body temperature (36.5° C.-37.5° C.) during the surgical procedures. A 24-gauge catheter was inserted into the tail vein for administration of fluids and supplemental anesthesia. The animal was positioned in a stereotaxic frame (Kopf Instruments, frame #9) and the head flexed to 50 degrees. For the brief surgical procedure, anesthesia was supplemented with isoflurane (0.8-1.2%) delivered in an 1:1 $O_2$:Air mixture.

The atlanto-occipital membrane was exposed via a midline dorsal neck incision and a small incision was made to expose the underlying dura mater. A polyethylene catheter (6-cm long, 0.28 mm ID×0.61 mm OD, (Solomon Scientific, Plymouth Meeting, Pa.)) filled with normal saline was advanced 1-mm into the intrathecal space via a small durotomy made using a 23-gauge needle and was fixed and sealed with super glue. The skin incision was closed around the catheter.

MRI Imaging Protocol

Following surgery, the rats were flipped supine and positioned in a custom-made acrylic cradle fitted with a head fixation device and a snout mask for delivery of supplemental oxygen. The head of the animal was positioned on top of a 3.0 cm custom-made radio-frequency (rf) receiver coil. Non-invasive, MRI compatible monitors (pulse-oximetry, respiratory rate and rectal temperature probe, SA Instruments, Inc., Stony Brook, N.Y.) were repositioned for continuous monitoring of vital signs while the animal underwent MRI imaging. During imaging, body temperature was kept strictly within 36.5-37.5° C. during imaging using a computer assisted air heating system (SA Instruments, Inc., Stony Brook, N.Y.). The intrathecal catheter was connected to a long PE 20 line filled with paramagnetic MR contrast diluted in 0.9% NaCl attached to a 1 cc-syringe and micro-infusion pump (Baxter Model AS50 infusion Pump, Baxter Healthcare Corporation, Illinois, USA). The tail vein catheter was used for maintenance hydration (0.9% NaCl, 4 cc/kg/hr) and supplemental anesthesia (Nembutal®, 5-10 mg/kg IV) administered every 2 hrs as guided by the respiratory rate.

Two different paramagnetic contrast agents were used for the experiments: Magnevist®, (diethylenetriaminepentacetate (Gd-DTPA), Molecular Weight (MW) 938 D, Bayer HealthCare Pharmaceuticals Inc., Wayne, N.J. 07470) and GadoSpin™ P (polymeric Gd-chelate, MW 200 kDa, Miltenyi Biotec Inc., Auburn, Calif.). To visualize the glymphatic pathways by contrast-enhanced MRI (T1 shortening effects the initial concentrations were first established at which the two different paramagnetic contrast agents are matched so that decreasing concentrations produced over time in brain tissue far from the injection site were comparable. In other words, the T1 effects induced by the two paramagnetic contrast agents are important to match since after they are injected into the cisterna magna they will travel through the brain-wide glymphatic pathways and become progressively diluted over time. To accomplish this, phantom experiments were carried out.

All imaging protocols were performed on a 9.4T/20 MRI instrument interfaced to a Bruker Advance console and controlled by Paravision 5.0 software (Bruker Bio Spin, Billerica, Mass.). A custom-made 3-cm surface radio-frequency coil was used as a receiver and a 16-cm diameter volume coil (Bruker) was used as a transmitter. Following localizer anatomical scout scans, a 3D T1-weighted FLASH sequence (TR=15 msec, TE=3.4 ms, Flip angle 15°, NA=1, FOV=3.0×3.0×3.2 cm, scanning time=4 minutes 5 sec, acquisition matrix size of 256×128×128 interpolated to 256×256×256 yielding an image resolution of 0.12×0.12× 0.13 mm) were acquired in the sagittal or coronal plane. For all experiments a 60 mM (1:8 volume ratio diluted in 0.9% NaCl) Gd-DTPA phantom placed in the vicinity of animal's head was used for image intensity normalization over the time series. The scanning protocol consisted of three baseline scans followed by intrathecal paramagnetic contrast (0.17 mM GadoSpin™ and 21 mM Gd-DTPA) delivery via the indwelling catheter while MRI acquisitions continued. A total of 80 µl of the paramagnetic contrast agent was delivered intrathecally at an infusion rate of 1.6 µl/min (total infusion time: 50 min). After completion of the intrathecal infusion, the 3D MRI acquisitions continued over 3.9 hrs. At the end of the experiment the animal was euthanized with an overdose of Nembutal.

Data Processing

The general MRI image processing procedure consisted of head motion correction, intensity normalization, smoothing and voxel-by-voxel conversion to % of baseline signal. SPM8 (World Wide Web at fil.ion.ucl.ac.uk/spm) was used for this. First, the acquired T1-weighted MRI images were exported as DICOM files and converted to 3D Nlfti image format. Second, scan to scan misregistration caused by head movement was corrected by rigid-body alignment of each scan to the time-averaged (mean) image. Third, image intensity was normalized over the time-series by dividing voxel intensity by the mean intensity of the reference phantom using the following expression: img_normalized=img_original/phantom*1000; followed by 0.1 mm full width at half maximum isotropic Gaussian smoothing. Finally, all time-series images were subtracted and divided by the baseline average image using the following expression: $(P(l,j,k)=(l(l,j,k)-base(l,j,k))/base(l,j,k)*100)$ to ensure that voxel intensity represents percentage change relative to the average baseline images.

The signal changes measured on the T1-weighted MRIs over time in pre-selected anatomical areas were used to obtain the time 'activity' curves (TACs) of regional tissue uptake of the paramagnetic contrast agents. The T1-weighted averaged baseline images as well as the contrast-enhanced T1-weighted MRIs were used to anatomically guide placement of the regions-of-interest (ROIs). From near-midline sagittal MRIs, ROIs were drawn on four sagittal slices in each hemisphere and the signals from each of the anatomical ROIs were averaged using PMOD software (PMOD Version 3.307, PMOD Technologies, Ltd, Zurich, Switzerland). The ROIs included the pituitary recess, pineal recess, olfactory bulb, cerebellum, pontine nucleus and aqueduct. The TACs for each ROI were extracted via the PKMod module. The area under the curve (AUC) for each ROI's TAC was calculated using the 'trapezoidal rule'. The calculated AUCs were normalized by dividing each animal's AUC by the number of the corresponding time intervals used for that particular study referred to as 'mean Area Under the Curve (mAUC)' calculated as: $(mAUC=AUC/(n-1))$. Furthermore, to minimize potential differences in the amount of paramagnetic contrast delivered to each animal within groups the mAUC of the pituitary recess (which represent the major input and source of contrast) was used to normalize the other regions mAUCs. Subsequently, the mean mAUC-ratios were compared between the two groups for each anatomical location using a two-sided independent t-test.

Cluster Analysis

Non-parametric segmentation to group voxels in the MRI images on the basis of similar kinetics was performed using a k-means cluster algorithm (PMOD Version 3.307, PMOD Technologies, Ltd, Zurich, Switzerland) on four sagittal slices at the level of the aqueduct from each of the 4D T1-weighted MRIs. A volume-of-interest mask containing the brain only was created for the cluster analysis. The number of clusters (K) used was determined by the K which was able to segment out voxels adjacent to the large vessels such as basilar artery (including pituitary recess) and olfactory artery complex. This was done on an interactive, per animal basis. Each analysis was performed using a 50% percentile threshold (i.e. only 50% of the pixels with the highest signal changes (sum of squared TAC values were used). The number of clusters which provided the most ideal visualization of para-vascular inflow conduits was 4 clusters. The four clusters were examined visually and co-registered with the corresponding contrast-enhanced and anatomical MRIs to verify the positions of the clusters in relation to the large vessels. The number of voxels and TACs for each cluster was extracted for further processing.

Fluorescent Intrathecal Tracer Imaging

To evaluate the movement of intrathecal tracers into the rat brain with higher resolution ex vivo fluorescence imaging was conducted of fluorescein isothiocyanate-conjugated dextran (MW 500 kD, FITC-d500) and Texas Red-conjugated dextran (MW 3 kD, TR-d3) in fixed brain slices. FITC-d500 and TR-d3 were selected to roughly correspond with the molecular weights of Gd-DTPA (MW ~1 kD) and GadoSpin™ (MW 200 kD). Intrathecal injections were conducted as detailed above. A mixture of 0.1% FITC-d500 and TR-d3 dissolved in artificial CSF was injected. 30, 60 and 180 min post-injection, animals were trans-cardially perfused with 4% paraformaldehyde and the brains removed and post-fixed overnight at 4° C. 100 μm sagittal vibratome sections were cut and mounted with Prolong Antifade Gold reagent with DAPI (Invitrogen). A subset of coronal slices were additionally counter-labeled with biotinylated Griffonia (Brandeiraea) *Simplicifolia* Lectin I Isolectin B4 (IB4, a vascular endothelial marker; 1:100, Vector Laboratories) overnight at 4° C. Secondary detection was conducted using Cy5-conjugated streptavidin (1:250, Jackson Immunoresearch). Three-channel whole-slice montages were generated using a conventional epifluorescence microscope (Olympus) at 10× objective power with a motorized stage and Microlucida software (Microbrightfield). High-power imaging was conducted at 40× objective power by laser scanning confocal microscopy (Olympus).

Statistics Overview

All data are presented as mean±SD. Statistical analyses were performed using SAS version 9.2 (SAS Institute Inc, USA) and XLSTAT Version 2011 (Addinsoft, N.Y., USA) with p-value<0.05 described as significantly different. Differences in regional tissue uptake (as represented by the average ratio between the mean 'Area Under Curve' (mAUC) of the anatomical region of interest and the average mAUC of the pituitary recess) between the Gd-DTPA and GadoSpin™ rats were compared using a two-sided t-test for independent groups. From the K-means cluster analysis the following parameters were derived: 1) total number of voxels in each of the three anatomical zones, 2) the time-weighted cluster number of each zone (#voxels*AUC) and 3) ratios of zone 2's and 3's total time-weighted cluster number to that of zone 1's time-weighted cluster number. Differences in average values of each of these parameters derived from the cluster analysis between the Gd-DTPA and GadoSpin™ rats were compared using a two-sided t-test for independent groups.

Phantom MRI Experiments

Phantoms of different concentrations of the two contrast agents (i.e. Gd-DTPA and the Gd-Chelate GadoSpin™ P) were prepared and their T1 s were calculated at 37° C. GadoSpin™ P was prepared according to the manufacturer's instruction; and to reconstitute the lyophilizate, 1 cc sterile 0.9% NaCl was injected into each vial containing 33 mg GadoSpin™ P, yielding a 0.165 mM solution. Magnevist® injection is a 0.5M solution of 1-deoxy-1(methylamino)D-glucitol dihydrogen [N,N-bis[2-[bis(carboxymethyl)amino] ethyl]glycinato (5-)]gadolinite(2-)(2:1); and 0.01 ml of this solution was diluted with 0.23 ml of 0.9% sterile NaCl yielding a 20.8 mM Gd-DTPA solution. The undiluted, reconstituted GadoSpin™ P and 20.8 mM Gd-DTPA represented the initial solutions from which the phantoms of different concentrations were made. Thus, Gd-DTPA phantoms were prepared by serially diluting 20.8 mM Gd-DTPA with sterile 0.9% NaCl to obtain 1:10, 1:20, 1:40, 1:80, 1:160, 1:320, 1:640 and 1:1280 volume ratios. Similarly, from the reconstituted GadoSpin™ P solution, phantoms were prepared using the same volume ratios (1:91:1279) as for Gd-DTPA. Each phantom (0.5 ml of a given dilution) was scanned at 37° C. using identical MR parameters as the animal study: 2D single slice FLASH sequence, (TR=15 msec, TE=3.8 ms, NA=5), and 26 flip angles (2°~80°). T1 was calculated by a standard spoiled gradient echo sequence (FLASH) expressed as:

$$S(\theta \cdot TE) = S_0 \frac{(1 - e^{-TR/T1})\sin\theta}{(1 - e^{-TR/T1}\cos\theta)} e^{-TE/T_2^*}$$

where $S_0$, TR, TE, T1, $T_2^*$T1, $\theta$ denote proton density, repetition time, echo time, transverse relaxation time, longitudinal relaxation time, and flip angle, respectively. Nelder-Mead simplex algorithm built into MATLAB 7.1 was employed in the fitting procedure. FIG. 16 (volume ratio of 1:20) depicts detected signal changes over the range of flip angles for the two contrast agents. In FIG. 17, calculated T1s are plotted as a function of paramagnetic contrast concentrations ranging from 0.1 (1:10 ratio) and 0.01 (1:100 ratio). As can be seen from FIG. 17, the T1's of the two different contrast agents are comparable over a wide range of decreasing concentrations. Based on these experiments it was assumed that 0.165 mM GadoSpin™ and 20.8 mM Gd-DTPA would yield near-equivalent T1 effects at the start of the experiment (initiation of intrathecal infusion).

Results

Figure 18A:
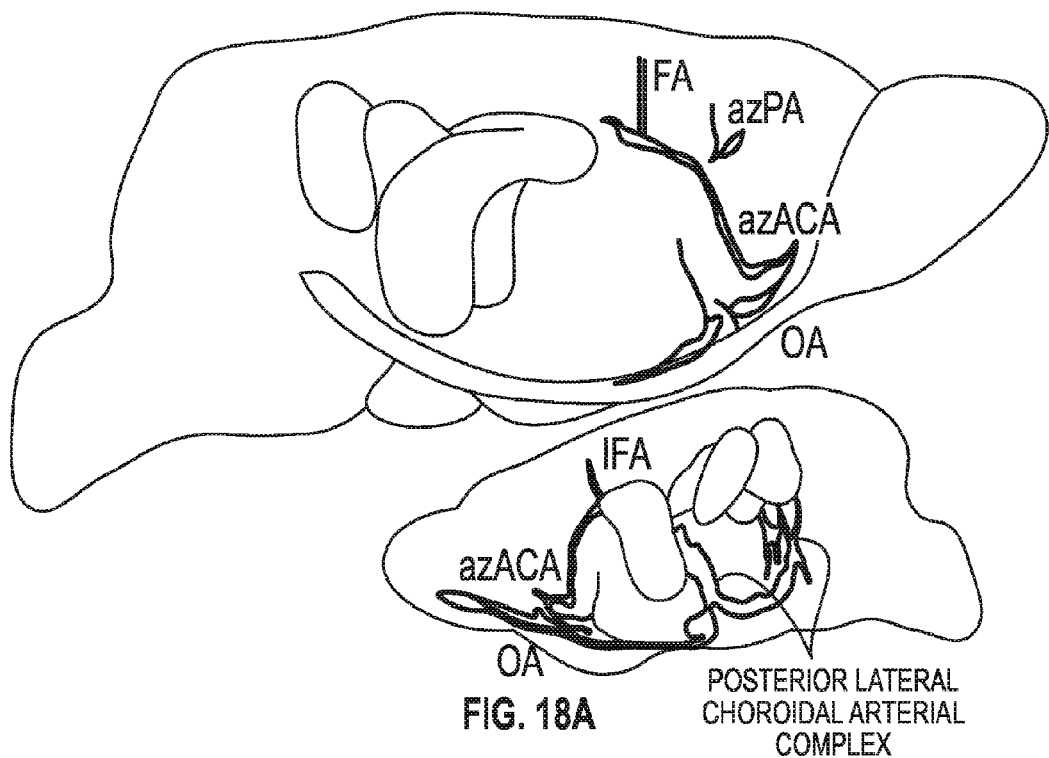
Figure 18B:
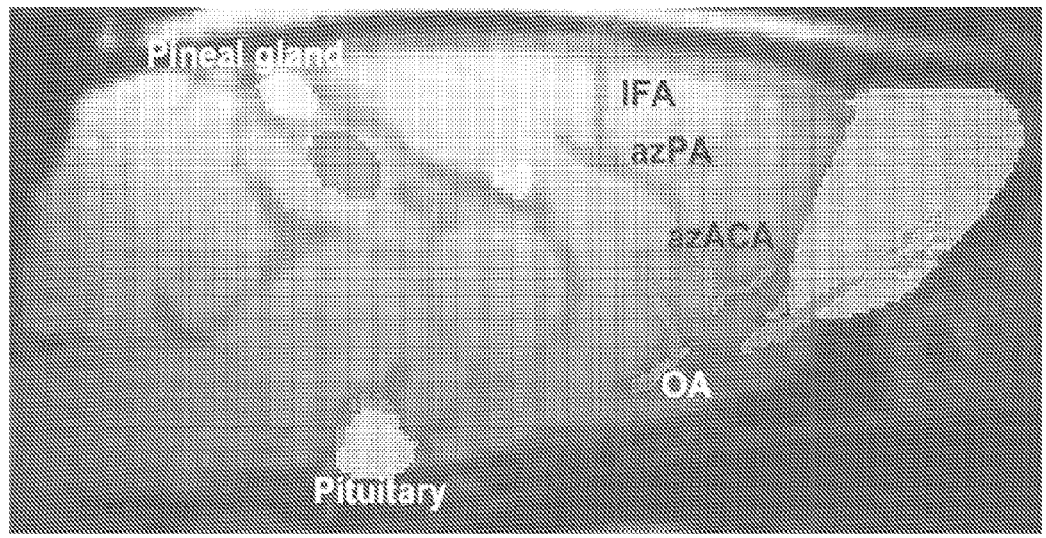
Figure 18C:
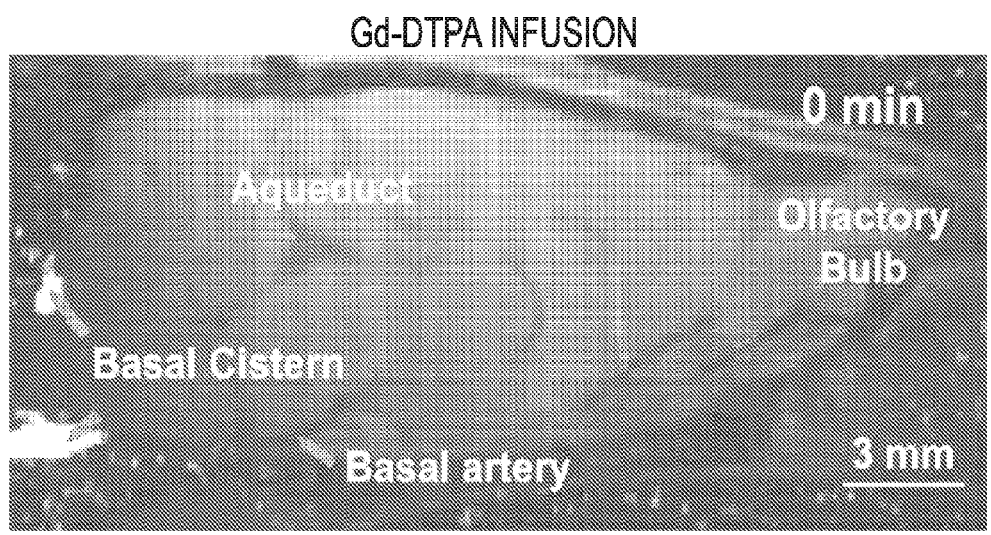
Figure 18D:
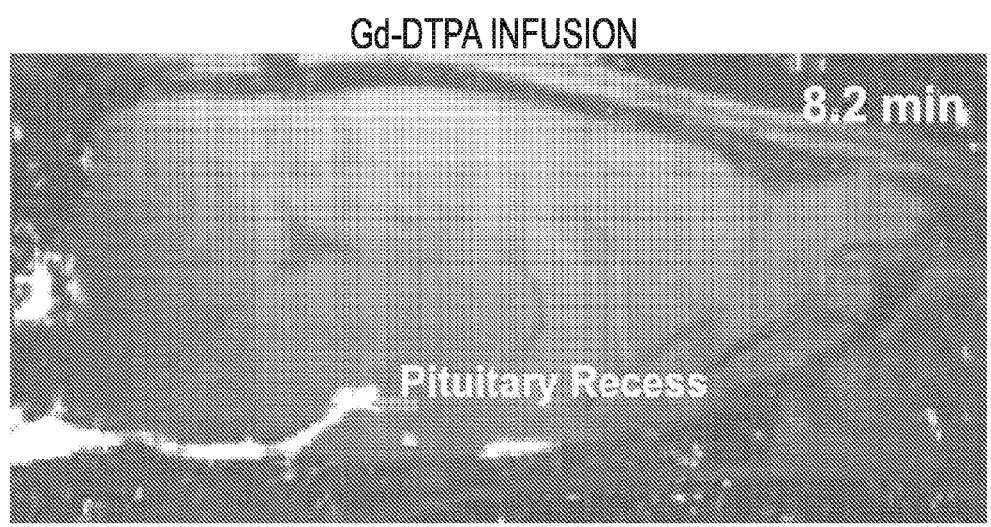
Figure 18E:
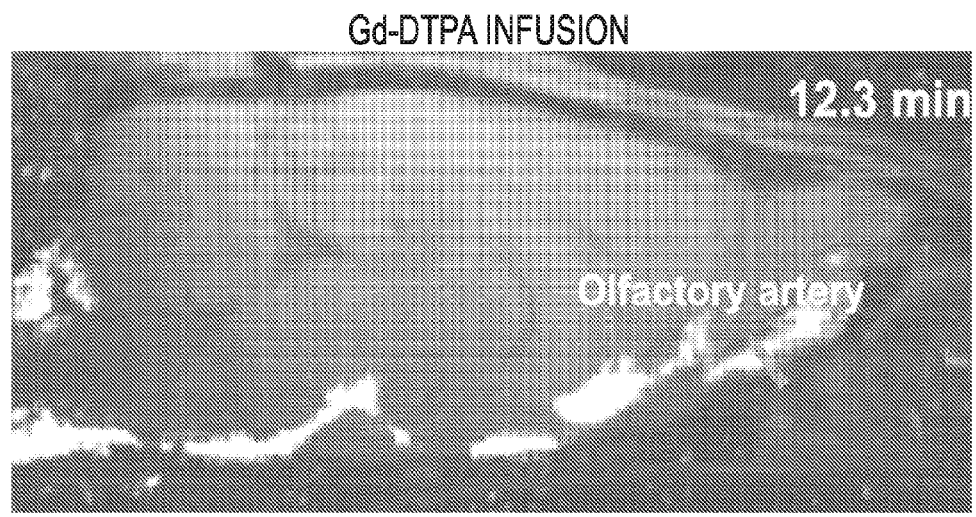
Figure 18F:
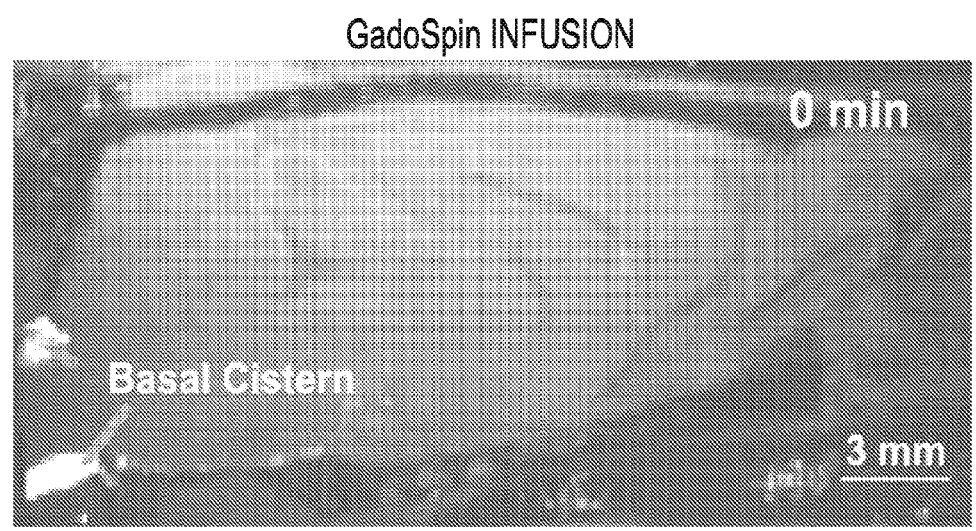
Figure 18G:
Figure 18H:
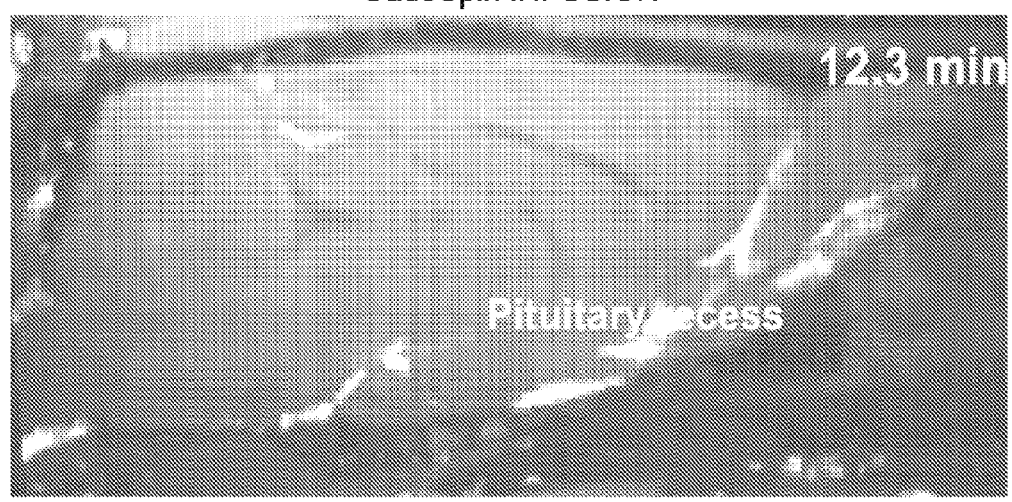
Figure 18:
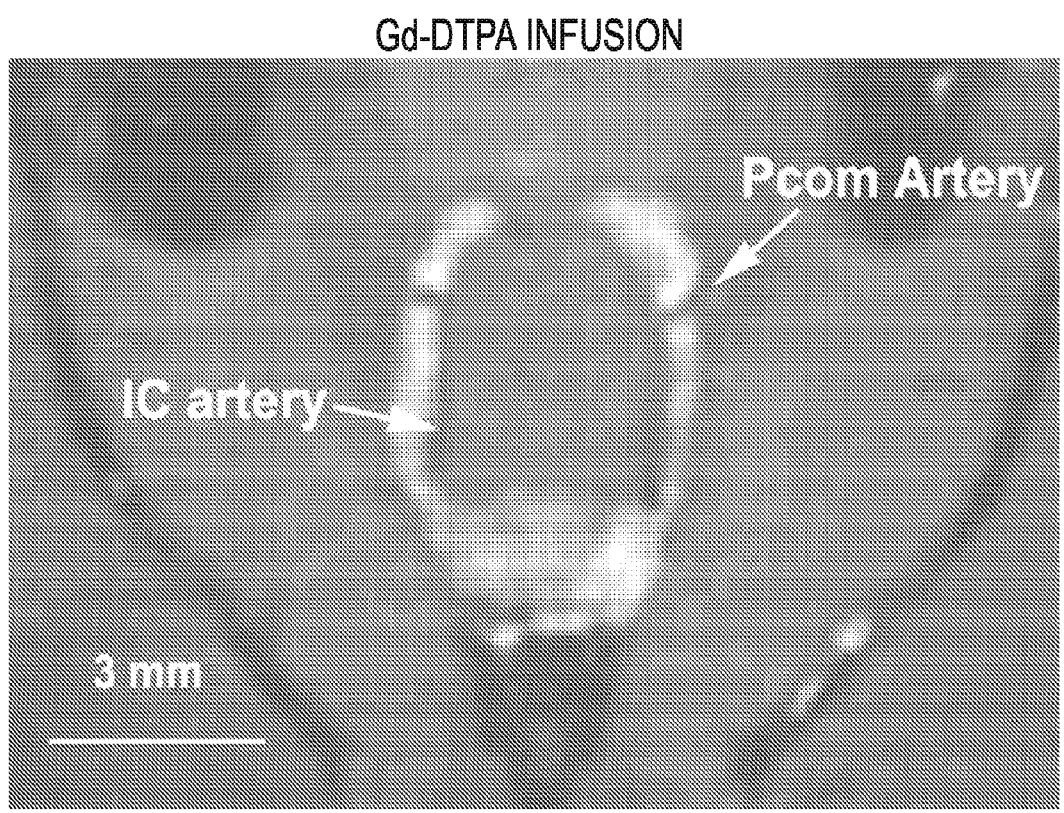

All rats included in the study remained physiologically stable during the 6 hr imaging experiment with respiratory rates in the range of 50-60 breaths/min, $O_2$-saturation ~98-100%, heart rate ~300-370 beats/min and body temperature 36.5-37.5° C. Several major anatomical structures such as the olfactory bulb, hippocampus, pineal gland, superior colliculus, inferior colliculus, pituitary gland and cerebellum could be identified although the grey-white matter contrast was limited in the 3D FLASH T1-weighted sequence obtained prior to administration of paramagnetic contrast (FIGS. 18A-B). Larger arteries such as the olfactory artery, azygos of the anterior cerebral artery, azygos pericallosal artery, middle internal frontal arteries, in addition to the posterior lateral choroidal arterial complex, were easily visualized in the near-midline sagittal plane (FIGS. 18A and B).

Paravascular Influx of Paramagnetic Contrast

Example 1 demonstrates that in the mouse, CSF from the subarachnoid space rapidly enters the brain via the Virchow-Robin spaces, along para-arterial channels to exchange with the interstitial fluid compartment. Such an extensive 'retrograde' flux of CSF into the brain parenchyma is contrary to the classical model of CSF secretion and reabsorption (1, 2). In this example, the first goal was to determine whether the paravascular influx of CSF into the brain could be observed by contrast-enhanced MRI following intrathecal delivery of different paramagnetic contrast agents.

FIGS. 18A-J show influx of small molecular weight Gd-DTPA (FIGS. 18C-E) and large molecular weight GadoSpin™ (FIGS. 18F-H) over the early infusion period in two representative rats. The dynamic time-series of T1-weighted MRIs clearly reveal the time-dependent anatomical routes of paravascular influx including 1) arrival of paramagnetic contrast agent in the cisterna magna (FIGS. 18C and F) and transport along the basilar artery (FIGS. 18D and G), 2) appearance of contrast in the pituitary recess (FIGS. 18D and G), 3) continued transport along the olfactory arterial complex and into the olfactory bulb (FIGS. 18E and H), and 4) transport via the posterior choroidal arterial complex (FIG. 18A) to the pineal recess.

Figure 18J:
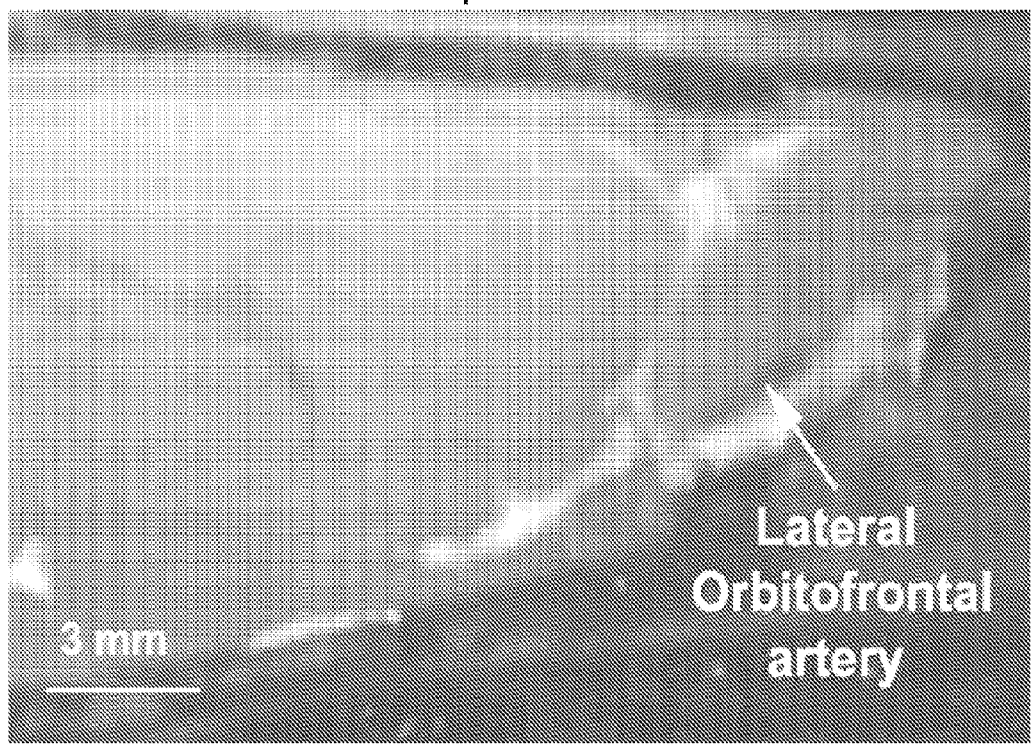

Movies of the dynamic time series capturing transport through the glymphatic system of Gd-DTPA and GadoSpin™ clearly demonstrate the difference in brain-wide distribution of the small and larger molecules (data not shown; still images from movies shown in FIGS. 19 and 20). For example, signal-changes induced by GadoSpin™ appear and preferentially remain along the para-arterial/para-vascular conduits and parenchymal uptake is sparse, while the small molecular weight Gd-DTPA contrast agent has much more diffuse access to the brain parenchyma (data not shown). It is also evident that although the molecular weights of the two paramagnetic contrast agents are different, the passage via the para-vascular conduits is largely similar from the time the contrast appears in the cisterna magna (defined as '0' min in FIGS. 18C and F). Some variability exists as to the amount of paramagnetic contrast that appears in the pineal recess; and in 2 animals injected with Gd-DTPA no signal changes were observed in the pineal recess. However, the para-vascular nature of the influx along the glymphatic pathway is clearest at the level of the Circle of Willis, where high intensity signal outlines the exit of the posterior communicating arteries (FIG. 18I); as well as along the lateral orbitofrontal artery (FIG. 18J).

Based upon the dynamic time-series, it is evident that although Gd-DTPA and GadoSpin™ differ in molecular weight by more than 2 orders of magnitude, they appear to transit the paravascular conduits at largely similar rates (FIGS. 18C-H). Contrast appeared to move sluggishly through the pineal recess, typically remaining in this cistern even after more than 2 hrs of wash-out (data not shown). The observation that paravascular contrast movement did not appreciably differ based upon agent molecular weight is consistent with bulk flow-mediated fluid transport, which is known to be independent of molecular size (7). These data confirm using contrast-enhanced MRI the first basic finding in Example 1 that bulk flow of CSF from the subarachnoid space into the brain parenchyma occurs primarily along para-arterial pathways.

Effect of Molecular Size on Brain-wide Gd-DTPA and GadoSpin™ Transport

In Example 1, it was demonstrated that although both small and large molecular weight tracers were able to move along the proximal para-arterial influx pathway, access from the para-arterial space into the surrounding brain interstitium was restricted based upon molecular size. Specifically, smaller molecular weight tracers such as TR-d3 (MW 3 kD) or ALEXA647-conjugated ovalbumin (MW 45 kD) passed readily into the interstitium while larger molecular weight tracers such as FITC-conjugated 2000 kD dextran (FITC-d2000, MW 2000 kD) remained confined to the paravascular spaces. It was surmised that overlapping astrocytic endfeet which completely ensheathe the cerebral microcirculation (8) function to restrict the access of larger molecular weight substances from the interstitium. Based upon these findings, it was predicted that as a result of better access to the brain interstitium Gd-DTPA (MW 938 Da) would be expected to induce signal changes (T1 shortening) in a larger total brain tissue volume compared to the larger GadoSpin™ (MW 200 kD) molecule. This hypothesis was tested using different quantitative image processing strategies.

Figure 21A:
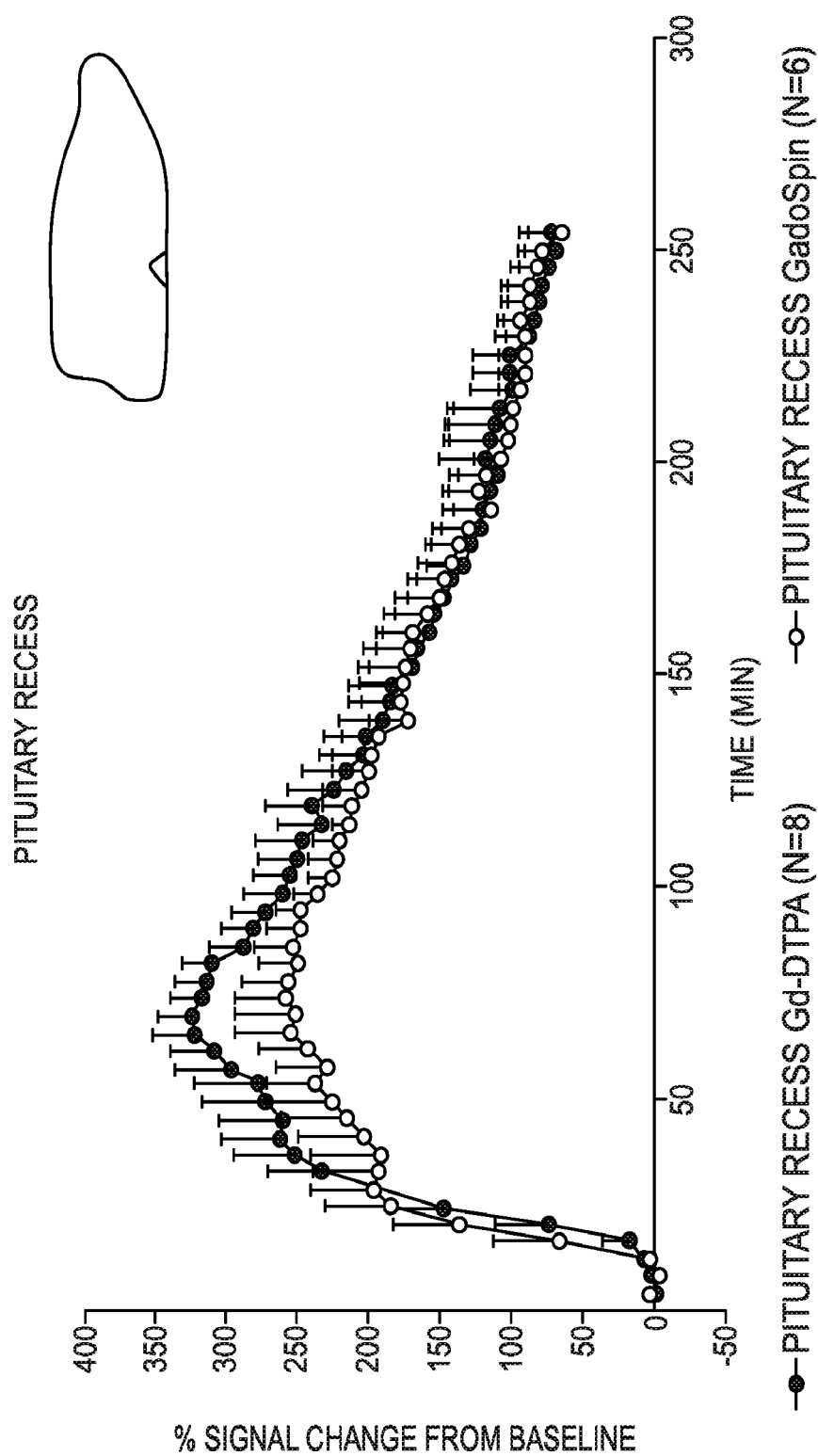
Figure 21B:
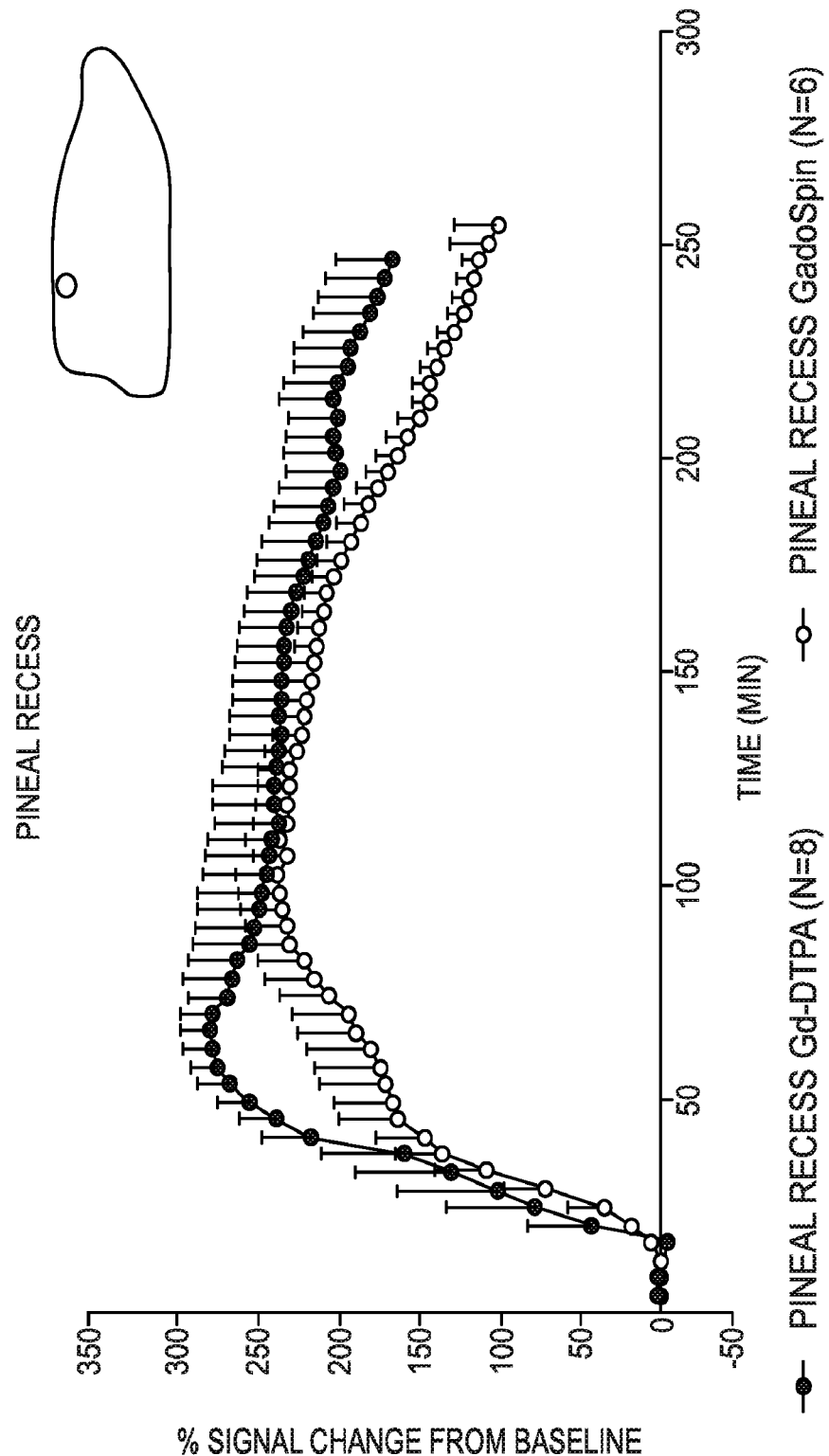
Figure 21C:
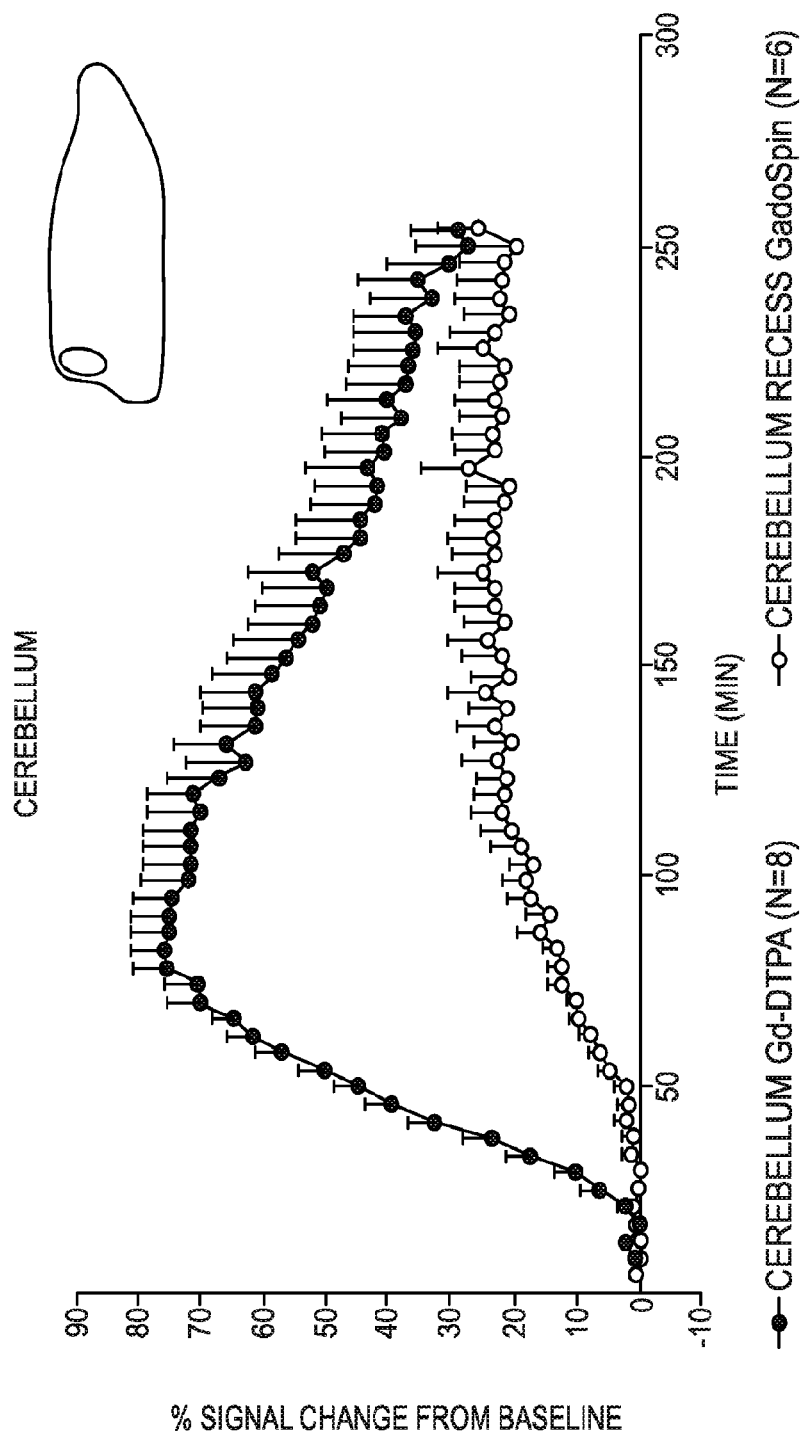
Figure 21D:
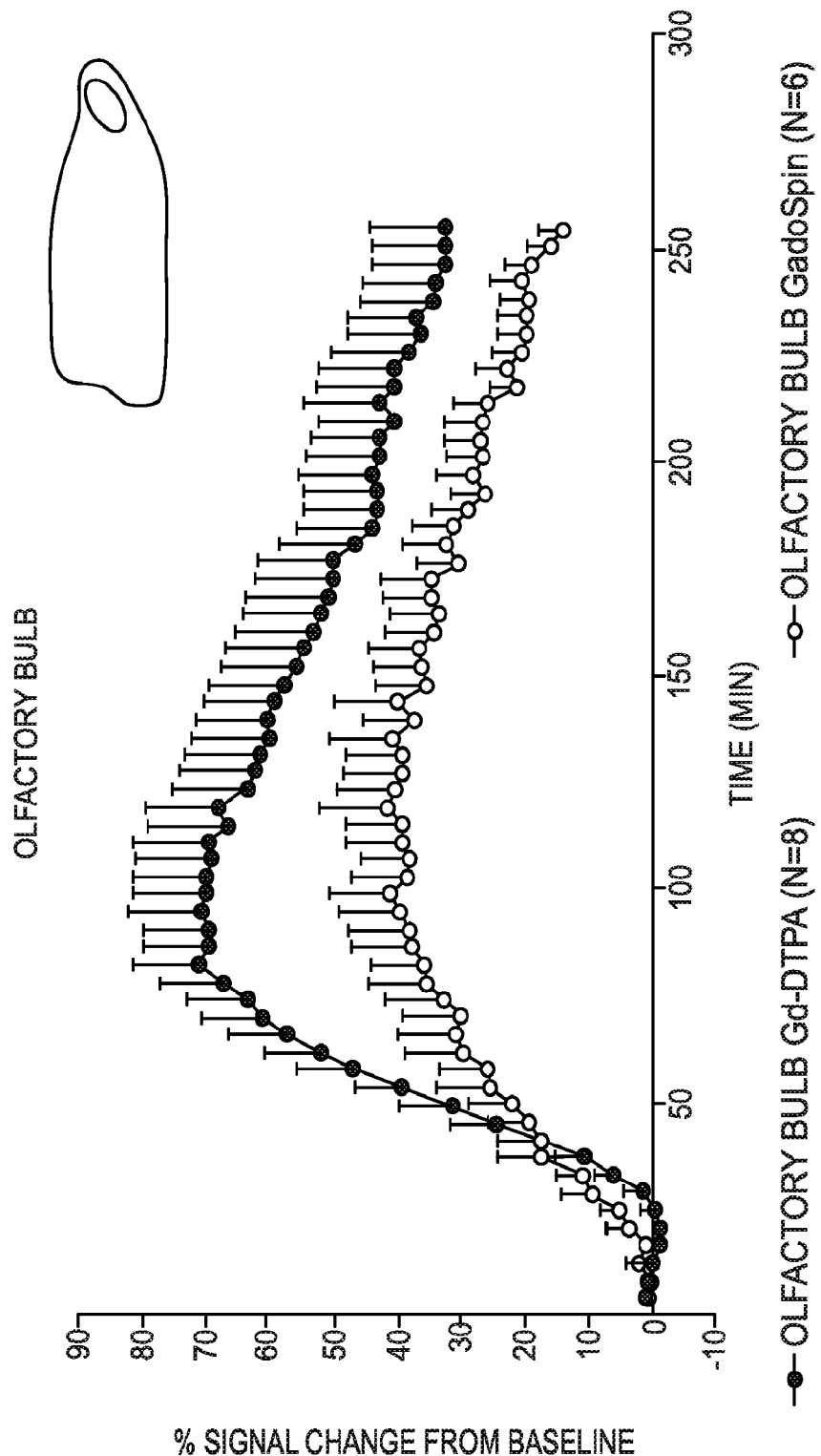
Figure 21E:
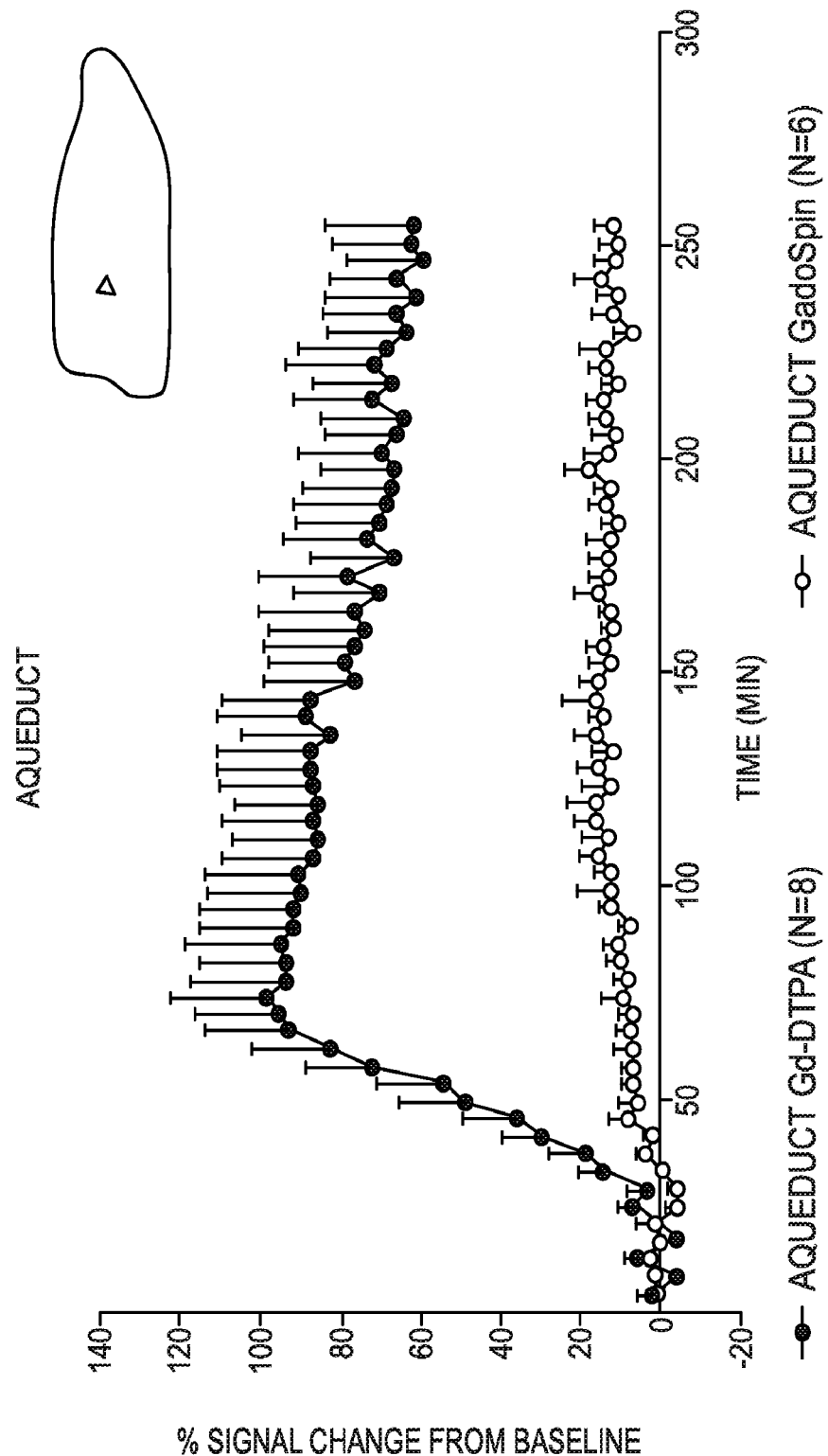
Figure 21F:
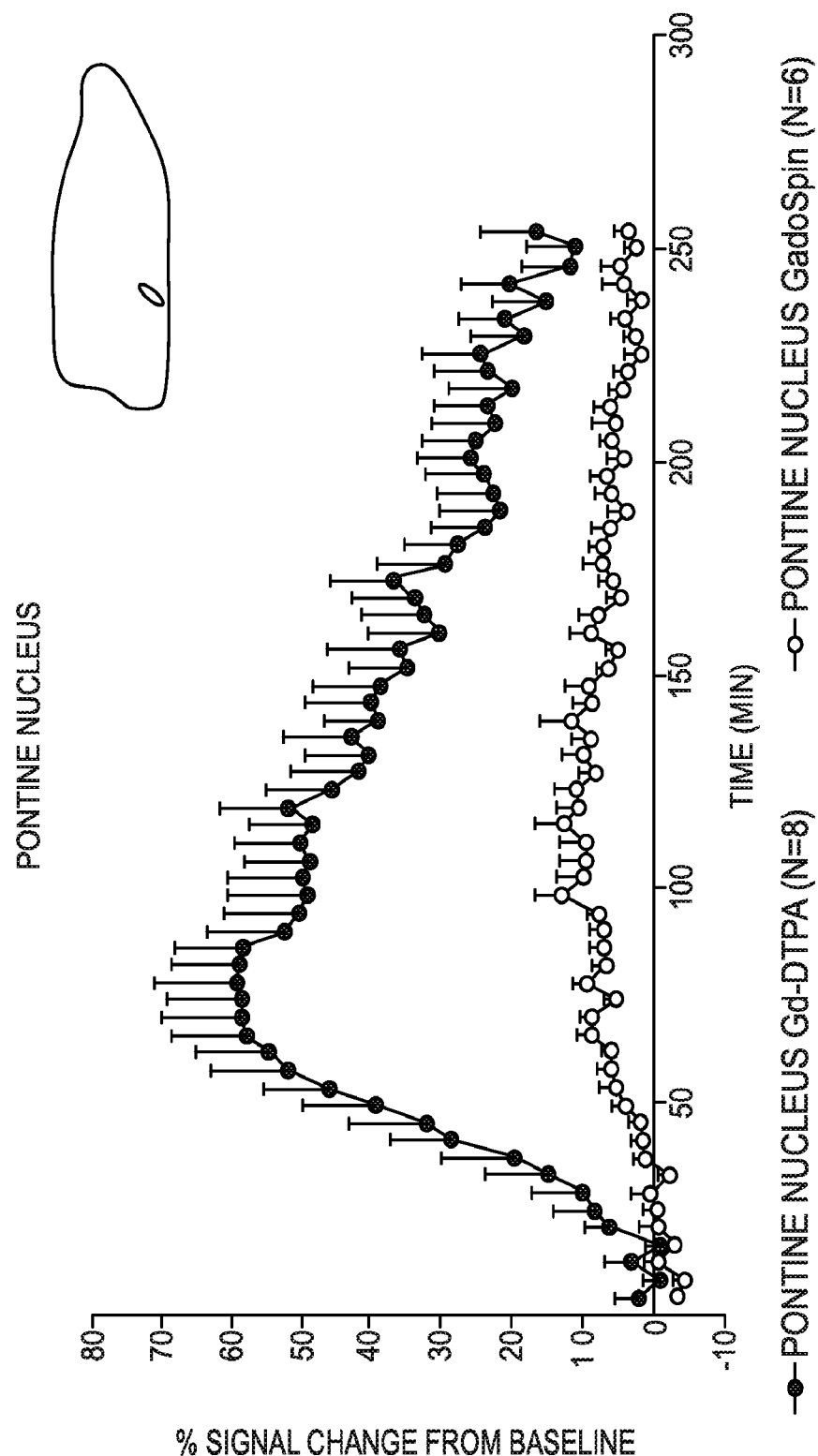

The total 'time-exposure' of paramagnetic contrast was first measured at key anatomical sites near large paravascular inflow conduits where contrast uptake was clearly visualized over time. Specifically, ROIs were sub-divided into the most proximal glymphatic inflow conduits (i.e., the pituitary recess and pineal recess) and 'parenchymal' ROIs such as the pontine nucleus, cerebellum, olfactory bulb and aqueduct. To compare the relative kinetics within these sub-regions, average TACs for Gd-DTPA and GadoSpin™ were calculated and plotted in FIGS. 21A-F. Within the pituitary recess, the average time course of signal intensity changes induced by Gd-DTPA and GadoSpin™ were largely identical over the entire study period (FIG. 21A). Similar findings were observed for the pineal recess (FIG. 21B). This confirms that within the proximal portions of the glymphatic pathway, defined as the subarachnoid spaces and proximal paravascular channels, contrast agent access and flux is largely independent of molecular size. In contrast, the average TACs for Gd-DTPA and GadoSpin™ within the cerebellum (FIG. 21C), aqueduct (FIG. 21E) and pontine nucleus (FIG. 21F) demonstrated clear intra-agent differences in influx rate, time-to-peak, and efflux rates. In each case, the apparent influx of large molecular weight GadoSpin™ into these regions lagged considerably behind that of Gd-DTPA. For example, in rats infused with Gd-DTPA, the average uptake in the cerebellum peaked at ~90 min post-injection, whereas in rats infused with GadoSpin™, the average cerebellar tissue uptake reached an apparent plateau at ~120 min post-injection.

Mean AUC values (mAUC), reflecting transit and uptake rates, were also calculated for Gd-DTPA and GadoSpin™ within each of these regions. At the pituitary recess, mAUC values derived for Gd-DTPA and GadoSpin™ were 743±266% signal change per time interval and 685±217% signal change per time interval, respectively (p-value=0.45). As the total amount of paramagnetic contrast passing through the pituitary recess varied among rats within each group, to minimize variability when comparing tissue uptake of paramagnetic contrast within and between groups, all regional mAUCs were normalized to the mAUC of the pituitary recess (representing the most proximal portion of the glymphatic pathway and main 'source' of contrast delivery). Table 1 shows the results of the regional mAUC ratio analysis and demonstrates that tissue uptake of Gd-DTPA was significantly higher than that of GadoSpin™ in the cerebellum, aqueduct and the pontine nucleus when compared to GadoSpin™

TABLE 1

Differences in total tissue uptake between rats injected with Gd-DTPA and GadoSpin ™

| Region | Gd-DTPA (N = 8) mAUC | Gado-Spin (N = 6) mAUC | P-value |
| --- | --- | --- | --- |
| Pineal recess[#] | 1.01 ± 0.35 | 1.13 ± 0.53 | 0.629 |
| Cerebellum | 0.28 ± 0.11 | 0.11 ± 0.08 | 0.007* |
| Olfactory Bulb | 0.24 ± 0.11 | 0.16 ± 0.06 | 0.113 |
| Aqueduct | 0.34 ± 0.23 | 0.06 ± 0.04 | 0.012* |
| Pontine Nucleus | 0.17 ± 0.09 | 0.03 ± 0.02 | 0.002* |

[#]2 rats in the Gd-DTPA group did not have contrast in the pineal recess. The data represents the ratio between the average mAUC of the anatomical region of interest and the average mAUC of pituitary recess. Results are presented as mean ± SD;
*P < 0.05.

Figure 22A:
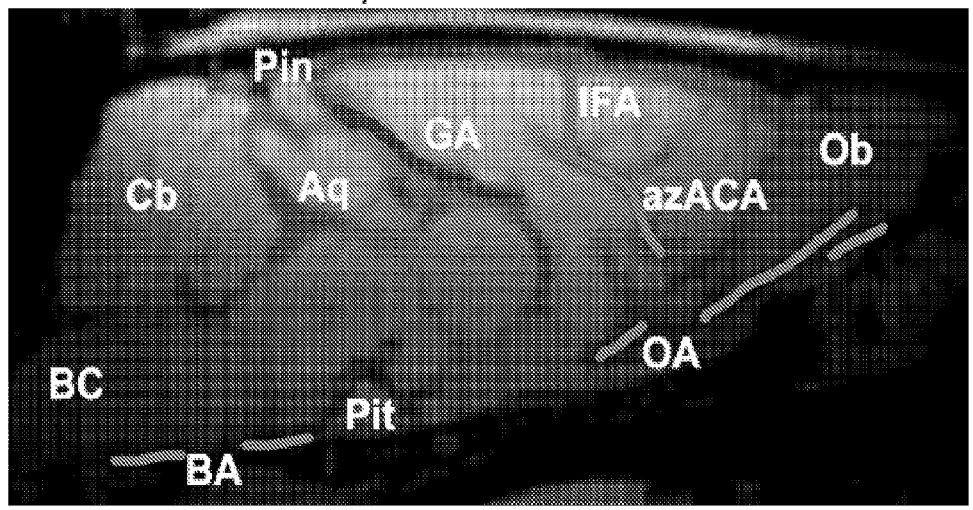
Figure 22B:
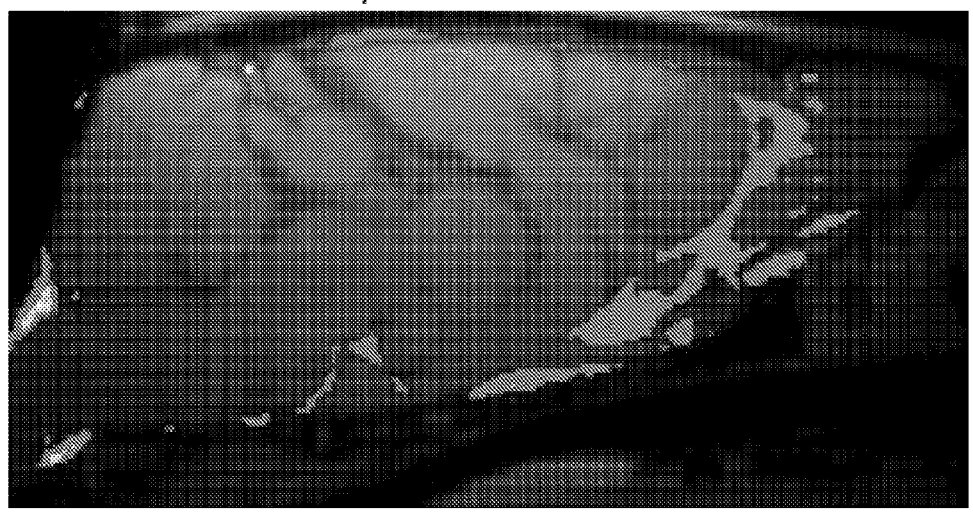
Figure 22C:
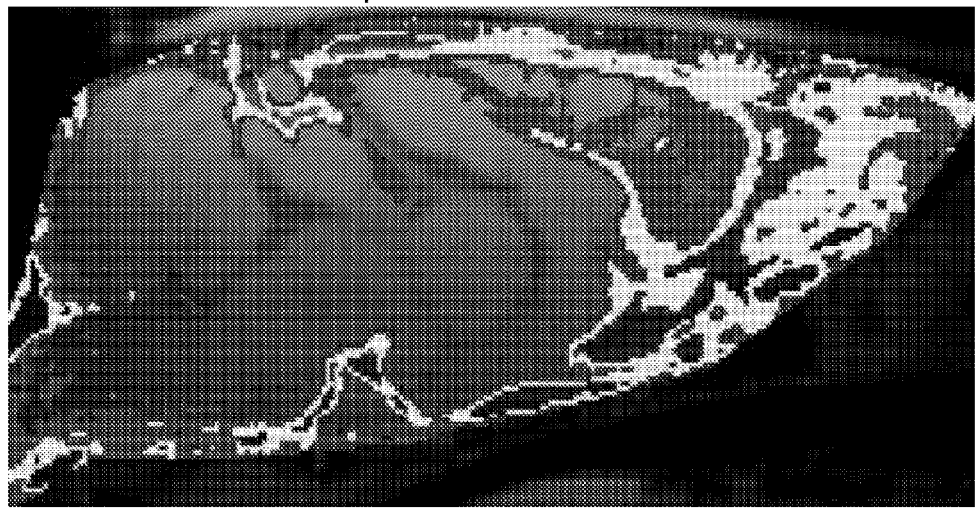
Figure 22D:
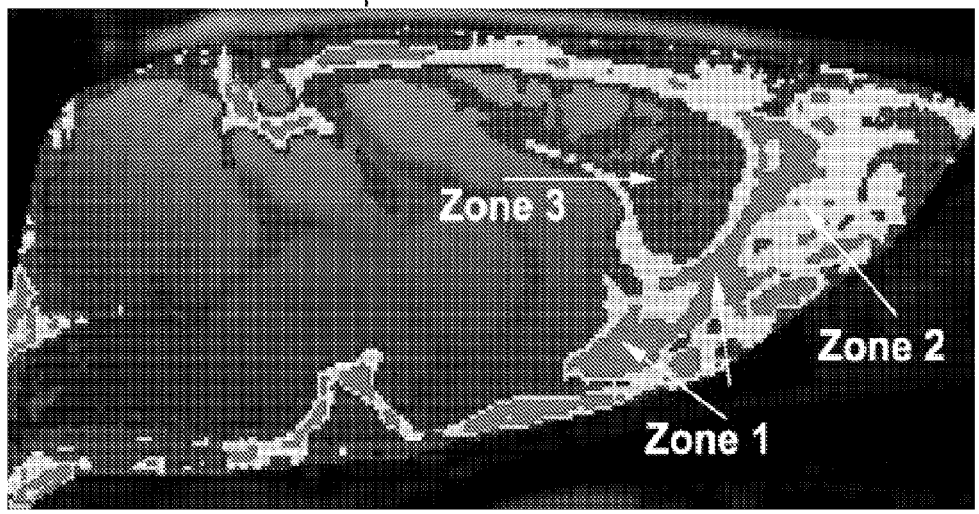
Figure 22E:
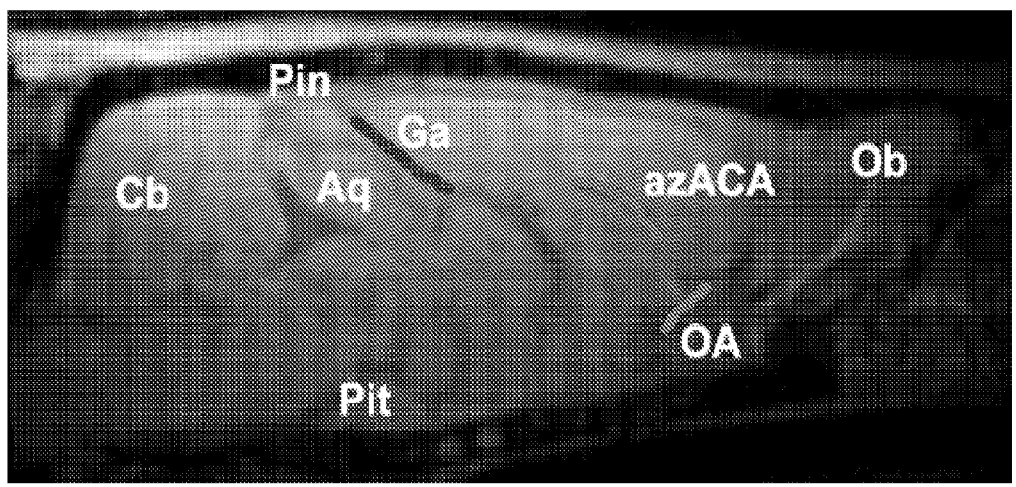
Figure 22F:
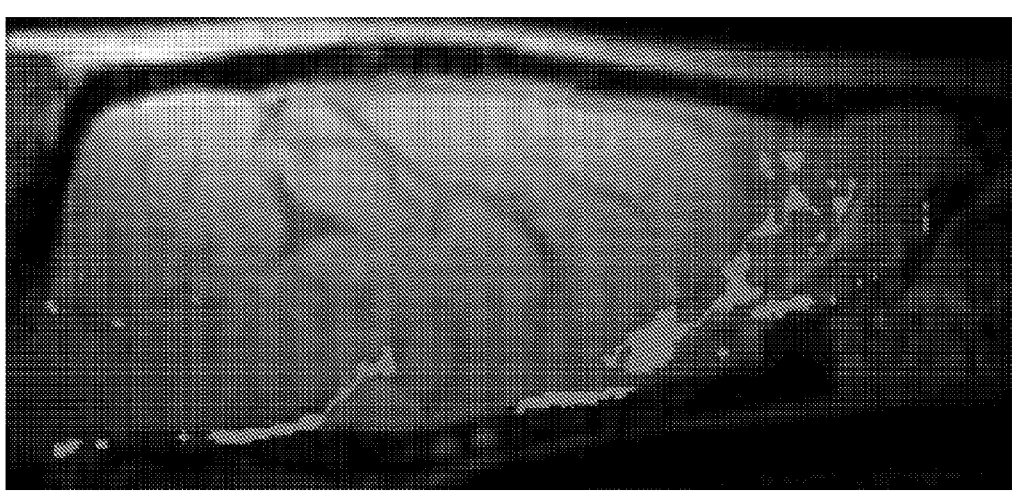

As a second non-parametric approach to analyze brain tissue uptake and distribution patterns of Gd-DTPA compared to GadoSpin™, a cluster analysis was performed on a series of 4 midline sagittal slices at the level of the aqueduct from each animal. The results of this analysis are shown in FIGS. 22A-J. Four clusters (K=4) were used for optimal visualization of the peri-vascular conduits. The different clusters were associated with different anatomical areas including tissue immediately associated with para-vascular areas (zone 1), tissue immediately adjacent to zone 1 (zone 2) and the most distally labeled voxels next to zone 2 (zone 3). The distribution pattern of the clusters and corresponding zones are shown in FIGS. 22A-J. In the GadoSpin™ rats, the para-vascular zone 1 includes the red and the orange clusters (FIG. 22B) and the green and blue clusters comprise zone 2 and zone 3, respectively, and represents the slower parenchymal glymphatic pathways such as the olfactory bulb and tissue adjacent to the pituitary recess and pineal recess (FIG. 22C, D). The TACs of the four clusters from the GadoSpin™ rat show that the most proximal para-vascular conduits (red and orange clusters) are represented by the highest signal changes (>300% signal change from baseline) when compared to the green and blue clusters; and furthermore that they represent the smallest compartment (FIG. 22I).

Figure 22G:
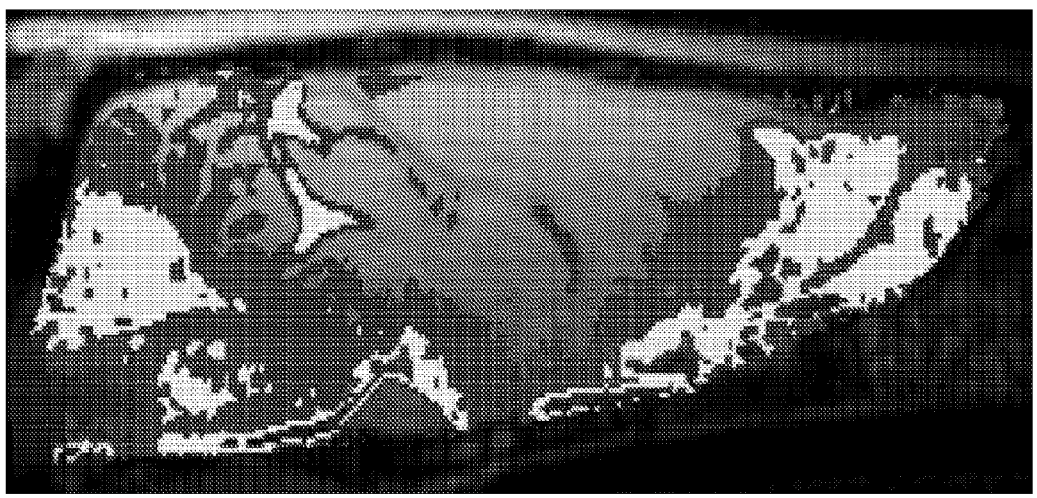
Figure 22H:
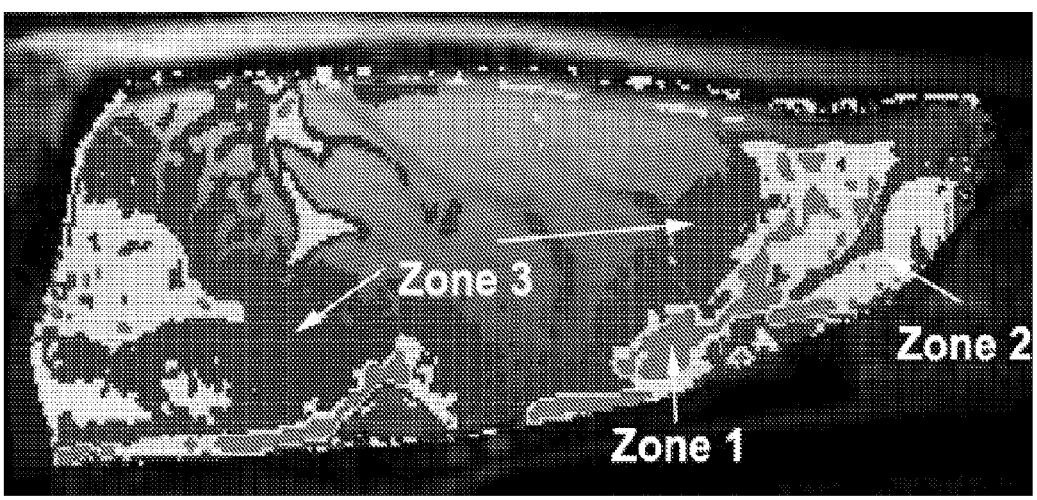
Figure 22J:
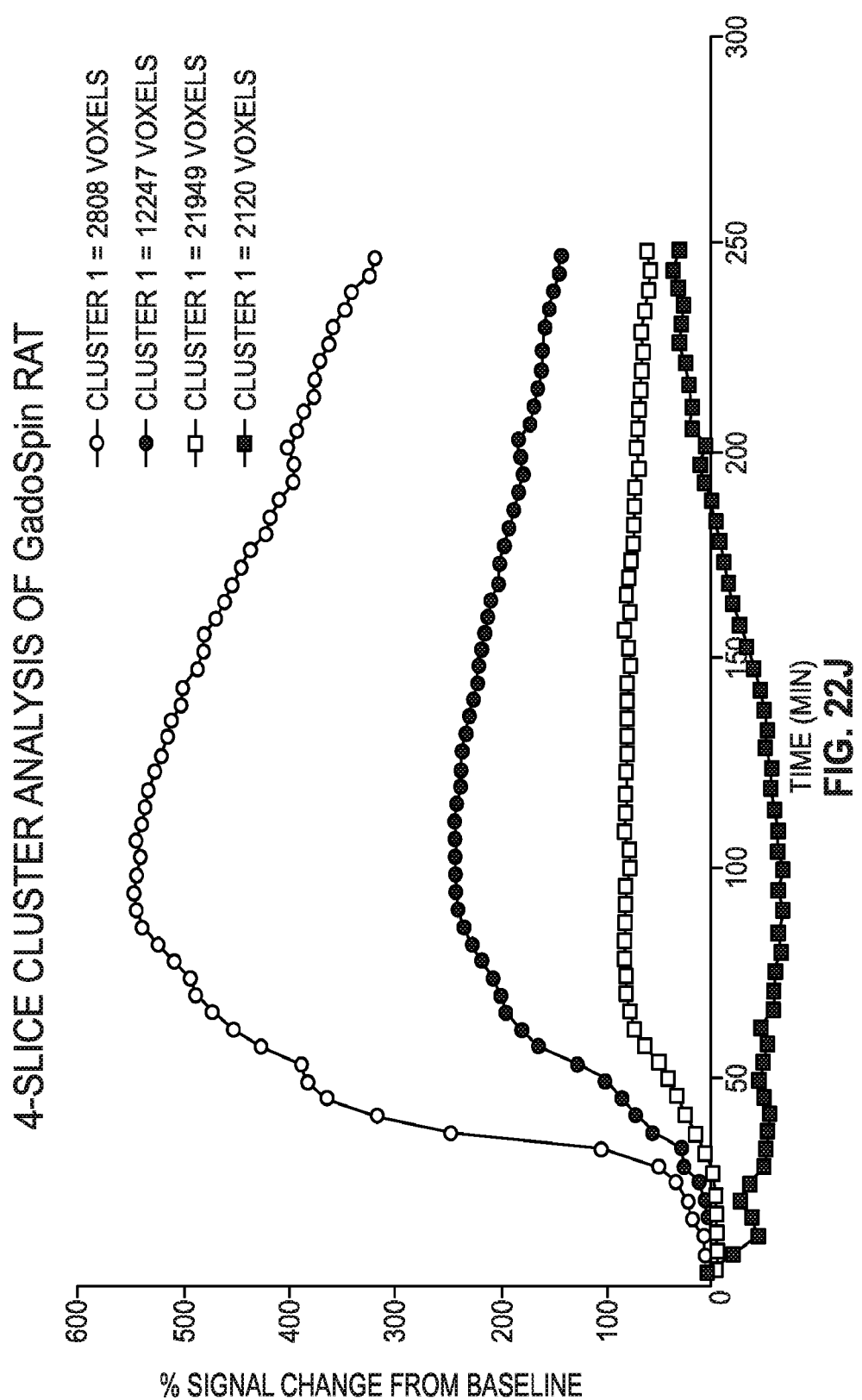

In the Gd-DTPA rats the cluster analysis similarly resulted in clusters distributed among three major anatomical zones, however, it included overall more brain tissue when compared to GadoSpin™. As shown in FIGS. 22A-J, in the Gd-DTPA rat the red clusters are located in para-vascular conduits as observed for GadoSpin™ (compare FIGS. 22B and F); and the green clusters are associated with deeper tissue areas such as the olfactory bulb and cerebellum (FIG. 22G). However, in contrast to GadoSpin™, the blue cluster voxels of the Gd-DTPA rats included most of the cerebellum and pontine nucleus (FIG. 22G-H) suggesting that the large molecular weight GadoSpin™ does not gain access to the brain interstitial space as readily as the small molecular weight Gd-DTPA. The TACs of the four different clusters from the Gd-DTPA rat are shown in FIG. 22J. The time-to-peak of the para-vascular red cluster is ~90 min, which is similar to that observed for the para-vascular red cluster of the GadoSpin™ rat. In other words, para-vascular transport of Gd-DTPA and GadoSpin™ share similar kinetics.

The quantitative results of the cluster analysis for Gd-DTPA and GadoSpin™ rats are presented in Table 2.

TABLE 2

Cluster analysis for 4 mid-sagittal slices

| Parameter | Gd-DTPA (N = 6) | GadoSpin™ (N = 6) | P-value |
|---|---|---|---|
| #Voxels - Zone 1, mean (SD) | 4048 (2146) | 5112 (2028) | 0.399 |
| #Voxels - Zone 2, mean (SD) | 15835 (5690) | 12759 (4162) | 0.310 |
| #Voxels - Zone 3, mean (SD) | 18295 (7407) | 6180 (3311) | 0.004 |
| #Voxels*AUC - Zone 1, mean (SD) | $22646 \times 10^4$ ($15816 \times 10^4$) | $19777 \times 10^4$ ($7368 \times 10^4$) | 0.695 |
| #Voxels*AUC - Zone 2, mean (SD) | $30037 \times 10^4$ ($10068 \times 10^4$) | $18335 \times 10^4$ ($5889 \times 10^4$) | 0.033 |
| #Voxels*AUC - Zone 3, mean (SD) | $12800 \times 10^4$ ($4448 \times 10^4$) | $4092 \times 10^4$ ($3458 \times 10^4$) | 0.003 |
| Zone $2_{\#Voxels*AUC}$/Zone $1_{\#Voxels*AUC}$, mean (SD) | 1.62 (0.60) | 1.01 (0.46) | 0.077 |
| Zone $3_{\#Voxels*AUC}$/Zone $1_{\#Voxels*AUC}$, mean (SD) | 0.89 (0.56cistern) | 0.25 (0.22) | 0.027 |

Table 2 sets forth the average total number of voxels of each cluster derived from the four mid-sagittal brain slices included in the analysis, the AUCs of the three different cluster/zone TACs*voxel number product for each cluster/zone. As can be seen from Table 2, the number of voxels allocated to zone 1 (para-vascular areas) are within similar range for Gd-DTPA and GadoSpin™ rats. However, in the Gd-DTPA rats the average total number of voxels in zone 3 (blue voxels in FIG. 22D), is significantly higher than observed for GadoSpin™ (blue voxels in FIG. 22H; P-value <0.05).

To further compare the relationships between clusters within the two groups, the ratio was calculated of zone 2's total time-weighted cluster number to that of the first (Zone $2_{\#Voxels*AUC}$/Zone $1_{\#Voxels*AUC}$) and the ratio of zone 3's total time-weighted cluster number to the first (Zone $3_{\#Voxels*AUC}$/Zone $1_{\#Voxels*AUC}$). These ratios represent the relationship between the contrast (Gd-DTPA and GadoSpin™) that passes through the paravascular regions (zone 1) and that which passes through parenchymal voxels (zones 2 and 3) over the study period. They represent a way to quantify the relative ease with which contrast agent can transit from the proximal glymphatic influx pathway (red and/or orange clusters) into the deeper brain interstitium (green and blue clusters). As can be seen in Table 2, the average Zone $3_{\#Voxels*AUC}$/Zone $1_{\#Voxels*AUC}$ ratio obtained in Gd-DTPA rats is significantly higher than that obtained in GadoSpin™ rats (Gd-DTPA: 0.89±0.56 vs. GadoSpin™: 0.25±0.22; p=0.027, t-test). Thus, this non-parametric cluster analysis clearly confirms that while small molecular weight Gd-DTPA and large molecular weight GadoSpin™ enjoy largely equivalent access to the proximal glymphatic pathway (including the subarachnoid and initial paravascular compartments), the access of the large molecular weight GadoSpin™ to the brain interstitial space is dramatically reduced compared to Gd-DTPA.

Fluorescence-based Imaging of Glymphatic Pathway Function

The volume of brain parenchyma exhibiting signal changes (T1-shortening) upon intrathecal contrast injection in rats was considerably more restricted than the penetration of fluorescent CSF tracers into the brain parenchyma detected by fluorescence-based imaging in mice (Example 1). This discrepancy stemmed from differences in total amount of contrast delivered intrathecally combined with the relative insensitivity (compared to fluorescence-based imaging) of T1-weighted MRI to detect signal changes induced by low concentrations of contrast agent when dispersed throughout the brain parenchyma. To test this, fluorescent dextrans (FITC-d500 and TR-d3; MW 500 kD and 3 kD, respectively) were co-injected by the same protocol used for the MRI study, and evaluated the routes and extent of tracer penetration into the brain by ex vivo fluorescence microscopy.

Figure 23A:
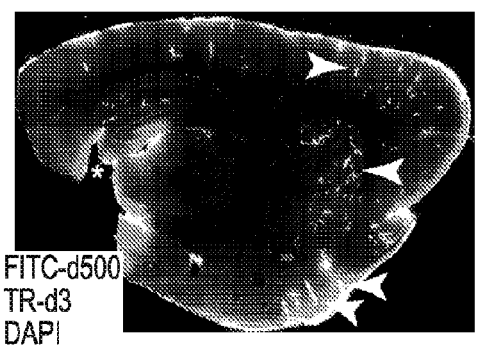

When imaged at low power (4×) by conventional epifluorescence microscopy, gross fluorescent tracer distribution was in broad agreement with the findings of the MRI imaging study. 30 to 60 min after tracer infusion, intense fluorescence labeling was apparent below the pial surface throughout the brain (FIGS. 23A, F). Tracer intensity was greatest along the ventral brain surface and along the margins of the pineal recess as it extends into the brain and connects with the hippocampal fissure. At these locations, CSF tracer penetration into the tissue was largely dependent upon molecular size, as the small molecular weight TR-d3 readily entered the parenchyma from the subarachnoid space while the large molecular weight FTIC-d500 did not penetrate beyond the pial surface (FIG. 23A, F).

Figure 23B:
Figure 23C:
Figure 23D:
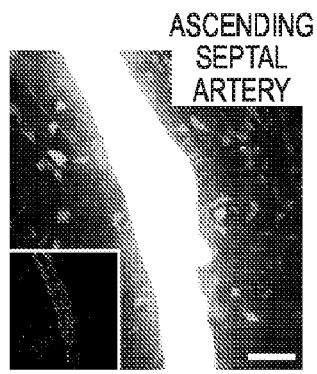
Figure 23E:
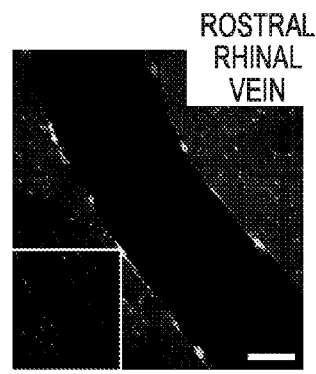
Figure 23F:
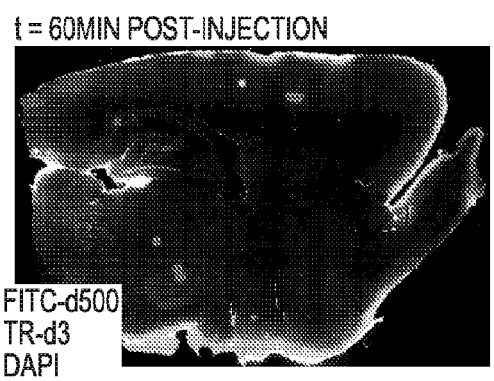

At 30 min post-injection, paravascular CSF influx into the brain was clearly evident (FIG. 23A-B). As observed in Example 1, paravascular influx occurred almost exclusively along the spaces surrounding penetrating arteries (FIGS. 23C-D) rather than along veins (FIG. 23E). This included smaller penetrating cortical arteries in addition to large caliber arteries originating at the ventral brain surface. Consistent with the differences in distribution observed between Gd-DTPA and GadoSpin™, TR-d3 and FITC-d500 distribution through the brain differed markedly. At 30 min post-injection, FITC-d500 remained restricted to the paravascular spaces and did not enter the surrounding parenchyma. In contrast, TR-d3 spread readily from the paravascular spaces into the surrounding parenchyma and was taken up by nearby neurons (FIGS. 23C-D).

Figure 23G:
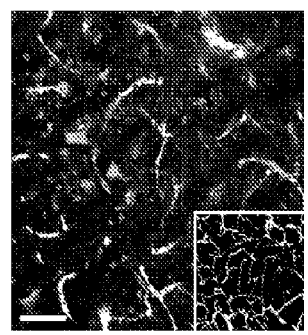
Figure 23H:
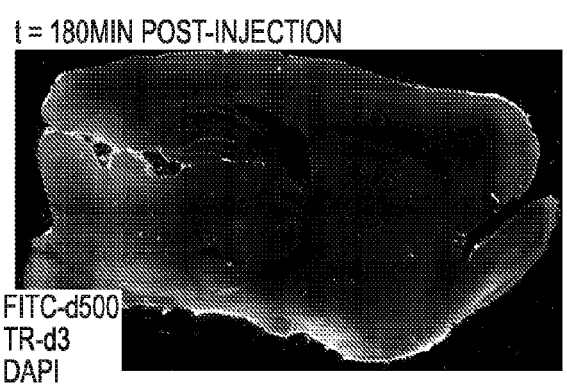
Figure 23I:

Signal changes induced within the parenchyma by Gd-DTPA peaked between 60-80 min post-injection (FIGS. 21C-D), then declined as contrast was cleared from the brain parenchyma. Between 30 and 60 min post-injection, brain-wide TR-d3 fluorescence appeared to increase as the tracer spread from the proximal pial surface and paravascular pathways to distribute diffusely throughout the parenchyma (FIGS. 23A, F). FITC-d500 remained confined to paravascular spaces, extending into capillary beds throughout the brain (FIG. 23G). At 180 min post-injection, brain fluorescence intensity had declined from values at 30 and 60 min (FIG. 23H), however tracer persisted in the surrounding para-venous pathways near the pineal recess (FIG. 23I).

Discussion

Example 1 demonstrated that the glymphatic pathway is a key contributor to the clearance of soluble amyloid β from the brain interstitium and proposed that the failure of this clearance might contribute to amyloid plaque deposition and AD progression. In light of these findings, there is great value in the development of a clinical prognostic test for measuring glymphatic pathway function throughout the human brain, and evaluating whether suppression of this system contributes to the development and progression of AD. This example demonstrates that glymphatic pathway function can be measured using a clinically relevant imaging technique, contrast-enhanced MRI, to visualize brain-wide CSF-ISF exchange. It demonstrates that following intrathecal administration, contrast moves rapidly by bulk flow through para-arterial pathways to reach major influx nodes at the pituitary recess, the olfactory bulb and the pineal recess. Furthermore, parametric and non-parametric data analysis of signal changes (T1 shortening) within different regions of the brain parenchyma clearly demonstrates that contrast movement into and through the interstitium is highly dependent upon the molecular weight of the paramagnetic contrast molecule. From the dynamic series of contrast-enhanced MRI images, kinetic parameters were developed and defined to characterize glymphatic system function that reflect rates of CSF-ISF exchange throughout the brain.

Example 1 demonstrated that subarachnoid CSF rapidly enters the brain parenchyma along paravascular channels surrounding penetrating arteries. The present findings demonstrate that external brain surface arteries such as the basilar artery, communicating arteries of the Circle of Willis and olfactory arteries constitute a rapid transport pathway for CSF within the wider subarachnoid space and ultimately the brain proper. Anatomically, these CSF transport pathways likely correspond to the leptomeningeal paravascular sheathes described in electron microscopy studies by Weller and colleagues (9-11). Both small (<1 kD) and large (~200 kD) molecular weight contrast moved through these para-arterial spaces at comparable rates, suggesting that bulk flow is driving CSF flux transport along these pathways (7, 12, 13). Analysis of intrathecal fluorescently labeled tracer influx into the rat brain confirmed that the bulk flow pathways surrounding the surface arteries are continuous with those surrounding smaller penetrating arteries and provide a direct route for the rapid influx of CSF into and through the brain interstitium. These para-arterial bulk flow pathways comprise the major component of a brain-wide system that facilitates that clearance of solutes and wastes from the brain interstitium.

The exchange of CSF and ISF between paravascular spaces and the interstitium occurs across perivascular astrocytic endfeet, which extend nearly complete coverage over the brain microvasculature (8). As a result, solutes that lack a specific molecular transport pathway (such as ion transporters or channels) across the endfeet must instead pass through the ~20 nm cleft between overlapping endfoot processes to gain access to the interstitial space. In Example 1, small tracers such as TR-d3 (diameter of hydration ($d_H$)=6.1 nm (14)) were observed to pass readily into and through the interstitium, whereas large tracers such as FITC-d2000 ($d_H$>32 nm (14)) remained largely confined to paravascular spaces. In this example, these findings were confirmed in the rat using fluorescence-based imaging. In addition, intrathecal administration of two different sized contrast agents, Gd-DTPA (MW ~1 kD) and GadoSpin™ (MW 200 kD), was used to demonstrate a similar effect of tracer size by dynamic contrast-enhanced MRI. For example, when TACs for the two contrast agents are compared at different anatomical locations, the large molecular weight GadoSpin™ entered the brain parenchyma at a dramatically lower rate than did the small molecular weight Gd-DTPA (compare red and blue curves, FIGS. 21A-F). Moreover, an independent cluster analysis clearly revealed that while both tracers had ready access to paravascular spaces, the brain volume accessible to Gd-DTPA was markedly larger than that accessed by GadoSpin™ (compare blue Zone 3, FIGS. 22D, H). Although the observed differences in CSF-ISF exchange patterns between Gd-DTPA and GadoSpin™ can be attributed to differences in molecular size, other possibilities exist. For example, other intrinsic molecular properties such as shape, electrostatic forces, size (radius of gyration), conformation or physical/chemical interactions may contribute to the dissimilar CSF-ISF exchange patterns observed with the two contrast molecules.

One apparent discrepancy between fluorescence-based and contrast enhanced MR-based imaging under the experimental protocol in this example is the inability to detect the small molecular weight contrast agent (Gd-DTPA) in the entire brain parenchyma after intrathecal injection. This is in contrast to the widespread parenchymal labeling with small molecular weight fluorescent CSF tracers in the mouse (Example 1). To confirm that these differences did not reflect species differences in CSF-ISF exchange, ex vivo fluorescence imaging in rat brain slices was conducted following intrathecal injection of similarly-sized fluorescent CSF tracers (compare FITC-d500 (500 kD) to GadoSpin™ (200 kD), and TR-d3 (MW 3 kD) to Gd-DTPA (MW ~1 kD)) using an injection protocol that was otherwise identical to that used for the MRI experiments. This fluorescence-based imaging confirmed the permeation of small molecular weight CSF tracer throughout the rat brain parenchyma, and restriction of the large molecular weight tracer to the paravascular spaces. Thus Gd-DTPA, like TR-d3, does in fact move throughout the brain parenchyma. However, the Gd-DTPA contrast concentrations achieved under the current intrathecal infusion protocol within the broader parenchyma simply were not sufficiently high to induce detectable signal changes (T1 shortening).

Notwithstanding these limitations, the intrinsic 3D nature of MRI permitted the visualization of the entire paravascular CSF-ISF exchange pathway throughout the whole brain, allowing us to define key nodes of CSF influx into the brain at the pituitary recess, olfactory artery, and pineal recess and to assess CSF-ISF exchange at many anatomically distinct locations simultaneously (FIG. 24). Through the dynamic image acquisitions, the kinetics of CSF tracer influx into and clearance from the paravascular and interstitial spaces could be measured and characterized for a given contrast molecule. For example, TACs generated for the subarachnoid pituitary recess and pineal recess after Gd-DTPA injection exhibit similar influx profiles whereas efflux from the pineal recess is markedly slowed compared to that of the pituitary recess (compare FIGS. 21A and B). Similarly, TACs generated for the cerebellum and aqueduct show similar influx kinetics, while the clearance of contrast from the aqueduct is prolonged compared to the cerebellar region (compare FIGS. 21C and E). One possible explanation for the protracted clearance from the pineal recess and the aqueduct is that these anatomical regions constitute primary ISF clearance sites, and thus appear to retain contrast (by accumulating it from other regions) for longer durations.

Analysis of the dynamic time series data also allowed the essential comparison of CSF-ISF exchange between a small (Gd-DTPA) and a large (GadoSpin™) molecular weight contrast agents. Here it is particularly important to note that within the pituitary recess, Gd-DTPA and GadoSpin™ influx and clearance are virtually identical (compare red and blue curves, FIG. 21A), whereas in the parenchymal pontine nucleus, GadoSpin™ movement into and through the region is dramatically reduced compared to Gd-DTPA (compare red and blue curves, FIG. 21F). Using a second approach, cluster analysis, the spatial distribution pattern of CSF-ISF exchange between the two contrast agents can be evaluated at the level of the aqueduct. Comparing either the raw brain volume occupied by Zone 3 (corresponding to the most distal compartment), or the normalized average Zone $3\#_{Voxels*AUC}/\text{Zone } 1_{\#Voxels*AUC}$ ratio (which reflects tracer penetration from the paravascular space into the brain parenchyma), GadoSpin™ penetration into and through the brain interstitium is dramatically restricted compared to Gd-DTPA (Table 2). Thus, dynamic contrast-enhanced MRI following intrathecal contrast agent administration provides an approach to characterizing both the kinetics and spatial distribution of glymphatic CSF-ISF exchange throughout the whole brain.

Example 1 demonstrates glymphatic pathway is an important contributor to the clearance of interstitial solutes such as soluble amyloid β, a peptide widely believed to be a critical driver of AD pathogenesis (15, 16). Example 1 indicates that failure of glymphatic pathway function may contribute to the deposition of amyloid β plaques and the progression of AD. The work discussed in this example, evaluating glymphatic pathway function by contrast-enhanced MRI in rats, provides the experimental groundwork for evaluating glymphatic pathway function in the human brain and whether its failure contributes to AD progression in man. To accomplish this, a safe, minimally invasive imaging approach to measuring glymphatic pathway function was necessary.

Contrast-enhanced MR cisternography is currently used clinically to visualize CSF leaks in patients undergoing treatment for spontaneous intracranial hypotension and CSF rhinorrhea (4, 5) and the Gd-DTPA utilized in the present study is already clinically approved for this purpose. While the current injection route via the cisterna magna and scan time required (>2 hrs) is not clinically relevant, Example 3 demonstrates the suitability of single-shot intrathecal lumbar injections for evaluating glymphatic pathway function in the brain.

The present example demonstrates that in the rat, this potentially clinically acceptable approach can be used to visualize and evaluate glymphatic pathway function, permitting assessment of kinetics and anatomical distribution patterns of paravascular CSF-ISF exchange throughout the whole brain. This approach can provide the basis for a wholly new prognostic strategy for evaluating AD susceptibility and disease progression.

REFERENCES CITED IN EXAMPLE 2

1. Brown, P. D., Davies, S. L., Speake, T., and Millar, I. D. 2004. Molecular mechanisms of cerebrospinal fluid production. Neuroscience 129:957-970.
2. Praetorius, J. 2007. Water and solute secretion by the choroid plexus. Pflugers Arch 454:1-18.
3. Battal, B., Kocaoglu, M., Bulakbasi, N., Husmen, G., Tuba Sanal, H., and Tayfun, C. 2011. Cerebrospinal fluid flow imaging by using phase-contrast MR technique. Br J Radiol 84:758-765.
4. Schick, U., Musahl, C., and Papke, K. 2010. Diagnostics and treatment of spontaneous intracranial hypotension. Minim Invasive Neurosurg 53:15-20.
5. Aydin, K., Terzibasioglu, E., Sencer, S., Sencer, A., Suoglu, Y., Karasu, A., Kiris, T., and Turantan, M. I. 2008. Localization of cerebrospinal fluid leaks by gadolinium-enhanced magnetic resonance cisternography: a 5-year single-center experience. Neurosurgery 62:584-589; discussion 584-589.
6. Example 1
7. Cserr, H. F., Cooper, D. N., Suri, P. K., and Patlak, C. S. 1981. Efflux of radiolabeled polyethylene glycols and albumin from rat brain. Am J Physiol 240:F319-328.
8. Mathiisen, T. M., Lehre, K. P., Danbolt, N. C., and Ottersen, O. P. 2010. The perivascular astroglial sheath provides a complete covering of the brain microvessels: an electron microscopic 3D reconstruction. Glia 58:1094-1103.
9. Pollock, H., Hutchings, M., Weller, R. O., and Zhang, E. T. 1997. Perivascular spaces in the basal ganglia of the human brain: their relationship to lacunes. J Anat 191 (Pt 3):337-346.
10. Weller, R. O. 2005. Microscopic morphology and histology of the human meninges. Morphologie 89:22-34.
11. Zhang, E. T., Inman, C. B., and Weller, R. O. 1990. Interrelationships of the pia mater and the perivascular (Virchow-Robin) spaces in the human cerebrum. J Anat 170:111-123.
12. Groothuis, D. R., Vavra, M. W., Schlageter, K. E., Kang, E. W., Itskovich, A. C., Hertzler, S., Allen, C. V., and Lipton, H. L. 2007. Efflux of drugs and solutes from brain: the interactive roles of diffusional transcapillary transport, bulk flow and capillary transporters. J Cereb Blood Flow Metab 27:43-56.
13. Abbott, N. J. 2004. Evidence for bulk flow of brain interstitial fluid: significance for physiology and pathology. Neurochem Int 45:545-552.
14. Sykova, E., and Nicholson, C. 2008. Diffusion in brain extracellular space. Physiol Rev 88:1277-1340.

15. Hardy, J. 2009. The amyloid hypothesis for Alzheimer's disease: a critical reappraisal. J Neurochem 110:1129-1134.
16. Hardy, J., and Selkoe, D. J. 2002. The amyloid hypothesis of Alzheimer's disease: progress and problems on the road to therapeutics. Science 297:353-356.

6.3. Example 3

Evaluating Glymphatic Pathway Function Utilizing Clinically Relevant Intrathecal Injection of CSF Tracer This example demonstrates that lumbar intrathecal contrast delivery is a clinically useful approach that can be used in conjunction with dynamic nuclear imaging to assess glymphatic pathway function in humans.

Summary

Neurodegenerative diseases such as Alzheimer's disease (AD) are associated with the aggregation of endogenous peptides and proteins that are thought to contribute to neuronal dysfunction and loss. As demonstrated in Examples 1 and 2 above, the glymphatic system is a key contributor to the clearance of interstitial solutes from the brain, including amyloid β. These findings suggest that measuring changes in glymphatic pathway function may be an important prognostic for evaluating neurodegenerative disease susceptibility or progression. However, no clinically acceptable approach to evaluate glymphatic pathway function in humans has yet been developed.

Time sequenced ex vivo fluorescence microscopy of coronal rat and mouse slices was performed at 30, 60, 120, and 180 min, following intrathecal injection of Texas Red-conjugated dextran-3 (TR-d3, MW 3 kD) and FITC-conjugated dextran-500 (FITC-d500, MW 500 kD) into the foramen magnum or lumbar spine. Tracer content in different brain regions (cortex, white matter, subcortical structures, and hippocampus) were then quantified in the anterior and posterior rat brain to map the movement of tracer following both injection routes.

Following both intracisternal and lumbar intrathecal injections, small molecular weight TR-d3 entered the brain along perivascular pathways and exchanged broadly with the brain parenchyma, consistent with the initial characterization of the glymphatic pathway in mice. Larger molecular weight FITC-d500 remained largely confined to the perivascular space. Lumbar intrathecal injections exhibited a reduced and delayed peak fluorescence intensity compared to intracisternal injections.

Background

Fatal neurodegenerative disorders such as Alzheimer's disease (AD) are characterized by progressive loss of neurons, sensory and motor impairments, and severe cognitive decline. Extracellular depositions of soluble amyloid β (Aβ) peptides and accumulation of hyperphosphorylated tau in neurofibrillary tangles are believed to contribute to the pathophysiology of AD (Hardy and Selkoe, 2002, Small and Duff, 2008, Maccioni et al., 2010), while analogous misfolded proteins aggregate in other neurodegenerative diseases, including Huntington's disease and amyotrophic lateral sclerosis (ALS) (Bruijn et al., 1998, Scherzinger et al., 1999, Ross and Poirier, 2004). In the case of AD, it is widely believed that Amyloid deposition results from an age-related failure of soluble Aβ clearance from the brain (Deane and Zlokovic, 2007). Although neuroimaging approaches are now widely available to detect the deposition of amyloid plaques and the evolution of plaque burden (Nordberg et al., 2010), no approach yet exists that allows the efficiency of Aβ clearance to be directly measured. The ability to detect changes in the efficiency of Aβ clearance would be a significant advance in evaluating susceptibility to and progression of AD and other neurodegenerative disorders.

Example 1 demonstrated that a large portion of subarachnoid CSF recirculates through the brain parenchyma along paravascular spaces, exchanging with brain interstitial fluid (ISF) of the brain parenchyma before being cleared via para-venous pathways. The continuous circulation of CSF along this pathway facilitates the clearance of extracellular solutes, including soluble Aβ, from the brain. This brain-wide pathway has been termed the 'glymphatic system', based upon the critical role that astroglial water transport through the astrocytic aquaporin-4 water channel plays in facilitating CSF-ISF exchange and solute clearance (Example 1). One implication of these findings is that changes in glymphatic pathway function may contribute to the failure of Aβ clearance in the pre-clinical stages of AD, while a method to measure glymphatic pathway function in clinical populations might allow AD disease susceptibility and progression to be evaluated.

Initial characterization of the glymphatic system utilized in vivo two-photon microscopy and ex vivo fluorescence imaging of intracisternally injected CSF tracers to map the brain-wide pathway and to quantify the efficiency of solute clearance in mice. These approaches are not appropriate for clinical application, given the optical limitations of fluorescence-based imaging and the complications that are associated with intracisternal injections in humans (Keane, 1973). In the clinical setting, dynamic nuclear imaging modalities such as positron emission tomography (PET) and magnetic resonance imaging (MRI) are routinely used to monitor CSF flux in the diagnosis of spontaneous intracranial hypotension (SIH) and post-traumatic CSF rhinorrhea or otorrhea (Burns, 2008, Daele et al., 2011). These imaging modalities permit time-sequenced three-dimensional (3D) representation of the brain with high spatial and temporal resolution of tracer distribution. In Example 2, a follow-up pre-clinical study, contrast-enhanced magnetic resonance imaging (MRI) was successfully utilized after intrathecal injection of gadolinium-based contrast agent into the cisterna magna to measure glymphatic pathway function in rats.

In contrast to intracisternal injections, lumbar intrathecal injections of radio-tracer are presently used along with computer-tomography/myelography and digital subtraction myelography to diagnose dural leaks associated with SIH, pseudomeningocele, and superficial siderosis (Phillips et al., 2002, Hoxworth et al., 2012), as well as the integrity of the spinal cord in the setting of injury or tumor (Kapila, 1987, Adams et al., 1988). Lumbar intrathecal injections are additionally used in everyday practice for the delivery of anesthetics (Popping et al., 2012), and would thus provide an ideal delivery route for contrast agents that could then be used in conjunction with dynamic contrast-enhanced MRI to evaluate glymphatic clearance in humans. The present pre-clinical study evaluates whether lumbar intrathecal CSF tracer delivery permits the evaluation of glymphatic pathway function in the brain. The influx kinetics and parenchymal distribution of intracisternally and lumbar intrathecally injected fluorescent tracers in the rat brain are compared. The data demonstrate that CSF tracer injected via both routes enters the brain through paravascular spaces and exchanges with the parenchyma in a manner consistent with the previous characterization of the glymphatic pathway in mice in Example 1. This shows that the lumbar intrathecal injection is a clinically viable contrast delivery route to assess glymphatic function in humans.

Methods

Surgical Preparation

Female Sprague-Dawley rats (200-230 g; Charles River Labs, USA) were used in all experiments. The rats were housed under standard laboratory conditions, with access to food and water, ad libitum. All experiments were approved by the University Committee on Animal Resources of the University of Rochester and carried out according to guidelines from the National Institutes of Health. Rats were initially induced with isofluorane (3%), then anesthetized with sodium pentobarbital (50 mg/kg i.p.). Supplemental sodium pentobarbital was given as necessary. For intracisternal injections, anesthetized rats were fixed in a stereotaxic frame, the foramen magnum was surgically exposed, and a 30GA needle was inserted into the cistern magna. For lumbar injections, the lumbar spinal column was exposed, an $L_{2-3}$ laminectomy was performed, and 30GA needle was inserted into the subarachnoid space.

Tracer Injection

In the present study, two different fluorescent tracers were used: large molecular weight fixable fluorescein isothiocyanate (FITC)-conjugated dextran (500 kD, FITC-d500; Invitrogen) and small molecular weight fixable Texas Red-conjugated dextran (3k, TR-d3; Invitrogen). Tracers were constituted in artificial CSF at a concentration of 0.25%. For intracisternal and lumbar injection, tracers were infused at a rate of 1.6 µl/min for the 30 min injection groups, while injection was stopped at a total volume of 70 µl for injection times greater than or equal to 60 min. At t=30, 60, or 120 min after the start of injection, rats were transcardially perfused with ice-cold heparinized PBS, followed by 4% paraformaldehyde (PFA). Brains were removed, post-fixed overnight in 4% PFA at 4° C., and 50 µm coronal slices were cut on a vibratome (Leica) and mounted with PROLONG Anti-Fade Gold with DAPI (Invitrogen).

Immunofluorescence

Free floating immunofluorescent labeling was conducted on a separate set of 50 µm slices. For intracisternal injection, 8 slices from each animal from the 60 min time point were used. For lumbar injection, 8 slices from each animal from the 120 min time point were used. These time points were chosen because they corresponded with peak CSF tracer influx via the respective injection routes. Slices were blocked in 3% normal donkey serum (Jackson Immunoresearch) for 1.5 hrs at room temperature, incubated in mouse anti-glial fibrillary acidic protein (GFAP, an astrocytic marker; 1:1000, Millipore) or Biotinylated Griffonia (Brandeiraea) *Simplicifolia* Lectin I Isolectin B4 (Ib4, a vascular endothelial marker; 1:100, Vector Laboratories) overnight at 4° C. Secondary detection was conducted for mouse-anti GFAP using Cy5-conjugated donkey anti-mouse secondary antibody (1:500, Jackson Immunoresearch) and for Ib4 using Cy5-conjugated streptavidin (1:250, Jackson Immunoresearch). Slices were incubated for 2 hrs at room temperature in the secondary antibody solution. After washing, all slices were mounted with PROLONG Antifade Gold with DAPI (Invitrogen).

Fluorescence Imaging

Tracer movement into the brain was measured by conventional fluorescence microscopy. Whole slice 3-channel montages were generated at 4× magnification for 8 slices per animal using the Virtual Slice module of the Microlucida software (Microbrightfield), on an upright fluorescence microscope (Olympus) equipped with a motorized stage. This included separate DAPI, green (for FITC) and red (for Texas Red) emission channels. The gain and exposure settings were determined based on un-injected control slices and held constant throughout all imaging sessions. Slice fluorescence (fluorescent tracer accumulation) in the slices was quantified using ImageJ software (NIH) as described in Example 1. Anatomical brain regions of interest (ROIs) were generated based upon the DAPI emission channel for the cortex, white matter (including corpus callosum, internal and external capsule), subcortical structures (striatum, thalamus, hypothalamus) and hippocampus. The background fluorescence for each channel was uniformly subtracted and the mean pixel intensity for each region was measured. Distribution of large and small molecular weight CSF tracers throughout the brain parenchyma was evaluated under high power by laser scanning confocal microscopy (Olympus). Immunofluorescently-labeled slices were imaged at 40× objective power.

Statistical Analysis

All values were expressed as mean±SEM. Intensities were compared at each time point and across injection routes by 2-way analysis of variance (ANOVA) with Bonferroni's post-hoc test to evaluate differences at individual time points (Graphpad Prism software). A 'P' value <0.05 was considered significant.

Results and Discussion

Figure 25A:
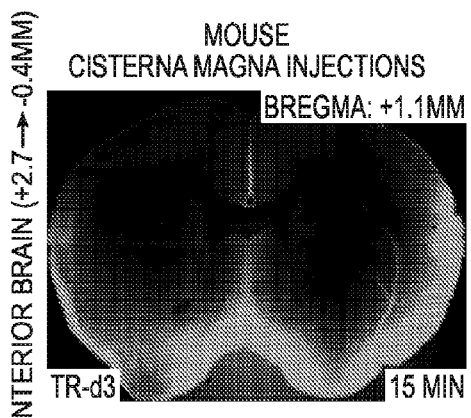
Figure 25B:
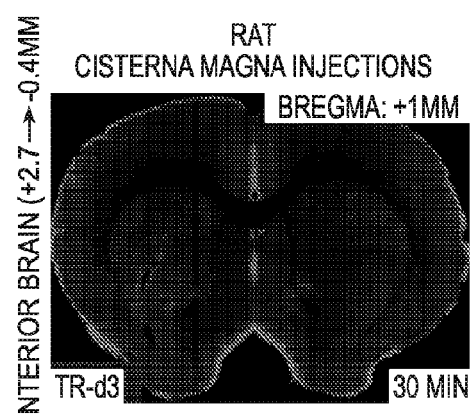
Figure 25C:
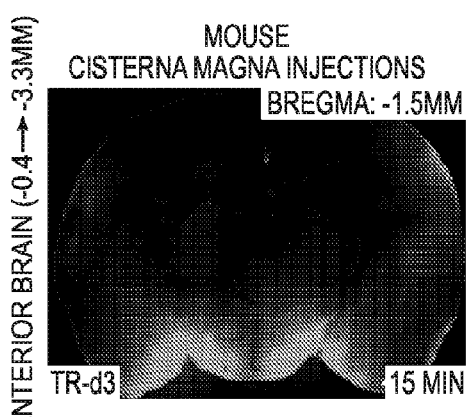
Figure 25D:
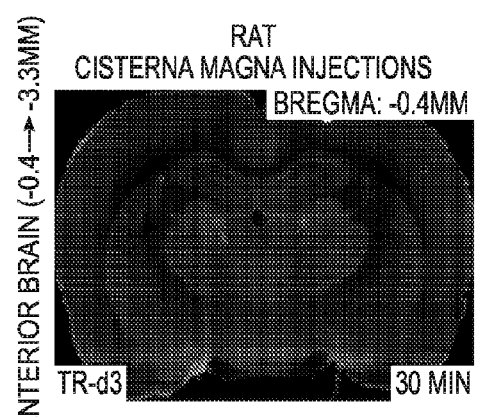
Figure 25E:
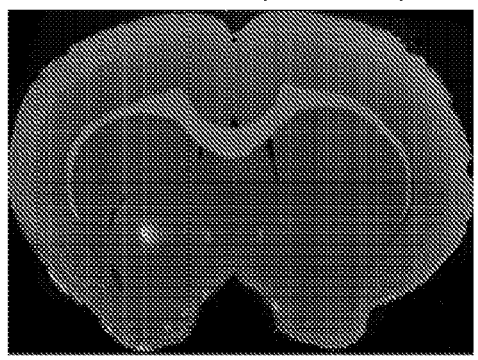
Figure 25F:
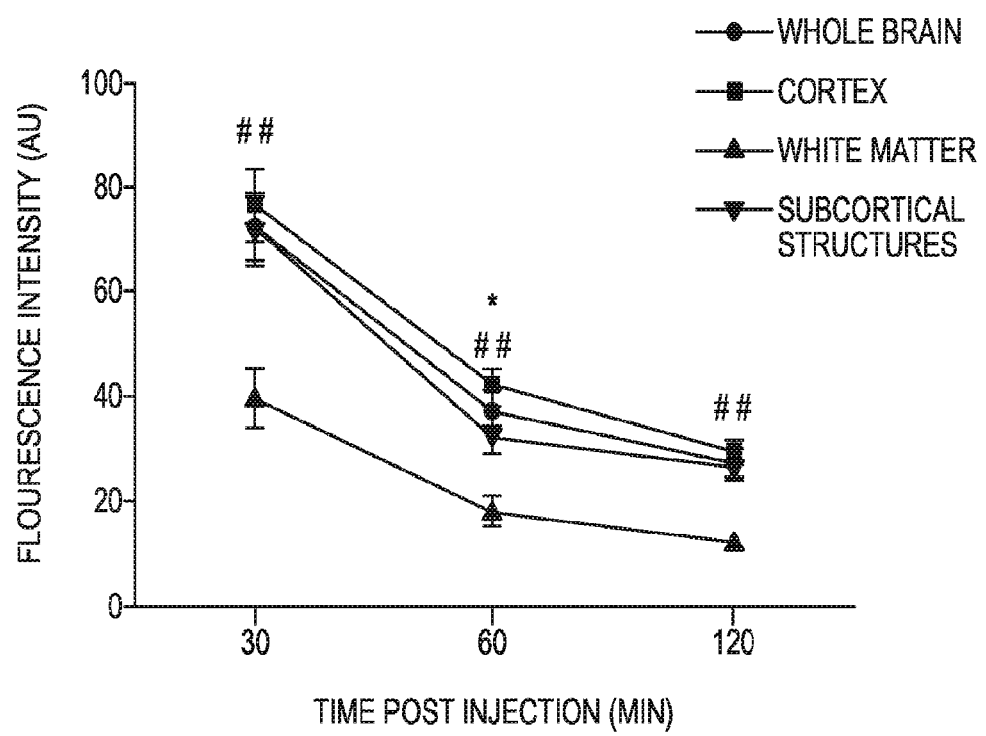
Figure 25G:
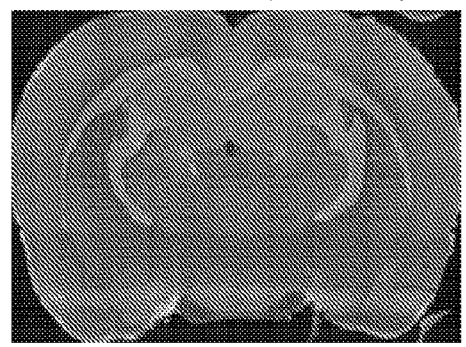
Figure 25H:
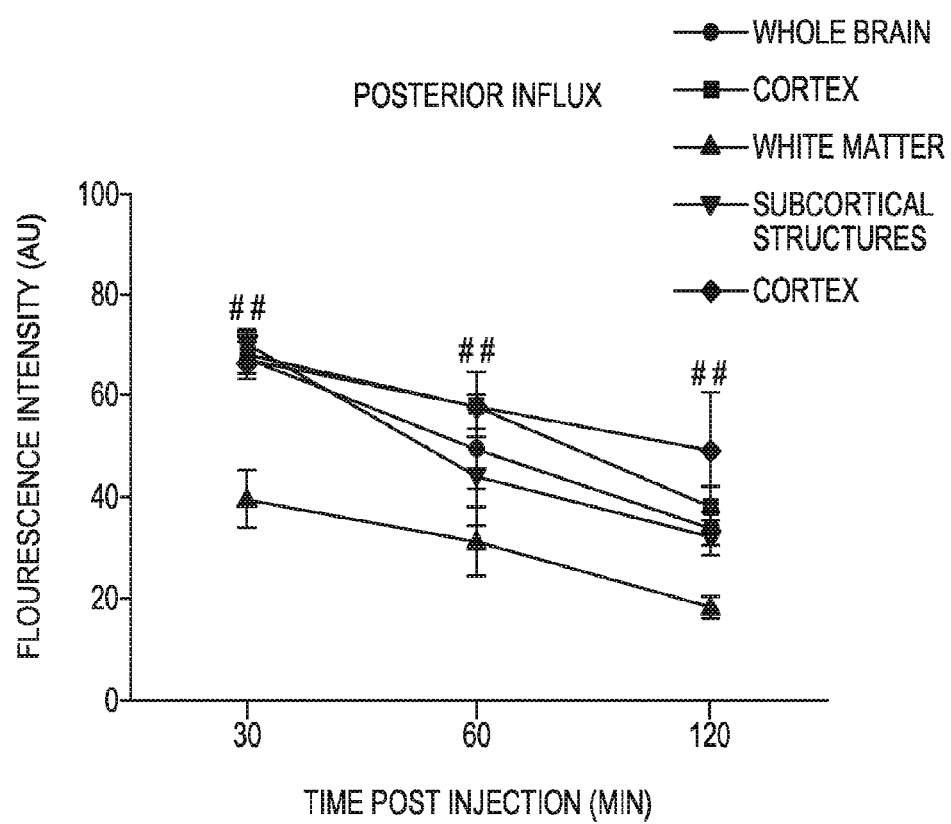

In the mouse study in Example 1, 2-photon in vivo imaging was used to demonstrate the existence of a brain-wide paravascular route that permits CSF to exchange with the ISF of the brain parenchyma termed the 'glymphatic' system. CSF-ISF exchange along these paravascular pathways was supported by astroglial aquaporin-4 water channels and the movement of fluid through this pathway facilitated the clearance of interstitial solutes, including soluble Aβ, from the brain. The purpose of the present study was to assess whether glymphatic pathway function could be similarly evaluated after lumbar intrathecal injection of fluorescent CSF tracers. In contrast to Example 1, which was performed on mice, the current study characterized glymphatic flow in the adult Sprague Dawley rat. This choice to characterize glymphatic flux in rat expands the understanding of glymphatic function into a rodent model recognized in the art as a pre-clinical model for human methods of treatment, while also moving to a model that makes it easier to perform lumbar intrathecal injections. Intracisternal CSF tracer injections were carried out in parallel to provide a direct comparison to the injection route used previously (Example 1). Imaging CSF-ISF exchange in mouse and rat by intracisternal tracer injection The movement of intrathecal CSF fluorescent tracer (TR-d3, MW 3 kD) into the rat brain parenchyma after Cisterna Magana injection was characterized. In FIGS. 25A-H, intracisternal CSF tracer influx and clearance were evaluated in mouse and rat. Representative anterior (FIGS. 25A-B) and posterior (FIGS. 25C-D) coronal slices are shown from mouse (FIGS. 25A, C) and rat (FIGS. 25B, D) brains following intracisternal injection of Texas Red-conjugated dextran (TR-d3, MW 3 kD; t=30 min post-injection) showed similar tracer distributions between species. (FIGS. 25E-H) Tissue fluorescence was evaluated in different brain regions: cortex (blue), white matter (grey), hippocampus (magenta), and subcortical structures (red) of the anterior (FIGS. 25E-F) and posterior (FIGS. 25G-H) brain. FIGS. 25F and H show quantification of mean fluorescence intensity within each region (*P<0.05 cortex vs. subcortical structures; ##P<0.01 vs. cortex; 2-way ANOVA; n=3-4 per time point).

FIGS. 25A-D shows representative images from mouse and rat brain slices, respectively taken 1.1 and 1.0 mm anterior and 1.5 and 0.4 mm posterior to the Bregma 0 point, that were fixed 30 min after injection (the time point of peak fluorescence intensity). Consistent with the prior study in mice (Example 1), intracisternally-injected TR-d3 was observed to move rapidly into the rat brain parenchyma, both across the pial surface and along paravascular pathways (FIGS. 25B, D) and exchanged broadly with the brain interstitium. To quantify tracer movement into different brain regions four anterior (FIGS. 25E-F) and posterior (FIGS. 25G-H) regions of interest were defined including the cortex, white matter, subcortical structures, and hippocampus (FIGS. 25E, G show the regions of interest). Analysis of TR-d3 fluorescence either within the whole ex vivo slice or within the cortex, white matter, or sub-cortical structures revealed that the influx of intracisternally-injected CSF tracer peaked around 30 min post-injection, then began to decline at later time points as the tracer was cleared from the brain tissue (FIG. 25F, H; n=3-4 animals per time point).

Analysis of tracer clearance between the four different anatomical regions suggested that tracer clearance from subcortical structures was faster than from the cortex (FIGS. 25F, H; *$P<0.05$ cortex vs. subcortical, 2-way ANOVA). This is consistent with the prior observation that subcortical regions enjoy the largest influxes of subarachnoid CSF along large caliber penetrating arteries from the ventral brain surface (Example 1). Furthermore, these regions are most proximate to the para-venous clearance pathways that drain medially along the internal cerebral veins. When anterior versus posterior tracer fluxes were compared, both peak values at 30 min and the rate of clearance between 30-120 min post-injection were lower in the posterior brain compared to the anterior brain (compare FIGS. 25F, H). These observations are consistent with MRI findings in the rat in which glymphatic fluxes along anterior penetrating arteries were both faster and greater in magnitude than those that followed branches of mediolateral arteries such as the middle cerebral artery (Example 2). In both the anterior and posterior brain, TR-d3 fluorescence intensity in the white matter was significantly lower than the cortex at all time points (FIGS. 25F, H; ##$P<0.01$ vs. cortex, 2-way ANOVA), while the rate of tracer clearance from the white matter did not appear to consistently differ from other brain regions. The shift in white matter fluorescence intensity likely stems from lower levels of tissue autofluorescence of white matter compared to gray matter. Alternatively, this may reflect the lower levels of CSF tracer penetration into the subcortical white matter observed in the prior study (Example 1).

Imaging Rat CSF-ISF Exchange Following Lumbar Intrathecal Injections

Figure 26A:
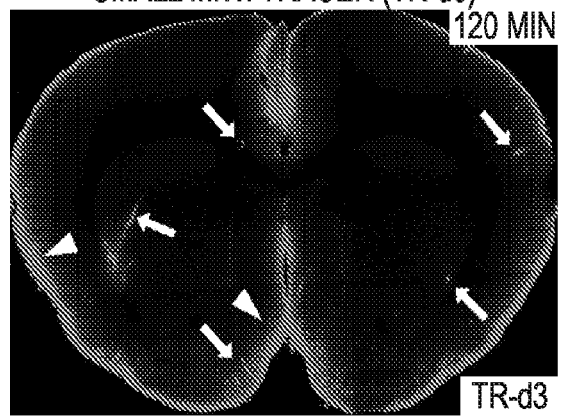
Figure 26B:
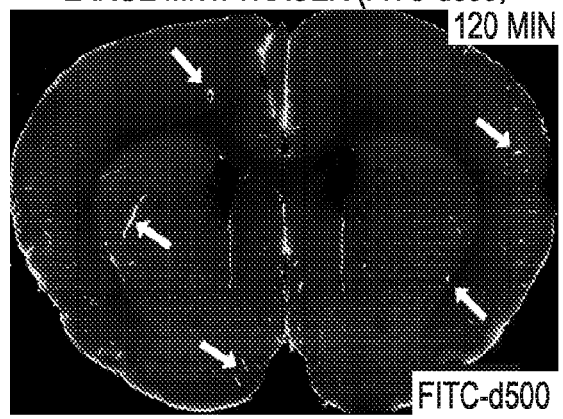

FIGS. 26A-F show the effect of molecular weight on tracer influx into the brain after lumbar intrathecal injection. FIGS. 26A-B show coronal brain slices that show penetration of large molecular weight FITC-conjugated dextran (FITC-d500, MW 500 kD) and small molecular weight Texas Red-conjugated dextran (TR-d3, MW 3 kD) 120 min after lumbar intrathecal co-injection. FITC-d500 is largely confined to paravascular spaces (FIG. 26B, arrows), while TR-d3 moves readily though the brain parenchyma from paravascular spaces (FIG. 26A, arrows) or from the pial surface (arrowheads). FIGS. 26C-F show quantification of fluorescent tracer influx into anterior (FIGS. 26C-D) and posterior (FIGS. 26E-F) brain after lumbar intrathecal injection, anatomically subdivided into cortex, white matter, subcortical structures, and hippocampus. (*$P<0.05$, *$P<0.01$ cortex vs. subcortical structures; ##$P<0.01$ cortex vs. white matter; †$P<0.05$, ††$P<0.01$ cortex vs. hippocampus; 2-way ANOVA; n=3-4 per time point).

Figure 26C:
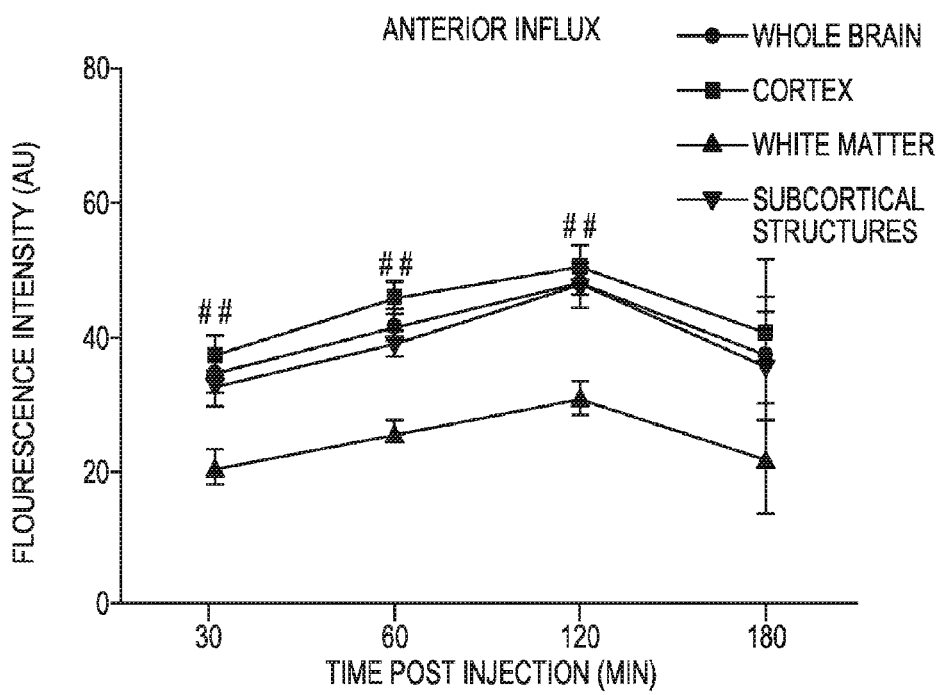
Figure 26D:
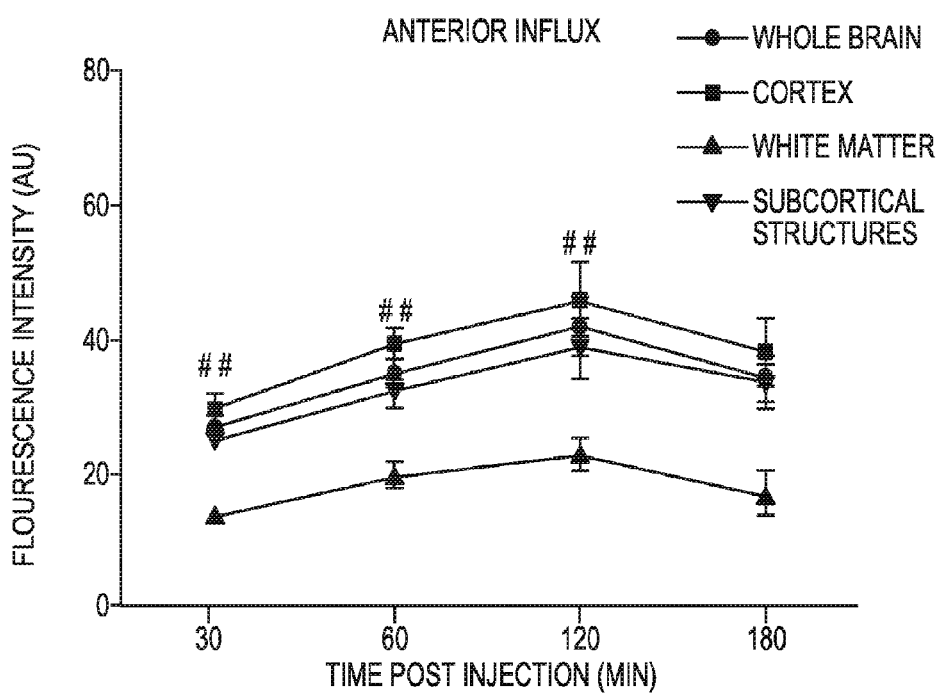
Figure 26E:
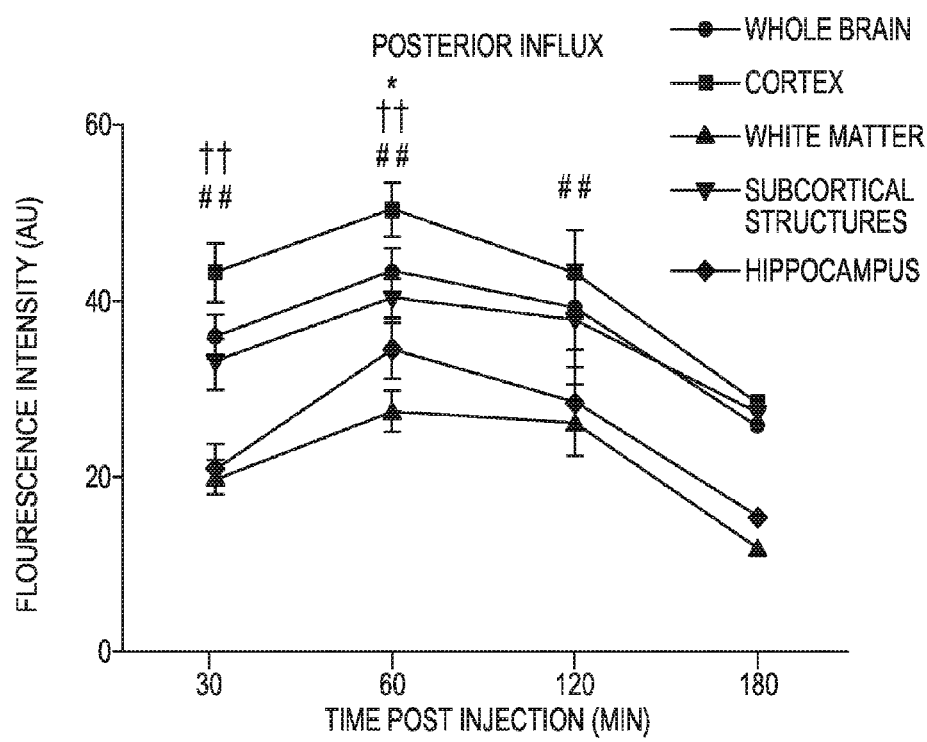
Figure 26F:
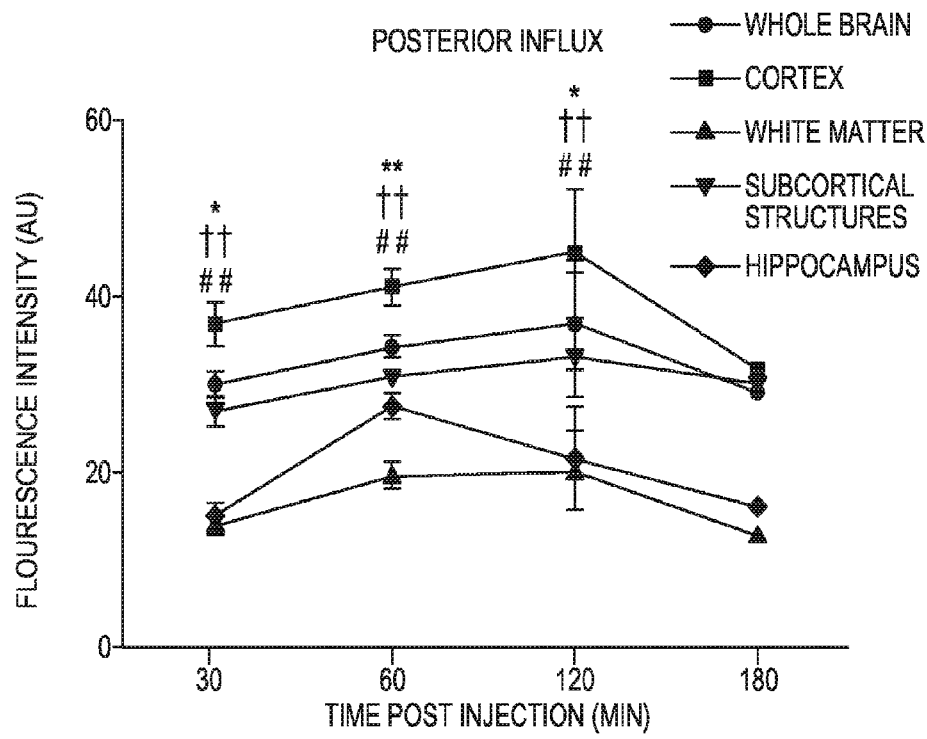
Figure 27A:
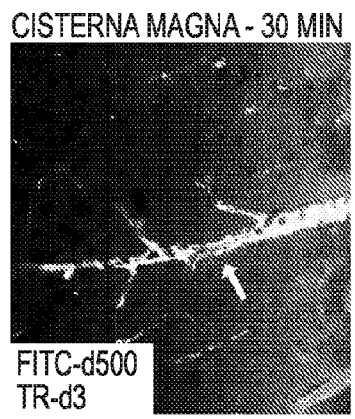
Figure 27B:
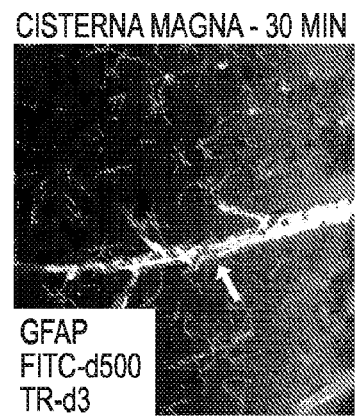
Figure 27C:
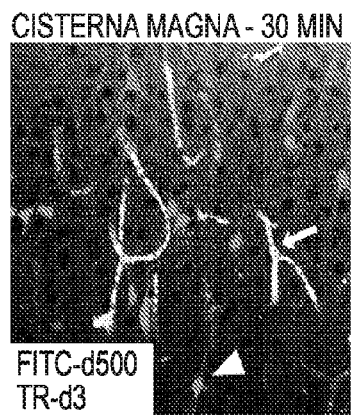
Figure 27D:
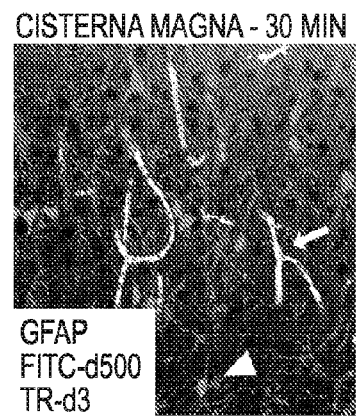
Figure 27E:
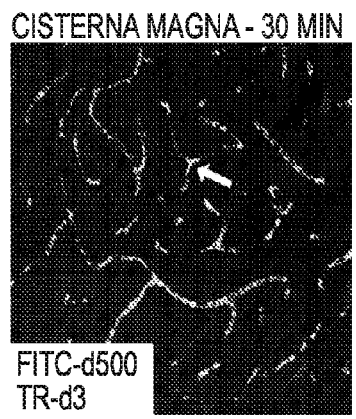
Figure 27F:
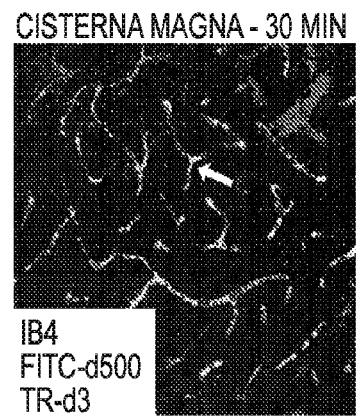
Figure 27G:
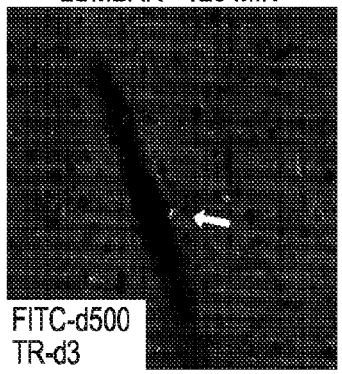
Figure 27H:
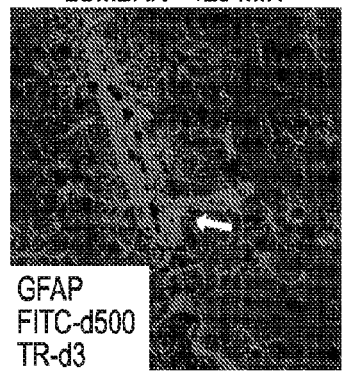
Figure 27I:
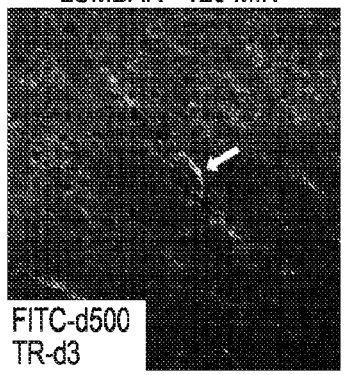
Figure 27J:
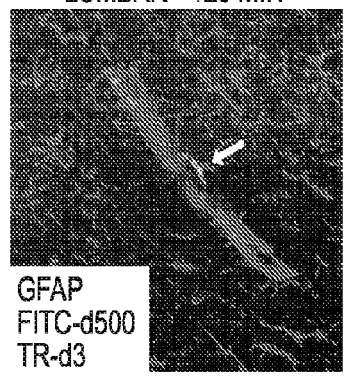
Figure 27K:
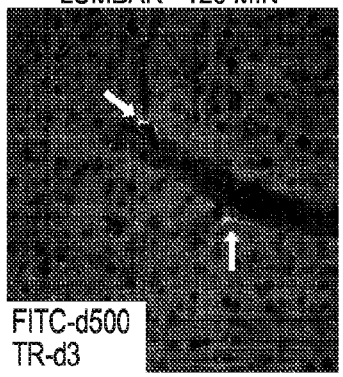
Figure 27L:
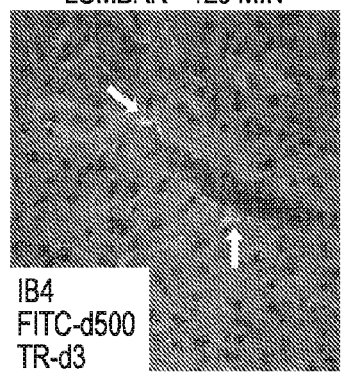

Compared to intracisternally-injected TR-d3 (FIGS. 25F, H), the influx of CSF tracer delivered by the lumbar route was significantly delayed, peaking in the posterior brain 60 min after injection, and in the anterior brain 120 min after injection (compare FIGS. 25F, H to FIGS. 26C, E). This delay in CSF tracer influx kinetics was likely attributable to two factors. First, the distance from the site of lumbar injection to the cisterna magna was ~32 mm. Second, the prevailing direction of CSF bulk flow within the spinal subarachnoid was rostral-to-caudal (Enzmann and Pelc, 1991), suggesting that during infusion, CSF tracer must traverse the intervening distance against the bulk CSF flow generated from CSF secretion in the cerebral ventricles. In addition to the delay in fluorescent CSF tracer influx, the overall magnitude of tracer influx into the brain was markedly reduced after lumbar infusion compared to intracisternal infusion. This difference was most likely the result of CSF reabsorption that occurs along the spinal column via the peripheral nerve roots (Edsbagge et al., 2004). As CSF tracer is infused into the lumbar subarachnoid space and moves rostrally towards the brain, a portion will be lost along each vertebral segment along the natural CSF clearance pathway, resulting in a reduced delivery of tracer to the distant cisternal spaces surrounding the brain which form the entrance to the brain-wide glymphatic system (Examples 1 and 2). Despite these differences in influx magnitude and kinetics, tracer distribution after lumbar and intracisternal injection followed a similar pattern and encompassed the entire brain parenchyma (compare FIGS. 25B, D and FIG. 26A). These findings demonstrate that fluorescent intrathecal tracer influx into and through the brain parenchyma can be readily visualized after injection via a lumbar route.

Rat Lumbar Intrathecal Tracer Influx is Independent of Molecular Weight

CSF moves through the ventricular and subarachnoid compartment through the process of bulk flow (Cserr, 1971, Abbott, 2004, Praetorius, 2007). Because under bulk flow, the movement of the solvent is typically more rapid than the movement of the solute by passive diffusion, bulk flow-dependent movement is largely independent of molecular weight (Cserr, 1971). To evaluate whether the rate of intrathecal lumbar tracer influx into the brain parenchyma was dependent upon molecular size, large molecular weight fluorescent FITC-d500 (MW 500 kD) and small molecular weight TR-d3 (MW 3 kD) were co-injected. Representative images from this study are shown in FIGS. 26A-B. When FITC-d500 and TR-d3 movement into the brain parenchyma were quantified within the anterior and posterior cortex, white matter, subcortical structures and hippocampus, no significant differences were observed between either the time course or the magnitude of influx of the small and large molecular weight tracers (FIGS. 26C-F). This finding is consistent with the movement of fluorescent tracer from the lumbar site of injection to the brain subarachnoid and paravascular spaces via bulk flow rather than by simple diffusion (Cserr, 1971).

Paravascular Pathway of Intrathecal CSF Tracer Influx

In the prior study in mice (Example 1), it was noted that while CSF tracers of all sizes moved rapidly into the brain along paravascular spaces, large molecular weight tracers such as FITC-d2000 (MW 2000 kD) became trapped in the paravascular space and could not move freely into and through the brain interstitium. According to one recent study, astrocytic endfoot processes completely cover the cerebral microcirculation; the only routes between the paravascular spaces and the wider brain interstitium being through ~20 nm clefts between overlapping astroglial endfeet (Mathiisen et al., 2010). It was surmised that the perivascular astrocytic endfeet acted as a sieve to restrict the movement of large solutes from the paravascular spaces into the brain interstitium (Example 1).

In the present example, confocal microscopy was utilized to evaluate small (TR-d3) and large (FITC-d500) fluorescent CSF tracer exchange between the paravascular influx pathway and the surrounding brain interstitium. Slices from intracisternally-injected animals and lumbar-injected animals were fixed at 30 and 120 min after injection, respectively. These time points corresponded to the peak influx values observed for each injection route (FIGS. 26A-F and 27A-L).

FIGS. 27A-L demonstrate CSF tracer localization after intracisternal and lumbar intrathecal injection. FIGS. 27A-L show localization of FITC-conjugated dextran (FITC-d500, MW 500 kD) and Texas Red-conjugated dextran (TR-d3, MW 3 kD) 30 min after intracisternal injection. Large molecular weight FITC-d500 remained restricted to paravascular spaces (arrows) surrounding penetrating arteries (FIGS. 27A-B) and extending to the level of the terminal capillary beds (FIGS. 27C-F, arrows). Small molecular weight TR-d3 moved quickly into the brain interstitium and was taken up by subpopulations of neurons (arrowheads). FIGS. 27G-L show that 120 min after lumbar intrathecal injection of tracers, large molecular weight FITC-d500 accumulated in perivascular spaces (arrows), but not as uniformly as observed after intracisternal injection. Small molecular weight TR-d3 moved readily throughout the brain parenchyma. GFAP: glial fibrillary acidic protein (astrocytic marker); IB4: isolectin B4 (vascular endothelial marker).

Following intracisternal injection, FITC-d500 covered the pial surface and distributed into deeper brain tissue along paravascular pathways, extending to the level of the terminal capillary beds (FIGS. 27A-F). It did not move appreciably from the paravascular spaces into the surrounding interstitium. When FITC-d500 distribution was evaluated after lumbar injection, the large molecular weight tracer in a similar manner remained confined to paravascular spaces (FIGS. 27G-L), however the overall fluorescence intensity was reduced compared to intracisternal injections. After both intracisternal and lumbar injection, small molecular weight tracer moved readily into the interstitium surrounding paravascular spaces (FIGS. 27A-L). These data demonstrate that after both intracisternal and lumbar intrathecal injection in the rat, large molecular weight fluorescent tracers move into the brain along paravascular spaces, but remain confined to this space. Small molecular weight CSF tracers, in contrast, are able to move into and through the brain interstitium.

CONCLUSION

This pre-clinical study demonstrates three findings.

First, when glymphatic paravascular CSF-ISF exchange is evaluated after fluorescent CSF tracer injection into the rat cisterna magna, tracer distribution and kinetics within the brain are in general agreement with the initial characterization of this paravascular pathway in the mouse (Example 1).

Second, it was observed that CSF-ISF exchange within the brain can be readily evaluated after injection of fluorescent CSF tracer via a lumbar, in addition to the intracisternal route.

Third, it was found that after lumbar intrathecal infusion, fluorescent CSF tracer movement along paravascular pathways is dependent upon bulk flow, whereas fluorescent tracer movement from these paravascular spaces into and through the surrounding brain interstitium is constrained by tracer size.

Example 1 describes a brain-wide paravascular pathway along which CSF and ISF exchange to facilitate the clearance of interstitial solutes, including amyloid β, from the brain. These present findings suggest that the failure of amyloid β clearance by the glymphatic pathway contributes to the onset of amyloid plaque deposition and AD progression. If true, the ability to clinically measure glymphatic pathway function in patients will provide an effective approach to evaluate AD susceptibility and progression.

To translate the initial characterization of the glymphatic pathway to a clinical setting, a clinically relevant imaging modality for evaluation of glymphatic pathway function can be used. The analysis in Example 2 demonstrates that the glymphatic system can be evaluated in the rats using contrast-enhanced MRI following intracisternal gadolinium-based contrast injection. However, intracisternal injections are rarely used in a clinical setting due to their high potential for iatrogenic complications, including traumatic tissue injury (Keane, 1973). In contrast, the lumbar intrathecal delivery route is routinely employed for administration of radio-tracers for CT-myelography (Adams et al., 1988, Hoxworth et al., 2012), spinal anesthetics and post-operative analgesics (Hong and Lee, 2005, Gehling and Tryba, 2009), as well as chemotherapeutics (Kerr et al., 2001). In this example, it has been demonstrated glymphatic pathway function can be effectively evaluated using tracer injection via this clinically relevant pathway.

REFERENCES CITED IN EXAMPLE 3

Abbott N J (2004) Evidence for bulk flow of brain interstitial fluid: significance for physiology and pathology. Neurochemistry international 45:545-552.

Adams C, Babyn P S, Logan W J (1988) Spinal cord birth injury: value of computed tomographic myelography. Pediatric neurology 4:105-109.

Bruijn L I, Houseweart M K, Kato S, Anderson K L, Anderson S D, Ohama E, Reaume A G, Scott R W, Cleveland D W (1998) Aggregation and motor neuron toxicity of an ALS-linked SOD1 mutant independent from wild-type SOD1. Science 281:1851-1854.

Burns B J (2008) Images in emergency medicine. Traumatic cerebrospinal fluid leak. Annals of emergency medicine 51:704, 706.

Cserr H F (1971) Physiology of the choroid plexus. Physiological reviews 51:273-311.

Daele J J, Goffart Y, Machiels S (2011) Traumatic, iatrogenic, and spontaneous cerebrospinal fluid (CSF) leak: endoscopic repair. B-Ent 7 Suppl 17:47-60.

Deane R, Zlokovic B V (2007) Role of the blood-brain barrier in the pathogenesis of Alzheimer's disease. Current Alzheimer research 4:191-197.

Edsbagge M, Tisell M, Jacobsson L, Wikkelso C (2004) Spinal CSF absorption in healthy individuals. American journal of physiology Regulatory, integrative and comparative physiology 287:R1450-1455.

Enzmann D R, Pelc N J (1991) Normal flow patterns of intracranial and spinal cerebrospinal fluid defined with phase-contrast cine M R imaging. Radiology 178:467-474.

Gehling M, Tryba M (2009) Risks and side-effects of intrathecal morphine combined with spinal anaesthesia: a meta-analysis. Anaesthesia 64:643-651.

Hardy J, Selkoe D J (2002) The amyloid hypothesis of Alzheimer's disease: progress and problems on the road to therapeutics. Science 297:353-356.

Hong J Y, Lee I H (2005) Comparison of the effects of intrathecal morphine and pethidine on shivering after Caesarean delivery under combined-spinal epidural anaesthesia. Anaesthesia 60:1168-1172.

Hoxworth J M, Trentman T L, Kotsenas A L, Thielen K R, Nelson K D, Dodick D W (2012) The role of digital subtraction myelography in the diagnosis and localization of spontaneous spinal CSF leaks. AJR American journal of roentgenology 199:649-653. Kapila A (1987) Lumbar intraspinal epidermoid tumor. Evaluation with computed tomography and myelography. Spine 12:817-820.

Keane J R (1973) Cisternal puncture complications. Treatment of coccidioidal meningitis with amphotericin B. California medicine 119:10-15.

Kerr J Z, Berg S, Blaney S M (2001) Intrathecal chemotherapy. Critical reviews in oncology/hematology 37:227-236.

Maccioni R B, Farias G, Morales I, Navarrete L (2010) The revitalized tau hypothesis on Alzheimer's disease. Archives of medical research 41:226-231.

Mathiisen™, Lehre K P, Danbolt N C, Ottersen O P (2010) The perivascular astroglial sheath provides a complete covering of the brain microvessels: an electron microscopic 3D reconstruction. Glia 58:1094-1103.

Nordberg A, Rinne J O, Kadir A, Langstrom B (2010) The use of PET in Alzheimer disease. Nature reviews Neurology 6:78-87.

Phillips C D, Kaptain G J, Razack N (2002) Depiction of a postoperative pseudomeningocele with digital subtraction myelography. AJNR American journal of neuroradiology 23:337-338.

Popping D M, Elia N, Marret E, Wenk M, Tramer M R (2012) Opioids added to local anesthetics for single-shot intrathecal anesthesia in patients undergoing minor surgery: a meta-analysis of randomized trials. Pain 153:784-793.

Praetorius J (2007) Water and solute secretion by the choroid plexus. Pflugers Archiv: European journal of physiology 454:1-18.

Ross C A, Poirier M A (2004) Protein aggregation and neurodegenerative disease. Nature medicine 10 Suppl: S10-17.

Scherzinger E, Sittler A, Schweiger K, Heiser V, Lurz R, Hasenbank R, Bates G P, Lehrach H, Wanker E E (1999) Self-assembly of polyglutamine-containing huntingtin fragments into amyloid-like fibrils: implications for Huntington's disease pathology. Proceedings of the National Academy of Sciences of the United States of America 96:4604-4609.

Small S A, Duff K (2008) Linking Abeta and tau in late-onset Alzheimer's disease: a dual pathway hypothesis. Neuron 60:534-542.

6.4. Example 4

Restoration or Augmentation of Cerebrospinal Fluid (CSF) Secretion to Clear the Aging Brain of Toxins Normal cerebrospinal fluid (CSF) secretion and the flow associated with cerebrospinal fluid (CSF)/interstitial fluid (ISF) exchange removes waste byproducts of metabolism and toxins from the brain. This example relates to restoring or augmenting reduced cerebrospinal fluid (CSF) secretion and/or reduced flow associated with cerebrospinal fluid (CSF)/interstitial fluid (ISF) exchange in the aging brain. To accomplish this, a mechanical pumping system was used to promote faster clearance.

In human patients, CSF infusion is carried out, for example, via the lateral ventricle or the subarachnoid space. Alzheimer's disease (AD) is major application for this approach. Currently, there is no treatment that will slow or stop the progression of this devastating disease.

Background

Accumulation of toxic dysfunctional proteins in the mammalian brain is associated with many neurodegenerative diseases, including Alzheimer's, Parkinson's, Huntington's and amyotrophic lateral sclerosis (ALS) in humans. However, the mechanism that leads to the accumulation of toxins in the aging brain is not completely known. In the case of Alzheimer's disease (AD) the two hallmarks are senile plaques, which are extracellular deposits of amyloid β (Aβ) toxins, and intracellular neurofibrillary tangles (hyperphosphorylated tau). The "amyloid cascade" hypothesis suggests that the cognitive decline and the distinct pathogenic features in AD are related to abnormal accumulation of these toxins (Selkoe, 2001; Hardy, 2006).

Aβ is produced by many cells in the body, including nerve cells in the brain, from a large protein called amyloid β precursor protein (APP), which is cleaved by proteases, β-secretase and γ-secretase, to produce Aβ (Selkoe, 2001). In normal individuals, these toxins are present at low concentrations in the brain, but in AD they accumulate and their presence is a major event initiating AD pathogenesis (Hardy & Selkoe, 2002). In a small number of cases (<1%), Aβ accumulation is due to its overproduction (early onset AD), while in the majority of cases, Aβ accumulation is due to faulty clearance from the brain (late on-set AD) (Tanzi, 2005; Tanzi et al., 2004; Mawuenyega et al., 2010). Increased levels of Aβ in the brain results in formation of neurotoxic Aβ oligomers and progressive synaptic, neuritic and neuronal dysfunction (Masters and Selkoe, 2012). Aβ peptides are the main constituent of amyloid β in the brain parenchyma and in the vasculature (cerebral amyloid angiopathy). Aβ extracted from senile plaques is mainly peptides $A\beta_{1-40}$ (Aβ40) and $A\beta_{1-42}$ (Aβ42) while vascular amyloid is mainly peptides $A\beta_{1-39}$ and Aβ40. The major soluble form of Aβ present in cerebrospinal fluid (CSF) and brain is Aβ40. Soluble Aβ, which is circulating in CSF and brain interstitial fluid (ISF), may exist as free peptide and/or associated with different binding proteins (carriers), such as apolipoprotein E (apoE), apolipoprotein J (apoJ), transthyretin, albumin, and a2-macroglobulin ($\alpha_2$M) (Deane et al., 2009). Therapies based only on lowering brain Aβ levels have, so far, been unsuccessful in clinical trials (Hardy, 2009).

Aβ is eliminated from brain ISF through various routes, including cellular uptake and degradation, ISF bulk flow, and blood-brain barrier (BBB)-mediated transport (Deane et al., 2009). The glymphatic system—a macroscopic brain-wide path of CSF/ISF exchange—facilitates clearance of neurotoxic metabolic by-products, including Aβ. The glymphatic system regulates convective flow of brain ISF and functions similarly to the peripheral lymphatic system. The glymphatic system comprises three main pathways: (1) CSF via the peri-arterial space, (2) astrocytic aquaporin 4 (AQP4)-dependent convective flow of brain ISF through the brain parenchyma, and (3) efflux via peri-venous clearance. However, since the CSF rapidly and specifically enters the brain parenchyma along penetrating arteries, the glymphatic system may also act as a distribution path for brain-wide delivery of essential compounds as well as removing toxic compounds. Also, the glymphatic system may be a mechanism that clears the brain of all forms of Aβ, bound and free.

In the aging brain and in AD, CSF secretion is reduced (Serot et al., 2003). Reduced CSF secretion is associated with accumulation of Aβ and tau in rodent brains (Chiu et al., 2012; Silverberg et al., 2010). Continuous drainage of CSF via a shunt, in mild to severe AD patients, had no benefits (Silverberg et al., 2008).

This example demonstrates that restoring or augmenting the flow of CSF and the CSF/ISF exchange via the glymphatic system and using a mechanical pump or infusion system increases, augments or restores the removal of toxic substances from brain and thus, may prevent loss of neuronal function in the aging brain. This system can also restore the delivery of essential substances to brain. Since the glymphatic system is a fundamental brain-wide system, it has applications to many diseases associated with accumulation of toxic substances in brain.

In this example, artificial CSF was infused using a mechanical infusion system into the cisterna magna at a low rate (0.1 pl/min) and the recovery of exogenous $^{125}$I-Aβ and $^{14}$C-inulin at different time-points (15, 30 and 60 min) was measured after their injection into the brain and prior to the CSF infusion. $^{125}$I-Aβ was used because Aβ represented a peptide associated with AD and $^{14}$C-inulin was used because inulin is an inert molecule and a marker of bulk flow of molecules.

In a second series of experiments, the rate of CSF infusion was varied (0.1 μL/min, 0.5 μL/min and 1.0 μL/min) and recovery of $^{125}$I-Aβ and $^{14}$C-inulin was determined 30 min after their injection into the brain. To show that the glymphatic system is a brain-wide process, $^{125}$I-Aβ and $^{14}$C-inulin were injected into two brain regions, the caudate nucleus and the frontal cortex. The normal rate of CSF secretion in mice is 0.37 μL/min (Oshio et al., 2003). The data obtained demonstrates that restoring or augmenting the flow of CSF and the CSF/ISF exchange via the glymphatic system restores the removal of toxic substances from brain and suggests that loss of neuronal function in the aging brain can be delayed, reduced, decreased or prevented by increasing the flow of CSF and CSF/ISF exchange via the glymphatic system.

Methods

Brain Clearance Studies

Briefly, a stainless steel guide cannula was implanted stereotaxically into the right caudate-putamen or frontal cortex of anesthetized mice (ketamine (100 mg/kg) and xylazine (10 mg/kg). For the caudate-putamen, the coordinate of the cannula tip was 0.9 mm anterior and 1.9 mm lateral to the bregma, and 2.9 mm below the surface of the brain. For the frontal cortex, the coordinate of the cannula tip was 0.7 mm anterior and 3.0 mm lateral to the bregma, and 1.3 mm below the surface of the brain. Animals were allowed to recover after surgery. The experiments were performed before substantial chronic process occurred, but allowing time for the BBB repair to large molecules, as reported (Deane et al., 2004).

Injection of the Mixture of Tracers

Mock CSF (0.5 μL) containing $^{125}$I-labeled Aβ40 (10 nM monomer) together with $^{14}$C-inulin (0.05 μCi, an inert molecule for bulk flow) was microinfused into brain ISF over 5 minutes using a mechanical infusion system. Such infusion systems are well known in the art.

Tissue Sampling

At the end of the experiments brain was removed and prepared for radioactivity analysis and trichloroacetic acid (TCA) analyses using standard methods known in the art.

Analysis of Radioactivity $^{125}$I-radioactivities were determined in a gamma counter (Wallac Vizard Gamma Counter, Perkin Elmer). For $^{14}$C-counting, the samples were solubilized in 0.5 ml tissue solubilizer (Perkin Elmer) overnight, followed by addition of 5 ml of scintillation cocktail (Packard Ultima Gold) and analyzed in a liquid scintillation counter (Packard Tri-Carb 2100TR, Perkin Elmer).

Calculations

All calculations of clearance parameters were carried out using standard methods as disclosed hereinabove and in Deane et al., 2004. Briefly, the percentage of radioactivity remaining in the brain after microinjection was determined as % recovery in brain=$100 \times (N_b/N_i)$, where, $N_b$ is the radioactivity remaining in the brain at the end of the experiment and $N_i$ is the radioactivity injected into the brain ISF, i.e., the d.p.m. for $^{14}$C-inulin and the c.p.m. for the trichloroacetic acid (TCA)-precipitable $^{125}$I-radioactivity. Inulin was used as a metabolically inert polar molecule which is neither transported across the BBB nor retained by the brain; its clearance rate provides a measure of the ISF bulk flow.

Results

Effect of CSF Infusion Rate on Recovery of $^{125}$I-Aβ40 and $^{14}$C-inulin in Brain after their Injection into the Caudate Nucleus A small volume (0.5 μL) of mock CSF containing $^{125}$I-Aβ40 (10 nM) and $^{14}$C-inulin (0.05 μCi) was first microinjected into the caudate nucleus and immediately CSF was infused into the cisterna magna at 0.1, 0.5 or 1.0 μL/min for 30 min. At the end of the experiment the brain was removed and analyzed for radioactivity. FIG. 28 shows that there was a progressive reduction in the levels of Aβ40 and inulin remaining in brain with CSF infusion rate. Brain clearance of Aβ40 and inulin increased with CSF infusion rate.

Effect of CSF infusion on recovery of $^{125}$I-Aβ40 and $^{14}$C-inulin in brain after their injection into the caudate nucleus FIGS. 29A-B shows that at a CSF infusion rate of 0.1 pl/min, the levels of Aβ40 (FIG. 29A) and inulin (FIG. 29B) remaining in brain after their injection into the caudate nucleus were progressively reduced with the duration of infusion. Thus brain clearance of Aβ40 (A) and inulin (B) increased with CSF infusion duration.

Effect of duration of CSF infusion on recovery of $^{125}$I-Aβ40 and $^{14}$C-inulin in brain after their injection into the frontal cortex FIGS. 30A-B show the levels of Aβ40 and inulin remaining in brain 30 minutes (FIG. 30A) and 60 minutes (FIG. 30B) after their injection into the frontal cortex and at a CSF infusion rate of 0.1 μL/min into the cisterna magna. CSF infusion increased clearance of Aβ and inulin from brain. Therefore, infusion of CSF into the CSF compartment can be used to ameliorate, increase or restore the clearance of toxic substances from the aging brain. Since CSF secretion rate is reduced in aging brains and in the brains of individuals suffering from Alzheimer's disease, restoring this flow and CSF/ISF exchange can be used to reduce the accumulation of Aβ and delay the onset of, decrease or prevent cognitive decline and/or neuronal dysfunction. This approach can potentially be applied to any age-dependent neurological disorder.

REFERENCES CITED IN EXAMPLE 4

Chiu, C., M. C. Miller, I. N. Caralopoulos, M. S. Worden, T. Brinker, Z. N. Gordon, C. E. Johanson and G. D. Silverberg. "Temporal Course of Cerebrospinal Fluid Dynamics and Amyloid Accumulation in the Aging Rat Brain from Three to Thirty Months." *Fluids Barriers CNS* 9, no. 1 (2012): 3.

Deane, R., R. D. Bell, A. Sagare and B. V. Zlokovic. "Clearance of Amyloid-Beta Peptide across the Blood-Brain Barrier: Implication for Therapies in Alzheimer's Disease." *CNS Neurol Disord Drug Targets* 8, no. 1 (2009): 16-30.

Hardy, J. "A Hundred Years of Alzheimer's Disease Research." *Neuron* 52, no. 1 (2006): 3-13.

Hardy, J. "The Amyloid Hypothesis for Alzheimer's Disease: A Critical Reappraisal." *J Neurochem* 110, no. 4 (2009): 1129-34.

Hardy, J. and D. J. Selkoe. "The Amyloid Hypothesis of Alzheimer's Disease: Progress and Problems on the Road to Therapeutics." *Science* 297, no. 5580 (2002): 353-6.

Johanson, C., P. McMillan, R. Tavares, A. Spangenberger, J. Duncan, G. Silverberg and E. Stopa. "Homeostatic Capabilities of the Choroid Plexus Epithelium in Alzheimer's Disease." *Cerebrospinal Fluid Res* 1, no. 1 (2004): 3.

Masters, C. L. and D. J. Selkoe. "Biochemistry of Amyloid Beta-Protein and Amyloid Deposits in Alzheimer Disease." *Cold Spring Harb Perspect Med* 2, no. 6 (2012): a006262.

Mawuenyega, K. G., W. Sigurdson, V. Ovod, L. Munsell, T. Kasten, J. C. Morris, K. E. Yarasheski and R. J. Bateman. "Decreased Clearance of Cns Beta-Amyloid in Alzheimer's Disease." *Science* 330, no. 6012 (2010): 1774.

Oshio, K., Y. Song, A. S. Verkman and G. T. Manley. "Aquaporin-1 Deletion Reduces Osmotic Water Permeability and Cerebrospinal Fluid Production." *Acta Neurochir Suppl* 86, (2003): 525-8.

Selkoe, D. J. "Clearing the Brain's Amyloid Cobwebs." *Neuron* 32, no. 2 (2001): 177-80.

Serot, J. M., M. C. Bene and G. C. Faure. "Choroid Plexus, Aging of the Brain, and Alzheimer's Disease." *Front Biosci* 8, (2003): s515-21.

Silverberg, G. D., M. Mayo, T. Saul, J. Fellmann, J. Carvalho and D. McGuire. "Continuous Csf Drainage in Ad: Results of a Double-Blind, Randomized, Placebo-Controlled Study." *Neurology* 71, no. 3 (2008): 202-9.

Silverberg, G. D., M. C. Miller, J. T. Machan, C. E. Johanson, I. N. Caralopoulos, C. L. Pascale, A. Heile and P. M. Klinge. "Amyloid and Tau Accumulate in the Brains of Aged Hydrocephalic Rats." *Brain Res* 1317, (2010): 286-96.

Tanzi, R. E. "The Synaptic Abeta Hypothesis of Alzheimer Disease." *Nat Neurosci* 8, no. 8 (2005): 977-9.

Tanzi, R. E., R. D. Moir and S. L. Wagner. "Clearance of Alzheimer's Abeta Peptide: The Many Roads to Perdition." *Neuron* 43, no. 5 (2004): 605-8.

6.5 Example 5

Methods for Evaluating Brain-wide Paravascular Pathway for Waste Clearance Function Using Positron Emission Tomography (PET) in Combination with Intrathecal 2-Deoxy-2-($^{18}$F)Fluoro-D-glucose ($^{18}$FDG)

This example demonstrates methods for mapping glymphatic transport in the live rodent brain using dynamic integrated MRI-PET imaging in combination with intrathecal administration of a paramagnetic contrast agent and two different $^{18}$F-labeled radioisotopes. In certain embodiments, these methods are used evaluate waste clearance via the glymphatic pathway into the clinical arena.

This example also describes a clinical protocol that can be used to implement this technique in humans.

6.5.1 Glymphatic Transport in Rodent Brain Imaged Via Dynamic Integrated MRI-PET Sprague Dawley rats (2-3 month old females) were anesthetized with phenobarbital and lumbar intrathecal catheters placed. Imaging was performed using a custom-built, MRI-compatible PET scanner for the rat brain in combination with a 9.4T microMRI (ref). The PET camera used inside the 9.4 TmicroMRI instrument has been described in detail elsewhere (Refs). Briefly, it is a modification of the initial RatCap detector (ref) and designed with non-magnetic materials (ref). The PET ring (ID 38 mm and accommodating the head of a rat) consists of 12 detector blocks consisting of a 4×8 array of 2.22×2.22×5 mm$^3$ lutetium oxyorthosilicate (LSO) crystals assembled with a thin reflective foil and coupled to a matching non-magnetic S8550 APD array (ref). PET data are transferred via optical fibers to an external (PCI)-based data acquisition board (ref). For simultaneous PET/MRI imaging a custom-made volume RF coil which fits inside the PET ring was used. The 9.4T microMRI used in all experiments is a superconducting horizontal bore magnet (Bruker Biospin 94/20, 400 MHz, Magnex scientific) interfaced to a Bruker Advance console and controlled by Paravision 5.0 software (Bruker Bio Spin, Billerica, Mass.). The magnet is equipped with an actively shielded combined RT-shim and gradient system (B-GA 12S) that can produce a maximum gradient strength of 200 mT/m. The 9.4T magnet is also rigged with a specially designed plastic support tube extending through the magnet's entire bore, which is isolated from the gradient set with noise-reducing concentric foam liners (this configuration reduces the noise from vibrations generated by the gradients during imaging). The support tube is big enough to accommodate two other plastic tube assemblies which are used for PET-MRI imaging; One tube is used to secure the RF coil inside the PET ring and the other is used to position the animal accurately within the PET-MRI device positioned in the center of the magnet (FIGS. 31A-C).

The rats were imaged in the supine position during and following intrathecal infusion (total volume: 60 µl) of a mixture of Gd-DTPA and $^{18}$F tagged isotopes. Dynamic MRI and PET images were acquired synchronously; including a 3D T1-weighted FLASH sequence (TR=15 msec, TE=3.8 ms, NA=1, FOV=3.0×3.0×3.2 cm, scanning time=4.1 min, image resolution of 0.12×0.12×0.13 mm) and a PET acquisition in singles listmode, spatial resolution of 1.2 mm. Two different $^{18}$F tagged isotopes mixed with Gd-DTPA (20.8 mM in artificial CSF) were tested: i) 0.5 mCi [$^{18}$F]fluoride and ii) 0.5 mCi 2-deoxy-2-($^{18}$F)fluoro-D-glucose ($^{18}$FDG). MRI data were reconstructed as previously described (ref). PET data was reconstructed using an iterative, maximum likelihood by expectation maximization (MLEM) approach and included the final corrections for decay and live time. PET-MRI image fusion was executed and normalized and registered to a segmented rat brain atlas template (PMOD).

Figure 32A:
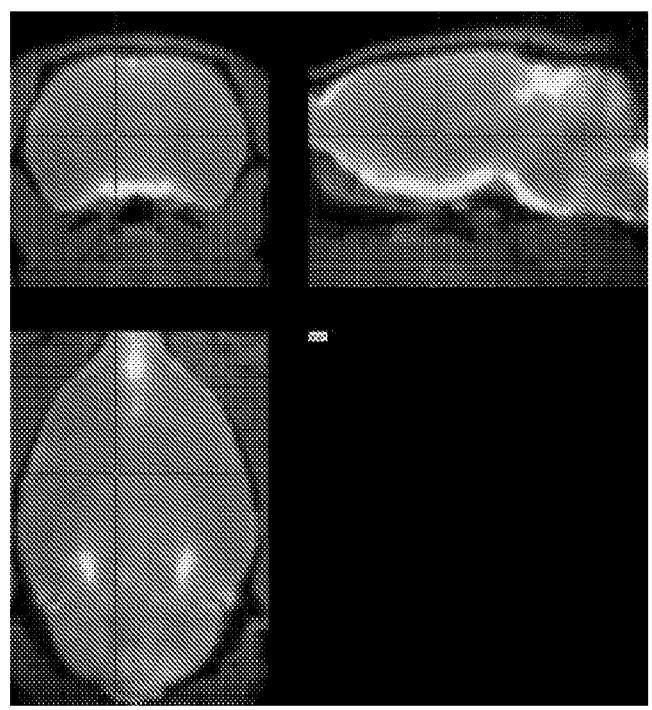
Figure 32B:
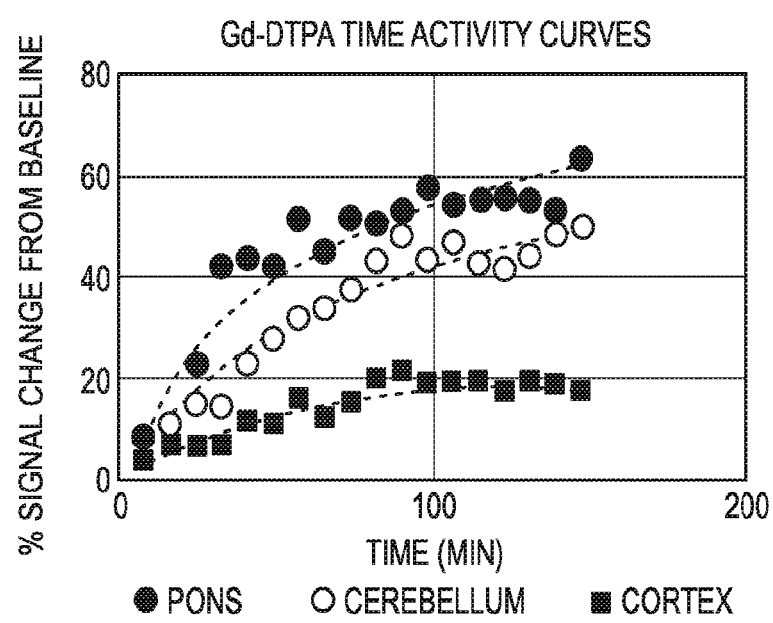
Figure 32C:
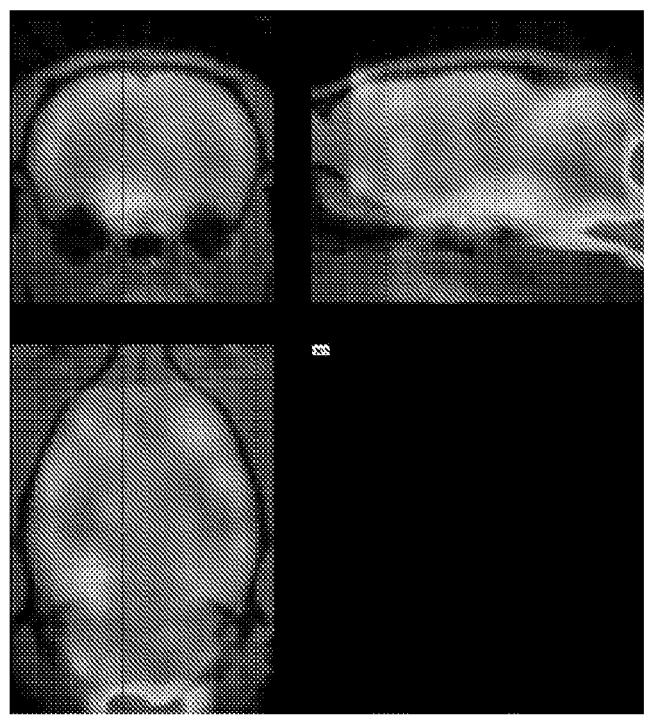
Figure 32D:
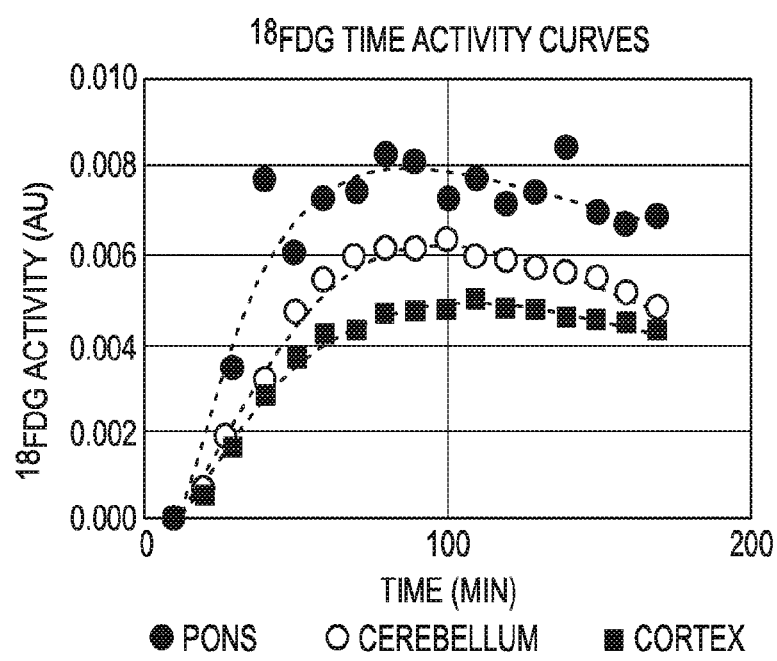
Figure 32E:
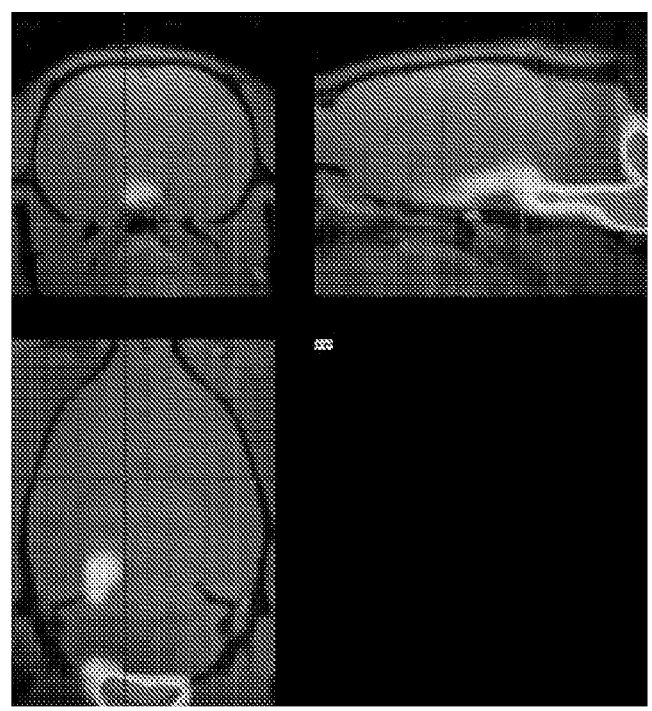
Figure 32F:
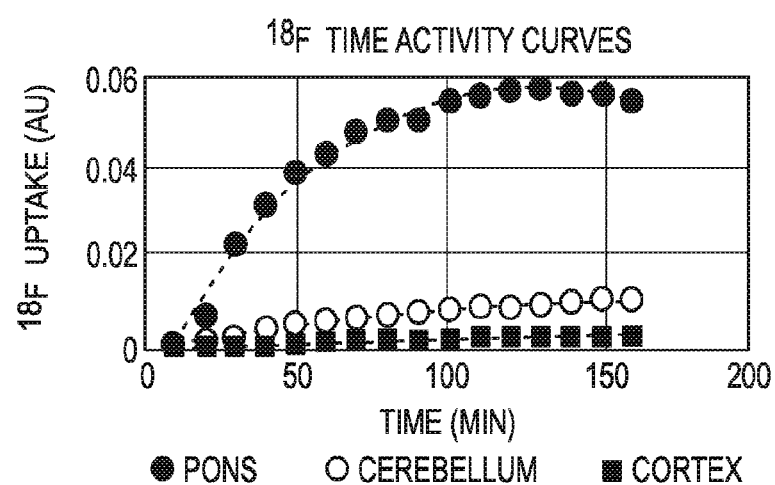
Figure 33A:
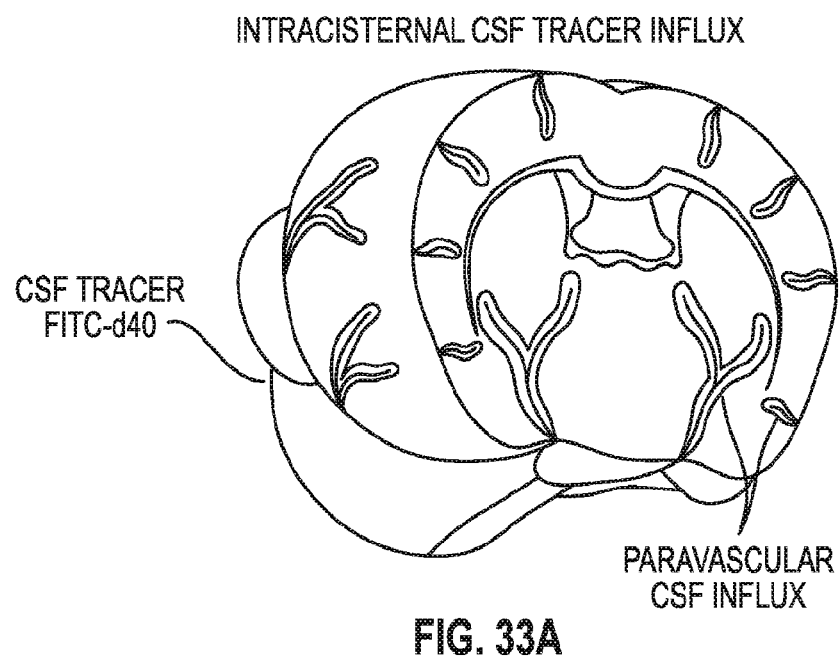
Figure 33B:
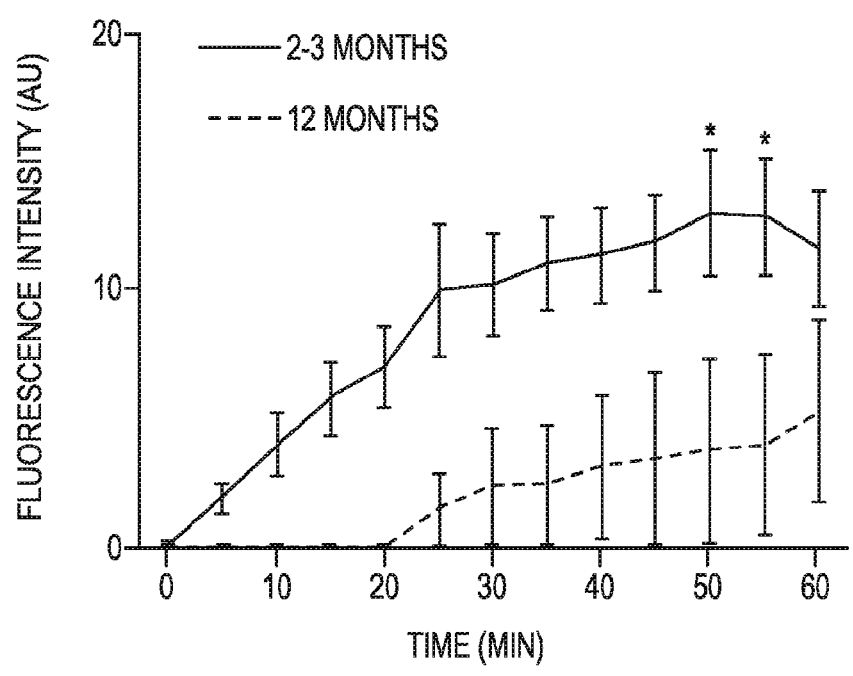
Figure 34A:
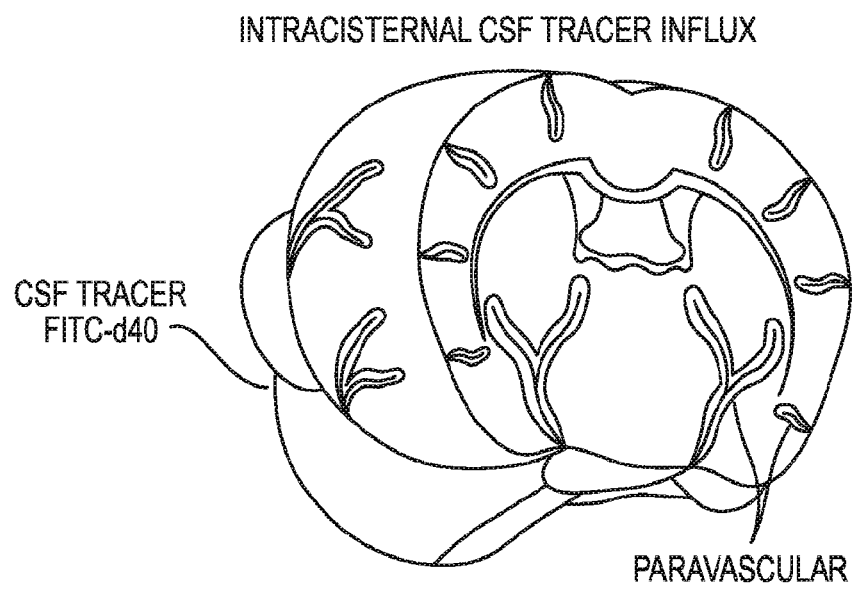
Figure 34B:
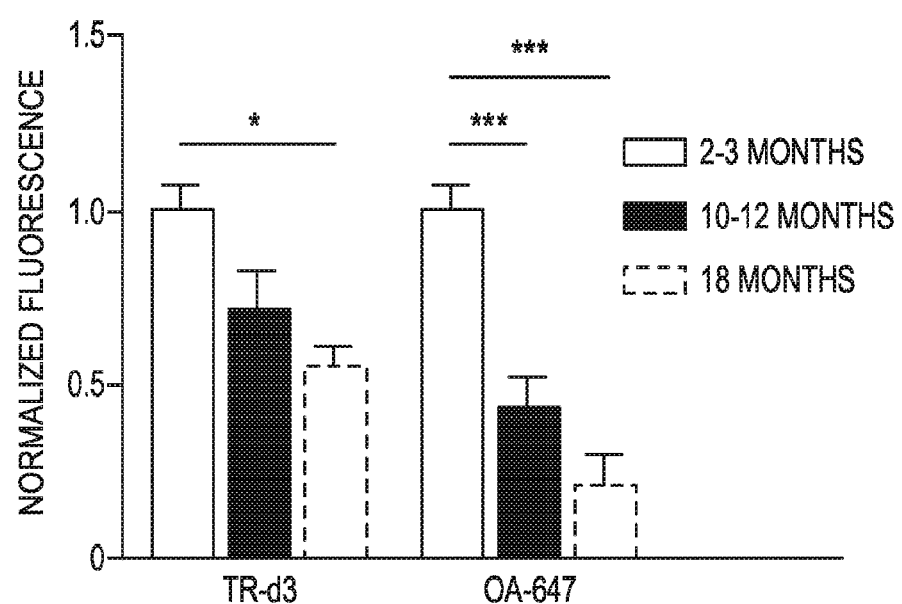
Figure 34C:
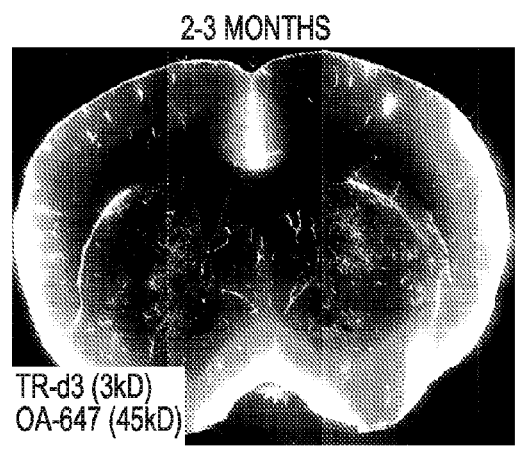
Figure 34D:
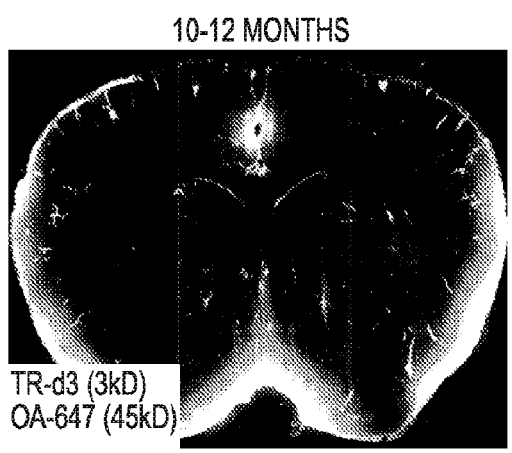
Figure 34E:
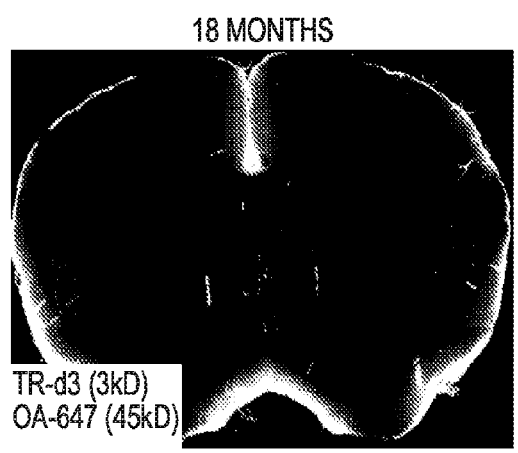
Figure 35A:
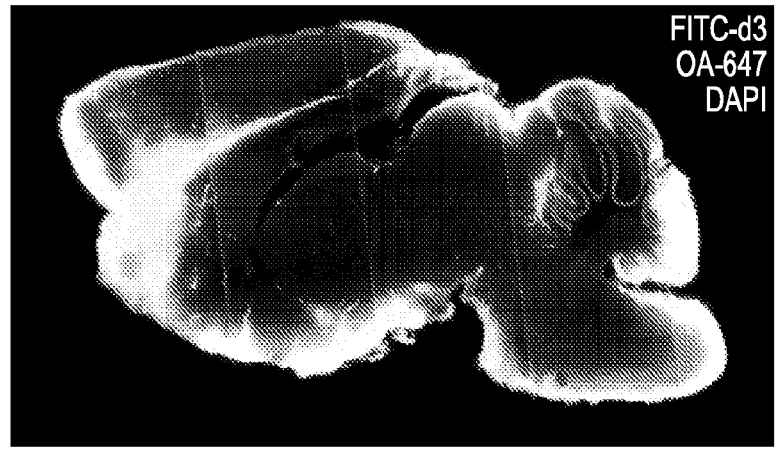
Figure 35B:
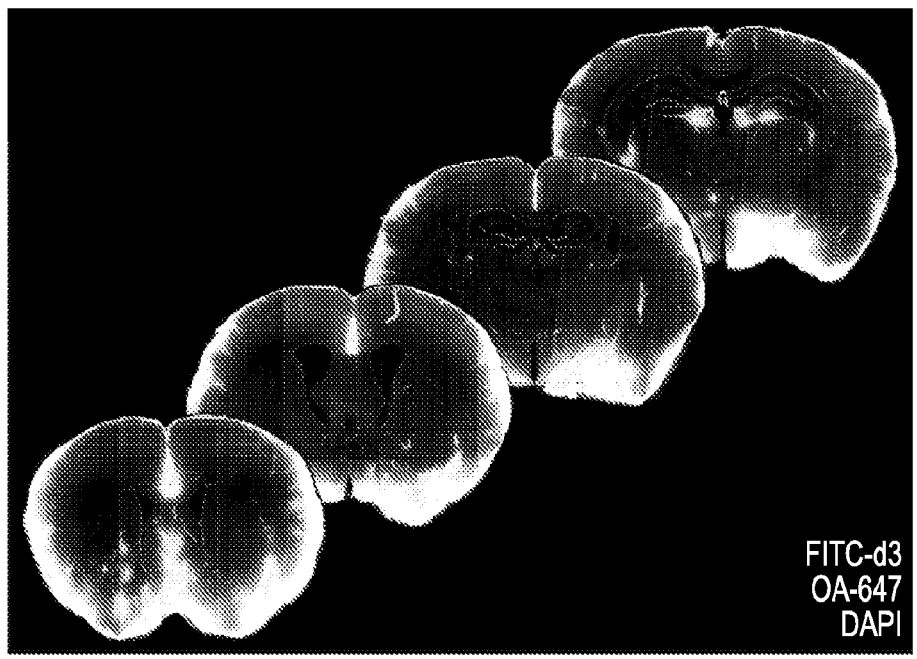
Figure 35C:
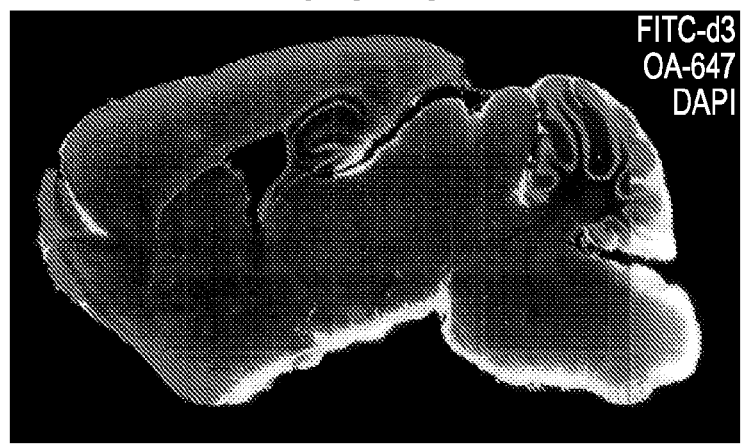
Figure 35D:
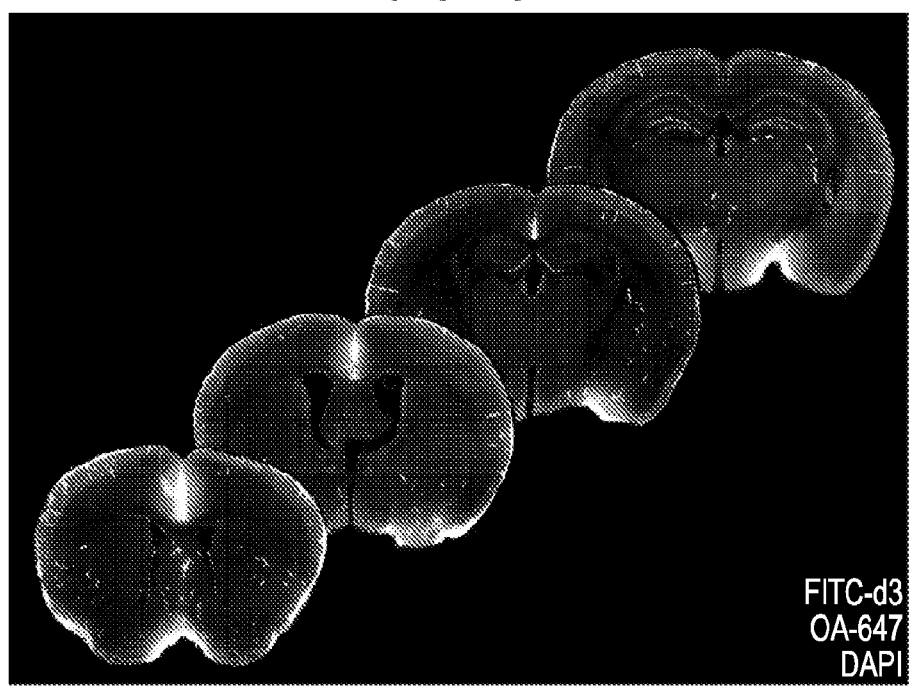
Figure 35E:
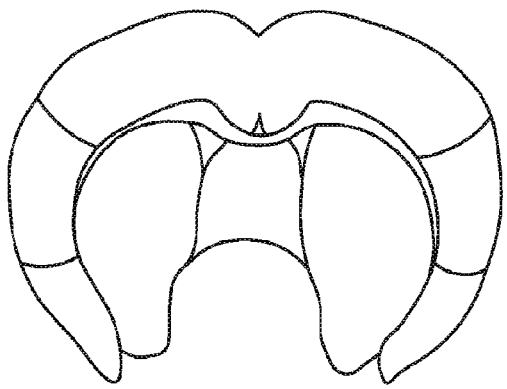
Figure 35F:
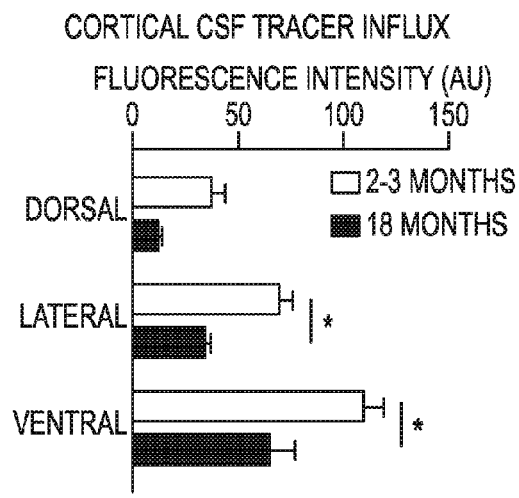
Figure 35G:
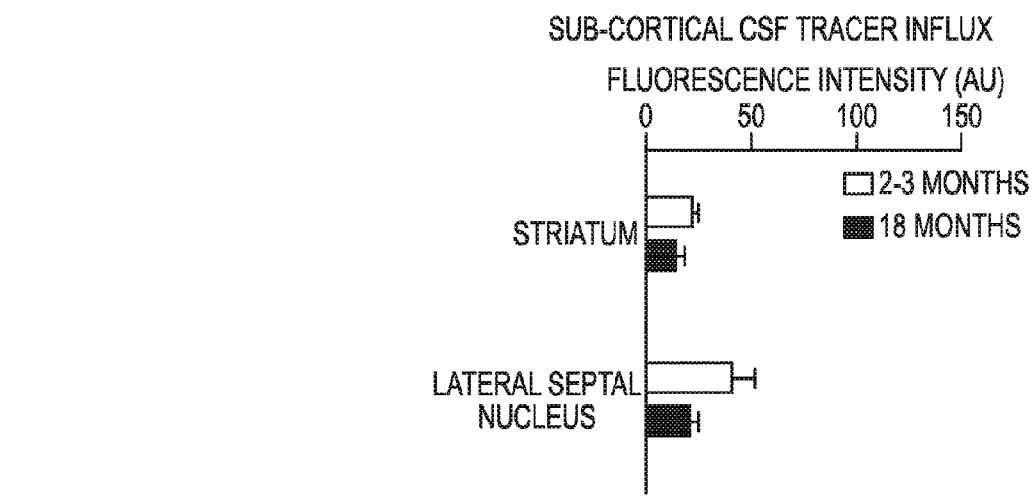
Figure 35H:
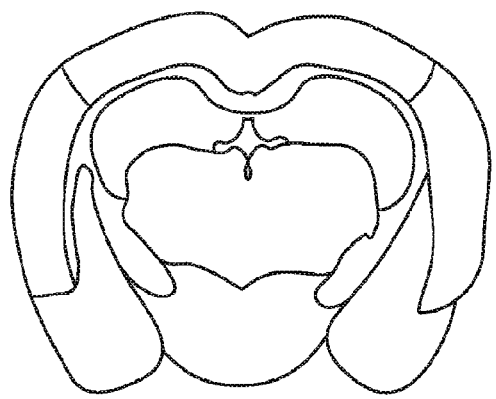
Figure 35I:
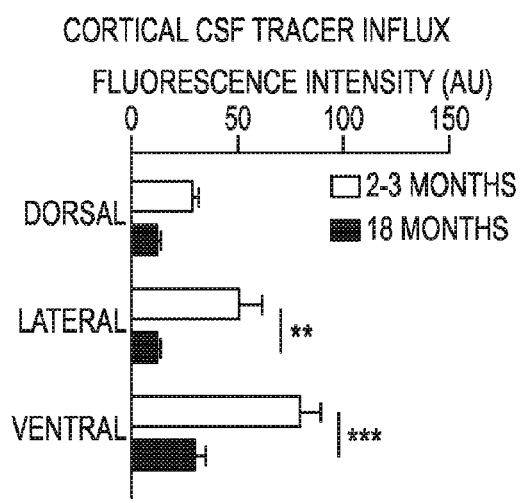
Figure 35J:
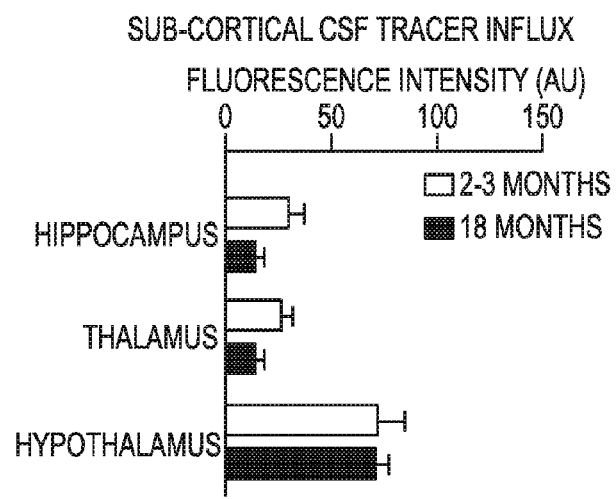

The results of the experiments, shown in FIGS. 32A-F, demonstrate that intrathecal $^{18}$FDG moves rapidly through the brain-wide glymphatic pathway as illustrated by FIG. 32D, showing that $^{18}$FDG time-activity curves are near identical for major brain regions. In contrast, DTPA and $^{18}$F moves through the glymphatic pathway with some 'restriction'. These data provide proof-of-principle that intrathecal administered $^{18}$FDG can provide a rapid, quantitative and transient estimate of glymphatic pathway function. These features of $^{18}$FDG administered intrathecally make it ideal for clinical application.

6.5.2 Clinical Protocol to Assess Glymphatic Transport in Human Brain

The approach presented in the pre-clinical data section (Section 6.5.1 above) is translated to humans as follows. A step-wise trial is conducted. In the first step, brain uptake of $^{111}$-In DTPA injected intrathecally (using routine methods) in human patients undergoing radionuclear cisternography is studied using combined SPET-CT. In the second step, intrathecally injected $^{18}$FDG in human patients is similarly studied. The advantage of using intrathecal $^{18}$FDG for this purpose is:

Uptake and transport via the glymphatic pathway occurs much more rapidly compared with DTPA; and this expedites the test.

If $^{18}$FDG works for cisternography in human patients, it can then be used diagnostically in multiple clinical settings, for example, in evaluation of normal pressure hydrocephalus (NPH), cerebrospinal fluid (CSF) leaks, and for evaluation of glymphatic waste clearance in patients at risk for AD.

6.6 Example 6

Brain-wide glymphatic pathway Function is Impaired in the Aging Brain

This example demonstrates that brain-wide glymphatic pathway function is impaired in the aging brain.

FIGS. 33A-F. Glymphatic Paravascular CSF Influx is Impaired in the Aging Brain.

(A) Paravascular CSF influx was evaluated by in vivo 2-photon microscopy in the anesthetized mouse cortex. The cerebral vasculature was defined by intra-arterial Texas Red dextran (70 kD, TR-d70) and cortical arteries (arrows) and veins (arrowheads) were defined morphologically. 10 µl Fluorescent CSF tracer (FITC-conjugated dextran, 40 kD; FITC-d40) was injected intracisternally while paravascular tracer influx was visualized via a closed cranial window preparation. (B) Quantification of paravascular CSF influx into the cortex 100 µm below the cortical surface shows that compared to the young (2-3 month old) brain, paravascular CSF influx into the aged (12 months) cortex is significantly slowed (*$P<0.05$, 12 month vs. 2-3 month, 2-way repeated measures ANOVA; n=4 per group). (C-D) Representative serial imaging of CSF tracer as it enters the cortex initially along cerebral surface arteries (C1-C6), then along penetrating arterioles as it moves into the surrounding interstitium imaged here at 100 µm below the cortical surface (D1-D6). (E-F) Representative serial imaging of CSF tracer entry into the cortex of aged mice (12 months) shows slowed movement of CSF tracer first along the paravascular spaces of the cerebral surface vasculature (E1-E6) as well as its movement into the cortical interstitium (F1-F6). These data demonstrate that glymphatic pathway function is dramatically reduced in the aged mouse cortex.

FIGS. 34A-E. Brain-Wide Glymphatic Pathway Function is Impaired in the Aging Brain.

Glymphatic pathway function was evaluated in the anesthetized mouse brain by ex vivo fluorescence imaging. (A) Two different fluorescent CSF tracers (Texas Red-conjugated dextran, MW 3 kD, TR-d3; ovalbumin-conjugated ALEXA 647, MW 45 kD, OA-647) were co-injected into the cisterna magna. 30 min later, animals were perfusion fixed, the brains sliced on a vibratome, and coronal sections imaged by 2-channel conventional fluorescence microscopy. (B) Quantification of CSF tracer influx revealed an age-related impairment of glymphatic pathway function, as influx of both low molecular weight TR-d3 and high molecular weight OA-647 were significantly impaired in the old (18 months) compared to the young (2-3 months) mouse brain (*$P<0.05$, ***$P<0.001$ vs. 2-3 months; ANOVA; n=5-8 per group). CSF tracer influx into the middle-aged (10-12 months) brain was intermediate between that of the young and old brains. (C-E) Representative images showing differences in fluorescent CSF tracer influx between the 2-3 month (C), 10-12 month (D), and 18 month (E) brain show marked impairment of tracer influx with progressing age, particularly with increasing distance from the pial surface.

FIGS. 35A-J. Region-specific Age-related Impairment of Glymphatic Pathway Function.

Glymphatic pathway function was evaluated in the anesthetized mouse brain by ex vivo whole slice fluorescence imaging of CSF tracer influx. Small (Texas Red-conjugated dextran, MW 3 kD, TR-d3) and large molecular weight (ovalbumin-conjugated ALEXA 647, MW 45 kD, OA-647) tracers were injected into the cisterna magna, and the animals were perfusion fixed 30 min later. Fluorescent CSF tracer influx was evaluated in sagittal (A, C) and coronal (B, D) slices counterstained with the nuclear stain DAPI. Assessment of CSF tracer influx across the whole brain revealed differences in CSF influx between regions within the young brain, in addition to distinct susceptibilities to age-related glymphatic pathway failure between regions in the aged brain. (E-J) Both the anterior (E) and posterior (H) brain were divided into gross regions of interest and OA-647 influx was evaluated on a regional basis. In general, glymphatic pathway function was most dramatically impaired in the aged (18 months) cortex compared to the young (2-3 months) cortex, with greater attenuation observed in the posterior cortex (I) compared to the anterior cortex (F) (*$P<0.05$, $P<0.01$, *$P<0.001$ vs. 2-3 months, ANOVA; n=4 per group). In comparison, glymphatic CSF influx into subcortical regions was comparatively small compared to that observed in the cortex, while age-related impairment within these subcortical regions was similarly muted (G, J).

FIGS. 36A-B. Impairment of Interstitial amyloid β Clearance in the Aged Brain.

The clearance of interstitial solutes from the aging brain was evaluated by a radio-tracer clearance assay. (A) Trace amounts of radio-labeled $^{125}$I-Amyloid $β_{1-40}$ and $^{14}$C-Inulin were co-injected into the caudate nucleus of young (2-3 months), middle aged (10-12 months) and old (18 months) anesthetized mice. 1 hr later, the animals were sacrificed, the brains harvested, and the residual radioactivity within the brain tissue was quantified by gamma particle counting and liquid scintillation counting. (B) In the old brain, the clearance of both $^{125}$I-Amyloid $β_{1-40}$ and $^{14}$C-Inulin were significantly slowed compared to the clearance in the young brain (***$P<0.001$ vs. young, ANOVA; n=8 per group). The clearance of $^{125}$I-Amyloid $β_{1-40}$ and $^{14}$C-Inulin from the middle aged brain was intermediate between that of the young and the old brain. These data demonstrate that glymphatic pathway function, including the function of interstitial amyloid β clearance, is markedly reduced in the aging brain.

FIGS. 37A-E. Cerebral Arterial Pulsation is Reduced in the Aging Brain.

Cerebral vascular pulsatility was evaluated in anesthetized mice by in vivo 2-photon microscopy. (A-B) The cerebral vasculature was visualized by intra-arterial injection of fluorescent Texas Red-conjugated dextran (70 kD). Cerebral surface arteries and veins (A), and penetrating arteries and ascending veins (B) were identified morphologically. Insets in (B) show orthogonal XZ and YZ projections of the XYZ volume imaged for the experiment. (C-D) Cerebral surface arteries and veins, penetrating arteries and ascending veins were identified and imaged by high-frequency linescanning. The resulting X-t (time) plot were thresholded to improve contrast, allowing changes in vessel diameter resulting from each cardiac cycle to be measured. Changes in vascular diameter were integrated about the average vessel diameter over a 3 s interval to define a parameter termed vascular Pulsatility'. (E) Pulsatility measured in penetrating arteries was reduced in the aged (18 months) compared to the young (2-3 months) brain (n=2-4 per group). No obvious differences were observed in other elements of the cerebrovascular tree. These data demonstrate that one of the driving forces of glymphatic pathway function, arterial pulsatility, is reduced in the aging brain.

FIGS. 38A-D. Aging does not Alter Cortical Extracellular Volume Fraction but does Alter Tortuosity.

Diffusion parameters (extracellular volume fraction, alpha; tortuosity, lambda) were evaluated by in vivo tetramethyl ammonia electrophysiology in the waking and anesthetized cortex in vivo as described previously (Xie et al. Science 2013, incorporated herein by reference in its entirety). (A-B) No differences in extracellular volume fraction were observed between old (18 months) and young (2-3 month) brains (A); while the marked enlargement of the extracellular space in the sleeping versus the waking brain were preserved unaltered in the aged brain (B) (*P<0.001, awake vs. asleep, 2-way ANOVA, n=9-20 per group). (C-D) While no overall differences in either waking or sleeping tortuosity in the old versus the young cortex were noted (C), a change in the sleep-wake relationship in tortuosity values was observed in the aging brain (D). In the young brain, tortuosity values did not differ between the waking and the sleeping state. In contrast, in the aged brain, the onset of sleep was accompanied by a significant increase in extracellular tortuosity (*P<0.001 awake vs. asleep, 2-way ANOVA, n=9-20 per group). These data demonstrate that the composition (both material and spatial) of the brain extracellular space is altered in the aged brain, which may underlie the impairment of glymphatic pathway function observed in the aging brain.

FIGS. 39A-F. Altered Perivascular AQP4 Expression in the Aged Brain.

Changes in cortical AQP4 and GFAP expression were evaluated by immunofluorescence double labeling followed by laser scanning confocal microscopy. (A-B) Representative images show that in the young brain (2-3 months), AQP4 expression is restricted almost exclusively to perivascular astrocytic endfeet (arrows). In the aging cortex (18 months), AQP4 localization shifts to include fine astrocytic processes (arrowheads) that are not strictly perivascular. (C) Quantification of AQP4 expression in endfoot domains shows that in the aged brain, a slight reduction in perivascular AQP4 expression is observed surrounding large cerebral vessels, but not surrounding cerebral capillaries (*P<0.05, 18 months vs. 2-3 months, t-test; n=4 per group). (D) In contrast, the localization of AQP4 shifts dramatically in the aged brain. In the young brain, AQP4 polarization is very pronounced, with low levels of AQP4 expression save only in perivascular endfeet. In the aged brain, global AQP4 expression increases slightly, while regions immediately surrounding large cerebral vessels exhibit strongly increased AQP4. Thus, in the aged brain, AQP4 surrounding large cerebral vessels loses its strict perivascular polarization, while microvascular polarization remains largely intact. (E) Such specificity is not observed for the marker of reactive astrogliosis, GFAP. In the aged brain, perivascular GFAP expression was significantly elevated both surrounding large cerebral vessels and cerebral microvessels (***P<0.001, 18 months vs. 2-3 months, t-test; n=4 per group). (F) Similarly, when GFAP expression is evaluated spatially, increased GFAP expression is observed globally throughout the cortex, and differences in GFAP expression are not observed between large vessels and microvessels.

FIGS. 40A-C. Regional Differences in AQP4 Expression and Polarization.

Changes in AQP4 expression (A), AQP4 polarization (B) and GFAP expression (C) were evaluated throughout defined regions of interest within the anterior and posterior brain slices by immunofluorescence double labeling, laser scanning confocal microscopy, and an image analysis approach defined previously (Wang et al. *J Neurosci* 2012; Ren et al. *J Cereb Blood Flow Metab* 2013). (A) Color intensity maps depict regional mean AQP4 immunofluorescence intensity for the 2-3 month and 18 month brain. When AQP4 expression is quantified in each region, no signifcant changes in AQP4 expression are noted between the young and old brain. (B) AQP4 "depolarization" is defined as the tissue area with AQP4 immunofluorescence that is equal to or greater than perivascular AQP4 immunoreactivity (more detailed description provided in Ren et al. *J Cereb Blood Flow Metab* 2013). Thus higher values reflect loss of perivascular AQP4 polarization, or AQP4 "depolarization". As shown in color intensity maps, marked loss of AQP4 polarization occured in the aged brain. Significant loss of polarization wsa evident throughout the cortex and subcortical structures (*P<0.05, **P<0.01 vs. 2-3 month; 2-way ANOVA; n=4 per group). (C) GFAP expression was evaluated based upon the area covereage of GFAP-positive astrocytic processes. Color intensity maps show an increase in GFAP coverage in the aged brain. These changes were most pronounced in the cortex, but were also observed in subcortical structures (*P<0.05, **P<0.01 vs. 2-3 month; 2-way ANOVA; n=4 per group).

FIGS. 41A-J. AQP4 Polarization is a Key Determinant of Cortical Glymphatic Pathway Function.

The interrelationship between reactive astrogliosis (GFAP expression), AQP4 expression, AQP4 polarization and glymphatic pathway function (influx of intracisternally injected CSF tracer) were evaluated thoughout different anterior and posterior brain regions. Animals were injected intracisternally with ovalbumin-conjugated ALEXA-647 (OA-647, MW 45 kD). 30 min later, animals were fixed, and brains sliced. Anterior and posterior brain slices were labeled by immunofluorescnce double-labeling for AQP4 and GFAP. OA-647 influx (A), AQP4 expression (B), AQP4 depolarization (C) and GFAP expression (D) were evaluated in different regions of interest throughout the anterior and posterior brain. (A-D) Color intensity maps depict the relative increase (red values) versus decrease (blue values) in glymphatic OA-647 influx, AQP4 expression, AQP4 depolarization, and GFAP expression between 2-3 months of age and 18 months of age. This is a graphical representation of data presented in columnar form in FIGS. 40A-C above. (E-I) The relationship between AQP4 expression, AQP4 depolarization, and GFAP expression were evaluated within each region were evaluated pooling 2-3 month and 18 month values, then subjecting paired OA-647/AQP4 expression, OA-647/AQP4 depolarization, and OA-647/GFAP expression values to linear regression analysis. The strongest associations are depicted in each figure with trendlines, and the corresponding $r^2$ and P values (for non-zero slopes) are provided. (E) In the cortex, changes in AQP4 polarization were most strongly associated with glymphatic pathway function, with loss of AQP4 polarization corresponding strongly to impaired glymphatic CSF tracer influx. (F) Within the hippocampus, no strong associations between glymphatic pathway function, AQP4 expression, AQP4 polarization or GFAP expression were evident. (G-J) Within the striatum, lateral septal nuclei, thalamus and hypothalamus, AQP4 expression (not polarization) was most strongly associated with glymphatic pathway function. Interestingly, this was a positive correlation, with increasining AQP4 expression associated with increased glymphic CSF influx within these regions. These data demonstrate that perivascular AQP4 polarization is key determinant of paravascular CSF influx in the cerebral cortex, while in subcortical tissues global AQP4 expression may be a more important determinant of glymphatic pathway function.

FIGS. 42A-F. Traumatic Brain Injury (TBI) Causes Loss of Polarized Localization of AQP4 Perivascular Astrocytic Endfeet.

(A) Schematic depicting mouse model of moderate TBI. Mouse is briefly anesthetized with isofluorane, suspended by its incisors from a string, and calibrated temporal impact is delivered by a pneumatic controlled cortical impactor device. The animal falls to an underlying pad and rapidly awakens from anesthesia. (B-F) 28 days after TBI, AQP4 localization and GFAP expression are evaluated by immunofluorescence double-labeling and laser scanning confocal microscopy. As shown in the whole-slice montage (B-C) a region of persistent reactive astrogliosis remains in the ipsilateral temporal cortex 28 days after TBI. Evaluating AQP4 localization under high objective power, no obvious change in AQP4 polarization is apparent when control cortex (D) is compared to the contralateral cortex after TBI (E) as AQP4 localization remains restricted primarily to perivascular astrocytic endfeet (arrows). In the ipsilateral cortex (F), GFAP-positive reactive astrocytes exhibit profound loss of AQP4 polarization, with AQP4 expression being evenly distributed between fine processes and those surrounding cerebral vessels (arrows). These findings demonstrate that TBI results in the chronic loss of perivascular AQP4 polarization.

FIGS. 43A-J. Glymphatic Clearance of Interstitial Solutes is Chronically Impaired after TBI.

(A) Paravascular CSF-ISF exchange was evaluated by intracisternal injection of CSF tracer (Ovalbumin-conjugated ALEXA-555) 1, 3, 7 and 28 days after TBI. (B-F) Ex vivo whole-slice fluorescence imaging shows paravascular CSF influx evaluated 30 min post-injection was dramatically reduced 7 days after TBI. Interestingly, reduced glymphatic influx was observed bilaterally despite the unilateral traumatic injury. Quantification of tracer influx into the cortex (G) show that the effect of TBI upon CSF influx peaks at 7 days post-injury, however a significant impairment of glymphatic function remains 28 days after injury (*$P<0.05$, **$P<0.01$ vs. control; #$P<0.05$ vs. contralateral structure; 2-way ANOVA, n=5-12 animals per group). Although impaired CSF influx is observed bilaterally in the cortex, the impairment is greatest in the ipsilateral cortex. (H) The effect of TBI upon interstitial solute clearance from the cortex was evaluated 7 days post-injury. The clearance of radio-labeled $^3$H-mannitol (MW 182 Da) (I) and $^{14}$C-inulin (MW-5 kDa) (J) was measured 60 min after infusion into contralateral frontal cortex. In wild type mice, TBI significantly slowed the clearance of both $^3$H-mannitol and $^{14}$C-inulin (#$P<0.05$, ####$P<0.001$ vs sham; 2-way ANOVA, n=6 animals per group). Clearance studies conducted in Aqp4$^{-/-}$ mice demonstrated that impairment of solute clearance after TBI was exacerbated by Aqp4 gene deletion (*$P<0.05$, ***$P<0.001$ vs. WT; 2-way ANOVA, n=6 animals per group). These data demonstrate that glymphatic pathway function, including interstitial solute clearance, is profoundly and chronically impaired after TBI.

FIGS. 44A-E. Interstitial Tau Cleared from the Brain Along Paravascular Pathways.

(A) Recombinant human monomeric tau (hTau) was injected into the cortex of NG2-DsRed transgenic mice, which express DsRed fluorescent protein in cerebral vascular smooth muscle and pericytes. (B-E) Movement of interstitial hTau through the brain was evaluated 30 min post-injection by immunofluorescence followed by laser scanning confocal microscopy. hTau moved diffusely from the injection site (B), accumulating along the capillary basal lamina (C). Projections of fluorescence intensity depict hTau accumulations in these spaces relative to surrounding interstitial compartments. (D-E) 30 min post-injection, hTau moved rapidly through the brain interstitium to reach paravascular spaces surrounding the large-caliber internal cerebral veins in the roof of the $3^{rd}$ ventricle. These data demonstrate that soluble interstitial tau is cleared from the brain along paravascular pathways of the brain-wide glymphatic system.

FIGS. 45A-C. AQP4 Immunoreactivity is Absent in Aqp4$^{-/-}$ Mice.

To ensure the specificity of the anti-AQP4 primary antibody utilized in the present study, we conducted in immunolabeling of control and TBI-treated brains from Aqp4$^{-/-}$ mice perfused 7 days after injury. Although GFAP expression was readily detectable control (A), contralateral TBI (B) and ipsilateral TBI (C) cortex, no AQP4 immunoreactivity was detectable.

FIGS. 46A-C. Aqp4 Gene Deletion does not Alter TBI Lesion Volume.

The effect of Aqp4 gene deletion upon traumatic lesion volume was evaluated in brains harvested 28 days after TBI. (A-B) Brains were serially sliced and brain structure was evaluated by H & E staining. Red arrow indicates site of traumatic impact and area of greatest cortical damage. Ipsilateral and contralateral cortical areas were measured for each slice, then integrated through serial slices to derive a cortical volume. Cortical volume expressed as a ratio to the contralateral volume (C). No significant difference was observed in ipsilateral lesion volume between wild type and Aqp4$^{-/-}$ mice.

FIGS. 47A-F. Aqp4 Gene Deletion Exacerbates Development of Tauopathy after TBI.

The effect of impairing glymphatic pathway function by Aqp4 gene deletion upon the development of tauopathy after TBI was evaluated. (A) Wild type and Aqp4$^{-/-}$ brains were harvested 28 days post-injury and probed for the presence of phosphorylated tau (P-tau) epitopes. Representative blots are presented showing effect of mouse genotype (wild type vs. Aqp4$^{-/-}$), injury status (sham vs. TBI) and hemisphere (contralateral (C) vs. ipsilateral (I)) upon labeling by various P-tau monoclonal antibodies targeting different tau phosphorylation epitopes. Total tau was also measured (Pan-tau) and all P-tau levels were normalized to P-tau levels within each biological sample. (B-F) Across all epitopes, TBI tended to increase P-tau labeling, particularly on the ipsilateral side. Similarly, labeling tended to be stronger in Aqp4$^{-/-}$ mice after TBI compared to wild type mice after TBI. Specifically, antibodies recognizing the pThr231 and pSer396 P-tau epitopes registered significant increases in P-tau labeling in Aqp4$^{-/-}$ mice compared to wild type animals ($^{\dagger}P<0.05$, $^{\dagger\dagger\dagger}P<0.001$ vs. Aqp4$^{-/-}$ sham, $^{\ddagger}P<0.05$ vs. wild type TBI; *P<0.05 vs. wild type sham; $^{\#}P<0.05$ vs. contralateral structure; 1-way ANOVA; n=4 animals per group). These data demonstrate that when glymphatic pathway function is impaired beyond what is seen with TBI alone, chronic tau aggregation is promoted.

FIGS. 48A-F. Impairment of Glymphatic Pathway Function Promotes Tau Aggregation after TBI.

(A) The effect of impairment of glymphatic pathway function by Aqp4 gene deletion upon the development of tauopathy after TBI was evaluated. Wild type and Aqp4$^{-/-}$ mice were subjected to TBI and the accumulation of phosphorylated tau (P-tau) was evaluated by immunofluorescence and Western blot (presented in FIGS. 47A-F) 28 days post-injury. (B-D) Double labeling with the AT8 P-tau antibody (specific for pSer202/pThr205 epitopes) and the neuronal marker NeuN showed that in the wild type cortex, P-tau immunoreactivity was not observed. In the Aqp4$^{-/-}$ cortex, marked P-tau labeling was observed, both within neuronal soma (arrows) and in surrounding neurites (arrowheads). (E-F) Quantification of P-tau staining revealed that 28 days after TBI, P-tau immunoreactivity was evident within the ipsilateral cortex, and to a lesser extent the underlying striatum, of Aqp4$^{-/-}$ mice. These data demonstrate that impairment of glymphatic pathway function after TBI promotes tau aggregation and the deposition of P-tau both within neurons and extra-neurally.

FIGS. 49A-L. Impaired Glymphatic Pathway Function Sustains Neuroinflammation after TBI.

The effect of Aqp4 gene deletion upon the persistence of neuroinflammation after TBI was evaluated. (A-F) Wild type and Aqp4$^{-/-}$ mice were subjected to TBI and reactive astrogliosis (GFAP expression) and microgliosis (Iba1 expression) was evaluated by immunofluorescence 28 days post-injury. Markedly elevated GFAP- and Iba1-immunoreactivity was observed solely in the ipsilateral cortex of Aqp4 mice after TBI. (G-H) Quantification of GFAP labeling demonstrated significantly increased reactive astrogliosis in the cortex and underlying striatum of Aqp4$^{-/-}$ but not wild type mice (*P<0.05, **P<0.01 vs. wild type; $^{\#}P<0.05$, $^{\#\#}P<0.01$ vs. contralateral structure; 2-way ANOVA; n=4 animals per group). (I) No differences in GFAP immunoreactivity were observed in the hippocampus. (J-K) Quantification of Iba1 labeling showed that microglial activation persisted in the ipsilateral cortex and striatum of Aqp4$^{-/-}$ mice, but had resolved in wild type mice within 28 days post-injury ($^{\#}P<0.05$ vs. contralateral structure; 2-way ANOVA; n=4 animals per group). (L) Increased Iba1 labeling was observed in the CA3 region of the hippocampus in both wild type and Aqp4$^{-/-}$ mice ($^{\#}P<0.05$ vs. contralateral structure; 2-way ANOVA; n=4 animals per group).

FIGS. 50A-E. Aqp4 Gene Deletion Exacerbates Post-Traumatic Cognitive Impairment.

(A) The effect of impairing the glymphatic pathway upon post-traumatic cognitive deficits was evaluated in wild type and Aqp4 mice subjected to TBI. Animals underwent baseline behavioral testing 2 days prior to injury, then weekly after TBI. (B) Gross motor behavior was assessed by the open field test. TBI did not alter performance in the open field test in either wild type of Aqp4$^{-/-}$ mice. (C) Motor coordination and learning was evaluated by the rotarod test. While TBI did not significantly impair rotarod performance in wild type animals, in Aqp4 mice TBI significantly impaired test performance (*P<0.05 Aqp4$^{-/-}$ sham vs. Aqp4$^{-/-}$ TBI; 2-way repeated measures ANOVA, n=9-14 animals per group). Cognitive function was evaluated with the novel object recognition test (D) and the Barnes maze test (E). In both tests, TBI impaired cognitive performance among both wild type and Aqp4$^{-/-}$ mice (*P<0.05, P<0.01, *P<0.001 TBI vs. Sham; 2-way repeated-measures ANOVA, n=9-14 animals per group). Post-traumatic cognitive impairment was exacerbated in Aqp4$^{-/-}$ mice compared to wild type animals (**P<0.01 wild type TBI vs. Aqp4$^{-/-}$ TBI; 2-way repeated measures ANOVA; n=9-14 per group).

FIGS. 51A-D. AQP4-M1 Variant as a Determinant of Perivascular AQP4 Polarization.

(A) The Aqp4 gene has two transcription initiation site, with transcription initiated at each site resulting in two AQP4 mRNA variants: AQP4-M1 which includes Exons 0-4 of the Aqp4 gene and AQP4-M23 which lacks Exon 0. (B) AQP4-M23 (the predominant form in the CNS under physiological conditions) permits perivascular AQP4 packing while AQP4-M1 prevents it; thus increasing AQP4-M1 expression impairs AQP4 polarization (Crane et el. *J Biol Chem* 2009; Furman et al. *Proc Nat Acad Sci* 2003). (C) The expression of AQP4-M1 was evaluated by real-time quantitative PCR (qPCR) in the mouse ipsilateral cortex 3 days after TBI using PCR primers specifically targeting Exon 0 of the AQP4-M1 transcript. Compared to AQP4-M1 expression in the control (sham) cortex, TBI increased AQP4-M1 expression by approximately two-fold (*P<0.05, t-test; n=5 per group). (D) Using an siRNA-based approach targeting Exon 0 of the AQP4-M1 variant, the expression of AQP4-M1 could be efficiently knocked down in cultured primary mouse cortical astrocytes. Three siRNA duplexes were designed to target Exon 0 of the AQP4-M1 transcript, and primary mouse astrocytes were transfected with these siRNA duplexes for six days. After siRNA treatment, AQP4-M1 expression was evaluated by qPCR, showing efficient knockdown of AQP4-M1 by siRNA targeting of Exon 0 ($^{\#\#\#}P<0.001$, siAQP4-M1 vs. Control, 1-way ANOVA; n=3). In silico screening of the Aqp4 gene promoter revealed two binding sites for the transcription factor signal transducer and activator of transcription (STAT)-3 upstream of the AQP4-M1 transcription initiation site. Thus, we tested whether inhibition of STAT3 signaling in primary mouse cortical astrocytes could reduce AQP4-M1 expression. Treatment of primary astrocytes with the STAT3-specific inhibitor STATTIC significantly reduced AQP4-M1 expression (**P<0.01 STATTIC vs. control, 1-way ANOVA; n=3). These data demonstrate that AQP4-M1 expression is increased after TBI while AQP4-M1 expression can be reduced either by siRNA targeting of the AQP4-M1 transcript or by STAT3 inhibition in astrocytes. These findings are consistent with the notion that the loss of AQP4 polarization after brain injury (such as traumatic brain injury or ischemic brain injury) could be prevented through these approaches.

FIGS. 52A-E. Glymphatic Pathway Function is Impaired after Diffuse Ischemic Injury.

Using a mouse model of multiple microinfarcts (M. Wang et al., Cognitive Deficits and Delayed Neuronal Loss in a Mouse Model of Multiple Microinfarcts, J. Neuroscience, 12 Dec. 2012, 32(50): 17948-17960), the effect of diffuse ischemic injury was evaluated by in vivo 2-photon imaging. (A) Animals were subjected to diffuse ischemic injury. 3 days later, glymphatic pathway function was evaluated by imaging the influx of intracisternally-injected fluorescent CSF tracer (Texas Red-conjugated dextran, MW 70 kD) into the cerebral cortex via a closed cranial window. (B-D) Representative 2-photon images acquired 100 μm below the cortical surface show fluorescent CSF tracer movement into the cortical parenchyma 20 min after intracisternal injection.

(E) Quantification of fluorescence intensity 3 days post-injury 100 μm below the cortical surface by serial 2-photon imaging shows that in control animals, CSF tracer rapidly enters the cortex, peaking within 20 min of injection. In the ipsilateral cortex, CSF tracer influx is virtually abolished, while even in the contralateral cortex, CSF tracer influx is markedly impaired. These data demonstrate that diffuse ischemic injury, which causes loss of perivascular AQP4 polarization (Wang et al. *J Neurosci* 2012), also dramatically impairs glymphatic pathway function.

FIGS. 53A-B. Glymphatic Pathway Function is Impaired after Diffuse Ischemic Injury.

Using a mouse model of multiple microinfarcts described recently (Wang et al. *J Neurosci* 2012), the effect of diffuse ischemic injury was evaluated by whole-slice fluorescence imaging. Animals were subjected to diffuse ischemic injury. 3 days later, glymphatic pathway function was evaluated by intracisternal injection of CSF tracer (ovalbumin-conjugated ALEXA-647, OA-647, MW 45 kD). 30 min after tracer injection, animals were fixed, brains were sliced, and CSF tracer influx was evaluated by conventional fluorescence microscopy. (A) In the control brain, CSF tracer moves rapidly into the brain parenchyma along paravascular spaces. (B) After diffuse ischemic injury CSF influx into the brain is dramatically reduced. Ipsilaterally, CSF movement into the parenchyma is virtually abolished. In the contralateral hemisphere, although paravascular CSF influx is present, its rate and extent of exchange with the surrounding interstitial space is dramatically reduced.

6.7 Example 7

Glymphatic System: Target for Brain-wide Clearance in the Aging Brain and in Alzheimer's Disease As disclosed herein, increasing brain clearance of toxic or waste substances by modulating the brain's normal mechanisms controlling the convective flow of brain interstitial fluid (ISF) and cerebrospinal fluid (CSF)/ISF exchange in the aging brain, removes waste byproducts of metabolism and toxin associated with neurodegenerative diseases, such as Alzheimer's disease (AD).

As disclosed in this example, a method is provided for modulating the brain's renin-angiotensin system (RAS) to enhance clearance of substances, such as amyloid-β, from brain. Alzheimer's disease is one major target for treatment by this method. Currently, there is no treatment that will slow or stop the progression of this devastating disease.

This example also demonstrates that art-known antagonists of AVP (vasopressin) (e.g., tolvaptan, conivaptan, or VPA-985), of atrial natriuretic peptide (ANP) (e.g., anantin), of Angiotensin II (e.g., losartan), of AT2R receptors (e.g., PD123319), or of AT1 receptors (e.g., valsartan) can be used to increase or promote glymphatic clearance.

Background

Accumulation of toxic dysfunctional proteins in the brain is associated with many neurodegenerative diseases, including Alzheimer's, Parkinson's, Huntington's and amyotrophic lateral sclerosis (ALS). However, the mechanism that leads to the accumulation of toxins in the aging brain is not completely known. In the case of AD, the two hallmarks are senile plaques, which are extracellular deposits of amyloid-β toxins (Aβ), and intracellular neurofibrillary tangles (hyperphosphorylated tau). The "amyloid cascade" hypothesis suggests that the cognitive decline and the distinct pathogenic features in AD are related to abnormal accumulation of these toxins (Selkoe, 2001; Hardy, 2006).

Aβ is produced by many cells in the body, including nerve cells in the brain, from a large protein called amyloid-β precursor protein (APP), which is cleaved by proteases, β-secretase and γ-secretase, to produce Aβ (Selkoe, 2001). In normal individuals, these toxins are present at low concentrations in the brain, but in AD they accumulate and their presence is a major event associated AD pathogenesis (Hardy & Selkoe, 2002). In a small number of cases (<1%) the Aβ accumulation is due to it overproduction (early onset AD) while in the majority of cases its due to faulty clearance from brain (late on-set AD) (Tanzi, 2005; Tanzi et al., 2004; Mawuenyega et al., 2010). Increased levels of Aβ in the brain result in formation of neurotoxic Aβ oligomers, progressive synaptic loss and neuronal dysfunction (Masters and Selkoe, 2012). Aβ peptides are the main constituent of amyloid-β in the brain parenchyma and in the vasculature (cerebral amyloid angiopathy, CAA). Aβ extracted from senile plaques is mainly peptides $A\beta_{1-40}$ ($A\beta 40$) and $A\beta_{1-42}$ ($A\beta 42$) while vascular amyloid is mainly peptides $A\beta_{1-39}$ and $A\beta 40$. The major soluble form of Aβ present in cerebrospinal fluid (CSF) and brain is $A\beta 40$. Soluble Aβ which is circulating in CSF, and brain interstitial fluid (ISF) may exist as free peptide and/or associated with different binding proteins (carriers), such as apolipoprotein E (apoE), apolipoprotein J (apoJ), transthyretin, albumin, and α2-macroglobulin ($\alpha_2 M$) (Deane et al., 2009). Therapies based only on lowering brain Aβ production have, so far, been unsuccessful in clinical trials (Hardy, 2009).

Aβ is eliminated from brain ISF through various routes, including cellular uptake and degradation, ISF convective flow, and blood-brain barrier (BBB)-mediated transport (Deane et al., 2009). As disclosed herein, the glymphatic system is a macroscopic brain-wide path of CSF/ISF exchange that facilitates clearance of metabolic by-products, including Aβ. The glymphatic system is fundamental for the convective flow of brain ISF, mediated by astrocytes and functions similar to the peripheral lymphatic system. The glymphatic system consists of three main pathways: (1) CSF from the subarachnoid space re-enters brain via the para-arterial space, (2) astrocytic aquaporin 4 (AQP4, water channels specific in astrocytes) drives convective flow of brain ISF through the brain parenchyma, and (3) efflux via para-venous clearance. However, since the CSF rapidly enters the brain parenchyma along penetrating arteries, the glymphatic system may also act as a distribution path for brain-wide delivery of essential compounds as well as removing toxic compounds. Also, it is an appropriate mechanism that could clear the brain of all forms of Aβ, bound and free.

Fluid Balance in the Periphery

In the periphery, plasma volume and composition of salts (sodium chloride) and blood pressure are maintained by interacting systems, including hormones (aldosterone and vasopressin), the renin-angiotensin system (RAS), and the sympathetic nervous system. These mechanisms are well established (Dinh et al., 2001; Zucker, 2002; Persson, 2003; Burnier, 2003; Arnold et al., 2013; Ohshima et al., 2013). Reduced plasma volume causes the release of renin from the kidneys which in turn proteolytically cleave angiotensin I (a decapeptide) from the precursor angiotensinogen (produce in the liver) in plasma. Angiotensin I is further processed to angiotensin II by angiotensin converting enzymes (ACE). Furthermore, the cascade diverges with the procession of angiotensin I and angiotensin II to other active metabolites, including angiotensin (1-7), with contrasting biological actions (FIG. 54) Angiotensin-converting enzyme 2 catalyzes the conversion of angiotensin I to angiotensin (1-9) and angiotensin II to angiotensin (1-7). Other enzymes may also play a role in the cascade of active metabolites of the RAS, such as cathepsin and neprilysin. Angiotensin II acts on two class of pharmacological G protein-couples receptors, angiotensin 1 receptor (AT1R) and angiotensin 2 receptor (AT2R), whereas angiotensin (1-7) acts on the recently identified mas receptor. Angiotensin II stimulates the secretion of aldosterone from the adrenal cortex, which retains sodium in plasma by reducing its excretion mainly by the kidneys. Angiotensin II also causes vasoconstriction (maintain perfusion pressure). Simultaneously vasopressin is secreted from the posterior pituitary gland and promotes water retention by reducing water excretion by the kidneys. Collectively, these mechanisms maintain blood pressure, plasma (extracellular volume) volume and plasma salts concentrations. The reverse occurs when plasma volume is increased. In contrast to angiotensin II, Angiotensin (1-7) cause vasodilation by acting on receptor called Mas (Santos et al., 2003).

Angiotensin II actions on AT2 receptor also cause vasodilation. Thus a balance between angiotensin II and angiotensin (1-7) modulate the outcomes of the RAS. One of the key enzyme in this balancing of the RAS effects is believe to be the angiotensin-converting enzyme 2, since it plays a major role in the conversion of angiotensin I and angiotensin II to angiotensin (1-7) (Gallagher et al., 2006).

Brain Renin Angiotensin System (RAS).

The brain RAS is believed to be independent of the RAS in the periphery (Mogi et al., 2012; Ohshima et al., 2013. The brain plays a major role is controlling blood pressure, plasma volume and salt composition by integration these established mechanisms. In addition, due to the BBB, it may control its own fluid environment (volume and composition of the ISF/ECF), perhaps in a similar way as the regulation of plasma volume and salts composition. In addition RAS has other roles not related to salt and water balance, such as neuroprotection, learning and inflammation. Activation of angiotensin 2 receptor and Mas receptor lead to vasodilation, neuroprotection, cognition, anti-proliferative effects and anti-hypertensive effects (Sudilovsky et al., 1987; Wang et al., 2007). In aging and in AD, the brain RAS is believed to be enhanced (Wright et al., 2010; Savaskan et al., 2001). Levels of angiotensin-converting enzyme is increased in the caudate nucleus and cortex in AD (Arregui et al., 1982), which may influence risk of AD (Hemming et al., 2005; Najjar et al., 2012; Saavedra et al., 2012; AbdAlla et al., 2013)

In brain, astrocytes are a major source of angiotensinogen, the precursor for angiotensin I, and of angiotensin-converting enzyme 2 for the conversion into angiotensin (1-7) (Gallagher et al., 2006). Astrocytes also possess angiotensin 1 receptor. Thus astrocytes may play a key role in controlling brain ISF volume and salts. Moreover, recently we have shown that blocking noradrenalin receptors ($\alpha 1$, $\alpha 2$ and $\beta$) increased clearance of A$\beta$ and inulin from brain via the glymphatic system, (Xie et al., 2013). Noradrenalin, a neurotransmitter of the activated sympathetic nervous system and adrenergic system, increases the activity of renin, the enzyme that converts angiotensinogen to angiotensin I (Michael et al., 2001; Campbell et al., 1979; Macova et al., 2009). Thus, increasing the activity of the brain adrenergic system (Locus Coeruleus) in arousal (wakefulness) may increase RAS activity. This is associated with reduced clearance via the glymphatic system during wake state (Xie et al., 2013). Blocking the adrenergic system, as in a sleep state, is associated with increased clearance of substances from brain (Xie et al., 2013).

Thus, the RAS may play a major role in controlling clearance of ISF substances via the glymphatic system. However the role of the RAS in the clearance of substance present in the ISF is unclear.

Brain RAS Conserves Brain ISF Fluid, as it does in the Periphery, and Blocking its Action Increases Clearance of ISF by the Glymphatic System.

Since this is a fundamental brain-wide system, it will have application to many diseases associated with accumulation of toxic substances in brain, including Aft This hypothesis was tested by using angiotensin II, angiotensin (1-7), blockers of angiotensin I receptor (Losartan, Valsartan) and blocker of angiotensin (1-7) receptor (A779) on clearance of $^{125}$I-A$\beta$1-40 (referred to as A$\beta$) and $^{14}$C-inulin (referred to as inulin), a molecule that is cleared only by convective blow of ISF (Xie et al., 2013). The role of RAS on clearance of exogenous $^{125}$I-A$\beta$ and $^{14}$C-inulin were determined at 30 minutes after their injection into the frontal cortex (Xie et al., 2013). The role of RAS on the influx of these molecules into brain was determined by injecting these molecules into the subarachnoid space (cisterna magna) and determining brain levels after 30 minutes. A$\beta$ represented a peptide associated with AD and inulin an inert molecule and marker of convective flow of molecules in the ISF. The data confirm the hypothesis.

Methods

Brain Clearance Studies:

Briefly, a stainless steel guide cannula was implanted stereotaxically into the right caudate-putamen or frontal cortex of anesthetized mice (ketamine (100 mg/kg) and xylazine (10 mg/kg). For the frontal cortex, the coordinate of the cannula tip was 0.7 mm anterior and 3.0 mm lateral to the bregma, and 1.3 mm below the surface of the brain. Animals were allowed to recover after surgery. The experiments were performed before substantial chronic process occurred, but allowing time for the BBB repair to large molecules, as reported (Deane et al., 2004). Drugs were pre-injected for 10 minutes before injection of the radiolabeled molecules.

Injection of the mixture of tracers: Mock CSF (0.5 µL) containing $^{125}$I-labeled A$\beta$40 (10 nM monomer) together with $^{14}$C-inulin (0.05 µCi, an inert molecule for bulk flow) was microinfused into brain ISF over 5 minutes.

Tissue Sampling:

At the end of the experiments brain was removed and prepared for radioactivity analysis and TCA analyses.

Analysis of Radioactivity:

$^{125}$I-radioactivities were determined in a gamma counter (Wallac Vizard Gamma Counter, Perkin Elmer). For $^{14}$C-counting, the samples were solubilized in 0.5 ml tissue solubilizer (Perkin Elmer) overnight, followed by addition of 5 ml of scintillation cocktail (Packard Ultima Gold) and analyzed in a liquid scintillation counter (Beckman Coulter Counter).

Calculations:

All calculations of clearance parameters were carried out as described above or by routine methods (Deane et al., 2004; Xie et al., 2013). Briefly, the percentage of radioactivity remaining in the brain after microinjection was determined as % recovery in brain=$100 \times (N_b/N_i)$, where $N_b$ is the radioactivity remaining in the brain at the end of the experiment and $N_i$ is the radioactivity injected into the brain ISF, i.e., the d.p.m. for $^{14}$C-inulin and the c.p.m. for the TCA-precipitable $^{125}$I-radioactivity. Inulin was used as a metabolically inert polar molecule which is neither transported across the BBB nor retained by the brain; its clearance rate provides a measure of the ISF convective bulk flow. For each group there were 3-6 mice, and data expressed as mean±SEM. $P<0.5$ was taken as statistically significant as determined using T-test.

Results

A. Pharmacological Intervention

1) Effect of Angiotensin and Losartan on the Recovery of $^{125}$I-Aβ40 and $^{14}$C-inulin in Brain after their Injection into the Frontal Cortex A small volume (0.5 µL) of mock CSF containing $^{125}$I-Aβ40 (10 nM) and $^{14}$C-inulin (0.05 µCi) was microinjected into the frontal cortex. At the end of the experiment (30 minutes) the brain was removed and analyzed for radioactivity. FIG. 55A shows that there was an increase in the levels of Aβ40 remaining in brain with angiotensin II (1 µM). In contrast losartan (1 µM), an antagonist of angiotensin 1 receptor, reduced the recovery of Aβ. FIG. 55B shows that there was also an increase in the levels of inulin remaining in brain with angiotensin II (1 µM). In contrast losartan (1 µM) reduced the recovery inulin. Thus, angiotensin II reduced clearance via convective flow of ISF.

2) Effect of Angiotensin and Losartan on the Influx of $^{125}$I-Aβ40 and $^{14}$C-Inulin in Brain after their Injection into the Cistern Magna A small volume (5 µL) of mock CSF containing $^{125}$I-Aβ40 (10 nM) and $^{14}$C-inulin (0.05 µCi) was microinjected into the cistern magna at 1 µL/min. At the end of the experiment (30 minutes) the brain was removed and analyzed for radioactivity. FIG. 56A shows that there was a decrease in the influx of Aβ40 into brain with angiotensin II (1 µM). In contrast losartan, injected into the cistern magna (1 µM) or intraperitoneally (IP; 1 mg) increased the influx of Aβ. FIG. 56B shows that there was also a decrease in the influx of inulin with angiotensin II (1 µM). In contrast losartan increased the influx of inulin.

3) Effect of Vasopressin on the Recovery of $^{125}$I-Aβ40 and $^{14}$C-inulin in Brain after their Injection into the Frontal Cortex FIG. 57 shows that vasopressin (1 µM), a hormone that retains water in the body, injected into the frontal cortex reduced clearance of both Aβ and inulin from brain compared to controls 4) Effect of Atrial Natriuretic Peptide (ANP) on the Recovery of $^{125}$I-Aβ40 and $^{14}$C-inulin in Brain after their Injection into the Frontal Cortex FIG. 58 show that atrial natriuretic peptide (ANP) (1 µM), a peptide that reduces body water and sodium, when injected into the frontal cortex, reduced clearance of Aβ and inulin. ANP secretion is stimulated by various factors, including increased sympathetic activation, as seem in conditions of wakefulness.

5) Effect of Angiotensin (1-7) (A7) on the Recovery of $^{125}$I-Aβ40 and $^{14}$C-inulin in Brain after their Injection into the Frontal Cortex Angiotensin (1-7) has been shown to have neuroprotective effects, and opposes the action of angiotensin II. The effect was determined of angiotensin (1-7) pre-injected into the frontal cortex on clearance of Aβ and inulin from brain. FIG. 59 shows that clearance of Aβ was increased progressively with dose.

To improve sensitivity, the time point was reduced. Using a 15 minute time point, there was a greater change between concentrations 10 nM and 1 nM angiotensin (1-7) (FIG. 60).

Figure 61:
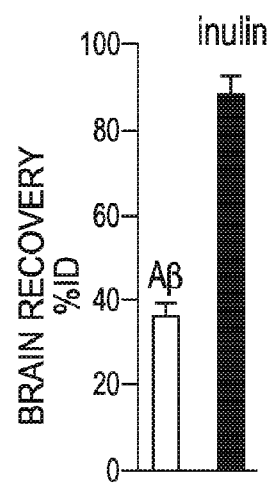

To confirm the effect of angiotensin (1-7), a blocker was used, A779, which antagonizes this ligand by blocking the receptor. A779 (I µM) was first injected into the cistern magna for 10 minutes, and then Aβ and inulin clearance from the frontal cortex were determined in the presence of A779 (1 µM) and angiotensin (1-7) (10 nM). FIG. 61 shows that the effect of angiotensin (1-7) was prevented with the blocker.

6) Effect of Blocking Nitric Oxide (NO) on the Glymphatic Pathways.

Since nitric oxide (NO) plays a key role in mediating the effects of many hormones, neurotransmitter and interacts with the RAS, the role of NO in the glymphatic system was determined.

Figure 62:
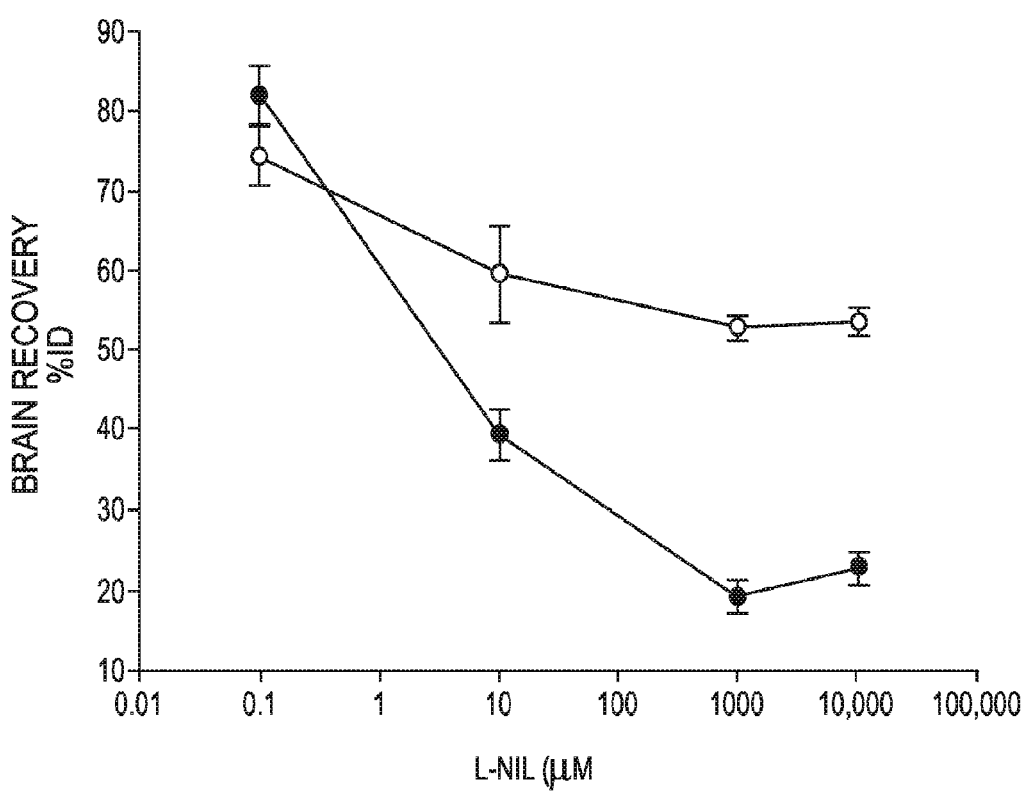

A selective inhibitor of the inducible nitric oxide synthase (iNOS), L-NIL, was used. FIG. 62 shows that L-NIL has a dose dependent effect on the clearance of Aβ and inulin. Clearance was increased at 1 mM L-NIL.

Figure 63:
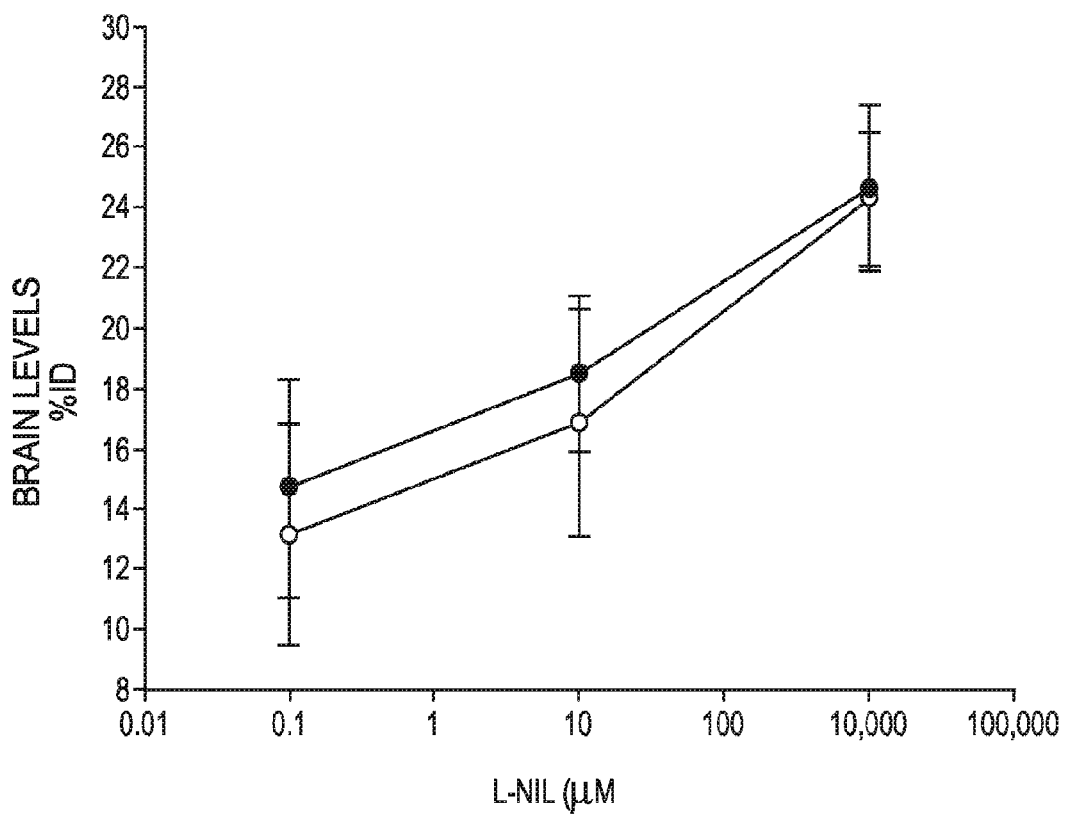

There was also a dose dependent increase in the influx of Aβ and inulin with L-NIL (FIG. 63).

B. Mechanical Disruption of the Glymphatic System

First, the cisterna magna was cannulated and CSF allowed to be drained continuously. After 10 minutes clearance of Aβ from the frontal cortex was determined for 30 minutes. FIG. 64 shown that Aβ clearance from the cortex was reduced while CSF was drained from the cistern magna. Thus, diverting CSF flow from brain may reduce its re-circulation into brain via the para-arterial space, and reduce convective flow through the parenchyma, which in turn reduce clearance.

C. Sleep Deprivation

Clearance of Aβ and inulin were increased under sleep conditions (see also Xie et al., 2013, incorporated by reference herein in its entirety). To establish whether sleep deprivation alters clearance, mice were deprived of sleep by gentle handling from 6 AM (light-on) for 6 hrs. Clearance of Aβ was then determined under wakefulness. FIG. 65 shows that clearance of Aβ was reduced during sleep deprivation.

Thus, to increase glymphatic clearance, in certain embodiments, an agent for use in the treatment of insomnia or an aid for sleep can be administered to the subject or patient using routine, clinically-accepted methods, including, but not limited to:

Antihistamines (e.g., Over-the-counter):
ALLEGRA® (Fexofenadine)
BENADRYL® (Diphenhydramine)
CLARITIN® or TAVIST® (loratadine)
CHLOR-TRIMETON® (chlorpheniramine maleate)
DIMETANE® (Brompheniramine, Phenylpropanolamine)
ZYRTEC® (Cetirizine)
Nonprescription Sleep Aids:
Unisom Nighttime Sleep-Aid
Dormin
Nytol
Simply Sleep
Sominex
Extra Strength Tylenol PM
Diphenhydramine hydrochloride
Excedrin P.M.
Benzodiazepines:
PROSUM® (estazolam)
DALMANE® (flurazepam)
DORAL® (quazepam)
RESTORIL® (temazepam)
HALCION® (triazolam)
VALIUM® (diazepam)

Non-Benzodiazepines:
Imidazopyridines: AMBIEN®, AMBIEN® CR, INTERMEZZO® (zolpidem) (class of its own)
SONATA® (pyrazolopyrimidine) (class of its own)
melatonin receptor stimulator:
ROZEREM® (ramelteon)
NOTEC® (chloral hydrate)
PRECEDEX® (dexmedetomidine hydrochloride)
LUNESTA® (eszopiclone)
Barbiturates:
NEMBUTAL® (phenobarbital)
MEBARAL® (mephobarbital)
Amytal Sodium (amobarbital sodium)
BUTISOL® (butabarbital sodium)
SECONAL® Sodium Pulvules (secobarbital sodium)

REFERENCES CITED IN EXAMPLE 7

AbdAlla, S., A. Langer, X. Fu and U. Quitterer. "Ace Inhibition with Captopril Retards the Development of Signs of Neurodegeneration in an Animal Model of Alzheimer's Disease." Int J Mol Sci 14, no. 8 (2013): 16917-42.

Arnold, A. C., P. E. Gallagher and D. I. Diz. "Brain Renin-Angiotensin System in the Nexus of Hypertension and Aging." Hypertens Res 36, no. 1 (2013): 5-13.

Arregui, A., E. K. Perry, M. Rossor and B. E. Tomlinson. "Angiotensin Converting Enzyme in Alzheimer's Disease Increased Activity in Caudate Nucleus and Cortical Areas." J Neurochem 38, no. 5 (1982): 1490-2.

Burnier, M. "Angiotensin Ii Type 1 Receptor Blockers." Circulation 103, no. 6 (2001): 904-12.

Campbell, W. B., R. M. Graham and E. K. Jackson. "Role of Renal Prostaglandins in Sympathetically Mediated Renin Release in the Rat." J Clin Invest 64, no. 2 (1979): 448-56.

Deane, R., R. D. Bell, A. Sagare and B. V. Zlokovic. "Clearance of Amyloid-Beta Peptide across the Blood-Brain Barrier: Implication for Therapies in Alzheimer's Disease." CNS Neurol Disord Drug Targets 8, no. 1 (2009): 16-30.

Dinh, D. T., A. G. Frauman, C. I. Johnston and M. E. Fabiani. "Angiotensin Receptors: Distribution, Signalling and Function." Clin Sci (Lond) 100, no. 5 (2001): 481-92.

Gallagher, P. E., M. C. Chappell, C. M. Ferrario and E. A. Tallant. "Distinct Roles for Ang II and Ang-(1-7) in the Regulation of Angiotensin-Converting Enzyme 2 in Rat Astrocytes." Am J Physiol Cell Physiol 290, no. 2 (2006): C420-6.

Najjar, I., L. Brown, W. J. Mack and H. Chui. "Impact of Angiotensin Receptor Blockers on Alzheimer Disease Neuropathology in a Large Brain Autopsy Series." Arch Neurol 69, no. 12 (2012): 1632-8.

Hardy, J. "A Hundred Years of Alzheimer's Disease Research." Neuron 52, no. 1 (2006): 3-13.

Hardy, J. "The Amyloid Hypothesis for Alzheimer's Disease: A Critical Reappraisal." J Neurochem 110, no. 4 (2009): 1129-34.

Hardy, J. and D. J. Selkoe. "The Amyloid Hypothesis of Alzheimer's Disease: Progress and Problems on the Road to Therapeutics." Science 297, no. 5580 (2002): 353-6.

Hemming, M. L. and D. J. Selkoe. "Amyloid Beta-Protein Is Degraded by Cellular Angiotensin-Converting Enzyme (Ace) and Elevated by an Ace Inhibitor." J Biol Chem 280, no. 45 (2005): 37644-50.

Macova, M., J. Pavel and J. M. Saavedra. "A Peripherally Administered, Centrally Acting Angiotensin Ii At2 Antagonist Selectively Increases Brain At1 Receptors and Decreases Brain Tyrosine Hydroxylase Transcription, Pituitary Vasopressin and ACTH." Brain Res 1250, (2009): 130-40.

Masters, C. L. and D. J. Selkoe. "Biochemistry of Amyloid Beta-Protein and Amyloid Deposits in Alzheimer Disease." Cold Spring Harb Perspect Med 2, no. 6 (2012): a006262.

Mawuenyega, K. G., W. Sigurdson, V. Ovod, L. Munsell, T. Kasten, J. C. Morris, K. E. Yarasheski and R. J. Bateman. "Decreased Clearance of CNS Beta-Amyloid in Alzheimer's Disease." Science 330, no. 6012 (2010): 1774.

Michael, R., F. Fam and A. Abadir. "Effect of Adrenergic Agonists and Antagonists on Renin Release." Proc West Pharmacol Soc 44 (2001): 113-5.

Mogi, M., J. Iwanami and M. Horiuchi. "Roles of Brain Angiotensin Ii in Cognitive Function and Dementia." Int J Hypertens 2012 (2012): 169649.

Ohshima, K., M. Mogi and M. Horiuchi. "Therapeutic Approach for Neuronal Disease by Regulating Renin-Angiotensin System." Curr Hypertens Rev 9, no. 2 (2013): 99-107.

Persson, P. B. "Renin: Origin, Secretion and Synthesis." J Physiol 552, no. Pt 3 (2003): 667-71.

Saavedra, J. M. "Angiotensin II at (1) Receptor Blockers as Treatments for Inflammatory Brain Disorders." Clin Sci (Lond) 123, no. 10 (2012): 567-90.

Santos, R. A., A. C. Simoes e Silva, C. Maric, D. M. Silva, R. P. Machado, I. de Buhr, S. Heringer-Walther, S. V. Pinheiro, M. T. Lopes, M. Bader, E. P. Mendes, V. S. Lemos, M. J. Campagnole-Santos, H. P. Schultheiss, R. Speth and T. Walther. "Angiotensin-(1-7) Is an Endogenous Ligand for the G Protein-Coupled Receptor Mas." Proc Natl Acad Sci USA 100, no. 14 (2003): 8258-63.

Savaskan, E., C. Hock, G. Olivieri, S. Bruttel, C. Rosenberg, C. Hulette and F. Muller-Spahn. "Cortical Alterations of Angiotensin Converting Enzyme, Angiotensin Ii and At1 Receptor in Alzheimer's Dementia." Neurobiol Aging 22, no. 4 (2001): 541-6.

Selkoe, D. J. "Clearing the Brain's Amyloid Cobwebs." Neuron 32, no. 2 (2001): 177-80.

Sudilovsky, A., B. Turnbull, S. H. Croog and T. Crook. "Angiotensin Converting Enzyme and Memory: Preclinical and Clinical Data." Int J Neurol 21-22 (1987): 145-62.

Tanzi, R. E. "The Synaptic Abeta Hypothesis of Alzheimer Disease." Nat Neurosci 8, no. 8 (2005): 977-9.

Tanzi, R. E., R. D. Moir and S. L. Wagner. "Clearance of Alzheimer's Abeta Peptide: The Many Roads to Perdition." Neuron 43, no. 5 (2004): 605-8.

Wang, J., L. Ho, L. Chen, Z. Zhao, W. Zhao, X. Qian, N. Humala, I. Seror, S. Bartholomew, C. Rosendorff and G. M. Pasinetti. "Valsartan Lowers Brain Beta-Amyloid Protein Levels and Improves Spatial Learning in a Mouse Model of Alzheimer Disease." J Clin Invest 117, no. 11 (2007): 3393-402.

Wright, J. W. and J. W. Harding. "The Brain Ras and Alzheimer's Disease." Exp Neurol 223, no. 2 (2010): 326-33.

Xie, L., H. Kang, Q. Xu, M. J. Chen, Y. Liao, M. Thiyagarajan, J. O'Donnell, D. J. Christensen, C. Nicholson, J. J. Miff, T. Takano, R. Deane and M. Nedergaard. "Sleep Drives Metabolite Clearance from the Adult Brain." Science 342, no. 6156 (2013): 373-7 (incorporated by reference herein in its entirety).

Zucker, I. H. "Brain Angiotensin Ii: New Insights into Its Role in Sympathetic Regulation." Circ Res 90, no. 5 (2002): 503-5.

6.8 Example 8

Modulation by Aquaporin 4 (AQP4) of Amyloid Beta Clearance from the Brain

Members of the aquaporin family of intrinsic membrane proteins function as water-selective channels in the plasma membranes of many cells. Aquaporin 4 (AQP4) is the predominant aquaporin found in brain. This example demonstrates that AQP4 modulates amyloid beta clearance from the brain. Either the activation of AQP4 can accelerate amyloid beta clearance from the brain, or the inhibition of AQP4 can exacerbate amyloid beta deposition in a transgenic mouse model of Alzheimer's disease. Based on the results disclosed in this example, neurodegenerative diseases, including Alzheimer's disease, can be treated with, ameliorated by, or prevented by, the drugs JNJ-17299425 or JNJ-17306861, which promote perivascular polarization of AQP4.

Neurodegenerative diseases including Alzheimer's disease are characterized by mis-aggregation of peptides and proteins into toxic aggregates and plaques, caused in part by the age- or injury-related failure of extracellular protein or peptide clearance. Extracellular protein and peptide clearance from the brain depends upon the perivascular localization of AQP4; polarization that is lost in the aging and injured brain. Maintaining perivascular polarization of AQP4 can be used to maintain the clearance of these solutes from the extracellular compartment, preventing or slowing the onset and progression of neurodegeneration.

Currently, no therapeutic approaches exist that prevent loss of AQP4 polarization in the aging brain. Instead, current approaches for dealing with these aggregates are aimed at preventing the production of their constituents or by targeting the aggregates for destruction. The former may be harmful, as these constituents are often physiologically active compounds that are necessary for normal function, while targeting of aggregates may take place too late in the pathological process to prevent neuronal loss. By maintaining 'normal' AQP4 polarization and clearance of these constituents, aggregation is prevented prior to the onset of disease and the loss of neurons.

JNJ-17299425 or JNJ-17306861 (Janssen Pharmaceuticals, Inc., Titusville, N.J. 08560) and their derivatives are known to prevent the loss of AQP4 polarization after traumatic brain injury, while no other drug has yet been reported that can maintain AQP4 polarization. In one embodiment, by treating with JNJ-17299425 or JNJ-17306861 early in the neurodegenerative process, protein and peptide aggregation can be prevented without the need to alter cellular processes responsible for their production.

Amyloid beta clearance along these pathways is dependent upon AQP4 polarization. In models of diffuse ischemic injury and mild and moderate traumatic brain injury, perivascular AQP4 localization is consistently lost after brain injury. In both the aging mouse and human brain, perivascular AQP4 polarization is lost. This is accompanied by a failure of interstitial amyloid beta clearance. Loss of perivascular AQP4 polarization contributes to the failure of interstitial amyloid beta and tau clearance. Therapeutic approaches that maintain this polarization can be effective in preventing the onset of amyloid beta or tau aggregation as well as down-stream neurodegenerative processes.

Proof-of-concept studies are conducted to determine whether activation of AQP4 accelerates amyloid beta clearance from the brain, or whether inhibition of AQP4 exacerbates amyloid beta deposition in a transgenic mouse model of Alzheimer's disease.

JNJ-17299425 and JNJ-17306861 are tested to determine whether they can prevent loss of AQP4 polarization in the aging brain or in the young brain after traumatic brain injury.

JNJ-17299425 may improve AQP4 function by retaining it at the perivascular endfeet after traumatic injury. Prevention of AQP4 mis-localization in the aging and neurodegenerating brain may prevent amyloid beta and tau aggregation. Thus AQP4-targeting compounds JNJ-17299425 or JNJ-17306861 may be effective in maintaining amyloid beta and tau clearance in the aging brain, and preventing their aggregation.

A sample of devices that are described herein are set forth in the following numbered paragraphs:

1. A method for measuring glio-vascular pathway (hereinafter "glymphatic system") function in the central nervous system (brain and/or spinal cord) of a mammal comprising the steps of:
   performing imaging of the central nervous system; and
   measuring cerebrospinal fluid-interstitial fluid (hereinafter "CSF-ISF") exchange in the central nervous system.

2. The method of paragraph 1 wherein the mammal is a human or a non-human primate.

3. The method of paragraph 1 wherein the mammal is a patient or a subject in need of treatment.

4. The method of paragraph 1 further comprising the step of administering an imaging agent prior to the step of performing imaging of the central nervous system.

5. The method of paragraph 4 wherein the imaging agent is administered intrathecally.

6. The method of paragraph 5 wherein the step of administering intrathecally the imaging agent comprises the step of administering a lumbar or an intracisternal intrathecal injection of the imaging agent.

7. The method of paragraph 4 wherein:
   the imaging agent is a negative or positive (paramagnetic) contrast agent, and the step of performing imaging of the central nervous system comprises the step of performing dynamic or contrast-enhanced magnetic resonance imaging (MRI) of the central nervous system.

8. The method of paragraph 7 wherein at least two different MRI contrast agents are administered, the different MRI contrast agents being matched in terms of their effects on T1 (paramagnetic) or T2 (negative contrast agents) so that their kinetic characteristics in brain tissue can be compared.

9. The method of paragraph 4 wherein:
   the imaging agent is a positron-emitting radionuclide tracer, and
   the step of performing imaging of the brain and spinal cord comprises the step of performing positron emission tomography (PET) scanning of the central nervous system.

10. The method of paragraph 1 wherein the step of measuring CSF-ISF exchange comprises measuring clearance of soluble amyloid β (Aβ), tau, a nanoparticle such as functionalized or therapeutic nanoparticle, a chemotherapy agent, a toxic product administered therapeutically, small interfering RNA (siRNA), alpha synuclein, a small molecule drug, a viral vector, an antibody-based therapeutic, a liposome or a therapeutic RNA construct.

11. The method of paragraph 1 wherein the step of measuring CSF-ISF exchange comprises measuring clearance of a therapeutic agent.

12. The method of paragraph 11 wherein the therapeutic agent is a chemotherapy agent, a functionalized nanoparticle or a toxic composition administered for a therapeutic use.

13. The method of paragraph 7 wherein the step of measuring CSF-ISF exchange comprises analyzing influx kinetics, parenchymal distribution and/or clearance of the paramagnetic or negative contrast agent in the brain.

14. The method of paragraph 1 wherein the step of measuring CSF-ISF exchange comprises measuring CSF-ISF exchange at the pituitary recess, the pineal gland recess, the cerebellum and/or the olfactory bulb.

15. The method of paragraph 1 wherein the step of measuring CSF-ISF exchange comprises the step of performing parametric or non-parametric data analysis of signal changes.

16. The method of paragraph 15 wherein the step of performing parametric or non-parametric data analysis of signal changes comprises the step of measuring T1 shortening or T2 changes, respectively.

17. The method of paragraph 1 wherein the step of measuring CSF-ISF exchange comprises the step of calculating an influx kinetic parameter, wherein the influx kinetic parameter reflects a rate of CSF-ISF exchange.

18. The method of paragraph 1 wherein the step of measuring CSF-ISF exchange comprises the single step of calculating a kinetic parameter from a static contrast-enhanced MRI or PET image, wherein the kinetic parameter reflects a rate of CSF-ISF exchange.

19. The method of paragraph 1, further comprising the step of calculating a risk of developing a neurodegenerative disease in the mammal.

20. The method of paragraph 19, wherein the neurodegenerative disease is Parkinson's disease (PD), Alzheimer's disease (AD), Alzheimer's disease with Lewy bodies, Lewy body dementia, mixed dementia, vascular dementia, frontotemporal dementia, chronic traumatic encephalopathy (CTE) or HIV associated dementia.

21. The method of paragraph 1, wherein the mammal is suffering from traumatic brain injury, further comprising the step of calculating a risk of developing chronic traumatic encephalopathy (CTE).

22. A method for treating onset of a neurodegenerative disease in the central nervous system (brain and/or spinal cord) of a mammal comprising the step of increasing glymphatic system clearance, whereby reactive gliosis is reduced or reactive gliosis onset delayed.

23. The method of paragraph 22 wherein the mammal is a human or a non-human primate.

24. The method of paragraph 22 wherein the mammal is a patient or a subject in need of treatment.

25. The method of paragraph 22, wherein the neurodegenerative disease is Parkinson's disease (PD), Alzheimer's disease (AD), Alzheimer's disease with Lewy bodies, Lewy body dementia, mixed dementia, vascular dementia, frontotemporal dementia, chronic traumatic encephalopathy (CTE) or HIV associated dementia.

26. The method of paragraph 22 further comprising the step of measuring glymphatic system function in the brain according to the method of paragraph 1.

27. The method of paragraph 22 wherein the step of increasing glymphatic clearance comprises the step of administering an agent to the mammal that increases glymphatic clearance.

28. The method of paragraph 27 wherein the agent is a Stat-3 inhibitor or molecules known in the art to be bone morphogenetic protein (BMP) signaling axis molecules.

29. The method of paragraph 27 wherein the agent that increases glymphatic clearance is an antagonist of AVP (vasopressin), an antagonist of atrial natriuretic peptide (ANP), an antagonist of Angiotensin II, an antagonist of AT2R receptors, or an antagonist of AT1 receptors.

30. The method of paragraph 27 wherein the agent that increases glymphatic clearance is an agent for use in the treatment of insomnia or as an aid for sleep.

31. The method of paragraph 27 wherein the agent that increases glymphatic clearance is an agent that prevents AQP4 depolarization or loss of AQP4 polarization.

32. The method of paragraph 31 wherein the agent that prevents AQP4 depolarization or loss of AQP4 polarization is JNJ-17299425 or JNJ-17306861.

33. The method of paragraph 22 wherein the step of increasing glymphatic clearance comprises the step of pumping fluid through the central nervous system interstitium.

34. A method for treating reactive gliosis in the central nervous system of a mammal comprising the step of increasing glymphatic system clearance, whereby reactive gliosis is reduced or reactive gliosis onset delayed.

35. The method of paragraph 34 wherein the mammal is a human or a non-human primate.

36. The method of paragraph 34 wherein the mammal is a patient or a subject in need of treatment.

37. The method of paragraph 34 further comprising the step of measuring glymphatic system function in the brain according to the method of paragraph 1.

38. The method of paragraph 34 wherein the step of increasing glymphatic clearance comprises the step of administering an agent to the mammal that increases glymphatic clearance.

39. The method of paragraph 38 wherein the agent is a Stat-3 inhibitor or molecules known in the art to be bone morphogenetic protein (BMP) signaling axis molecules.

40. The method of paragraph 38 wherein the agent that increases glymphatic clearance is an antagonist of AVP (vasopressin), an antagonist of atrial natriuretic peptide (ANP), an antagonist of Angiotensin II, an antagonist of AT2R receptors, or an antagonist of AT1 receptors.

41. The method of paragraph 38 wherein the agent that increases glymphatic clearance is an agent for use in the treatment of insomnia or as an aid for sleep.

42. The method of paragraph 38 wherein the agent that increases glymphatic clearance is an agent that prevents AQP4 depolarization or loss of AQP4 polarization.

43. The method of paragraph 42 wherein the agent that prevents AQP4 depolarization or loss of AQP4 polarization is JNJ-17299425 or JNJ-17306861.

44. The method of paragraph 34 wherein the step of increasing glymphatic clearance comprises the step of pumping fluid through the central nervous system interstitium.

45. A method for promoting clearance of a waste product from the central nervous system interstitium (brain interstitium and/or spinal cord interstitium) of a mammal comprising the step of:

administering an agent to the mammal that increases or promotes glymphatic clearance; or, pumping fluid through the central nervous system interstitium of the mammal.

46. The method of paragraph 45 wherein the mammal is a human or a non-human primate.

47. The method of paragraph 45 wherein the mammal is a patient or a subject in need of treatment.

48. The method of paragraph 45 wherein the brain waste product is soluble amyloid β (Aβ), tau, or alpha synuclein.

49. The method of paragraph 45 further comprising the step of measuring glymphatic system function in the brain according to the method of paragraph 1.

50. A method for treating the central nervous system of a mammal, comprising the step of increasing glymphatic clearance in the central nervous system of the mammal, thereby reducing, decreasing, delaying the onset of, or preventing accumulation of a waste product in the central nervous system of the mammal.

51. The method of paragraph 50 wherein the step of increasing glymphatic clearance in the central nervous system of the mammal comprises the step of:
administering an agent to the mammal that increases or promotes glymphatic clearance; or, pumping fluid through the central nervous system interstitium of the mammal.

52. The method of paragraph 50 wherein the mammal is a human or a non-human primate.

53. The method of paragraph 50 wherein the mammal is a patient or a subject in need of treatment.

54. The method of paragraph 53 wherein the patient or a subject in need of treatment is aged or elderly.

55. The method of paragraph 54 wherein the aged or elderly patient or subject is a human greater than 50, 60, 70 80 or 90 years old.

56. The method of paragraph 50 wherein the waste product is soluble amyloid β (Aβ), tau, or alpha synuclein.

57. The method of paragraph 50 further comprising the step of measuring glymphatic system function in the brain according to the method of paragraph 1.

58. A method for treating the brain of a mammal comprising the step of:
administering an agent to the mammal that increases or promotes glymphatic clearance; or pumping fluid through the central nervous system interstitium of the mammal, thereby decreasing, reducing, delaying onset of, or preventing amyloid β (Aβ), tau and/or alpha synuclein accumulation in the brain interstitium of the mammal.

59. The method of paragraph 58 wherein the brain of the mammal has been subjected to traumatic brain injury.

60. The method of paragraph 58 wherein the mammal is a human or a non-human primate.

61. The method of paragraph 58 wherein the mammal is a patient or a subject in need of treatment.

62. The method of paragraph 58 wherein the patient or a subject in need of treatment is aged or elderly.

63. The method of paragraph 62 wherein the aged or elderly patient or subject is a human greater than 50, 60, 70 80 or 90 years old.

64. The method of paragraph 58 wherein the therapeutic agent is an adrenergic receptor antagonist.

65. The method of paragraph 58 wherein the agent is a Stat-3 inhibitor or molecules known in the art to be bone morphogenetic protein (BMP) signaling axis molecules.

66. The method of paragraph 58 wherein the agent that increases glymphatic clearance is an antagonist of AVP (vasopressin), an antagonist of atrial natriuretic peptide (ANP), an antagonist of Angiotensin II, an antagonist of AT2R receptors, or an antagonist of AT1 receptors.

67. The method of paragraph 58 wherein the agent that increases glymphatic clearance is an agent for use in the treatment of insomnia or as an aid for sleep.

68. The method of paragraph 58 wherein the agent that increases glymphatic clearance is an agent that prevents AQP4 depolarization or loss of AQP4 polarization.

69. The method of paragraph 68 wherein the agent that prevents AQP4 depolarization or loss of AQP4 polarization is JNJ-17299425 or JNJ-17306861.

70. The method of paragraph 58 further comprising the step of measuring glymphatic system function in the brain according to the method of paragraph 1.

71. A method for decreasing or impeding clearance of a therapeutic or modulatory agent from the brain interstitium of a mammal comprising the step of decreasing or impeding glymphatic clearance.

72. The method of paragraph 71 wherein the mammal is a human or a non-human primate.

73. The method of paragraph 71 wherein the mammal is a patient or a subject in need of treatment.

74. The method of paragraph 71, wherein the step of decreasing or impeding glymphatic clearance comprises the step of administering an agent to the mammal that decreases or impedes glymphatic clearance.

75. The method of paragraph 71 wherein the agent is bumetanide, small interfering RNA (siRNA) directed against AQP4, an agonist of AVP (vasopressin), an agonist of atrial natriuretic peptide (ANP), an agonist of Angiotensin II, an agonist of AT2R receptors, or an agonist of AT1 receptors.

76. The method of paragraph 71 further comprising the step of measuring glymphatic system function in the brain according to the method of paragraph 1.

77. The method of paragraph 71 wherein the step of decreasing or impeding glymphatic clearance comprises the step of blocking or erecting a barrier to fluid flow through the central nervous system interstitium of the mammal.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

While embodiments of the present disclosure have been particularly shown and described with reference to certain examples and features, it will be understood by one skilled in the art that various changes in detail may be effected therein without departing from the spirit and scope of the present disclosure as defined by claims that can be supported by the written description and drawings. Further, where exemplary embodiments are described with reference to a certain number of elements it will be understood that the exemplary embodiments can be practiced utilizing either less than or more than the certain number of elements.

All references cited herein are incorporated herein by reference in their entirety and for all purposes to the same extent as if each individual publication, patent or patent application was specifically and individually indicated to be incorporated by reference in its entirety for all purposes.

The citation of any publication is for its disclosure prior to the filing date and should not be construed as an admission that the present invention is not entitled to antedate such publication by virtue of prior invention.

What is claimed is:

1. A method for treating reactive gliosis in the central nervous system (CNS) of a mammal comprising increasing glymphatic system clearance,
wherein increasing glymphatic clearance comprises
producing convective bulk fluid flow from the intracellular compartment to the extracellular compartment of the central nervous system, comprising pumping interstitial fluid (ISF) through the central nervous system interstitium to the cerebrospinal fluid (CSF),
whereby reactive gliosis is reduced or reactive gliosis onset delayed.

2. A method for promoting clearance of a waste product from the central nervous system interstitium, brain interstitium and/or spinal cord interstitium of a mammal comprising
   producing convective bulk fluid flow from the intracellular compartment to the extracellular compartment of the central nervous system, comprising pumping interstitial fluid (ISF) through the central nervous system interstitium to the cerebrospinal fluid (CSF) of the mammal,
thereby reducing or decreasing, accumulation of a waste product in the central nervous system of the mammal.

3. The method of claim 2 wherein the waste product is soluble amyloid β (Aβ), tau, or alpha synuclein.

4. A method for treating traumatic brain injury in the brain of a mammal comprising
   producing convective bulk fluid flow from the intracellular compartment to the extracellular compartment of the central nervous system, comprising pumping interstitial fluid (ISF) through the central nervous system interstitium to the cerebrospinal fluid (CSF) of the mammal,
thereby decreasing or reducing amyloid β (Aβ), tau and/or alpha synuclein accumulation in the brain interstitium of the mammal.

5. A method for treating a neurodegenerative disease in the central nervous system of a mammal comprising increasing glymphatic system clearance, wherein increasing glymphatic clearance comprises
   producing convective bulk fluid flow from the intracellular compartment to the extracellular compartment of the central nervous system, comprising pumping interstitial fluid (ISF) through the central nervous system interstitium to the cerebrospinal fluid (CSF),
whereby reactive gliosis is reduced.

6. The method of claim 5, wherein the neurodegenerative disease is Parkinson's disease (PD), Alzheimer's disease (AD), Alzheimer's disease with Lewy bodies, Lewy body dementia, mixed dementia, vascular dementia, frontotemporal dementia, chronic traumatic encephalopathy (CTE) or HIV associated dementia.

* * * * *